US008076488B2

(12) United States Patent
Dumas et al.

(10) Patent No.: US 8,076,488 B2
(45) Date of Patent: Dec. 13, 2011

(54) BICYCLIC UREA DERIVATIVES USEFUL IN THE TREATMENT OF CANCER AND OTHER DISORDERS

(75) Inventors: Jacques Dumas, Bethany, CT (US);
Stephen Boyer, Fairfield, CT (US);
Sharad Verma, New Haven, CT (US);
Lila Adnane, Madison, CT (US);
Yuanwei Chen, North Haven, CT (US);
Wendy Lee, Hamden, CT (US); Barton Phillips, New Haven, CT (US); Roger A. Smith, Madison, CT (US); William J. Scott, Guildford, CT (US); Jennifer Burke, New Haven, CT (US); Jianqing Chen, New Haven, CT (US); Zhi Chen, Hamden, CT (US); Jianmei Fan, Hamden, CT (US); Karl Miranda, North Haven, CT (US); Brian Raudenbush, Charlton, MA (US); Aniko Redman, Derby, CT (US); Jianxing Shao, Acton, MA (US); Ning Su, Hamden, CT (US); Gan Wang, Wallingford, CT (US); Lin Yi, Milford, CT (US); Qingming Zhu, West Haven, CT (US)

(73) Assignee: Bayer Healthcare LLC, Tarrytown, NY (US)

( * ) Notice: Subject to any disclaimer, the term of this patent is extended or adjusted under 35 U.S.C. 154(b) by 669 days.

(21) Appl. No.: 10/788,426

(22) Filed: Mar. 1, 2004

(65) Prior Publication Data
US 2005/0038031 A1 Feb. 17, 2005

Related U.S. Application Data

(60) Provisional application No. 60/450,323, filed on Feb. 28, 2003, provisional application No. 60/450,324, filed on Feb. 28, 2003, provisional application No. 60/450,348, filed on Feb. 28, 2003.

(51) Int. Cl.
*C07D 213/62* (2006.01)
*C07D 401/00* (2006.01)
*C07D 417/00* (2006.01)

(52) U.S. Cl. .................. 546/298; 546/270.1; 546/275.7; 544/365; 544/373

(58) Field of Classification Search .................. 544/336, 544/353, 365, 373; 514/338, 271.1, 253.09, 514/253.13, 346, 300; 546/271.7, 277.1, 546/275.7, 298, 270.1
See application file for complete search history.

(56) References Cited

U.S. PATENT DOCUMENTS

| | | | |
|---|---|---|---|
| 502,504 A | 8/1893 | Thoms | |
| 1,792,156 A | 2/1931 | Fitzky | |
| 2,046,375 A | 7/1936 | Goldstein et al. | |
| 2,093,265 A | 9/1937 | Coffey et al. | |
| 2,288,422 A | 6/1942 | Rohm | |
| 2,649,476 A | 8/1953 | Martin | |
| 2,683,082 A | 7/1954 | Hill et al. | |
| 2,722,544 A | 11/1955 | Martin | |
| 2,745,874 A | 5/1956 | Schetty et al. | |
| 2,781,330 A | 2/1957 | Downey | |
| 2,797,214 A | 6/1957 | Bossard | |
| 2,867,659 A | 1/1959 | Model et al. | |
| 2,877,268 A | 3/1959 | Applegath et al. | |
| 2,960,488 A | 11/1960 | Tamblyn et al. | |
| 2,973,386 A | 2/1961 | Weldon | |
| 3,151,023 A | 9/1964 | Martin | |
| 3,200,035 A | 8/1965 | Martin et al. | |
| 3,230,141 A | 1/1966 | Frick et al. | |
| 3,284,433 A | 11/1966 | Becker et al. | |
| 3,424,760 A | 1/1969 | Helsley et al. | |
| 3,424,761 A | 1/1969 | Helsley et al. | |
| 3,424,762 A | 1/1969 | Helsley | |
| 3,547,940 A | 12/1970 | Brantley | |
| 3,639,668 A | 2/1972 | AHes et al. | |
| 3,646,059 A | 2/1972 | Brantley | |
| 3,666,222 A | 5/1972 | Griggers | |
| 3,689,550 A | 9/1972 | Schehenbaurn et al. | |
| 3,743,498 A | 7/1973 | Brantley | |
| 3,754,887 A | 8/1973 | Brantley | |
| 3,823,161 A | 7/1974 | Lesser | |
| 3,828,001 A | 8/1974 | Broad et al. | |
| 3,860,645 A | 1/1975 | Nikawitz | |
| 3,990,879 A | 11/1976 | Soper | |
| 4,001,256 A | 1/1977 | Callahan et al. | |
| 4,009,847 A | 3/1977 | Aldrich et al. | |
| 4,042,372 A | 8/1977 | Harper | |
| 4,062,861 A | 12/1977 | Yukinaga et al. | |

(Continued)

FOREIGN PATENT DOCUMENTS

CA 2028536 4/1991

(Continued)

OTHER PUBLICATIONS

Silverman, R. "The Organic Chemistry of Drug Design and Drug Action," 2004, Elsevier, pp. 20-32.*
Avruch et al., "Raf meets Ras: completing the framework of a signal transduction pathway," TIBS 19; Jul. 1994, pp. 279-283.
Baka et al., "A review of the latest clinical compounds to inhibit VEGF in pathological angiogenesis," Expert Opinion Therapeutic Targets, 2006, vol. 10, No. 6, pp. 867-876.
Balani et al., "Metabolic Considerations in Prodrug Design," Chapter Twenty-Three In: Burger's Medicinal Chemistry and Drug Discovery, 5th ed. John Wiley & Sons, Inc., New York, 1995: vol. 1, pp. 949-982.
Berge et al., "Pharmaceutical Salts." Journal of Pharmaceutical Sciences. Jan. 1977:1-19, vol. 66, No. 1.

(Continued)

*Primary Examiner* — Janet Andres
*Assistant Examiner* — Heidi Reese
(74) *Attorney, Agent, or Firm* — Millen, White, Zelano & Branigan, P.C.

(57) ABSTRACT

This invention relates to novel diaryl ureas, pharmaceutical compositions containing such compounds and the use of those compounds or compositions for treating hyper-proliferative and angiogenesis disorders, as a sole agent or in combination with cytotoxic therapies.

32 Claims, No Drawings

U.S. PATENT DOCUMENTS

| | | |
|---|---|---|
| 4,063,928 A | 12/1977 | Johnston |
| 4,071,524 A | 1/1978 | Banitt |
| 4,103,022 A | 7/1978 | Sirrenberg et al. |
| 4,111,680 A | 9/1978 | Yukinaga et al. |
| 4,111,683 A | 9/1978 | Singer |
| 4,116,671 A | 9/1978 | Yukinaga et al. |
| 4,173,637 A | 11/1979 | Nishiyama et al. |
| 4,173,638 A | 11/1979 | Nishiyama et al. |
| 4,183,854 A | 1/1980 | Crossley |
| 4,212,981 A | 7/1980 | Yukinaga et al. |
| 4,240,820 A | 12/1980 | Dickore et al. |
| 4,279,639 A | 7/1981 | Okamoto et al. |
| 4,293,328 A | 10/1981 | Yukinaga et al. |
| 4,358,596 A | 11/1982 | Kruger |
| 4,405,644 A | 9/1983 | Kabbe et al. |
| 4,410,697 A | 10/1983 | Torok et al. |
| 4,437,878 A | 3/1984 | Acker et al. |
| 4,468,380 A | 8/1984 | O'Doherty et al. |
| 4,473,579 A | 9/1984 | Devries et al. |
| 4,499,097 A | 2/1985 | Tomcufcik et al. |
| 4,511,571 A | 4/1985 | Boger et al. |
| 4,514,571 A | 4/1985 | Nakai et al. |
| 4,526,997 A | 7/1985 | O'Doherty et al. |
| 4,540,566 A | 9/1985 | Davis et al. |
| 4,546,191 A | 10/1985 | Nishiyama et al. |
| 4,587,240 A | 5/1986 | Hider et al. |
| 4,623,662 A | 11/1986 | De Vries |
| 4,643,849 A | 2/1987 | Hirai et al. |
| 4,740,520 A | 4/1988 | Hallenbach et al. |
| 4,760,063 A | 7/1988 | Hallenbach et al. |
| 4,775,763 A | 10/1988 | Dalton et al. |
| 4,808,588 A | 2/1989 | King |
| 4,820,871 A | 4/1989 | Kissener et al. |
| 4,863,924 A | 9/1989 | Haga et al. |
| 4,921,525 A | 5/1990 | Grossman et al. |
| 4,963,605 A | 10/1990 | Fukui et al. |
| 4,973,675 A | 11/1990 | Israel et al. |
| 4,977,169 A | 12/1990 | Hausermann et al. |
| 4,985,449 A | 1/1991 | Haga et al. |
| 4,996,325 A | 2/1991 | Kristinsson |
| 5,036,072 A | 7/1991 | Nakajima et al. |
| 5,059,614 A | 10/1991 | Lepage et al. |
| 5,063,247 A | 11/1991 | Sekiya et al. |
| 5,096,907 A | 3/1992 | Carter et al. |
| 5,100,883 A | 3/1992 | Schiehser |
| 5,118,677 A | 6/1992 | Caufield |
| 5,118,678 A | 6/1992 | Kao et al. |
| 5,120,842 A | 6/1992 | Failli et al. |
| 5,130,331 A | 7/1992 | Pascual |
| 5,151,344 A | 9/1992 | Abe et al. |
| 5,151,413 A | 9/1992 | Caufield et al. |
| 5,162,360 A | 11/1992 | Creswell et al. |
| 5,177,110 A | 1/1993 | Oechslein et al. |
| 5,185,358 A | 2/1993 | Creswell et al. |
| 5,256,790 A | 10/1993 | Nelson |
| 5,258,389 A | 11/1993 | Goulet et al. |
| 5,270,458 A | 12/1993 | Lemischka |
| 5,283,354 A | 2/1994 | Lemischka |
| 5,312,820 A | 5/1994 | Ashton et al. |
| 5,319,099 A | 6/1994 | Kamata et al. |
| 5,378,725 A | 1/1995 | Bonjouklian et al. |
| 5,399,566 A | 3/1995 | Katano et al. |
| 5,423,905 A | 6/1995 | Fringeli |
| 5,429,918 A | 7/1995 | Seto et al. |
| 5,432,468 A | 7/1995 | Moriyama et al. |
| 5,441,947 A | 8/1995 | Dodge et al. |
| 5,447,957 A | 9/1995 | Adams et al. |
| 5,456,920 A | 10/1995 | Matoba et al. |
| 5,468,773 A | 11/1995 | Dodge et al. |
| 5,470,882 A | 11/1995 | Dixon et al. |
| 5,480,906 A | 1/1996 | Creemer et al. |
| 5,500,424 A | 3/1996 | Nagamine et al. |
| 5,508,288 A | 4/1996 | Forbes et al. |
| 5,547,966 A | 8/1996 | Atwal et al. |
| 5,559,137 A | 9/1996 | Adams et al. |
| 5,596,001 A | 1/1997 | Hamanaka |
| 5,597,719 A | 1/1997 | Freed et al. |
| 5,624,937 A | 4/1997 | Reel et al. |
| 5,656,612 A | 8/1997 | Monia |
| 5,658,903 A | 8/1997 | Adams et al. |
| 5,667,226 A | 9/1997 | Janich |
| 5,696,138 A | 12/1997 | Olesen et al. |
| 5,698,581 A | 12/1997 | Kleemann et al. |
| 5,710,094 A | 1/1998 | Minami et al. |
| 5,721,237 A | 2/1998 | Myers et al. |
| 5,726,167 A | 3/1998 | Dodge et al. |
| 5,747,498 A | 5/1998 | Schnur et al. |
| 5,773,459 A | 6/1998 | Tang et al. |
| 5,777,097 A | 7/1998 | Lee et al. |
| 5,780,262 A | 7/1998 | Brent et al. |
| 5,780,483 A | 7/1998 | Widdowson et al. |
| 5,783,664 A | 7/1998 | Lee et al. |
| 5,786,362 A | 7/1998 | Krongrad |
| 5,801,794 A | 9/1998 | Lehureau et al. |
| 5,807,876 A | 9/1998 | Armistead et al. |
| 5,807,891 A | 9/1998 | Bold et al. |
| 5,808,080 A | 9/1998 | Bell et al. |
| 5,814,646 A | 9/1998 | Heinz et al. |
| 5,869,043 A | 2/1999 | McDonnell et al. |
| 5,871,934 A | 2/1999 | Lee et al. |
| 5,886,044 A | 3/1999 | Widdowson et al. |
| 5,891,895 A | 4/1999 | Shiraishi et al. |
| 5,908,865 A | 6/1999 | Doi et al. |
| 5,919,773 A | 7/1999 | Monia et al. |
| 5,929,250 A | 7/1999 | Widdowson et al. |
| 5,955,366 A | 9/1999 | Lee et al. |
| 5,965,573 A | 10/1999 | Petrie et al. |
| 6,004,965 A | 12/1999 | Breu et al. |
| 6,005,008 A | 12/1999 | Widdowson et al. |
| 6,015,908 A | 1/2000 | Widdowson et al. |
| 6,017,692 A | 1/2000 | Brent et al. |
| 6,020,345 A | 2/2000 | Vacher et al. |
| 6,022,884 A | 2/2000 | Mantlo et al. |
| 6,025,151 A | 2/2000 | Peterson |
| 6,033,873 A | 3/2000 | McDonnell et al. |
| 6,040,339 A | 3/2000 | Yoshida et al. |
| 6,043,374 A | 3/2000 | Widdowson et al. |
| 6,080,763 A | 6/2000 | Regan et al. |
| 6,093,742 A | 7/2000 | Salituro et al. |
| 6,103,692 A | 8/2000 | Avruch et al. |
| 6,114,517 A | 9/2000 | Monia et al. |
| 6,130,053 A | 10/2000 | Thompson et al. |
| 6,133,319 A | 10/2000 | Widdowson |
| 6,136,779 A | 10/2000 | Foulkes et al. |
| 6,143,764 A | 11/2000 | Kubo et al. |
| 6,147,107 A | 11/2000 | Dent et al. |
| 6,147,116 A | 11/2000 | Barbachyn et al. |
| 6,150,415 A | 11/2000 | Hammock et al. |
| 6,159,901 A | 12/2000 | Kanno et al. |
| 6,174,901 B1 | 1/2001 | Mantlo et al. |
| 6,177,401 B1 | 1/2001 | Ullrich et al. |
| 6,178,399 B1 | 1/2001 | Takebayashi et al. |
| 6,180,631 B1 | 1/2001 | McMahon et al. |
| 6,180,675 B1 | 1/2001 | Widdowson et al. |
| 6,187,799 B1 | 2/2001 | Wood et al. |
| 6,193,965 B1 | 2/2001 | Karin et al. |
| 6,204,267 B1 | 3/2001 | Tang et al. |
| 6,210,710 B1 | 4/2001 | Skinner |
| 6,211,373 B1 | 4/2001 | Widdowson et al. |
| 6,218,539 B1 | 4/2001 | Widdowson |
| 6,228,881 B1 | 5/2001 | Regan et al. |
| 6,235,764 B1 | 5/2001 | Larson et al. |
| 6,236,125 B1 | 5/2001 | Oudet et al. |
| 6,242,601 B1 | 6/2001 | Breu et al. |
| 6,262,113 B1 | 7/2001 | Widdowson et al. |
| 6,271,261 B1 | 8/2001 | Widdowson |
| 6,294,350 B1 | 9/2001 | Peterson |
| 6,297,381 B1 | 10/2001 | Cirillo et al. |
| 6,310,068 B1 | 10/2001 | Bottcher et al. |
| 6,316,462 B1 | 11/2001 | Bishop et al. |
| 6,319,921 B1 | 11/2001 | Cirillo et al. |
| 6,329,415 B1 | 12/2001 | Cirillo et al. |
| 6,333,341 B1 | 12/2001 | Mantlo et al. |
| 6,339,045 B1 | 1/2002 | Kanno et al. |
| 6,344,476 B1 | 2/2002 | Ranges et al. |
| 6,352,977 B1 | 3/2002 | Astles et al. |
| 6,358,525 B1 | 3/2002 | Guo et al. |

| | | |
|---|---|---|
| 6,358,945 B1 | 3/2002 | Breitfelder et al. |
| 6,361,773 B1 | 3/2002 | Lee et al. |
| 6,372,773 B1 | 4/2002 | Regan |
| 6,372,933 B1 | 4/2002 | Baine et al. |
| 6,380,218 B1 | 4/2002 | Marfat et al. |
| 6,383,734 B1 | 5/2002 | Marshall et al. |
| 6,387,900 B1 | 5/2002 | Pevarello et al. |
| 6,391,917 B1 | 5/2002 | Petrie et al. |
| 6,403,588 B1 | 6/2002 | Hayakawa et al. |
| 6,414,011 B1 | 7/2002 | Hogenkamp et al. |
| 6,444,691 B1 | 9/2002 | Oremus et al. |
| 6,448,079 B1 | 9/2002 | Monia et al. |
| 6,479,519 B1 | 11/2002 | Astles et al. |
| 6,492,393 B1 * | 12/2002 | Breitfelder et al. ............ 514/319 |
| 6,495,331 B1 | 12/2002 | Gelfand et al. |
| 6,500,863 B1 | 12/2002 | Jin et al. |
| 6,511,800 B1 | 1/2003 | Singh |
| 6,511,997 B1 | 1/2003 | Minami et al. |
| 6,521,407 B1 | 2/2003 | Warenius et al. |
| 6,521,592 B2 | 2/2003 | Ko et al. |
| 6,524,832 B1 | 2/2003 | Kufe et al. |
| 6,525,046 B1 | 2/2003 | Cirillo et al. |
| 6,525,065 B1 | 2/2003 | Caldwell et al. |
| 6,525,091 B2 | 2/2003 | Robinson et al. |
| 6,583,282 B1 | 6/2003 | Zhang et al. |
| 6,608,052 B2 | 8/2003 | Breitfelder et al. |
| 6,617,324 B1 | 9/2003 | Naraian et al. |
| 6,635,421 B1 | 10/2003 | Klagsbrun et al. |
| 6,653,320 B2 | 11/2003 | Hayakawa et al. |
| 6,656,963 B2 | 12/2003 | Firestone et al. |
| 6,673,777 B1 | 1/2004 | Tracey et al. |
| 6,689,560 B1 | 2/2004 | Rapp et al. |
| 6,797,823 B1 | 9/2004 | Kubo et al. |
| 6,958,333 B1 | 10/2005 | Hayama et al. |
| 7,070,968 B2 | 7/2006 | Kufe et al. |
| 7,202,244 B2 * | 4/2007 | Boyle et al. ................... 514/247 |
| 7,235,576 B1 | 6/2007 | Riedl et al. |
| 7,253,286 B2 | 8/2007 | Funahashi et al. |
| 7,307,071 B2 | 12/2007 | Lyons et al. |
| 7,329,670 B1 | 2/2008 | Dumas et al. |
| 7,351,834 B1 | 4/2008 | Riedl et al. |
| 7,371,763 B2 | 5/2008 | Dumas et al. |
| 7,517,880 B2 | 4/2009 | Miller et al. |
| 7,528,255 B2 | 5/2009 | Riedl et al. |
| 7,547,695 B2 | 6/2009 | Hoelzemann et al. |
| 7,557,129 B2 | 7/2009 | Scott et al. |
| 7,605,261 B2 | 10/2009 | Deprez et al. |
| 7,612,092 B2 | 11/2009 | Funahashi et al. |
| 7,678,811 B2 | 3/2010 | Dumas et al. |
| 2001/0006975 A1 | 7/2001 | Wood et al. |
| 2001/0011135 A1 | 8/2001 | Riedl et al. |
| 2001/0011136 A1 | 8/2001 | Riedl et al. |
| 2001/0016659 A1 | 8/2001 | Riedl et al. |
| 2001/0027202 A1 | 10/2001 | Riedl et al. |
| 2001/0034447 A1 | 10/2001 | Riedl et al. |
| 2001/0038842 A1 | 11/2001 | Achen et al. |
| 2002/0037276 A1 | 3/2002 | Ptasznik et al. |
| 2002/0042517 A1 | 4/2002 | Uday et al. |
| 2002/0062763 A1 | 5/2002 | Macholdt et al. |
| 2002/0065283 A1 | 5/2002 | McMahon et al. |
| 2002/0065296 A1 | 5/2002 | Dumas et al. |
| 2002/0082255 A1 | 6/2002 | Eastwood |
| 2002/0085857 A1 | 7/2002 | Kim et al. |
| 2002/0085859 A1 | 7/2002 | Hashimoto et al. |
| 2002/0103253 A1 | 8/2002 | Ranges et al. |
| 2002/0111495 A1 | 8/2002 | Magee et al. |
| 2002/0128321 A1 | 9/2002 | Widdowson et al. |
| 2002/0137774 A1 | 9/2002 | Riedl et al. |
| 2002/0161014 A1 | 10/2002 | Sadhu et al. |
| 2002/0165275 A1 | 11/2002 | Wu et al. |
| 2002/0165349 A1 | 11/2002 | Kirsch et al. |
| 2002/0165394 A1 | 11/2002 | Dumas et al. |
| 2002/0173507 A1 | 11/2002 | Santora et al. |
| 2002/0188027 A1 | 12/2002 | Robinson et al. |
| 2002/0197256 A1 | 12/2002 | Grewal |
| 2003/0069284 A1 | 4/2003 | Keegan et al. |
| 2003/0105091 A1 | 6/2003 | Riedl et al. |
| 2003/0125359 A1 | 7/2003 | Lyons et al. |
| 2003/0130309 A1 | 7/2003 | Moss et al. |
| 2003/0139605 A1 | 7/2003 | Riedl et al. |
| 2003/0144278 A1 | 7/2003 | Riedl et al. |
| 2003/0157104 A1 | 8/2003 | Waksal |
| 2003/0181442 A1 | 9/2003 | Riedl et al. |
| 2003/0207870 A1 | 11/2003 | Dumas et al. |
| 2003/0207872 A1 | 11/2003 | Riedl et al. |
| 2003/0207914 A1 | 11/2003 | Dumas et al. |
| 2003/0216396 A1 | 11/2003 | Dumas et al. |
| 2003/0216446 A1 | 11/2003 | Dumas et al. |
| 2003/0232400 A1 | 12/2003 | Radka et al. |
| 2003/0232765 A1 | 12/2003 | Carter et al. |
| 2004/0023961 A1 | 2/2004 | Dumas et al. |
| 2004/0052880 A1 | 3/2004 | Kobayashi et al. |
| 2004/0096855 A1 | 5/2004 | Stratton et al. |
| 2004/0147541 A1 | 7/2004 | Lane et al. |
| 2004/0192770 A1 | 9/2004 | Kozikowski et al. |
| 2004/0197256 A1 | 10/2004 | Rogers et al. |
| 2004/0209905 A1 | 10/2004 | Kubo et al. |
| 2004/0224937 A1 | 11/2004 | Furness et al. |
| 2004/0229937 A1 | 11/2004 | Dumas et al. |
| 2004/0235829 A1 | 11/2004 | Scott et al. |
| 2005/0032798 A1 | 2/2005 | Boyer et al. |
| 2005/0038031 A1 | 2/2005 | Dumas et al. |
| 2005/0038080 A1 | 2/2005 | Boyer et al. |
| 2005/0059703 A1 | 3/2005 | Wilhelm et al. |
| 2005/0069963 A1 | 3/2005 | Lokshin et al. |
| 2005/0096344 A1 | 5/2005 | Fraley et al. |
| 2005/0175737 A1 | 8/2005 | Knobel |
| 2005/0256174 A1 | 11/2005 | Wood et al. |
| 2005/0288286 A1 | 12/2005 | Flynn et al. |
| 2006/0058358 A1 | 3/2006 | Dumas et al. |
| 2006/0078617 A1 | 4/2006 | Schueckler |
| 2006/0211738 A1 | 9/2006 | Mitchell et al. |
| 2006/0234931 A1 | 10/2006 | Biggs, III et al. |
| 2006/0241301 A1 | 10/2006 | Hoelzemann et al. |
| 2006/0247186 A1 | 11/2006 | Carter et al. |
| 2006/0281762 A1 | 12/2006 | Staehle et al. |
| 2007/0020704 A1 | 1/2007 | Wilhelm et al. |
| 2007/0105142 A1 | 5/2007 | Wilhelm |
| 2007/0178494 A1 | 8/2007 | Elting et al. |
| 2007/0244120 A1 | 10/2007 | Dumas et al. |
| 2007/0265315 A1 | 11/2007 | Dumas et al. |
| 2008/0009527 A1 | 1/2008 | Dumas et al. |
| 2008/0027061 A1 | 1/2008 | Riedl et al. |
| 2008/0032979 A1 | 2/2008 | Riedl et al. |
| 2008/0045589 A1 | 2/2008 | Kelley |
| 2008/0108672 A1 | 5/2008 | Riedl et al. |
| 2008/0153823 A1 | 6/2008 | Riedl et al. |
| 2008/0194580 A1 | 8/2008 | Dumas et al. |
| 2008/0214545 A1 | 9/2008 | Lee et al. |
| 2008/0227828 A1 | 9/2008 | Dumas et al. |
| 2008/0242707 A1 | 10/2008 | Schuckler et al. |
| 2008/0269265 A1 | 10/2008 | Miller et al. |
| 2008/0300281 A1 | 12/2008 | Dumas et al. |
| 2008/0311601 A1 | 12/2008 | Elting et al. |
| 2008/0311604 A1 | 12/2008 | Elting et al. |
| 2009/0068146 A1 | 3/2009 | Wilhelm |
| 2009/0093526 A1 | 4/2009 | Miller et al. |
| 2009/0118268 A1 | 5/2009 | Riedl et al. |
| 2009/0192127 A1 | 7/2009 | Scheuring et al. |
| 2009/0215835 A1 | 8/2009 | Wilhelm |
| 2009/0221010 A1 | 9/2009 | Elting et al. |
| 2009/0227637 A1 | 9/2009 | Weber et al. |
| 2009/0306020 A1 | 12/2009 | Scheuring et al. |
| 2010/0063088 A1 | 3/2010 | Wood et al. |

FOREIGN PATENT DOCUMENTS

| | | |
|---|---|---|
| CA | 2 146 707 | 10/1995 |
| CH | 479557 | 11/1969 |
| CL | 38688 | 6/1993 |
| DD | 253997 | 2/1988 |
| DE | 487014 | 11/1929 |
| DE | 511468 | 10/1930 |
| DE | 523437 | 4/1931 |
| DE | 3305866 | 8/1984 |
| DE | 2436179 | 4/1986 |
| DE | 3529247 | 11/1986 |
| DE | 3540377 | 5/1987 |
| DT | 2436179 | 2/1975 |

| | | | | | |
|---|---|---|---|---|---|
| DT | 2501648 | 7/1975 | WO | WO-93/04170 | 3/1993 |
| EP | 0016371 | 10/1980 | WO | WO-93/18028 | 9/1993 |
| EP | 0107214 | 5/1984 | WO | WO-93/24458 | 12/1993 |
| EP | 0116932 6932 | 8/1984 | WO | WO-94/02136 | 2/1994 |
| EP | 0192263 | 8/1986 | WO | WO-94/02485 | 2/1994 |
| EP | 0202538 | 11/1986 | WO | WO-94/04541 | 3/1994 |
| EP | 0230400 | 7/1987 | WO | WO-94/14801 | 7/1994 |
| EP | 0233559 | 8/1987 | WO | WO-94/18170 | 8/1994 |
| EP | 0242666 | 10/1987 | WO | WO-94/22807 | 10/1994 |
| EP | 0264904 | 4/1988 | WO | WO-94/23755 | 10/1994 |
| EP | 0314615 | 5/1989 | WO | WO-94/25012 | 11/1994 |
| EP | 0335156 | 10/1989 | WO | WO-95/02136 | 1/1995 |
| EP | 0359148 | 3/1990 | WO | WO-95/02591 | 1/1995 |
| EP | 0371876 | 6/1990 | WO | WO-95/07922 | 3/1995 |
| EP | 0379915 | 8/1990 | WO | WO-95/13067 | 5/1995 |
| EP | 0380048 | 8/1990 | WO | WO-95/14023 | 5/1995 |
| EP | 0381987 | 8/1990 | WO | WO-95/16691 | 6/1995 |
| EP | 0405233 | 1/1991 | WO | WO-95/19169 | 7/1995 |
| EP | 0425443 | 5/1991 | WO | WO-95/31451 | 11/1995 |
| EP | 0459887 | 12/1991 | WO | WO-95/33458 | 12/1995 |
| EP | 0233559 | 5/1992 | WO | WO-95/33460 | 12/1995 |
| EP | 0192263 | 7/1992 | WO | WO-96/02112 | 1/1996 |
| EP | 0502504 | 9/1992 | WO | WO-96/10559 | 4/1996 |
| EP | 0509795 | 10/1992 | WO | WO-96/13632 | 5/1996 |
| EP | 0676395 | 10/1992 | WO | WO-96/251 57 | 8/1996 |
| EP | 0690344 | 1/1996 | WO | WO-96/40673 | 12/1996 |
| EP | 0709220 | 5/1996 | WO | WO-96/40675 | 12/1996 |
| EP | 0709225 | 5/1996 | WO | WO-96/41807 | 12/1996 |
| EP | 0709225 | 8/1998 | WO | WO-97/03069 | 1/1997 |
| EP | 0860433 | 8/1998 | WO | WO-97/09973 | 3/1997 |
| EP | 1056725 | 12/2000 | WO | WO-97/17267 | 5/1997 |
| EP | 1199306 | 4/2002 | WO | WO-97/17329 | 5/1997 |
| EP | 1256587 | 11/2002 | WO | WO-97/30992 | 6/1997 |
| EP | 1537075 | 6/2005 | WO | WO-97/29743 | 8/1997 |
| FR | 1457172 | 9/1966 | WO | WO-97/34146 | 9/1997 |
| GB | 771333 | 3/1957 | WO | WO-97/40028 | 10/1997 |
| GB | 828231 | 2/1960 | WO | WO-97/40842 | 11/1997 |
| GB | 921682 | 3/1963 | WO | WO-97/45400 | 12/1997 |
| GB | 1110099 | 4/1968 | WO | WO-97/49399 | 12/1997 |
| GB | 111554 | 5/1968 | WO | WO-97/49400 | 12/1997 |
| GB | 1 590 870 | 6/1981 | WO | WO-98/17207 | 4/1998 |
| HU | P0004437 | 6/2001 | WO | WO-98/17267 | 4/1998 |
| IR | 26555 | 1/2000 | WO | WO-96/20668 | 5/1998 |
| JP | 44-2569 | 2/1969 | WO | WO-98/22103 | 5/1998 |
| JP | 50-76072 | 6/1975 | WO | WO-98/22432 | 5/1998 |
| JP | 50-77375 | 6/1975 | WO | WO-98/32439 | 7/1998 |
| JP | 50-149668 | 11/1975 | WO | WO-98/34929 | 8/1998 |
| JP | 51-63170 | 6/1976 | WO | WO-98/45268 | 10/1998 |
| JP | 51-80862 | 7/1976 | WO | WO-98/49150 | 11/1998 |
| JP | 53-86033 | 7/1978 | WO | WO-98/52558 | 11/1998 |
| JP | 54-32468 | 9/1979 | WO | WO-98/52559 | 11/1998 |
| JP | 55-98152 | 7/1980 | WO | WO-98/52937 | 11/1998 |
| JP | 55-124763 | 9/1980 | WO | WO-98/52941 | 11/1998 |
| JP | 55-162772 | 12/1980 | WO | WO-96/56377 | 12/1998 |
| JP | 57-53785 | 11/1982 | WO | WO-99/00357 | 1/1999 |
| JP | 58-21626 | 5/1983 | WO | WO-99/00370 | 1/1999 |
| JP | 61-20039 | 1/1986 | WO | WO-99/20617 | 4/1999 |
| JP | 63 -214752 | 9/1988 | WO | WO-99/21835 | 5/1999 |
| JP | 64-9455 | 1/1989 | WO | WO-99/23091 | 5/1999 |
| JP | 1-102461 | 4/1989 | WO | WO-99/24398 | 5/1999 |
| JP | 1-132580 | 5/1989 | WO | WO-99/24635 | 5/1999 |
| JP | 1-200254 | 8/1989 | WO | WO-99124035 | 5/1999 |
| JP | 1-259360 | 10/1989 | WO | WO-99/26657 | 6/1999 |
| JP | 2-22650 | 1/1990 | WO | WO-99/28305 | 6/1999 |
| JP | 2-23337 | 1/1990 | WO | WO-99/32109 | 7/1999 |
| JP | 2-35450 | 2/1990 | WO | WO-99/32110 | 7/1999 |
| JP | 2-105146 | 4/1990 | WO | WO-99/32111 | 7/1999 |
| JP | 2-108048 | 4/1990 | WO | WO-99/32436 | 7/1999 |
| JP | 2-150840 | 6/1990 | WO | WO-99/32455 | 7/1999 |
| JP | 3-53247 | 3/1991 | WO | WO-99/32463 | 7/1999 |
| JP | 3-144634 | 6/1991 | WO | WO-99/33458 | 7/1999 |
| JP | 3-198049 | 8/1991 | WO | WO-99/35132 | 7/1999 |
| JP | 6-75172 | 9/1994 | WO | WO-99132106 | 7/1999 |
| JP | 8-301841 | 11/1996 | WO | WO-99/40673 | 8/1999 |
| JP | 10-306078 | 11/1998 | WO | WO-99/56502 | 11/1999 |
| LB | 6124 | 1/2000 | WO | WO-99/62890 | 12/1999 |
| WO | WO-90/02112 | 3/1990 | WO | WO-00/12497 | 3/2000 |
| WO | WO-92103413 | 3/1992 | WO | WO-00/17175 | 3/2000 |
| WO | WO-92/05179 | 4/1992 | WO | WO-00/19205 | 4/2000 |

| | | |
|---|---|---|
| WO | WO-00/26203 | 5/2000 |
| WO | WO-00/27414 | 5/2000 |
| WO | WO-00/31238 | 6/2000 |
| WO | WO-00/34303 | 6/2000 |
| WO | WO-00/35454 | 6/2000 |
| WO | WO-00/35455 | 6/2000 |
| WO | WO-00/39101 | 7/2000 |
| WO | WO-00/39116 | 7/2000 |
| WO | WO-00/41698 | 7/2000 |
| WO | WO-00/42012 | 7/2000 |
| WO | WO-00/43366 | 7/2000 |
| WO | WO-00/43384 | 7/2000 |
| WO | WO-00/47577 | 8/2000 |
| WO | WO-00/50425 | 8/2000 |
| WO | WO-00/55139 | 9/2000 |
| WO | WO-00/55152 | 9/2000 |
| WO | WO-00/56331 | 9/2000 |
| WO | WO-00/71506 | 11/2000 |
| WO | WO-00/71532 | 11/2000 |
| WO | WO-01/04115 | 1/2001 |
| WO | WO-01/07411 | 2/2001 |
| WO | WO-01/09088 | 2/2001 |
| WO | WO-01/12188 | 2/2001 |
| WO | WO-01/36403 | 5/2001 |
| WO | WO-01/47892 | 7/2001 |
| WO | WO-99/32437 | 7/2001 |
| WO | WO-01/54723 | 8/2001 |
| WO | WO-01/54727 | 8/2001 |
| WO | WO-01/57008 | 8/2001 |
| WO | WO-01/63403 | 8/2001 |
| WO | WO-01/66099 | 9/2001 |
| WO | WO-01/66540 | 9/2001 |
| WO | WO-01/80843 | 11/2001 |
| WO | WO-02/06382 | 1/2002 |
| WO | WO-02/07747 | 1/2002 |
| WO | WO-02/07772 | 1/2002 |
| WO | WO-02/10141 | 2/2002 |
| WO | WO-02/14281 | 2/2002 |
| WO | WO-02/14311 | 2/2002 |
| WO | WO-02/18346 | 3/2002 |
| WO | WO-02/24635 | 3/2002 |
| WO | WO-02/25286 | 3/2002 |
| WO | WO-02/32872 | 4/2002 |
| WO | WO-02/40445 | 5/2002 |
| WO | WO-02/42012 | 5/2002 |
| WO | WO-02/44156 | 6/2002 |
| WO | WO-02/44158 | 6/2002 |
| WO | WO-02/50091 | 6/2002 |
| WO | WO-02/059081 | 8/2002 |
| WO | WO-02/059102 | 8/2002 |
| WO | WO-02/060900 | 8/2002 |
| WO | WO-02/062763 | 8/2002 |
| WO | WO-02/070008 | 9/2002 |
| WO | WO-02/065657 | 10/2002 |
| WO | WO-02/076930 | 10/2002 |
| WO | WO-02/076977 | 10/2002 |
| WO | WO-02/083628 | 10/2002 |
| WO | WO-02/083642 | 10/2002 |
| WO | WO-02/085859 | 10/2002 |
| WO | WO-02/088090 | 11/2002 |
| WO | WO-02/092576 | 11/2002 |
| WO | WO-03/004523 | 1/2003 |
| WO | WO-03/005999 | 1/2003 |
| WO | WO-03/047523 | 6/2003 |
| WO | WO-03/047579 | 6/2003 |
| WO | WO-03/066228 | 6/2003 |
| WO | WO-03/056036 | 7/2003 |
| WO | WO-03/059373 | 7/2003 |
| WO | WO-03/060111 | 7/2003 |
| WO | WO-03/065995 | 8/2003 |
| WO | WO-03/068223 | 8/2003 |
| WO | WO-03/068229 | 8/2003 |
| WO | WO-03/068746 | 8/2003 |
| WO | WO-03/082272 | 10/2003 |
| WO | WO-03/094626 | 11/2003 |
| WO | WO-03/097854 | 11/2003 |
| WO | WO-03/099771 | 12/2003 |
| WO | WO-2004/004720 | 1/2004 |
| WO | WO-2004/019941 | 3/2004 |
| WO | WO-2004/037789 | 5/2004 |
| WO | WO-2004/043374 | 5/2004 |
| WO | WO-2004/045578 | 6/2004 |
| WO | WO-2004/052880 | 6/2004 |
| WO | WO-2004/078128 | 9/2004 |
| WO | WO-2004/078746 | 9/2004 |
| WO | WO-2004/078747 | 9/2004 |
| WO | WO-2004/078748 | 9/2004 |
| WO | WO-2004/085399 | 10/2004 |
| WO | WO-2004/085425 | 10/2004 |
| WO | WO-2004/108713 | 12/2004 |
| WO | WO-2004/108715 | 12/2004 |
| WO | WO-2004/113274 | 12/2004 |
| WO | WO-2005/000284 | 1/2005 |
| WO | WO-2005/002673 | 1/2005 |
| WO | WO-2005/004863 | 1/2005 |
| WO | WO-2005/004864 | 1/2005 |
| WO | WO-2005/005389 | 1/2005 |
| WO | WO-2005/005434 | 1/2005 |
| WO | WO-2005/009367 | 2/2005 |
| WO | WO-2005/009961 | 2/2005 |
| WO | WO-2005/011700 | 2/2005 |
| WO | WO-2005/016252 | 2/2005 |
| WO | WO-2005/019192 | 3/2005 |
| WO | WO-2005/032548 | 4/2005 |
| WO | WO-2005/037273 | 4/2005 |
| WO | WO-2005/037285 | 4/2005 |
| WO | WO-2005/037829 | 4/2005 |
| WO | WO-2005/047283 | 5/2005 |
| WO | WO-2005/048948 | 6/2005 |
| WO | WO-2005/049603 | 6/2005 |
| WO | WO-2005/056764 | 6/2005 |
| WO | WO-2005/058832 | 6/2005 |
| WO | WO-2005/059179 | 6/2005 |
| WO | WO-2005/075425 | 8/2005 |
| WO | WO-2005/089443 | 9/2005 |
| WO | WO-2005/110994 | 11/2005 |
| WO | WO-2006/026500 | 3/2006 |
| WO | WO-2006/026501 | 3/2006 |
| WO | WO-2006/027346 | 3/2006 |
| WO | WO-2006/034797 | 4/2006 |
| WO | WO-2006/094626 | 9/2006 |
| WO | WO-2006/105844 | 10/2006 |
| WO | WO-2006/125540 | 11/2006 |
| WO | WO-2007/015947 | 2/2007 |
| WO | WO-2007/03940 | 4/2007 |
| WO | WO-2007/039403 | 4/2007 |
| WO | WO-2007/047955 | 4/2007 |
| WO | WO-2007/053573 | 5/2007 |
| WO | WO-2007/054215 | 5/2007 |
| WO | WO-2007/056011 | 5/2007 |
| WO | WO-2007/056012 | 5/2007 |
| WO | WO-2007/059094 | 5/2007 |
| WO | WO-2007/059154 | 5/2007 |
| WO | WO-2007/059155 | 5/2007 |
| WO | WO-2007/064872 | 6/2007 |
| WO | WO-2007/123722 | 11/2007 |
| WO | WO-2007/139930 | 12/2007 |
| WO | WO-2006/079972 | 7/2008 |
| WO | WO-2008/079968 | 7/2008 |
| WO | WO-2008/089389 | 7/2008 |
| WO | WO-2005/042520 | 5/2012 |

OTHER PUBLICATIONS

Martin-Blanco. "p38 MAPK signalling cascades: ancient roles and new functions," BioEssays, 22:637-645, 2000.

Foussard-Blarpin, Odette, "Comparative pharmacological study of substituted carboxamides upon central nervous system," Ann. Pharm. Fr. (1982), 40 (4), pp. 339-350.

Boliag et al., "Raf pathway inhibitors in oncology," Current Opinion in Investigational Drugs (2003) 4(12): pp. 1436-1441.

Bolton et al., "Chapter 17. *Ras* Oncogene Directed Approaches in Cancer Chemotherapy," Annual Reports in Medicinal Chemistry, vol. 29, 1994, pp. 165-174.

Boyer, S.J., "Small Molecule Inhibitors of KDR (VEGFR-2) Kinase: An Overview of Structure Activity Relationships," Current Topics in Medicinal Chemistry, 2002, vol. 2, pp. 973-1000.

Coperet et al., "A Simple And Efficient Method for the Preparation of Pyridine-*N*-oxides II," Tetrahedron Letters, Elsevier Science Ltd., Pergamon Press, Oxford, UK 1998: vol. 39, pp. 761-764.

Crump, Micheal, "Inhibition of raf kinase in the treatment of acute myeloid leukemia," Medline Abstract ISSN.1381-6128, Current Pharmaceutical Design, vol. 8, Issue 25, 2002, pp. 2243-2248.

Daum et al., "The ins and outs of Raf kinases," TIBS 19, Nov. 1994, pp. 474-480.

Dumas, J. "Protein kinase inhibitors from the urea class," Curr. Opin. in Drug Discovery and Dev., 5(s):718-727, 2002.

Dumas et al., "Discovery of a New Class of p38 Kinase Inhibitors," Bioorganic & Medicinal Chemistry Letters vol. 10, (2000), pp. 2047-2050.

Dumas et al., "1-Phenyl-5-pyrazolyl Ureas: Potent and Selective p38 Kinase Inhibitors," Bioorganic & Medicinal Chemistry Letters, 2000, vol. 10, pp. 2051-2054.

Dumas, J., "Growth factor receptor Kinase inhibitors: Recent progress and clinical impact," Current Opinion in Drug Discovery & Development, 2001, vol. 4, No. 4, pp. 378-389.

Dumas, J., "Protein kinase inhibitors: emerging pharmacophores 1997-2000," Expert Opinion on Therapeutic Patents (2001) vol. 11, No. 3, pp. 405-429.

Dumas et al., "Orally Active p38 Kinase Inhibitors from the Urea Class," Poster, 222nd American Cancer Society National Meeting 2001, Med I 256, 1 page.

Dumas, J., "Raf Kinase Inhibitors," Expert Opinion on Therapeutic Patients, vol. 8, No. 12, pp. 1749-1750, 1998.

Dumas et al., "Recent developments in the discovery of protein kinase inhibitors from the urea class." *Current Opinion in Drug Discovery & Development*, 2004, vol. 7, No. 5, pp. 600-616.

Martin-Blanco, " p38 MAPK signalling cascades: ancient roles and new functions." BioEssays, 22:637-645, 2000.

Dumas et al., "Synthesis and Pharmacological Characterization of a Potent, Orally Active p38 Kinase Inhibitor," *Bioorganic & Medicinal Chemistry Letters*, 2002, vol. 12, pp. 1559-1562.

Gura, "Systems for identifying new drugs are often faulty." *Science*, 1997, vol. 278, (5340), pp. 1041-1042. MEDLINE with Full text.

Kubo et al., "Synthesis and structure-activity relationship of quinazoline-urea derivatives as novel orally active VEGF receptor tyrosine kinase selective inhibitors," Proceedings of the American Association of Cancer Res., 2002, vol. 43, p. 182, abstract No. 913.

Kumar et al., "Drugs targeted against protein kinases" Expert Opin. Emerging Drugs 6(2):303-315 (2001).

Lyons et al., "Discovery of a novel Rat kinase inhibitor," *Endocrine-Related Cancer*, 2001, vol. 6, pp. 219-225.

Regan et al., "Pyrazole Urea-Based inhibitors of p38 MAP kinase: From Lead Compound to Clinical Candidate," J. Med. Chem. 45:2994-3006, 2002.

Smith et al., "Discovery of Heterocyclic Ureas as a New Class of Raf Kinase Inhibitors: Identification of a Second Generation Lead by a Combinatorial Chemistry Approach," Bioorganic & Medicinal Chemistry Letters, 2001, vol. 11 pp. 2775-2778.

Smith et al., (Abstract) "Recent Advances in the Research and Development of RAF Kinase Inhibitors," Current Topics in Medicinal Chemistry 6(11):1071-1089 (2006).

Thaimattam et al., "3D-OSAR CoMFA, CoMSIA studies on substituted ureas as Raf-1 kinase inhibitors and its confirmation with structure-based studies," *Bioorganic & Medicinal Chemistry*, 2004, vol. 12, pp. 6415-6425.

Thompson et al., "Recent progress in targeting the Raf/MEK/ERK pathway with inhibitors in cancer drug discovery," Curr. Opin. Pharmacol., Aug. 2005, vol. 5, No. 4, pp. 350-356.

Wilson et al., "The structural basis for the specificity of pyridinylimidazole inhibitors of p38 MAP kinase," Chemistry & Biology, 1997, vol. 4, No. 6, pp. 423-431.

Kubo et al., "Synthesis and Structure-Activity Relafionship of Quinazoline-Urea Derivatives as Novel Orally Active VEGF Receptor Tyrosine Kinase Selective Inhibitors," Proceedings of the American Association of Cancer Res., 2002, vol. 43, p. 182, abstract No. 913.

Riedl et al., # 4956 "Potent *Raf* Kinase Inhibitors from the Diphenylurea Class: Structure Activity Relationships," Proceedings of the American Association for Cancer Research, vol. 42, Mar. 2001, p. 923, 92nd Annual Meeting of the American Association for Cancer Research; New Orleans, LA, USA; Mar. 24-28, 2001.

Abstract of DE 3305866 A1, Aug. 23, 1984, BASF AG et al.

Abstract of EP 4931 A (Equivalent 4,240,820), Bayer AG, 1 page, 1980.

Abstract of EP 16371 (1980), 1 page, Hoffmann-La Roche AG.

Abstrac of EP 16371, Oct. 1, 1980, 1 page.

Abstract of EP 6932, Aug. 29, 1984, 2 pages.

Abstract of EP 116932, (1984), 2 pages, BASF AG.

Abstract of EP 0202536, (1986), 3 pages.

Abstract of EP 0202538 A1, Growth Promoting Agents, Nov. 26, 1986, 4 pages, Bayer AG.

Abstract of EP 0405233A1. Mitsubishi Kasei Corp., 2 pages, 1991.

Abstract of EP 0405233A1, Tetsuo Sekiya et al., 1 page, 1991.

Abstract of EP 0676395A2, (1995), 3 pages, Hoechst AG.

Abstract of EP 676395, (U.S. equivalent 5,698,581). Dec. 16. 1997, 1 page.

Patent Abstracts of Japan 02-022650, Jan. 25, 1990, 2 pages, Konica Corp.

esp@cenet Abstracts of Japan 02-022650, Jan. 25, 1990,1 page.

Patent Abstracts of Japan 02-023337, Jan. 25, 1990, 2 pages, Konica Corp.

Patent Abstracts of Japan 63-214752, Sep. 7, 1988, 2 pages, family member of JP 6-07512 B4, Fuji Photo Film Co. Ltd.

esp@cenet Abstract of Japan 02-023337, 1 page, 1990.

Abstract of JP 55162772 A2. Preparation of Substtuted Acetic Acid Derivatives, Shlongi & Co., Ltd. Dec. 1980, 1 page.

Esp@cenet Abstract of WO 9822103, May 28, 1998, Philip Hedge et al.

Abstract of WO 9822098 A2, QLT Phototherapeufics Inc. et al., May 28, 1998, 1 page.

Abstract of WO 9822103 A1, Zeneca Limited, published May 28, 1998, 1 page.

Abstract of WO 9852559 A1, Bayer Corp. et al., published Nov. 26, 1998, 1 page.

Abstract of WO 9852562 A1, Verkaik, MSE, et al., published Nov. 26, 1998, 1 page.

Abstract of WO 9900357 A1, Vertex Pharm. Inc., published Jan. 7, 1999 page.

Abstract of WO 9900364 A1, Pharmacia & Upjohn S.P.A. et al., published Jan. 7, 1999, 1 page.

Abstract of WO 9932098 A2, Janssen Pharm NV, published Jul. 1, 1999, 1 page.

Abstract of WO 9932106 A1, Bayer Corp., published Jul. 1, 1999, 1 page.

Abstract of WO 9932148 A1, Beth Israel Deaconess Medical Center et al., pub. Jul. 1, 1999, 1 page.

Abstract of WO 9932436 A1, Bayer Corp., published Jul. 1, 1999, 1 page.

Abstract of WO 9932455 A1, Bayer Corp., published Jul. 1, 1999, 1 page.

Abstract of WO 9932457 A1, Hoechst Marion Roussel Deutschland GmbH et al., published Jul. 1, 1999, 1 page.

Caplus 72:79046, Abstract of CH 479557, "Tuberculostatic and cancerostatic polybasic ureas," Dr. A. Wander, Oct. 15, 1969, 6 pages.

Caplus 84:180049, Abstract JP 56029871, "Substituted acetic acid derivatives," Hamada, Yoshinori et al Jul. 10, 1981, 1 page.

Caplus 84:43857, Abstract JP 58021626, "Alkanoic acid derivatives containing a pyridine ring," Maeda, Ryozo et al., May 2, 1983, 1 page.

Abstract Caplus 86:72448 JP 57053785, "Pyridine derivatives," Maeda, Ryozo et al., Nov. 15, 1982, 1 page.

Caplus 98:78152, Abstract of JP 57185219, "Antitumor benzophenone derivatives." Nov. 15, 1982, 1 page, Chugai Pharmaceutical Co., Ltd.

Caplus 113:106314, Abstract of JP 2022650, "Silver halide color photographic material containing a cyan coupler of 2-ureido-phenol type to improve dye developability and remove lecuo cyan dye," Noboru Mizukura et al. Jan. 25, 1990, 1 page.

Caplus 113:142130, Abstract of JP 2023337, "Silver halide photographic material containing phenolic cyan coupler a colorless cyan coupler," Toshihiko Yagi et al., Jan. 25, 1990, 1 page.

Caplus 127:34137I, "Preparation of quinoline and quinazoline derivatives inhibiting platelet-derived growth factor receptor autophosphorylation," Kazuo Kubo et al., May 15, 1997, WO 97/17329.
Caplus 131:58658k, "Inhibition of raf kinase using symmetrical and unsymmetrical substituted diphenyl ureas," Wen Scott, et al. Jul. 1, 1999, WO 99 32,436.
Caplus 131:73649b, "Preparation of pyrazolyl aryl ureas and related compounds as p38 kinase inhibitors," Jacques Dumas et al., Jul. 1, 1999, WO 99/32110.
"Beilsle lumber" Collection, 28 pp. (1997).
"Beilstein number" Collection, 4 pp. (1997).
Derwent World Patents Index Search, pp. 20-26. (1997).
Dumas, J. "CAS Substructure," May 6, 1997, pp. 1-29.
Scott, Bill, "Substructure (Patent Families)," Aug. 11, 1997, pp. 1-19.
Scott, Bill, "Substructure #2," Nov. 25,1997, pp. 1-3.
Scott, Bill"Substructure Search," Dec. 2, 1997, pp. 1-49.
Substructure Search, pp. 1-29. (1997).
Wild, Hanno, "Substructure #1," search, pp. 1-150, 1996.
A "Notice of References Cited" from the USPTO for U.S. Appl. No. 08/995,749, filing date of Dec. 22, 1997, inhibition of P38 Kinase Using Symmetrical and Unsymmetrical Diphenyl Ureas, 2 pages.
A "Notice of References Cited" from the USPTO for U.S. Appl. No. 09/083,399, filing date of May 22, 1998, Patent 6167799 issued Feb. 13, 2001, Inhibition of Raf Kinase Activity Using Aryl Ureas, 1 page.
A "Notice of References Cited" from the USPTO for U.S. Appl. No. 09/425,228, filing date of Oct. 22, 1999, Omega-Carboxyaryl Substituted Diphenyl Ureas As Raf Kinase inhibitors, 3 pages.
A "Notice of References Cited" from the USPTO for U.S. Appl. No. 09/425,229, filing date of Oct. 22, 1999, Omega-Carboxy Aryl Substituted Diphenyl Ureas As p38 Kinase Inhibitors, 1 page.
A "Notice of References Cited" from the USPTO for U.S. Appl. No. 09/458,015, filing date of Dec. 10, 1999, Inhibition of p38 Kinase Using Symmetrical and Unsymmetrical Diphenyl Ureas, 1 page.
A "Notice of References Cited" from the USPTO for U.S. Appl. No. 09/472,232, filing date of Dec. 27, 1999, Patent 7329670 issued Feb. 12, 2008, Inhibition of Raf Kinase Using Aryl and Heteroaryl Substituted Heterocyclic Ureas, 1 page.
A "Notice of References Cited" from the USPTO for U.S. Appl. No. 09/773,604, filing date of Feb. 2, 2001, Publication No. US 2001-0034447-A1, Publication Date Oct. 25, 2001, Omega-carboxyaryl Substituted Diphenyl Ureas as Raf Kinase Inhibitors, 1 page.
A "Notice of References Cited" from the USPTO for U.S. Appl. No. 09/773,659, filing date of Feb. 2, 2001, Publication No. US 2001-0011135 A1, Publication Date: Aug. 2, 2001, Omega-carboxyaryl Substituted Diphenyl Ureas As Raf Kinase Inhibitors, 1 page.
A "Notice of References Cited" from the USPTO for U.S. Appl. No. 09/773,672, filing date of Feb. 2, 2001, Publication No. US 2001-0016659 A1, Publication Date: Aug. 23, 2001, Omega-carboxyaryl substituted Diohenvl Ureas as Rat Kinase Inhibitors. 1 page.
A "Notice of References Cited" from the USPTO for U.S. Appl. No. 09/773,675, filing date of Feb. 2, 2001, Publication No. US 2001-0011136-A1 , Publication Date: Aug. 2, 2001, Omega-Carboxyaryl Substituted.
A "Notice of References Cited" from the USPTO for U.S. Appl. No. 09/776,935, filing date of Dec. 22, 1998, inhibition of p38 Kinase Using Aryl and Hetemaryl Substituted Heterocyclic Ureas, 1 page.
A "Notice of References Cited" from the USPTO for U.S. Appl. No. 09/376,936, filing date of Dec. 22, 1998, Inhibition of Raf Kinase Using Symmetrical and Unsymmetrical Substituted Diphenyl Ureas, 1 page.
A "Notice of References Cited" from the USPTO for U.S. Appl. No. 09/777,920, filing date of Feb. 7, 2001, Inhibition of Raf kinase using quinolyl, isoquinolyl or pyridyl ureas, 1 page.
A "Notice of References Cited" from the USPTO for U.S. Appl. No. 09/948,915, filing date of Sep. 10, 2001, OmegaCarboxyaryl Substituted Diphenyl Ureas As Rat Kinase Inhibitors, 1 page.
A "Notice of References Cited" from the USPTO for U.S. Appl. No. 10/042,226, filing date of Jan. 11, 2002, Omega-Carboxyaryl Substituted Diphenyl Ureas As Raf Kinase Inhibitors, 1 page.
Co-pending U.S. Appl. No. 09/458,014, filed Dec. 10, 1999, Dumas et al.
Abandoned U.S. Appl. No. 09/776,935, filed Dec. 22, 1998, Dumas et al.
Co-pending U.S. Appl. No. 09/776,936, filed Dec. 22, 1998, Miller et al.
Issued U.S. Appl. No. 09/869,227, filed Jul. 12, 2000, Riedl et al., issued as 7351834, Apr. 1, 2008.
Co-pending U.S. Appl. No. 09/993,647, filed Nov. 27, 2001. Riedl et al., published as 2003-0181442, Sep. 25, 2003.
Issued U.S. Appl. No. 10/060,396, filed Feb. 1, 2002, Adler et al., patent 7517880, issued Apr. 14, 2009, also published as 2004-0102636, May 27, 2004.
Issued U.S. Appl. No. 10/071,248, filed Feb. 11, 2002, Riedl et al., patent 7528255, issued May 5, 2009, also published as 2003-139605, Jul. 24, 2003.
Abandoned U.S. Appl. No. 10/086,417, filed Mar. 4, 2002, Riedl et al., published as 2003-0105091, Jun. 5, 2003.
Abandoned U.S. Appl. No. 10/125,369, filed Apr. 19, 2002, Dumas et al., published as 2003-0207914, Nov. 6, 2003.
Abandoned U.S. Appl. No. 10/308,167, filed Dec. 3, 2002, Carter et al., published as 2003-0232765, Dec. 18, 2003.
Abandoned U.S. Appl. No. 10/361,844, filed Feb. 11 , 2003, Dumas et al., published as 2004-0023961, Feb. 5, 2004.
Abandoned U.S. Appl. No. 10/361,850, filed Feb. 11, 2003, Dumas et al., published as US 2003-0216396, Nov. 20, 2003.
Co-pending U.S. Appl. No. 10/361,859, filed Feb. 11, 2003, Dumas et al., published as 2003-0216446,Nov. 20, 2003.
Co-Pending U.S. Appl. No. 10/895,985, filed Jul. 22, 2004, Boyer et al., published as US 2005-0038080, Feb. 17, 2005.
Co-Pending U.S. Appl. No. 11/932,548, filed Oct. 31, 2007, Dumas et al.
Co-Pending U.S. Appl. No. 12/084,662, filed May 7, 2008, Sandner et al., published as 2010-0035888, Feb. 11, 2010.
Co-Pending U.S. Appl. No. 12/086,454, filed Jun. 12, 2008, Weber et al.
Co-Pending U.S. Appl. No. 12/093,515, filed Nov. 13, 2008, Wilheim et al.
Co-Pending U.S. Appl. No. 12/095,611, filed May 30, 2008, Smith et al.
Co-Pending U.S. Appl. No. 2/158,524, filed Jun. 20, 2008, Smith et al.
Co-Pending U.S. Appl. No. 12/294,979, filed Sep. 29, 2006, Wilhelm et al.
Co-Pending U.S. Appl. No. 12/421,690, filed Apr. 10, 2009, Dumas et al.
Co-Pending U.S. Appl. No. 12/444,974, filed Apr. 9, 2009, Grunenberg et al.
Co-Pending U.S. Appl. No. 12/514,129, filed May 8, 2009, Gruenberg et al.
Co-Pending U.S. Appl. No. 12/514,715, filed May 13, 2009, Stiehl et al.
Co-Pending U.S. Appl. No. 12/520,618, filed Jun. 22, 2009, Smith et al.
Co-Pending U.S. Appl. No. 12/520,609, filed Jun. 22, 2009, Smith et al.
Co-pending U.S. Appl. No. 12/523,652, filed Jul. 17, 2009, Wilhelm et al.
Co-pending U.S. Appl. No. 12/523,697, filed Jul. 17, 2009, Wilhelm et al.
Co-Pending U.S. Appl. No. 12/628,735, filed Dec. 1, 2009, Dumas et al.
Co-Pending U.S. Appl. No. 12/692,845, filed Jan. 25, 2010, Dumas et al.
Co-Pending Application PCT/US09/61506 filed Oct. 21, 2009, Carol Pena.
International search report for International Application No. PCT/US98110375 dated Sep. 3, 1998, Inhibition Of p38 Kinase Activity by Aryl Ureas, publication No. 98/52558, publication date Nov. 26, 1998, 1 page.
international search report for International Application No. PCT/US98/10376 dated Jul. 30, 1998, Raf Kinase Inhibitors, publication No. WO 98/52559, publica.tion date Nov. 26, 1998,1 page.
International search report for International Application No. PCTIUS98/26078 dated Apr. 2, 4999, Inhibition of Raf Kinase Using Substituted Heterocyclic Ureas, publication No. WO 99/32106, publication date Jul. 1, 1999, 2 pages.
International search report for International Application No. PCT/US98/26079 dated Apr. 12, 1999, Inhibition Of p38 Kinase Activity Using Aryl and Heteroaryl Substituted Heterocyclic Ureas, publication No. WO 99/32110, publication date Jul. 1, 1999, 1 page.
International search report for International Application No. PCT/US98/26080 dated Apr. 12, 1999, Inhibition of p38 Kinase Using Substituted Heterocyclic Ureas, publication No. WO 99/32111, publication date Jul. 1, 1999,1 page.
International search report for International Application No. PCT/US98/26081 dated Apr. 2, 1999, Inhibition of Raf Kinase Using Symmetrical and Unsymmetrical, Substituted Diphenyl Ureas, publication No. WO 99/32436, publication date Jul. 1, 1999, 1 page.
International search report for International Application No. PCT/US98/26082 dated May 12, 1999, inhibition of Raf Kinase Using Aryl and Heteroaryl Substituted Heterocyclic Ureas, publication No. WO 99/32455, publication date Jul. 1, 1999, 1 page.
International search report for International Application No. PCT/US98/27265, dated Mar. 2, 1999, Inhibition of p38 kinase using symmetrical and unsymmetrical diphenyl ureas, publication No. WO 99/32463, publication date Jul. 1, 1999, 1 page.
International search report for International Application No. PCT/US00/00648 dated Jun. 29, 2000, Omega-Carboxyaryl Substituted Diphenyl Ureas as Raf Kinase inhibitors, publication No. WO 00/42012 A1, publication date Jul. 20, 2000, 2 pages.
International search report for International Application No. PCT/US00/00768 dated May 16, 2000, Omega-Carboxy Aryl Substituted Diphenyl Ureas As p38 Kinase Inhibitors, publication No. WO 00/41698 A1. publication date Jul. 20, 2000, 1 page.
International search report for International Application No. PCT/US02/12064 dated Sep. 20, 2002, Heteroaryl Ureas Containing Nitrogen Hetero-Atoms As p38 Kinase Inhibitors, publication No. 02/085859, publication date Oct. 31, 2002, 2 pages.
International search report for International Application No. PCT/US02/12066 dated Sep. 27, 2002, Inhibition Of Raf Kinase Quinolyl, Isoquinolyl or Ryridyl Ureas, publication No. 02/085857, publication date Oct. 31, 2002, 2 pages.
Supplemental search report from the EPO for European application EP 98963809.3 dated Mar. 30, 2001, Inhibition of Rat Kinase Using Symmetrical and Unsymmetrical Substituted Diphenyl Ureas, publication No. 1049664, publication date Jul. 1, 1999, granted Mar. 16, 2005, 4 pages.
Supplemental search report from the EPO for European application EP 98963810.1 dated Dec. 21, 2000, Inhibition Of Raf Kinase Using Aryl and Heteroaryl Substituted Heterocyclic Ureas, publication No. 1056725, publication date Jul. 1, 1999, granted Jun. 7, 2006, 4 pages.
Supplemental search report from the EPO for European application EP 98965981.8 dated Dec. 21, 2000, Inhibition Of Raf Kinase Using Substituted Heterocyclic Ureas, publication No. 1047418, publication date Jul. 1, 1999, granted Jul. 27, 2005, 8 pages.
Supplemental search report from the EPO for European application EP 00903239.2 dated Aug. 7, 2002, Omega-Carboxyaryl Substituted Diphenyl Ureas As Raf Kinase Inhibitors, publication No. EP 1140840, published Jul. 20, 2000, granted Mar. 22, 2006, 6 pages.
Supplemental search report from the EPO for European application EP 00905597.1 dated Feb. 7, 2008, Omega-Carboxyaryl Substituted Diphenyl Ureas As p38 Kinase Inhibitors, publication No. EP 1158985, Jul. 20, 2000, 9 pages.

English abstract of JP 10-306078, Nov. 17, 1998, Patent Abstracts of Japan, 2 pages.
English abstract of JP 08-301841, Nov. 19, 1996, Patent Abstracts of Japan, 2 pages.
English abstract of JP 03-196049, Aug. 29, 1991, Patent Abstracts of Japan, 1 page.
English abstract of JP 03-144634, Jun. 20, 1991, Patent Abstracts of Japan, 1 page.
English abstract of JP 03-053247, Mar. 7, 1991, Patent Abstracts of Japan, 1 page.
English abstract of JP 02-150840, Jun. 11, 1990, Patent Abstracts of japan, 1 page.
English abstract of JP 02-108048, Apr. 19, 1990, Patent Abstracts of Japan, 1 page.
English abstract of JP 02-105146, Apr. 17, 1990, Patent Abstracts of Japan, 1 page.
English abstract of JP 02-035450, Feb. 6, 1990, Patent Abstracts of Japan, 1 page.
English abstract of JP 01-200254, Aug. 11, 1939, Patent Abstracts of Japan, 1 page.
English abstract of JP 01-259360, Oct. 17, 1939, Patent Abstracts of Japan, 2 pages.
English abstract of JP 01-102461, Apr. 20, 1989, Patent Abstracts of Japan, 1 page.
English abstract of JP 06-120039, Apr. 28, 1994, Patent Abstracts of Japan, 1 page.
English abstract of JP 05-160862, Jul. 23, 1993, Patent Abstracts of Japan, 1 page.
English abstract of JP 05-163170, Jun. 29, 1993, Patent Abstracts of Japan, 1 page.
English abstract of JP 05-077375, Mar. 30, 1993, Patent Abstracts of Japan, 1 page.
English abstract of JP 05-076072, Mar. 26, 1993, Patent Abstracts of Japan, 2 pages.
English abstract of JP 50-149668 A and JP 56-29871 B, Derwen, World Patents Index, Dialog File No. 351, Acc. No. 1488399, 3 pages, 1974.
English abstract of JP 53-086033, Jul. 29, 1978, Patent Abstracts of Japan, 1 page.
English abstract of JP 54-032468, Mar. 9, 1979, Patent Abstracts of Japan, 1 page.
English abstract of JP 55-098152, Jul. 25, 1980, Patent Abstracts of Japan, 1 page.
English abstract of JP 64-009455, Jan. 12, 1989, Patent Abstracts of Japan, 1 page.
English abstract of JP 02-023337, Mar. 9, 1979, Patent Abstracts of Japan, 2 pages.
English abstract of EPA 0379915/EP-A1, Aug. 1, 1990, 2 pages.
English abstract of DD 253997 A, Feb. 10, 1988, 1 page.
English abstract of DE511468, European Patent Office, 2 pages; Oct. 30, 1930.
Co-Pending U.S. Appl. No. 12/619,913, filed Nov. 17, 2009, Ranges et al.
Arzneimitteltherapie, "Sorafenib" Oct. 6, 2006, Auflage 18498, 7 pages English translation.

* cited by examiner

BICYCLIC UREA DERIVATIVES USEFUL IN THE TREATMENT OF CANCER AND OTHER DISORDERS

RELATED APPLICATIONS

This application claims priority to Ser. No. 60/450,323, filed Feb. 28, 2003, Ser. No. 60/450,324 filed Feb. 28, 2003 and Ser. No. 60/450,348 filed Feb. 28, 2003 which are incorporated by reference herein.

FIELD OF THE INVENTION

This invention relates to novel compounds, pharmaceutical compositions containing such compounds and the use of those compounds or compositions for treating hyper-proliferative and angiogenesis disorders, as a sole agent or in combination with other active ingredients, e.g., cytotoxic therapies.

BACKGROUND OF THE INVENTION

Activation of the ras signal transduction pathway indicates a cascade of events that have a profound impact on cellular proliferation, differentiation, and transformation. Raf kinase, a downstream effector of ras, is recognized as a key mediator of these signals from cell surface receptors to the cell nucleus (Lowy, D. R.; Willumsen, B. M. Ann. Rev. Biochem. 1993, 62, 851; Bos, J. L. Cancer Res. 1989, 49, 4682). It has been shown that inhibiting the effect of active ras by inhibiting the raf kinase signaling pathway by administration of deactivating antibodies to raf kinase or by co-expression of dominant negative raf kinase or dominant negative MEK, the substrate of raf kinase, leads to the reversion of transformed cells to the normal growth phenotype (see: Daum et al. Trends Biochem. Sci. 1994, 19, 474-80; Fridman et al. J. Biol. Chem. 1994, 269, 30105-8. Kolch et al. (Nature 1991, 349, 426-28) have further indicated that inhibition of raf expression by antisense RNA blocks cell proliferation in membrane-associated oncogenes. Similarly, inhibition of raf kinase (by antisense oligodeoxynucleotides) has been correlated in vitro and in vivo with inhibition of the growth of a variety of human tumor types (Monia et al., Nat. Med. 1996, 2, 668-75). Some examples of small molecule inhibitors of Raf kinase activity are important agents for the treatment of cancer. (Naumann, U.; Eisenmann-Tappe, I.; Rapp, U. R. Recent Results Cancer Res. 1997, 143, 237; Monia, B. P.; Johnston, J. F.; Geiger, T.; Muller, M.; Fabbro, D. Nature Medicine 1996, 2, 668).

To support progressive tumor growth beyond the size of 1-2 mm$^3$, it is recognized that tumor cells require a functional stroma, a support structure consisting of fibroblast, smooth muscle cells, endothelial cells, extracellular matrix proteins, and soluble factors (Folkman, J., Semin Oncol, 2002. 29(6 Suppl 16), 15-8). Tumors induce the formation of stromal tissues through the secretion of soluble growth factors such as PDGF and transforming growth factor-beta (TGF-beta), which in turn stimulate the secretion of complimentary factors by host cells such as fibroblast growth factor (FGF), epidermal growth factor (EGF), and vascular endothelial growth factor (VEGF). These stimulatory factors induce the formation of new blood vessels, or angiogenesis, which brings oxygen and nutrients to the tumor and allows it to grow and provides a route for metastasis. It is believed some therapies directed at inhibiting stroma formation will inhibit the growth of epithelial tumors from a wide variety of histological types. (George, D. Semin Oncol, 2001. 28(5 Suppl 17), 27-33; Shaheen, R. M., et al., Cancer Res, 2001. 61(4), 1464-8; Shaheen, R. M., et al. Cancer Res, 1999. 59(21), 5412-6). However, because of the complex nature and the multiple growth factors involved in angiogenesis process and tumor progression, an agent targeting a single pathway may have limited efficacy. It is desirable to provide treatment against a number of key signaling pathways utilized by tumors to induce angiogenesis in the host stroma. These include PDGF, a potent stimulator of stroma formation (Ostman, A. and C. H. Heldin, Adv Cancer Res, 2001, 80, 1-38), FGF, a chemoattractant and mitogen for fibroblasts and endothelial cells, and VEGF, a potent regulator of vascularization.

PDGF is another key regulator of stromal formation which is secreted by many tumors in a paracrine fashion and is believed to promote the growth of fibroblasts, smooth muscle and endothelial cells, promoting stroma formation and angiogenesis. PDGF was originally identified as the v-sis oncogene product of the simian sarcoma virus (Heldin, C. H., et al., J Cell Sci Suppl, 1985, 3, 65-76). The growth factor is made up of two peptide chains, referred to as A or B chains which share 60% homology in their primary amino acid sequence. The chains are disulfide cross linked to form the 30 kDa mature protein composed of either M, BB or AB homo- or heterodimmers. PDGF is found at high levels in platelets, and is expressed by endothelial cells and vascular smooth muscle cells. In addition, the production of PDGF is up regulated under low oxygen conditions such as those found in poorly vascularized tumor tissue (Kourembanas, S., et al., Kidney Int, 1997, 51(2), 438-43). PDGF binds with high affinity to the PDGF receptor, a 1106 amino acid 124 kDa transmembrane tyrosine kinase receptor (Heldin, C. H., A. Ostman, and L. Ronnstrand, Biochim Biophys Acta, 1998. 1378(1), 79-113). PDGFR is found as homo- or heterodimer chains which have 30% homology overall in their amino acid sequence and 64% homology between their kinase domains (Heldin, C. H., et al. Embo J, 1988, 7(5), 1387-93). PDGFR is a member of a family of tyrosine kinase receptors with split kinase domains that includes VEGFR2 (KDR), VEGFR3 (Flt4), c-Kit, and FLT3. The PDGF receptor is expressed primarily on fibroblast, smooth muscle cells, and pericytes and to a lesser extent on neurons, kidney mesangial, Leydig, and Schwann cells of the central nervous system. Upon binding to the receptor, PDGF induces receptor dimerization and undergoes auto- and trans-phosphorylation of tyrosine residues which increase the receptors' kinase activity and promotes the recruitment of downstream effectors through the activation of SH2 protein binding domains. A number of signaling molecules form complexes with activated PDGFR including PI-3-kinase, phospholipase C-gamma, src and GAP (GTPase activating protein for p21-ras) (Soskic, V., et al. Biochemistry, 1999, 38(6), 1757-64). Through the activation of PI-3-kinase, PDGF activates the Rho signaling pathway inducing cell motility and migration, and through the activation of GAP, induces mitogenesis through the activation of p21-ras and the MAPK signaling pathway.

In adults, it is believed the major function of PDGF is to facilitate and increase the rate of wound healing and to maintain blood vessel homeostasis (Baker, E. A. and D. J. Leaper, Wound Repair Regen, 2000. 8(5), 392-8; Yu, J., A. Moon, and H. R. Kim, Biochem Biophys Res Commun, 2001. 282(3), 697-700). PDGF is found at high concentrations in platelets and is a potent chemoattractant for fibroblast, smooth muscle cells, neutrophils and macrophages. In addition to its role in wound healing PDGF is known to help maintain vascular homeostasis. During the development of new blood vessels, PDGF recruits pericytes and smooth muscle cells that are needed for the structural integrity of the vessels. PDGF is thought to play a similar role during tumor neovascularization. As part of its role in angiogenesis PDGF controls interstitial fluid pressure, regulating the permeability of vessels through its regulation of the interaction between connective tissue cells and the extracellular matrix. Inhibiting PDGFR activity can lower interstitial pressure and facilitate the influx of cytotoxics into tumors improving the anti-tumor efficacy of these agents (Pietras, K., et al. Cancer Res, 2002. 62(19), 5476-84; Pietras, K., et al. Cancer Res, 2001. 61(7), 2929-34).

PDGF can promote tumor growth through either the paracrine or autocrine stimulation of PDGFR receptors on stromal cells or tumor cells directly, or through the amplification of the receptor or activation of the receptor by recombination. Over expressed PDGF can transform human melanoma cells and keratinocytes (Forsberg, K., et al. Proc Natl Acad Sci USA., 1993. 90(2), 393-7; Skobe, M. and N. E. Fusenig, Proc Natl Acad Sci USA, 1998. 95(3), 1050-5), two cell types that do not express PDGF receptors, presumably by the direct effect of PDGF on stroma formation and induction of angiogenesis. This paracrine stimulation of tumor stroma is also observed in carcinomas of the colon, lung, breast, and prostate (Bhardwaj, B., et al. Clin Cancer Res, 1996, 2(4), 773-82; Nakanishi, K., et al. Mod Pathol, 1997, 10(4), 341-7; Sundberg, C., et al. Am J Pathol, 1997, 151(2), 479-92; Lindmark, G., et al. Lab Invest, 1993, 69(6), 682-9; Vignaud, J. M., et al, Cancer Res, 1994, 54(20), 5455-63) where the tumors express PDGF, but not the receptor. The autocrine stimulation of tumor cell growth, where a large faction of tumors analyzed express both the ligand PDGF and the receptor, has been reported in glioblastomas (Fleming, T. P., et al. Cancer Res, 1992, 52(16), 4550-3), soft tissue sarcomas (Wang, J., M. D. Coltrera, and A. M. Gown, Cancer Res, 1994, 54(2), 560-4) and cancers of the ovary (Henriksen, R., et al. Cancer Res, 1993, 53(19), 4550-4), prostate (Fudge, K., C. Y. Wang, and M. E. Stearns, Mod Pathol, 1994, 7(5), 549-54), pancreas (Funa, K., et al. Cancer Res, 1990, 50(3), 748-53) and lung (Antoniades, H. N., et al., Proc Natl Acad Sci USA, 1992, 89(9), 3942-6). Ligand independent activation of the receptor is found to a lesser extent but has been reported in chronic myelomonocytic leukemia (CMML) where the a chromosomal translocation event forms a fusion protein between the Ets-like transcription factor TEL and the PDGF receptor. In addition, activating mutations in PDGFR have been found in gastrointestinal stromal tumors in which c-Kit activation is not involved (Heinrich, M. C., et al., Science, 2003, 9, 9). Certain PDGFR inhibitors will interfere with tumor stromal development and are believed to inhibit tumor growth and metastasis.

Another major regulator of angiogenesis and vasculogenesis in both embryonic development and some angiogenic-dependent diseases is vascular endothelial growth factor (VEGF; also called vascular permeability factor, VPF). VEGF represents a family of isoforms of mitogens existing in homodimeric forms due to alternative RNA splicing. The VEGF isoforms are reported to be highly specific for vascular endothelial cells (for reviews, see: Farrara et al. Endocr. Rev. 1992, 13, 18; Neufield et al. FASEB J. 1999, 13, 9).

VEGF expression is reported to be induced by hypoxia (Shweiki et al. Nature 1992, 359, 843), as well as by a variety of cytokines and growth factors, such as interleukin-1, interleukin-6, epidermal growth factor and transforming growth factor. To date, VEGF and the VEGF family members have been reported to bind to one or more of three transmembrane receptor tyrosine kinases (Mustonen et al. J. Cell Biol., 1995, 129, 895), VEGF receptor-1 (also known as flt-1 (fms-like tyrosine kinase-1)), VEGFR-2 (also known as kinase insert domain containing receptor (KDR); the murine analogue of KDR is known as fetal liver kinase-1 (flk-1)), and VEGFR-3 (also known as flt-4). KDR and flt-1 have been shown to have different signal transduction properties (Waltenberger et al. J. Biol. Chem. 1994, 269, 26988); Park et al. Oncogene 1995, 10, 135). Thus, KDR undergoes strong ligand-dependant tyrosine phosphorylation in intact cells, whereas flt-1 displays a weak response. Thus, binding to KDR is believed to be a critical requirement for induction of the full spectrum of VEGF-mediated biological responses.

In vivo, VEGF plays a central role in vasculogenesis, and induces angiogenesis and permeabilization of blood vessels. Deregulated VEGF expression contributes to the development of a number of diseases that are characterized by abnormal angiogenesis and/or hyperpermeability processes. It is believed regulation of the VEGF-mediated signal transduction cascade by some agents can provide a useful mode for control of abnormal angiogenesis and/or hyperpermeability processes.

Angiogenesis is regarded as an important prerequisite for growth of tumors beyond about 1-2 mm. Oxygen and nutrients may be supplied to cells in tumor smaller lo than this limit through diffusion. However, it is believed every tumor is dependent on angiogenesis for continued growth after it has reached a certain size. Tumorigenic cells within hypoxic regions of tumors respond by stimulation of VEGF production, which triggers activation of quiescent endothelial cells to stimulate new blood vessel formation. (Shweiki et al. Proc. Nat'l. Acad. Sci., 1995, 92, 768). In addition, VEGF production in tumor regions where there is no angiogenesis may proceed through the ras signal transduction pathway (Grugel et al. J. Biol. Chem., 1995, 270, 25915; Rak et al. Cancer Res. 1995, 55, 4575). In situ hybridization studies have demonstrated VEGF mRNA is strongly upregulated in a wide variety of human tumors, including lung (Mattern et al. Br. J. Cancer 1996, 73, 931), thyroid (Viglietto et al. Oncogene 1995, 11, 1569), breast (Brown et al. Human Pathol. 1995, 26, 86), gastrointestinal tract (Brown et al. Cancer Res. 1993, 53, 4727; Suzuki et al. Cancer Res. 1996, 56, 3004), kidney and bladder (Brown et al. Am. J. Pathol. 1993, 1431, 1255), ovary (Olson et al. Cancer Res. 1994, 54, 1255), and cervical (Guidi et al. J. Nat'l Cancer Inst. 1995, 87, 12137) carcinomas, as well as angiosacroma (Hashimoto et al. Lab. Invest. 1995, 73, 859) and several intracranial tumors (Plate et al. Nature 1992, 359, 845; Phillips et al. Int. J. Oncol. 1993, 2, 913; Berkman et al. J. Clin. Invest., 1993, 91, 153). Neutralizing monoclonal antibodies to KDR have been shown to be efficacious in blocking tumor angiogenesis (Kim et al. Nature 1993, 362, 841; Rockwell et al. Mol. Cell. Differ. 1995, 3, 315).

Over expression of VEGF, for example under conditions of extreme hypoxia, can lead to intraocular angiogenesis, resulting in hyperproliferation of blood vessels, leading eventually to blindness. Such a cascade of events has been observed for a number of retinopathies, including diabetic retinopathy, ischemic retinal-vein occlusion, and retinopathy of prematurity (Aiello et al. New Engl. J. Med. 1994, 331, 1480; Peer et al. Lab. Invest. 1995, 72, 638), and age-related macular degeneration (AMD; see, Lopez et al. Invest. Opththalmol. Vis. Sci. 1996, 37, 855).

In rheumatoid arthritis (RA), the in-growth of vascular pannus may be mediated by production of angiogenic factors. Levels of immunoreactive VEGF are high in the synovial fluid of RA patients, while VEGF levels were low in the synovial fluid of patients with other forms of arthritis of with degenerative joint disease (Koch et al. J. Immunol. 1994, 152, 4149). The angiogenesis inhibitor AGM-170 has been shown to prevent neovascularization of the joint in the rat collagen arthritis model (Peacock et al. J. Exper. Med. 1992, 175, 1135).

Increased VEGF expression has also been shown in psoriatic skin, as well as bullous disorders associated with subepidermal blister formation, such as bullous pemphigoid, erythema multiforme, and dermatitis herpetiformis (Brown et al. J. Invest. Dermatol. 1995, 104, 744).

The vascular endothelial growth factors (VEGF, VEGF-C, VEGF-D) and their receptors (VEGFR2, VEGFR3) are not only key regulators of tumor angiogenesis, but also lymphangiogenesis. VEGF, VEGF-C and VEGF-D are expressed in most tumors, primarily during periods of tumor growth and, often at substantially increased levels. VEGF expression is stimulated by hypoxia, cytokines, oncogenes such as ras, or by inactivation of tumor suppressor genes (McMahon, G. Oncologist 2000, 5(Suppl. 1), 3-10; McDonald, N. Q.; Hendrickson, W. A. Cell 1993, 73, 421-424).

The biological activities of the VEGFs are mediated through binding to their receptors. VEGFR3 (also called Flt-4) is predominantly expressed on lymphatic endothelium in normal adult tissues. VEGFR3 function is needed for new lymphatic vessel formation, but not for maintenance of the pre-existing lymphatics. VEGFR3 is also upregulated on blood vessel endothelium in tumors. Recently VEGF-C and VEGF-D, ligands for VEGFR3, have been identified as regulators of lymphangiogenesis in mammals. Lymphangiogenesis induced by tumor-associated lymphangiogenic factors could promote the growth of new vessels into the tumor, providing tumor cells access to systemic circulation. Cells that invade the lymphatics could find their way into the bloodstream via the thoracic duct. Tumor expression studies have allowed a direct comparison of VEGF-C, VEGF-D and VEGFR3 expression with clinicopathological factors that relate directly to the ability of primary tumors to spread (e.g., lymph node involvement, lymphatic invasion, secondary metastases, and disease-free survival). In many instances, these studies demonstrate a statistical correlation between the expression of lymphangiogenic factors and the ability of a primary solid tumor to metastasize (Skobe, M. et al. Nature Med. 2001, 7(2), 192-198; Stacker, S. A. et al. Nature Med. 2001, 7(2), 186-191; Makinen, T. et al. Nature Med. 2001, 7(2), 199-205; Mandriota, S. J. et al. EMBO J. 2001, 20(4), 672-82; Karpanen, T. et al. Cancer Res. 2001, 61(5), 1786-90; Kubo, H. et al. Blood 2000, 96(2), 546-53).

Hypoxia appears to be an important stimulus for VEGF production in malignant cells. Activation of p38 MAP kinase is required for VEGF induction by tumor cells in response to hypoxia (Blaschke, F. et al. Biochem. Biophys. Res. Commun. 2002, 296, 890-896; Shemirani, B. et al. Oral Oncology 2002, 38, 251-257). In addition to its involvement in angiogenesis through regulation of VEGF secretion, p38 MAP kinase promotes malignant cell invasion, and migration of different tumor types through regulation of collagenase activity and urokinase plasminogen activator expression (Laferriere, J. et al. J. Biol. Chem. 2001, 276, 33762-33772; Westermarck, J. et al. Cancer Res. 2000, 60, 7156-7162; Huang, S. et al. J. Biol. Chem. 2000, 275, 12266-12272; Simon, C. et al. Exp. Cell Res. 2001, 271, 344-355).

Some diarylureas have been described as having activity as serine-threonine kinase and/or as tyrosine kinase inhibitors. The ultility of these diarylureas as an active ingredient in pharmaceutical compositions for the treatment of cancer, angiogenesis disorders, and inflammatory disorders has been demonstrated. See Redman et al., Bioorg. Med. Chem. Lett. 2001, 11, 9-12; Smith et al., Bioorg. Med. Chem. Lett. 2001, 11, 2775-2778; Dumas et al., Bioorg. Med. Chem. Lett. 2000, 10, 2047-2050; Dumas et al., Bioorg. Med. Chem. Lett. 2000, 10, 2051-2054; Ranges et al., Book of Abstracts, 220th ACS National Meeting, Washington, D.C., USA, MEDI 149; Dumas et al., Bioorg. Med. Chem. Lett. 2002, 12, 1559-1562; Lowinger et al., Clin. Cancer Res. 2000, 6(suppl.), 335; Lyons et al., Endocr.-Relat. Cancer 2001, 8, 219-225; Riedl et al., Book of Abstracts, 92nd AACR Meeting, New Orleans, La., USA, abstract 4956; Khire et al., Book of Abstracts, 93rd AACR Meeting, San Francisco, Calif., USA, abstract 4211; Lowinger et al., Curr. Pharm. Design 2002, 8, 99-110; Regan et al., J. Med. Chem. 2002, 45, 2994-3008; Pargellis et al., Nature Struct. Biol. 2002, 9(4), 268-272; Carter et al., Book of Abstracts, 92nd AACR Meeting, New Orleans, La., USA, abstract 4954; Vincent et al., Book of Abstracts, 38th ASCO Meeting, Orlando, Fla., USA, abstract 1900; Hilger et al., Book of Abstracts, 38th ASCO Meeting, Orlando, Fla., USA, abstract 1916; Moore et al., Book of Abstracts, 38th ASCO Meeting, Orlando, Fla., USA, abstract 1816; Strumberg et al., Book of Abstracts, 38th ASCO Meeting, Orlando, Fla., USA, abstract 121; Madwed J B: Book of Abstracts, Protein Kinases: Novel Target Identification and Validation for Therapeutic Development, San Diego, Calif., USA, March 2002; Roberts et al., Book of Abstracts, 38th ASCO Meeting, Orlando, Fla., USA, abstract 473; Tolcher et al., Book of Abstracts, 38th ASCO Meeting, Orlando, Fla., USA, abstract 334; and Karp et al., Book of Abstracts, 38th AACR Meeting, San Francisco, Calif., USA, abstract 2753.

Despite the advancements in the art, there remains a need for cancer treatments and anti-cancer compounds.

DESCRIPTION OF THE INVENTION

The present invention pertains to:
(i) urea compounds, salts, metabolites and prodrugs thereof, including diastereoisomeric forms,
(ii) pharmaceutical compositions containing any of such compounds, salts, metabolites and prodrugs thereof, including diastereoisomeric forms, and
(iii) use of those compounds or compositions for treating diseases, e.g., hyper-proliferative and angiogenesis disorders, as a sole agent or in combination with other active ingredients, e.g., cytotoxic therapies.

The compounds of formula (I), salts, metabolites and prodrugs thereof, including diastereoisomeric forms (both isolated stereoisomers and mixtures of stereoisomers) are collectively referred to herein as the "compounds of the invention". Formula (I) is as follows:

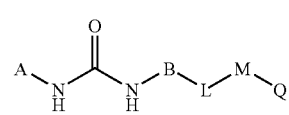

I wherein A is a bicyclic heterocycle which is:
(1) benzimidazolyl
(2) 1,3-benzothiazolyl
(3) 1,2,3-benzotriazolyl
(4) 1,3-benzoxazolyl
(5) 2,3-dihydro-1H-indolyl
(6) 2,3-dihydro-1H-indenyl
(7) 1,1-dioxido-2,3-dihydro-1-benzothienyl
(8) 1H-indazolyl
(9) 2H-indazolyl
(10) 1H-indolyl

(11) 2H-chromenyl
(12) quinoxalinyl or
(13) a group of the formula

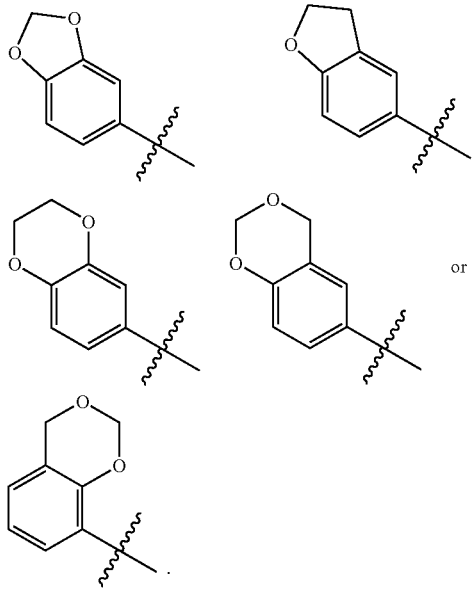

Compounds of formula I which are of interest include those where A is selected from:
(1) benzimidazol-5-yl
(2) benzimidazol-6-yl
(3) 1,3-benzothiazol-2-yl
(4) 1,3-benzothiazol-5-yl
(5) 1,3-benzothiazol-6-yl
(6) 1,2,3-benzotriazol-5-yl
(7) 1,3-benzoxazol-2-yl
(8) 1,3-benzoxazol-6-yl
(9) 2,3-dihydro-1H-indol-5-yl
(10) 2,3-dihydro-1H-indol-6-yl
(11) 2,3-dihydro-1H-inden-4-yl
(12) 2,3-dihydro-1H-inden-5-yl
(13) 1,1-dioxido-2,3-dihydro-1-benzothien-6-yl
(14) 1H-indazol-5-yl
(15) 2H-indazol-5-yl
(16) 1H-indazol-6-yl
(17) 1H-indol-5-yl
(18) 2H-chromen-7-yl
(19) quinoxalin-2-yl
(20) quinoxalin-6-yl, and
(21) a group of the formula

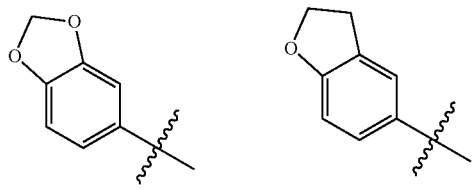

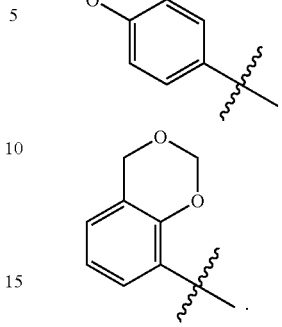

Preferred compounds of formula I have A selected from
(1) benzimidazol-5-yl
(2) benzimidazol-6-yl
(8) 1,3-benzoxazol-6-yl
(9) 2,3-dihydro-1H-indol-5-yl
(10) 2,3-dihydro-1H-indol-6-yl
(11) 2,3-dihydro-1H-inden-4-yl
(12) 2,3-dihydro-1H-inden-5-yl
(13) 1,1-dioxido-2,3-dihydro-1-benzothien-6-yl
(14) 1H-indazol-5-yl
(15) 2H-indazol-5-yl
(16) 1H-indazol-6-yl
(17) 1H-indol-5-yl
(18) quinoxalin-2-yl
(19) quinoxalin-6-yl, and
(20) a group of the formula

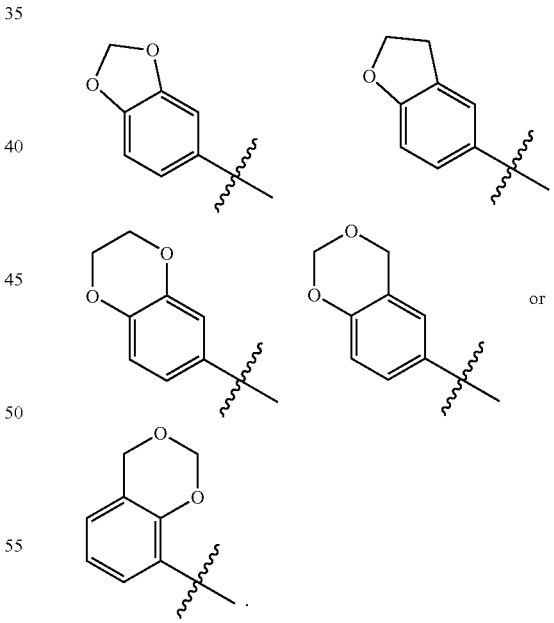

The bicyclic heterocycle A is optionally substituted with 1-4 substituents which are independently $R^1$, $OR^1$, $S(O)_pR^1$, $C(O)R^1$, $C(O)OR^1$, $C(O)NR^1R^2$, halogen, oxo, cyano, or nitro.

The preferred optional substituents on bicyclic heterocycle A are independently $R^1$, $OR^1$, and halogen.

B is phenyl, naphthyl, pyridyl, or quinolinyl optionally substituted with 1-4 substituents which are independently $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_6$ dialkylamino, carboxyamide, halogen, cyano, nitro or $S(O)_p R^7$.

B is preferably phenyl, pyridyl, or quinolinyl, more preferably phenyl or pyridyl, optionally substituted with 1-4 substituents which are independently $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_6$ dialkylamino, carboxyamide, halogen, cyano, nitro or $S(O)_p R^7$.

L is a bridging group which is:
(a) —$(CH_2)_m$—O—$(CH_2)_l$—,
(b) —$(CH_2)_m$—$(CH_2)_l$—,
(c) —$(CH_2)_m$—C(O)—$(CH_2)_l$—,
(d) —$(CH_2)_m$—$NR^3$$(CH_2)_l$—,
(e) —$(CH_2)_m NR^3 C(O)$—$(CH_2)_l$—,
(f) —$(CH_2)_m$—S—$(CH_2)_l$—,
(g) —$(CH_2)_m$—$C(O)NR^3$—$(CH_2)_l$—, or
(h) a single bond,
where m and l are integers independently selected from 0-4, and preferably selected from 0-2.

Most preferably, L is —O— or —S—.

M is a pyridine ring, optionally substituted with 1-3 substituents which are independently $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_6$ dialkylamino, halogen, or nitro Q is $C(O)R^4$, $C(O)OR^4$ or $C(O)NR^4R^5$.

Each of $R^1$, $R^2$, $R^3$, $R^4$ and $R^5$ is independently:
(a) hydrogen,
(b) $C_1$-$C_5$ alkyl, (linear, branched, or cyclic alkyl),
(c) phenyl,
(d) $C_1$-$C_3$ alkyl-phenyl,
(e) up to per-halo substituted $C_1$-$C_5$ linear or branched alkyl,
(f) —$(CH_2)_q$—X, wherein the substituent X is a 5 or 6 membered heterocyclic ring, containing at least one atom selected from oxygen, nitrogen and sulfur, which is saturated, partially saturated, or aromatic, or a 8-10 membered bicyclic heteroaryl having 1-4 heteroatoms which are O, N or S, or
(g) —$(CH_2)_q$—Y, where Y is $C(O)R^6$, $C(O)OR^6$ or $C(O)NR^6R^7$.

Each of $R^1$, $R^2$, $R^{13}$, $R^4$ and $R^5$ is preferably, independently:
(a) hydrogen,
(b) $C_1$-$C_5$ alkyl,
(c) phenyl,
(d) up to per-halo substituted $C_1$-$C_5$ linear or branched alkyl.

Each of $R^6$-$R^7$ is independently:
(a) hydrogen,
(b) $C_1$-$C_5$ linear, branched, or cyclic alkyl,
(c) phenyl,
(d) $C_1$-$C_3$ alkyl-phenyl, or
(e) up to per-halo substituted $C_1$-$C_5$ linear or branched alkyl.

Each of $R^1$, $R^2$, $R^3$, $R^4$, $R^5$, $R^6$ and $R^7$, other than per-halo substituted $C_1$-$C_5$ linear or branched alkyl, is optionally substituted with 1-3 substituents which are independently $C_1$-$C_5$ linear or branched alkyl, up to perhalo substituted $C_1$-$C_5$ linear or branched alkyl, $C_1$-$C_3$ alkoxy, hydroxy, carboxy, amino, $C_1$-$C_3$ alkylamino, $C_1$-$C_6$ dialkylamino, halogen, cyano, or nitro.

The variable p is an integer selected from 0, 1, or 2. The variable q is an integer selected from 1, 2, 3, or 4.

When any moiety is "substituted", it can have up to the highest number of indicated substituents, and each substituent can be located at any available position on the moiety and can be attached through any available atom on the substituent.

"Any available position" means any position on the moiety that is chemically accessible through means known in the art or taught herein and that does not create an unduly unstable molecule. When there are two or more substituents on any moiety, each substituent is defined independently of any other substituent and can, accordingly, be the same or different.

The term "optionally substituted" means that the moiety so modified may be either unsubstituted, or substituted with the identified substituent(s).

It is understood that since M is pyridine, the term "hydroxy" as a pyridine substituent includes 2-, 3-, and 4-hydroxypyridine, but also includes those structures referred to in the art as 1-oxo-pyridine, 1-hydroxy-pyridine and pyridine N-oxide.

Where the plural form of the word compounds, salts, and the like, is used herein, this is taken to mean also a single compound, salt, or the like.

The term $C_1$-$C_5$alkyl means straight or branched chain alkyl groups having from one to five carbon atoms, which may be linear or branched with single or multiple branching. Such groups include methyl, ethyl, n-propyl, isopropyl, n-butyl, isobutyl, sec-butyl, tert-butyl, and the like.

The term halo$C_1$-$C_5$ alkyl means a saturated hydrocarbon radical having up to five carbon atoms, which is substituted with a least one halogen atom, up to perhalo. The radical may be linear or branched with single or multiple branching. The halo substituent(s) include fluoro, chloro, bromo, or iodo. Fluoro, chloro and bromo are preferred, and fluoro and chloro are more preferred. The halogen substituent(s) can be located on any available carbon. When more than one halogen substituent is present on this moiety, they may be the same or different. Examples of such halogenated alkyl substituents include but are not limited to chloromethyl, dichloromethyl, trichloromethyl, fluoromethyl, difluoromethyl, trifluoromethyl, 2,2,2-trifluoroethyl, and 1,1,2,2-tetrafluoroethyl, and the like.

The term $C_1$-$C_3$ alkoxy means a straight or branched chain alkoxy group having from one to three saturated carbon atoms which may be linear or branched with single or multiple branching, and includes such groups as methoxy, ethoxy, n-propoxy, isopropoxy, and the like. It also includes halogenated groups such as 2,2-dichloroethoxy, trifluoromethoxy, and the like.

Halo or halogen means fluoro, chloro, bromo, or iodo. Fluoro, chloro and bromo are preferred, and fluoro and chloro are more preferred.

$C_1$-$C_3$alkylamine means methylamino, ethylamino, propylamino or isopropylamino. Examples of $C_1$-$C_6$ dialkylamine include but are not limited to diethylamino, ethyl-isopropylamino, means methylamino, methyl-isobutylamino, dihexylamino.

The term heteroaryl refers to both monocyclic and bicyclic heteroaryl rings. Monocyclic heteroaryl means an aromatic monocyclic ring having 5 to 6 ring atoms, at least one of which is a hetero atom selected from N, O and S, the remaining atoms being carbon. When more than one hetero atom is present in the moiety, they are selected independently from the other(s) so that they may be the same or different. Monocyclic heteroaryl rings include, but are not limited to pyrrole, furan, thiophene, imidazole, pyrazole, thiazole, oxazole, isoxazole, isothiazole, triazole, tetrazole, thiadiazole, oxadiazole, pyridine, pyrimidine, pyridazine, pyrazine, and triazine.

Bicyclic heteroaryl means fused bicyclic moieties where one of the rings is chosen from the monocyclic heteroaryl rings described above and the second ring is either benzene or another monocyclic heteroaryl ring described above. When both rings in the bicyclic moiety are heteroaryl rings, they may be the same or different, as long as they are chemically accessible by means known in the art. Bicyclic heteroaryl rings include synthetically accessible 5-5, 5-6, or 6-6 fused bicyclic aromatic structures including, for example but not by way of limitation, benzoxazole (fused phenyl and oxazole), quinoline (fused phenyl and pyridine), imidazopyrimidine (fused imidazole and pyrimidine), and the like.

The term "5 or 6 membered heterocyclic ring, containing at least one atom selected from oxygen, nitrogen and sulfur, which is saturated, partially saturated, or aromatic" includes, by no way of limitation, tetrahydropyrane, tetrahydrofurane, 1,3-dioxolane, 1,4-dioxane, morpholine, thiomorpholine, piperazine, piperidine, piperidinone, tetrahydropyrimidone, pentamethylene sulfide, tetramethylene sulfide, dihydropyrane, dihydrofurane, dihydrothiophene, pyrrole, furan, thiophene, imidazole, pyrazole, thiazole, oxazole, isoxazole, isothiazole, triazole, pyridine, pyrimidine, pyridazine, pyrazine, triazine, and the like.

The term "$C_1$-$C_3$ alkyl-phenyl" includes, by no way of limitation, 3-phenyl-propyl, 2-phenyl-1-methyl-ethyl. Substituted examples include 2-[2-chlorophenyl]ethyl, 3,4-dimethylphenyl-methyl, and the like.

The compounds of Formula I may contain one or more asymmetric centers, depending upon the location and nature of the various substituents desired. Asymmetric carbon atoms may be present in the (R) or (S) configuration or (R,S) configuration. In certain instances, asymmetry may also be present due to restricted rotation about a given bond, for example, the central bond adjoining two substituted aromatic rings of the specified compounds. Substituents on a ring may also be present in either cis or trans form. It is intended that all such configurations (including enantiomers and diastereomers), are included within the scope of the present invention. Preferred compounds are those with the absolute configuration of the compound of Formula I which produces the more desirable biological activity. Separated, pure or partially purified isomers or racemic mixtures of the compounds of this invention are also included within the scope of the present invention. The purification of said isomers and the separation of said isomeric mixtures can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivation, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivitization, are also useful. The optically active compounds of Formula I can likewise be obtained by chiral syntheses utilizing optically active starting materials.

The present invention also relates to useful forms of the compounds as disclosed herein, such as pharmaceutically acceptable salts, metabolites and prodrugs of all the compounds Formula (I).

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19. Pharmaceutically acceptable salts also include those in which the main compound functions as an acid and is reacted with an appropriate base to form, e.g., sodium, potassium, calcium, mangnesium, ammonium, and choline salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts are prepared by reacting the compounds of the invention with the appropriate base via a variety of known methods.

Representative salts of the compounds of this invention include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, tartrate, thiocyanate, tosylate, and undecanoate.

Base salts include alkali metal salts such as potassium and sodium salts, alkaline earth metal salts such as calcium and magnesium salts, and ammonium salts with organic bases such as dicyclohexylamine and N-methyl-D-glucamine. Additionally, basic nitrogen containing groups may be quaternized with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenylethyl bromides and others.

Certain compounds of this invention can be further modified with labile functional groups that are cleaved after in vivo administration to furnish the parent active agent and the pharmacologically inactive derivatizing (functional) group. These derivatives, commonly referred to as prodrugs, can be used, for example, to alter the physicochemical properties of the active agent, to target the active agent to a specific tissue, to alter the pharmacokinetic and pharmacodynamic properties of the active agent, and to reduce undesirable side effects.

Prodrugs of the invention include, e.g., the esters of appropriate compounds of this invention are well-tolerated, pharmaceutically acceptable esters such as alkyl esters including methyl, ethyl, propyl, isopropyl, butyl, isobutyl or pentyl esters. Additional esters such as phenyl-$C_1$-$C_5$ alkyl may be used, although methyl ester is preferred.

Methods for synthesizing prodrugs are described in the following reviews on the subject, which are incorporated herein by reference for their description of these methods:

Higuchi, T.; Stella, V. eds. *Prodrugs As Novel Drug Delivery Systems*. ACS Symposium Series. American Chemical Society: Washington, D.C. (1975).

Roche, E. B. *Design of Biopharmaceutical Properties through Prodrugs and Analogs*. American Pharmaceutical Association: Washington, D.C. (1977).

Sinkula, A. A.; Yalkowsky, S. H. *J Pharm Sci.* 1975, 64, 181-210.

Stella, V. J.; Charman, W. N. Naringrekar, V. H. *Drugs* 1985, 29, 455-473.

Bundgaard, H., ed. *Design of Prodrugs*. Elsevier: New York (1985).

Stella, V. J.; Himmelstein, K. J. *J. Med. Chem.* 1980, 23, 1275-1282.

Han, H-K; Amidon, G. L. *AAPS Pharmsci* 2000, 2, 1-11.

Denny, W. A. *Eur. J. Med. Chem.* 2001, 36, 577-595.

Wermuth, C. G. in Wermuth, C. G. ed. *The Practice of Medicinal Chemistry* Academic Press: San Diego (1996), 697-715.

Balant, L. P.; Doelker, E. in Wolff, M. E. ed. *Burgers Medicinal Chemistry And Drug Discovery* John Wiley & Sons: New York (1997), 949-982.

The metabolites of the compounds of this invention include oxidized derivatives of the compounds of Formulae I, wherein one or more of the nitrogens are substituted with a hydroxy group, which includes derivatives where the nitrogen atom of the pyridine group is in the oxide form, referred to in the art as 1-oxo-pyridine or has a hydroxy substituent, referred to in the art as 1-hydroxy-pyridine.

General Preparative Methods

The particular process to be utilized in the preparation of the compounds used in this embodiment of the invention depends upon the specific compound desired. Such factors as the selection of the specific substituents play a role in the path to be followed in the preparation of the specific compounds of this invention. Those factors are readily recognized by one of ordinary skill in the art.

The compounds of the invention may be prepared by use of known chemical reactions and procedures. Nevertheless, the following general preparative methods are presented to aid the reader in synthesizing the compounds of the present invention, with more detailed particular examples being presented below in the experimental section describing the working examples.

All variable groups of these methods are as described in the generic description if they are not specifically defined below. When a variable group or substituent with a given symbol is used more than once in a given structure, it is to be understood that each of these groups or substituents may be independently varied within the range of definitions for that symbol. It is recognized that compounds of the invention with each claimed optional functional group cannot be prepared with each of the below-listed methods. Within the scope of each method optional substituents are used which are stable to the reaction conditions, or the functional groups which may participate in the reactions are present in protected form where necessary, and the removal of such protective groups is completed at appropriate stages by methods well known to those skilled in the art.

The compounds of the invention can be made according to conventional chemical methods, and/or as disclosed below, from starting materials which are either commercially available or producible according to routine, conventional chemical methods. General methods for the preparation of the compounds are given below, and the preparation of representative compounds is specifically illustrated in examples.

Reaction Scheme 1:
Synthesis of Ureas of formula (I)

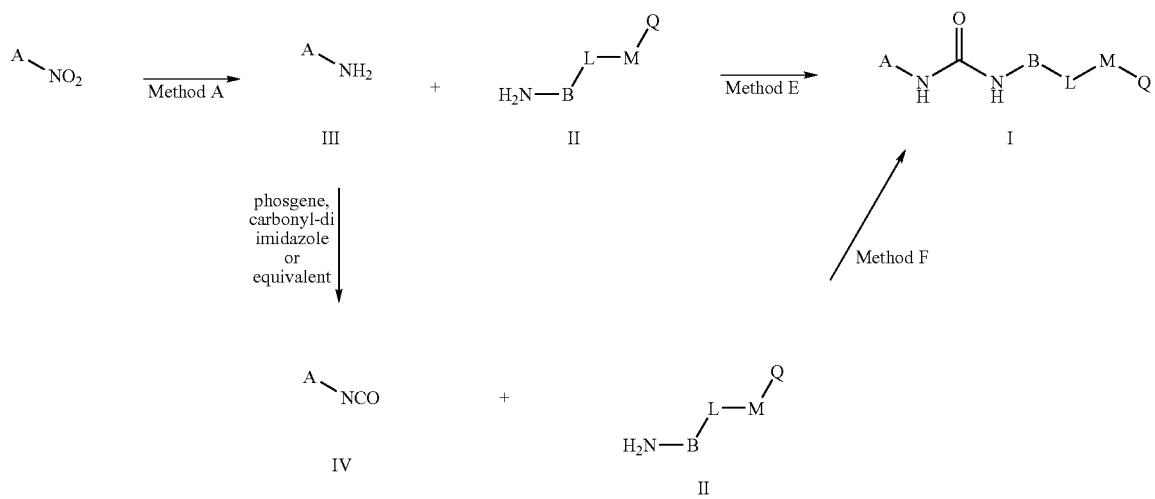

The preparation of ureas of formula (I) is depicted in Reaction Scheme 1, where A, B, L, M, and Q are broadly defined as above. Compounds (I) can be synthesized according to the reaction sequence shown in the General Methods E and F above. Using Method E, ureas of Formula (I) are prepared from the condensation of the two arylamine fragments (II) and (III) in the presence of phosgene, di-phosgene, tri-phosgene, carbonyldiimidazole, or equivalents in a solvent that does not react with any of the starting materials. Alternatively, compounds (I) can be synthesized by reacting amino compounds (II) with isocyanate compounds (IV) using Method F.

The isocyanates (IV) are commercially available or can be synthesized from heterocyclic amines of Formula (II) or (III), according to methods commonly known to those skilled in the art [e.g. from treatment of an amine with phosgene or a phosgene equivalent such as trichloromethyl chloroformate (diphosgene), bis(trichloromethyl)carbonate (triphosgene), or N,N'-carbonyldiimidazole (CDI); or, alternatively by a Curtius-type rearrangement of an amide, or a carboxylic acid derivative, such as an ester, an acid halide or an anhydride].

Reaction Scheme 2:
Synthesis of starting materials of formula (IV)

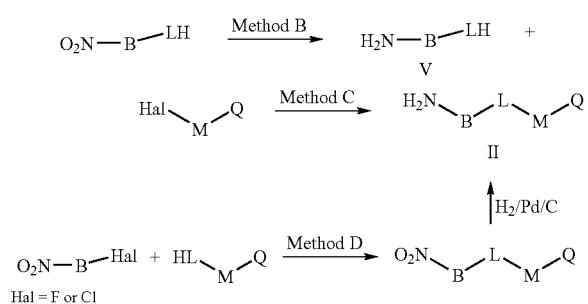

Aryl amines of formulas (III) or (V) are commercially available, or can be synthesized according to Method A or B, or methods commonly known to those skilled in the art. Aryl amines are commonly synthesized by reduction of nitroaryls using a metal catalyst, such as Ni, Pd, or Pt, and $H_2$ or a hydride transfer agent, such as formate, cyclohexadiene, or a borohydride (Rylander. Hydrogenation Methods; Academic Press: London, UK (1985)). Nitroaryls may also be directly reduced using a strong hydride source, such as $LiAlH_4$ (Seyden-Penne. Reductions by the Alumino- and borohydrides in Organic Synthesis; VCH Publishers: New York (1991)), or using a zero valent metal, such as Fe, Sn or Ca, often in acidic media. Many methods exist for the synthesis of nitroaryls (March. Advanced Organic Chemistry, $3^{rd}$ Ed.; John Wiley: New York (1985). Larock. Comprehensive Organic Transformations; VCH Publishers: New York (1989)). Nitro aryls are commonly formed by electrophilic aromatic nitration using $HNO_3$, or an alternative $NO_2^+$ source.

For the synthesis of compounds of formula (II) where L represents $—(CH_2)_mO—$, $—(CH_2)_mS—$, or $—(CH_2)_mNH—$, and B, M, Q, and m are broadly defined as above, the nitroaryls are further elaborated prior to reduction. In Reaction Scheme 2—method D, nitro aryls substituted with potential leaving groups such as F or Cl undergo substitution reactions on treatment with nucleophiles, such as phenoxide or thiolate, under basic conditions.

Another method for the preparation of the intermediate of Formula (II) is depicted in Reaction Scheme 2—Method C. The condensation of amine (V) with an appropriate substituted choropyridine has been previously described in the patent literatures, and can be adapted to the compounds of the present invention. For example, PCT Int. Appl., WO 99 32111, Dumas, J. et al., "Method for the Treatment of Neoplasm by inhibition of raf Kinase using N-Heteroaryl-N'-(hetero)arylureas", PCT Int. Appl., WO 99 32110, Dumas, J., et al., "Inhibition of raf Kinase using Aryl- and Heteroaryl-Substituted Heterocyclic Ureas".

Reaction Scheme 3:
Alternative Synthesis of Ureas of formula (I)

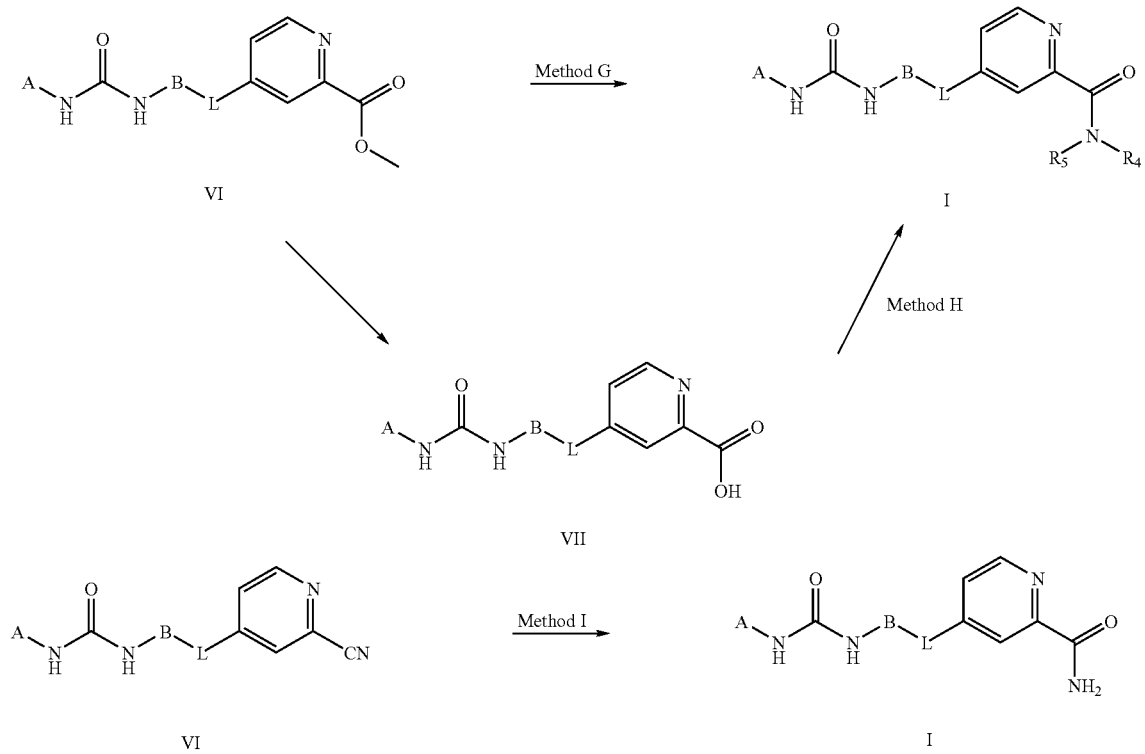

The compounds of the invention may also be prepared from compounds of formula (VII) according to the reaction sequence shown in the General Methods G and H above. Using Method G, ureas of Formula (VI) are treated with a Lewis acid such as magnesium chloride and the appropriate substituted amines, in a solvent such as THF at room temperature, to provide substituted amides. In Method H, ureas of Formula (VI) are deesterified with a base such as potassium hydroxide, lithium hydroxide, or sodium hydroxide. Carboxylic acids of formula (VII) are coupled with the appropriate amines according to methods commonly known to those skilled in the art [e.g. from treatment of a carboxylic acid with DCC/DMAP or EDCI/HOBT], in a solvent such as THF, AcCN, or DMF. In addition, compounds of formula (I) where $R_4$ and $R_5$ are hydrogens may be synthesized according to the reaction scheme shown in Method I. The cyano compound (VIII) can be hydrolyzed in the presence of NaOH or sodium percarbonate, in aqueous solvent such as acetone-water, and at temperature from 20 to 100° C. Compounds of formula (VI) and (VIII) are synthesized according to methods A to F, or methods commonly known to those skilled in the art.

Pyridine-1-oxides or Formula I where M carries a hydroxy substituent on its nitrogen atom, and A, B, L are broadly defined as above can be prepared from the corresponding pyridines using oxidation conditions know in the art. Some examples are as follows:

- peracids such as meta chloroperbenzoic acids in chlorinated solvents such as dichloromethane, dichloroethane, or chloroform (Markgraf et al., Tetrahedron 1991, 47, 183).
- $(Me_3SiO)_2$ in the presence of a catalytic amount of perrhenic acid in chlorinated solvents such as dichloromethane (Coperet et al., Terahedron Lett. 1998, 39, 761)
- Perfluoro-cis-2-butyl-3-propyloxaziridine in several combinations of halogenated solvents (Amone et al., Tetrahedron 1998, 54, 7831).
- Hypofluoric acid—acetonitrile complex in chloroform (Dayan et al., Synthesis 1999, 1427).
- Oxone, in the presence of a base such as KOH, in water (Robker et al., J. Chem. Res., Synop. 1993, 10, 412).
- Magnesium monoperoxyphthalate, in the presence of glacial acetic acid (Klemm et al., J. Heterocylic Chem. 1990, 6, 1537).
- Hydrogen peroxide, in the presence of water and acetic acid (Lin A. J., Org. Prep. Proced. Int. 1991, 23(1), 114).
- Dimethyldioxirane in acetone (Boyd et al., J. Chem. Soc., Perkin Trans. 1991, 9, 2189).

In addition, specific preparations of diaryl ureas and intermediate compounds (II) are already described in the patent literature, and can be adapted to the compounds of the present invention. For example, Miller S. et al, "Inhibition of p38 Kinase using Symmetrical and Unsymmetrical Diphenyl Ureas" PCT Int. Appl. WO 99 32463, Miller, S et al. "Inhibition of raf Kinase using Symmetrical and Unsymmetrical Substituted Diphenyl Ureas" PCT Int. Appl., WO 99 32436, Dumas, J. et al., "Inhibition of p38 Kinase Activity using Substituted Heterocyclic Ureas" PCT Int. Appl., WO 99 32111, Dumas, J. et al., "Method for the Treatment of Neoplasm by Inhibition of raf Kinase using N-Heteroaryl-N'-(hetero)arylureas" PCT Int. Appl., WO 99 32106, Dumas, J. et al., "Inhibition of p38 Kinase Activity using Aryl- and Heteroaryl-Substituted Heterocyclic Ureas" PCT Int. Appl., WO 99 32110, Dumas, J., et al., "Inhibition of raf Kinase using Aryl- and Heteroaryl-Substituted Heterocyclic Ureas" PCT Int. Appl., WO 99 32455, Riedl, B., et al., "O-Carboxy Aryl Substituted Diphenyl Ureas as raf Kinase Inhibitors" PCT Int. Appl., WO 00 42012, Riedl, B., et al., "O-Carboxy Aryl Substituted Diphenyl Ureas as p38 Kinase Inhibitors" PCT Int. Appl., WO 00 41698, Dumas, J. et al. "Heteroaryl ureas containing nitrogen hetero-atoms as p38 kinase inhibitors" U.S. Pat. Appl. Publ., US 20020065296, Dumas, J. et al. "Preparation of N-aryl-N'-[(acylphenoxy)phenyl]ureas as raf kinase inhibitors" PCT Int. Appl., WO 02 62763, Dumas, J. et al. "Inhibition of raf kinase using quinolyl, isoquinolyl or pyridyl ureas" PCT Int. Appl., WO 02 85857, Dumas, J. et al. "Preparation of quinolyl, isoquinolyl or pyridyl-ureas as inhibitors of raf kinase for the treatment of tumors and/or cancerous cell growth" U.S. Pat. Appl. Publ., US 20020165394. All the preceding patent applications are hereby incorporated by reference.

The reaction of the compounds (III) or (IV) with (II) is carried out preferably in a solvent. Suitable solvents comprise the customary organic solvents which are inert under the reaction conditions. Non-limiting examples include ethers such as diethyl ether, dioxane, tetrahydrofuran, 1,2-dimethoxy ethane; hydrocarbons such as benzene, toluene, xylene, hexane, cyclohexane, mineral oil fractions; halogenated hydrocarbons such as dichloromethane, trichloromethane, carbon tetrachloride, dichloroethane, trichloroethylene, chlorobenzene; alcohols such as methanol, ethanol, n-propanol, isopropanol; esters such as ethyl acetate; ketones such as acetone; nitriles such as acetonitrile; heteroaromatics such as pyridine; polar solvents such as dimethyl formamide and hexamethyl phosphoric acid tris-amide; and mixtures of the above-mentioned solvents. Toluene, benzene, and dichloromethane are preferred.

The compounds (III) are generally employed in an amount of from 1 to 3 mol per mol of compounds (II); an equimolar amount or slight excess of compounds (III) is preferred.

The reaction of the compounds (II) with (III) is generally carried out within a relatively wide temperature range. In general, they are carried out in a range of from −20 to 200° C., preferably from 0 to 100° C., and more preferably from 25 to 50° C. The steps of this reaction are generally carried out under atmospheric pressure. However, it is also possible to carry them out under superatmospheric pressure or under reduced pressure (for example, in a range of from 0.5 to 5 bar). The reaction time can generally be varied within a relatively wide range. In general, the reaction is finished after a period of from 2 to 24 hours, preferably from 6 to 12 hours.

Synthetic transformations that may be employed in the synthesis of compounds of Formula I and in the synthesis of intermediates involved in the synthesis of compounds of Formula I are known by or accessible to one skilled in the art. Collections of synthetic transformations may be found in compilations, such as:

- J. March. Advanced Organic Chemistry, $4^{th}$ ed.; John Wiley: New York (1992)
- R. C. Larock. Comprehensive Organic Transformations, $2^{nd}$ ed.; Wiley-VCH: New York (1999)
- F. A. Carey; R. J. Sundberg. Advanced Organic Chemistry, $2^{nd}$ ed.; Plenum Press: New York (1984)
- T. W. Greene; P. G. M. Wuts. Protective Groups in Organic Synthesis, $3^{rd}$ ed.; John Wiley: New York (1999)
- L. S. Hegedus. Transition Metals in the Synthesis of Complex Organic Molecules, $2^{nd}$ ed.; University Science Books: Mill Valley, Calif. (1994)
- L. A. Paquette, Ed. The Encyclopedia of Reagents for Organic Synthesis; John Wiley: New York (1994)
- A. R. Katritzky; 0. Meth-Cohn; C. W. Rees, Eds. Comprehensive Organic Functional Group Transformations; Pergamon Press: Oxford, UK (1995)
- G. Wilkinson; F. G A. Stone; E. W. Abel, Eds. Comprehensive Organometallic Chemistry; Pergamon Press: Oxford, UK (1982)
- B. M. Trost; I. Fleming. Comprehensive Organic Synthesis; Pergamon Press: Oxford, UK (1991)
- A. R. Katritzky; C. W. Rees Eds. Comprehensive Heterocylic Chemistry; Pergamon Press: Oxford, UK (1984)
- A. R. Katritzky; C. W. Rees; E. F. V. Scriven, Eds. Comprehensive Heterocyclic Chemistry II; Pergamon Press: Oxford, UK (1996)

C. Hansch; P. G. Sammes; J. B. Taylor, Eds. Comprehensive Medicinal Chemistry: Pergamon Press: Oxford, UK (1990).

In addition, recurring reviews of synthetic methodology and related topics include Organic Reactions; John Wiley: New York; Organic Syntheses; John Wiley: New York; Reagents for Organic Synthesis: John Wiley: New York; The Total Synthesis of Natural Products; John Wiley: New York; The Organic Chemistry of Drug Synthesis; John Wiley: New York; Annual Reports in Organic Synthesis; Academic Press: San Diego Calif.; and Methoden der Organischen Chemie (Houben-Weyl); Thieme: Stuttgart, Germany. Furthermore, databases of synthetic transformations include Chemical Abstracts, which may be searched using either CAS OnLine or SciFinder, Handbuch der Organischen Chemie (Beilstein), which may be searched using SpotFire, and REACCS.

Compositions of the Compounds of this Invention

This invention also relates to pharmaceutical compositions containing one or more compounds of the present invention. These compositions can be utilized to achieve the desired pharmacological effect by administration to a patient in need thereof. A patient, for the purpose of this invention, is a mammal, including a human, in need of treatment for the particular condition or disease. Therefore, the present invention includes pharmaceutical compositions which are comprised of a pharmaceutically acceptable carrier and a pharmaceutically effective amount of a compound, or salt thereof, of the present invention. A pharmaceutically acceptable carrier is preferably a carrier which is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule which can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents.

The compounds of this invention may also be administered parenterally, that is, subcutaneously, intravenously, intraocularly, intrasynovially, intramuscularly, or interperitoneally, as injectable dosages of the compound, preferably in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention preferably typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such material are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations which are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al, "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)-Part-1" PDA Journal of Pharmaceutical Science & Technology 1999, 53(6), 324-349; and Nema, S. et al, "Excipients and Their Use in Injectable Products" PDA Journal of Pharmaceutical Science & Technology 1997, 51(4), 166-171.

Commonly used pharmaceutical ingredients which can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC-CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavorants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono-or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate); tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

It is believed that one skilled in the art, utilizing the preceding information, can utilize the present invention to its fullest extent. Nevertheless, the following are examples of pharmaceutical formulations that can be used in the method of the present invention. They are for illustrative purposes only, and are not to be construed as limiting the invention in any way.

Pharmaceutical compositions according to the present invention can be illustrated as follows:

Sterile IV Solution: A 5 mg/ml solution of the desired compound of this invention is made using sterile, injectable water, and the pH is adjusted if necessary. The solution is diluted for administration to 1-2 mg/ml with sterile 5% dextrose and is administered as an IV infusion over 60 minutes.

Lyophilized powder for IV administration: A sterile preparation can be prepared with (I) 100-1000 mg of the desired compound of this invention as a lypholized powder, (ii) 32-327 mg/ml sodium citrate, and (iii) 300-3000 mg Dextran 40. The formulation is reconstituted with sterile, injectable saline or dextrose 5% to a concentration of 10 to 20 mg/ml, which is further diluted with saline or dextrose 5% to 0.2-0.4 mg/ml, and is administered either IV bolus or by IV infusion over 15-60 minutes.

Intramuscular suspension: The following solution or suspension can be prepared, for intramuscular injection:

50 mg/ml of the desired, water-insoluble compound of this invention
5 mg/ml sodium carboxymethylcellulose
4 mg/ml TWEEN 80
9 mg/ml sodium chloride
9 mg/ml benzyl alcohol Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 100 mg of active ingredient, 0.2 mg. Of colloidal silicon dioxide, 5 mg of magnesium stearate, 275 mg of microcrystalline cellulose, 11 mg. Of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Method of Treating Hyper-Proliferative Disorders

The present invention relates to a method for using the compounds described above (Compounds of Formula I), including salts and esters thereof and compositions thereof, to treat mammalian hyper-proliferative disorders. This method comprises administering to a mammal in need thereof, including a human, an amount of a compound of this invention, or a pharmaceutically acceptable salt or ester thereof, which is effective to treat the disorder. Hyper-proliferative disorders include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer.

Lymphomas include, but are not limited to AIDS-related lymphoma, non-Hodgkin's lymphoma, cutaneous T-cell lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

Based upon standard laboratory techniques known to evaluate compounds useful for the treatment of hyper-proliferative disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. It should be noted that the choice of dosing schedules is particularly important to maximize the efficacy and safety of drugs for the treatment of proliferative disorders such as cancer. Clinically useful dosing schedules will range from three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

The compounds of this invention can be administered as the sole pharmaceutical agent or in combination with one or more other pharmaceutical agents where the combination causes no unacceptable adverse effects. For example, the compounds of this invention can be combined with known anti-hyper-proliferative or other indication agents, and the like, as well as with admixtures and combinations thereof.

Optional anti-hyper-proliferative agents which can be added to the composition include but are not limited to compounds listed on the cancer chemotherapy drug regimens in the 11$^{th}$ Edition of the Merck Index, (1996), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other anti-hyper-proliferative agents suitable for use with the composition of the is invention include but are not limited to those compounds acknowledged to be used in the treatment of neoplastic diseases in Goodman and Gilman's The Pharmacological Basis of Therapeutics (Ninth Edition), editor Molinoff et al., publ. By McGraw-Hill, pages 1225-1287, (1996), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyladenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other anti-hyper-proliferative agents suitable for use with the composition of the invention include but are not limited to other anti-cancer agents such as epothilone and its derivatives, irinotecan, raloxifen and topotecan.

Generally, the use of cytotoxic and/or cytostatic agents in combination with a compound or composition of the present invention will serve to:

(1) yield better efficacy in reducing the growth of a tumor or even eliminate the tumor as compared to administration of either agent alone, (2) provide for the administration of lesser amounts of the administered chemotherapeutic agents, (3) provide for a chemotherapeutic treatment that is well tolerated in the patient with fewer deleterious pharmacological complications than observed with single agent chemotherapies and certain other combined therapies, (4) provide for treating a broader spectrum of different cancer types in mammals, especially humans, (5) provide for a higher response rate among treated patients, (6) provide for a longer survival time among treated patients compared to standard chemotherapy treatments, (7) provide a longer time for tumor progression, and/or (8) yield efficacy and tolerability results at least as good as those of the agents used alone, compared to known instances where other cancer agent combinations produce antagonistic effects.

| Abbreviations used in this specification | |
|---|---|
| DBU | 1,8-diazabicyclo[5.4.0]undec-7-ene |
| DMF | N,N-dimethyl formamide |
| DCM | dichloromethane |
| DCE | 1,2-dichloroethane |
| DMSO | dimethyl sulphoxide |
| HPLC | High pressure liquid chromatography |
| MPLC | Medium pressure liquid chromatography |
| LC-MS | liquid chromatography - coupled mass spectroscopy |
| RT | retention time |
| MP | melting point |
| NMR | nuclear resonance spectroscopy |
| TLC | thin layer chromatography |
| ES | electrospray |
| DMAC | N,N-dimethylacetamide |
| HRMS | high resolution mass spectroscopy |
| CDI | 1,1'-carbonyldiimidazole |
| HOBT | 1-hydroxybenzotriazole |
| DCC | 1,3-dicyclohexylcarbodiimide |
| EDCI | 1-[3-(dimethylamino) propyl]-3-ethylcarbodiimide hydrochloride |
| DMAP | 4-dimethylaminopyridine |
| TMSCI | Trimethylsilyl chloride |
| m-CPBA | 3-chloroperbenzoic acid |
| HEPES | N-(2-hydroxyethyl)-piperazine-N'-(2-ethanesulphonic acid) |
| Tris/hydrochloric acid | tris(hydroxymethyl)-aminomethane hydrochloride |
| ™ Triton X-100 ® | tert.-octyl-phenoxypolyethoxyethanol, Rohm & Haas, USA |

The yield percentages of the following examples refer to the starting component which was used in the lowest molar amount.

| LC-MS Methods | | | | |
| --- | --- | --- | --- | --- |
| LC-MS (Method 1): | | | | |
| MS equipment: | Micromass Quattro LCZ | | | |
| | ionization mode: ESI positive/negative | | | |
| HPLC equipment: | HP 1100 | | | |
| | UV detection: 208-400 nm | | | |
| | temperature: 40° C. | | | |
| Column: | ™ Symmetry C 18 | | | |
| | 50 mm × 2.1 mm 3.5 μm | | | |
| Supplier: | Waters | | | |
| Gradient: | Time | | | Flow |
| | [min.] | A: % | B: % | [mL/min.] |
| | 0.00 | 90.0 | 10.0 | 0.50 |
| | 4.00 | 10.0 | 90.0 | 0.50 |
| | 6.00 | 10.0 | 90.0 | 0.50 |

A: 0.05% strength solution of formic acid in water
B: 0.05% strength formic acid in acetonitrile

| LC-MS (Method 2): | | | | |
| --- | --- | --- | --- | --- |
| MS equipment: | Micromass LCZ | | | |
| | ionization mode: ESI | | | |
| HPLC equipment: | Gilson 215 | | | |
| | UV detection: 254 nm | | | |
| Column: | YMC pro C-18 | | | |
| | 23 mm × 2 mm 120 Å | | | |
| Supplier: | YMC | | | |
| Gradient: | Time | | | Flow |
| | [min.] | A: % | B: % | [mL/min.] |
| | 0.50 | 90.0 | 10.0 | 1.0 |
| | 3.50 | 5.0 | 95.0 | 1.0 |
| | 4.00 | 5.0 | 95.0 | 1.0 |
| | 4.01 | 90.0 | 10.0 | 1.0 |
| | 4.80 | 90.0 | 10.0 | 1.0 |

A: 0.02% strength solution of trifluoroacetic acid in 2% acetonitrile/98% water
B: 0.02% strength solution of trifluoroacetic acid in 98% acetonitrile/2% water

| HPLC (Method 3): | | | | |
| --- | --- | --- | --- | --- |
| HPLC Equipment: | Gilson 215 | | | |
| | UV Detection: 220 and 254 nM | | | |
| | Temperature: 25° C. | | | |
| Column: | YMC-Pack Pro C18 | | | |
| | 50 mm × 4.6 mm 5 μm | | | |
| Supplier: | Waters | | | |
| Gradient: | Time | | | Flow |
| | [min.] | A: % | B: % | [mL/min] |
| | 0.00 | 10.0 | 90.0 | 4.00 |
| | 3.50 | 90.0 | 10.0 | 4.00 |
| | 4.50 | 90.0 | 10.0 | 4.00 |
| | 4.60 | 10.0 | 90.0 | 4.00 |
| | 5.00 | 10.0 | 90.0 | 4.00 |

A: 0.1% strength solution of TFA in acetonitrile
B: 0.1% strength aqueous TFA

| HPLC (Method 4): | | | | |
| --- | --- | --- | --- | --- |
| HPLC Equipment: | Gilson 215 | | | |
| | UV Detection: 220 and 254 nM | | | |
| | Temperature: 25° C. | | | |
| Column: | YMC-Pack Pro C18 | | | |
| | 75 mm × 30 mm 5 μm | | | |
| Supplier: | Waters | | | |
| Gradient: | Time | | | Flow |
| | [min.] | A: % | B: % | [mL/min] |
| | 0.00 | 20.0 | 80.0 | 25.00 |
| | 20.00 | 80.0 | 20.0 | 25.00 |

A: acetonitrile
B: 0.1% strength aqueous TFA

Preparation of Starting Materials and Intermediates

General Method A: Preparations of Aminophenols

Aminophenols are either commercially available or may be prepared as described in one or more of the Examples below.

Method A-1

Preparation of 5-Nitroindazole-1-carboxylic acid tert-butyl ester

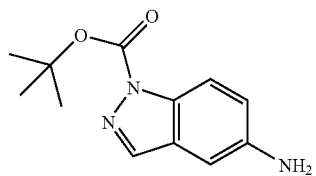

Step 1: Preparation of 5-Nitroindazole-1-carboxylic acid tert-butyl ester

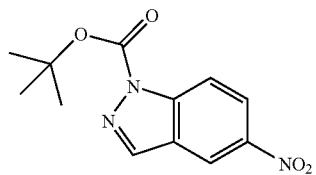

To a 0° C. slurry of 5-nitroindazole (5 g, 30.6 mmol), $Et_3N$ (4.7 mL, 33.7 mmol) and 4-dimethylaminopyridine (0.75 g, 6.1 mmol) in acetonitrile (60 mL) was added dropwise a solution of di-tert-butyl dicarbonate (8 g, 36.8 mmol) in acetonitrile (40 mL). The resulting mixture was stirred for 30 min, then concentrated under reduced pressure. The residue was dissolved in $Et_2O$ (200 mL) and $H_2O$ (100 mL). The pH of the aqueous layer was adjusted to 2 using a 1N HCl solution. The organic phase was separated, dried ($Na_2SO_4$) and concentrated under reduced pressure to give 5-nitroindazole-1-carboxylic acid tert-butyl ester (7.8 g, 96%) as a yellow solid: TLC (30% EtOAc/hex), $R_f$=0.70; ES-LCMS (rel abundance) m/z 264 ($MH^+$, 100%).

Step 2: Preparation of the title compounds
5-Aminoindazole-1-carboxylic acid tert-butyl ester Palladium on carbon (780 mg) was placed under an inert atmosphere and suspended in EtOH (15 mL). A solution of give 5-nitroindazole-1-carboxylic acid tert-butyl ester (7.78 g, 29.5) in EtOH (100 mL) and EtOAc (100 mL) was added. The reaction mixture was placed under $H_2$ atmosphere (1 Atm pressure) and stirred overnight. The resulting mixture was filtered through a pad of Celite®. The filtrate was concentrated under reduced pressure to get a greenish foamy solid. The crude product was dissolved in $CH_2Cl_2$ and purified by Biotage Flash 40M (gradient from 30% to 50% EtOAc/hex)

Method A-2a

Preparation of 1,1-Dioxo-2,3-dihydro-1H-benzo[b]thiophen-5-ylamine

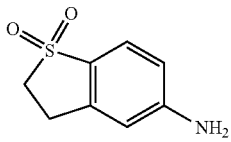

Palladium on carbon (25 mg) was placed under an inert atmosphere and suspended in 1:1 v/v EtOH/THF (10 mL). A solution of 5-nitrobenzo[b]thiophene 1,1-dioxide (250 mg, 1.18 mmol) in EtOH/THF (1:1) was then added, and the reaction mixture placed under $H_2$ atmosphere (1 Atm pressure) and stirred at RT for 3 h. Reaction is filtered through a Celite pad and washed well with MeOH to obtain the title compound (200 mg, 92%) as a brown solid: TLC (10% MeOH/DCM w/5% $NH_4OH$), $R_f$=0.40; LC MS m/z 184.1 ($MH^+$).

Method A-2b

Preparation of 2-Methyl-6-aminobenzoxazole

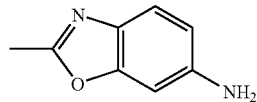

This compound was prepared from 2-methyl-6-nitrobenzoxazole (2.0 g, 13.5 mmol) in the same manner described for 5-aminobenxo[b[thiophene 1,1-dioxide, affording 1.57 (94%) of the title compound as a brown solid. MS LC-MS $(M+H)^+$=149.1, RT=0.77 min.

Method A-3a

Preparation of 1-(2-Diethylamino-ethyl)-1H-indol-5-ylamine

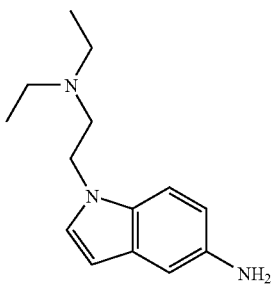

Step 1: Preparation of Diethyl-[2-(5-nitroindol-1-yl)ethyl]amine

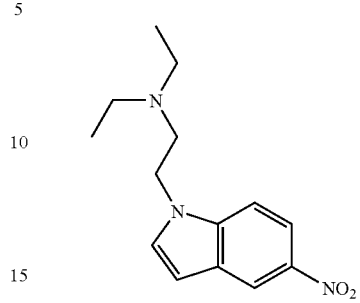

A slurry of 5-nitroindole (2.0 g, 12.3 mmol) and NaOH pellets (0.49 g, 1 eq) in $H_2O$ (2.0 mL) was stirred at RT. After 10 min, p-xylene (15.0 mL, 1.4 M), $K_2CO_3$ (2.55 g, 1.5 equ) and N-diethylaminoethyl chloride hydrochloride (2.12 g, 12.3 mmol, 1 eq) was added, and the reaction mixture was heated to 100° C. After 4 h the reaction mixture was cooled to ambient temperature and concentrated under reduced pressure. The crude residue was dissolved in p-xylene and washed with 1N NaOH (2×) and $H_2O$ (1×). The organic layer was dried over $MgSO_4$, filtered, and evaporated under reduced pressure to afford the nitro compound (1.79 g, 56%). TLC (5% MeOH/EtOAc), $R_f$=0.25; LC MS m/z 262.2 ($MH^+$).

Step 2: Preparation of the title compound 1-(2-Diethylamino-ethyl)-1H-indol-5-ylamine Diethyl-[2-(5-nitroindol-1-yl)ethyl]amine (1.6 g, 6.1 mmol) was dissolved in absolute EtOH (100 mL) and syringed into a flask containing 10% Pd over carbon (160 mg) under an argon atmosphere. The reaction mixture was placed under $H_2$ atmosphere (1 Atm pressure) and stirred at RT for 3 h. The reaction was filtered over a Celite pad and washed well with EtOH. Evaporation of the volatile solvent gave the title compound (1.4 g, 99%) as a brown solid. TLC (10% MeOH/DCM), $R_f$=0.20; LC MS m/z 232.3 ($MH^+$).

Method A-3b

Preparation of 1-(2-Diethylamino-ethyl)-1H-indazol-5-ylamine

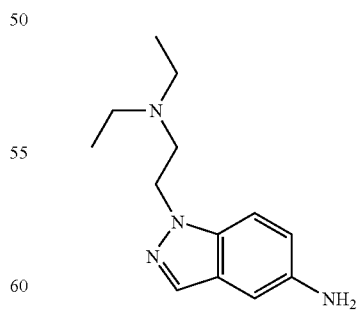

This compound was prepared from 5-nitroindazole (2.0 g, 12.3 mmol) in the manner described for 1-(2-diethylaminoethyl)-1H-indazol-5-ylamine, affording 2.0 g (70%) of the title compound. TLC (10% MeOH/DCM), $R_f$=0.20; LC MS m/z 233.2 ($MH^+$).

to give the title compound (6.55 g, 95%) as a white solid: TLC (50% EtOAc/hex), $R_f$=0.41; ES-LCMS (rel abundance) m/z 234 ($MH^+$, 66%).

General Method B: Preparations of Bicyclic Amines of Formula (III)

Compounds of formula (III) are either commercially available or may be prepared as described in one or more of the Examples below.

Method B-1a

Preparation of 4-Amino-3-fluorophenol

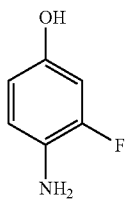

To a dry flask purged with argon was added 10% Pd/C (80 mg) followed by a solution of 3-fluoro-4-nitrophenol (1.2 g, 7.64 mmol) in EtOAc (40 mL). The mixture was stirred under an $H_2$ atmosphere for 4 h and filtered through a pad of Celite®. The filtrate was evaporated under reduced pressure to afford the desired product as a tan solid (940 mg, 7.39 mmol; 97% yield). $^1$H-NMR (DMSO-$d_6$) δ 8.76 (s, 1H), 6.62 to 6.52 (m, 1H), 6.41 (dd, J=2.5, 12.7 Hz, 1H), 6.35 to 6.29 (m, 1H), 4.38 (s, 2H).

Method B-1b

Preparation of 4-Amino-2-fluorophenol

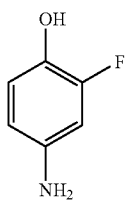

This compound was prepared from 2-fluoro-4-nitrophenol (2.0 g, 12.7 mmol) in is the manner described for 4-amino-3-fluorophenol, affording 1.58 g (98%) of 4-amino-2-fluorophenol as a tan solid. $^1$H-NMR (DMSO-$d_6$) □ 8.53 (s, 1H), 6.59 (dd, J=10.2, 8.5 Hz, 1H), 6.31 (dd, J=13.1, 2.8, Hz, 1H), 6.20 to 6.14 (m, 1H), 4.66 (s, 2H).

Method B-1c

Preparation of 4-Amino-3-trifluoromethylphenol

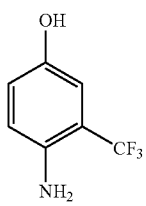

This compound was prepared from 4-nitro-3-trifluorophenol (5.0 g, 24.1 mmol) in the manner described for 4-amino-3-fluorophenol, affording 3.84 g (89.8%) of 4-amino-3-trifluoromethylphenol as a tan solid. $^1$H-NMR (DMSO-$d_6$) δ 8.89 (s, 1H), 6.78 to 6.67 (m, 3H), 4.85 (s, 2H); TLC (25% EtOAc/Hex), $R_f$=0.31.

Method B-1d

Preparation of 4-Amino-2-methoxyphenol

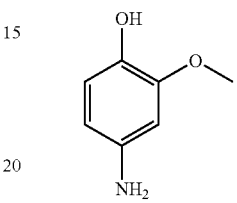

This compound was prepared from 4-nitro-2-methoxyphenol (10.0 g, 59.1 mmol) in the manner described for 4-amino-3-fluorophenol, affording 5.20 g (56.9%) of 4-amino-2-methoxyphenol as a dark brown solid. $^1$H-NMR (DMSO-$d_6$) δ 7.79 (br s, 1H), 6.44 (d, J=8.1 Hz, 1H), 6.21 (d, J=2.4 Hz, 1H), 5.97 (dd, J=8.4, 2.4 Hz, 1H), 4.43 (br s, 2H), 3.65 (s, 3H); TLC (66% EtOAc/Hex), $R_f$=0.42.

Method B-1e

Preparation of 5-Amino-8-hydroxyquinoline

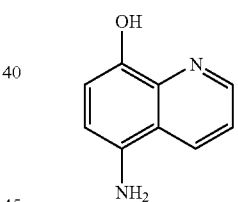

This compound was prepared from 8-hydroxy-5-nitroquinoline (5.0 g, 26.3 mmol) in the manner described for 4-amino-3-fluorophenol, affording 2.4 g (51.3%) of 5-amino-8-hydroxyquinoline. TLC (5% MeOH/DCM), $R_f$=0.52.

Method B-2a

Preparation of 3-Amino-2,4-difluorophenol

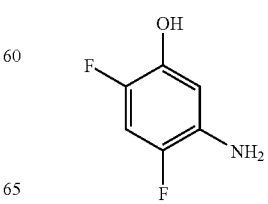

Step 1: Preparation of ethyl-2,4-difluorophenoxycarboxylate

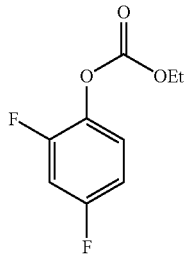

A solution of 2,4-difluorophenol (2.00 g, 15.4 mmol) in DCM (75 mL) at 0° C. was treated with triethylamine (2.6 mL, 18.5 mmol), followed by the dropwise addition of ethyl chloroformate (1.8 mL, 18.5 mmol). The reaction was stirred at 0 to 25° C. for 90 min, and the mixture was quenched with H$_2$O (75 mL). The organic layer was washed with brine (2×50 mL), dried over Na$_2$SO$_4$, and concentrated under reduced pressure to afford the desired product as a colorless oil in quantitative yield. $^1$H-NMR (DMSO-d$_6$) δ 7.22 to 7.14 (m, 1H), 6.97 to 6.83 (m, 2H), 4.34 (q, J=7.1 Hz, 2H), 1.41 (t, J=7.1 Hz, 3H).

Step 2: Preparation of 2,4-Difluoro-5-nitrophenol

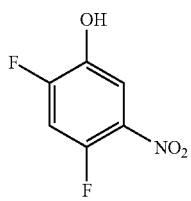

To a solution of ethyl 2,4-difluorophenoxycarboxylate (3.27 g, 16.2 mmol) in concentrated H$_2$SO$_4$ (11 mL) at 0° C. was added fuming HNO$_3$ (1.1 mL) dropwise, maintaining the internal temperature between 10 to 20° C. After stirring for 1 h, the mixture was poured over ice water (100 mL) and extracted with EtOAc (3×50 mL). The combined organic layers were washed with brine (2×40 mL), dried over MgSO$_4$, and concentrated in vacuo. The residue was dissolved in MeOH (50 mL), and sodium bicarbonate (2.72 g, 32.3 mmol) was added. The resultant mixture was stirred at room temperature for 64 h and the solid was filtered. The filtrate was concentrated and the residue was taken up in H$_2$O (100 mL). The pH was adjusted to 5 with the addition of conc. HCl, and the mixture was extracted with EtOAc (3×50 mL). The combined organic layers were washed with brine (2×40 mL), dried over MgSO$_4$, and evaporated under reduced pressure to give 2,4-difluoro-5-nitrophenol as a yellow solid (2.35 g, 13.4 mmol; 83% yield). $^1$H-NMR (DMSO-d$_6$) δ 10.88 (s, 1H), 7.70 to 7.61 (m, 2H),

Step 3: Preparation of the title compound 2,4-difluoro-5-aminophenol

This compound was prepared from 2,4-difluoro-3-nitrophenol (2.35 g, 13.4 mmol) in the manner described for 4-amino-3-fluorophenol, affording 1.89 g (97%) of 2,4-difluoro-5-aminophenol as a tan solid. $^1$H-NMR (DMSO-d$_6$) δ 9.26 (s, 1H), 6.89 (t, J=10.7 Hz, 1H), 6.33 (t, J=9.2 Hz, 1H), 4.82 (s, 2H).

Method B-2b

Preparation of 5-Amino-4-fluorophenol

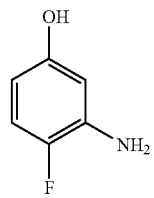

Step 1: Preparation of Ethyl-2-bromo-4-fluorophenoxycarboxylate

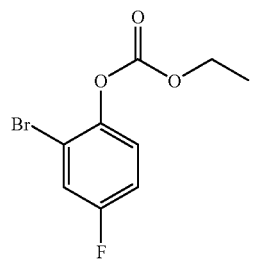

This compound was prepared from 2-bromo-4-fluorophenol (3.0 g, 15.7 mmol) in the manner described for ethyl 2,4-difluorophenoxycarboxylate, affording 4.0 g (96.8%) of ethyl-2-bromo-4-fluorophenoxycarboxlate as a light yellow oil. $^1$H-NMR (DMSO-d$_6$) δ 7.70 (dd, J=6.0, 2.1 Hz, 1H), 7.46 (dd, J=6.6, 3.9 Hz, 1H), 7.31 (dt, J=6.6, 2.1 Hz, 1H), 4.26 (q, J=5.4 Hz, 2H), 1.29 (t, J=5.4 Hz, 3H).

Step 2: Preparation of 2-Bromo-4-fluoro-5-nitrophenol

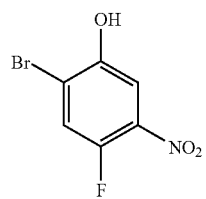

This compound was prepared from ethyl-2-bromo-4-fluorophenoxycarboxlate (4.0 g, 15.2 mmol) in the manner described for 2,4-difluoro-5-nitrophenol, affording 3.14 g (87.5%) of 2-bromo-4-fluoro-3-nitrophenol as a yellow solid. $^1$H-NMR (DMSO-d$_6$) δ 11.19 (s, 1H), 7.89 (d, J=8.4 Hz, 1H), 7.57 (d, J=5.1 Hz, 1H).

Step 3: Preparation of the title compound 3-Amino-4-fluorophenol

This compound was prepared from 2-bromo-4-fluoro-5-nitrophenol (3.1 g, 13.1 mmol) in the manner described for 4-amino-3-fluorophenol, affording quantitative yield of crude 3-amino-4-fluorophenol which was used without further purification. $^1$H-NMR (DMSO-$d_6$) δ 8.60 (br s, 2H), 7.12 (dd, J=7.8, 6.6 Hz, 1H), 6.82 (dd, J=5.1, 1.5 Hz, 1H), 6.55 to 6.61 (m, 1H).

Method B-2c

Preparation of 3-Amino-6-fluorophenol

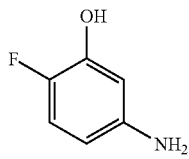

This compound was prepared from 4-bromo-2-fluorophenol (3.0 g, 15.71 mmol) in the manner described for 3-amino-4-fluorophenol, affording 1.79 g (86%) of 3-amino-6-fluorophenol. $^1$H-NMR (DMSO-$d_6$) δ 10.42 (s, 1H), 9.69 (br s, 2H), 7.22 (dd, J=8.4, 6.6 Hz, 1H), 6.93 (dd, J=5.7, 2.1 Hz, 1H), 6.74 to 6.99 (m, 1H).

Method B-3

Preparation of 4-Amino-2-chloro-6-fluorophenol

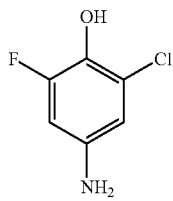

Step 1: Preparation of
2-Chloro-6-fluoro-4-nitrophenol

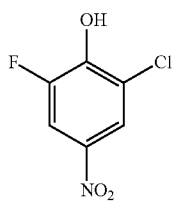

A solution of 2-chloro-6-fluorophenol (1.0 g, 6.82 mmol) in concentrated acetic acid (3.0 mL) was cooled to 0° C. Fuming nitric acid (559 mg, 8.87 mmol) was added dropwise, maintaining the reaction temperature between 10 to 20° C. The reaction was allowed to stir at 0° C. for 3 h. The mixture was poured over ice and was allowed to warm to room temperature. The aqueous was extracted with EtOAc (3×50 mL). The combined organic layers were washed with brine (1×50 mL), dried over Na$_2$SO$_4$, and evaporated under reduced pressure. The crude red solid was purified using the Biotage Quad 4 (25 M column) eluting with 9:1 Hexanes/EtOAc to afford the title compound as a yellow solid (326 mg, 1.70 mmol; 25% yield). $^1$H-NMR (DMSO-$d_6$) δ 11.74 to 12.77 (broad s, 1H), 8.10 to 8.16 (m, 2H).

Step 2: Preparation of the title compound
4-Amino-2-chloro-6-fluorophenol

This compound was prepared from 2-chloro-6-fluoro-4-nitrophenol (1.3 g, 6.79 mmol) in the manner described for 4-amino-3-fluorophenol, affording 0.34 g (40%) of 4-amino-2-chloro-6-fluorophenol. $^1$H-NMR (DMSO-$d_6$) δ 4.99 (s, 2H), 6.29-6.36 (m, 2H), 8.85 (s, 1H).

Method B-4a

Preparation of 4-Amino-3,5-difluorophenol

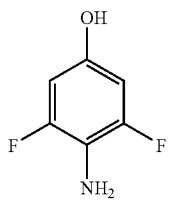

Step 1: Preparation of
5-Benzyloxy-1,3-difluoro-2-nitrobenzene

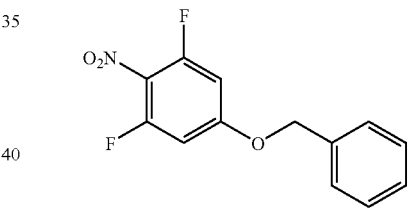

A mixture of 1,3,5-trifluoro-2-nitrobenzene (6.1 g, 34 mmol), benzyl alcohol (3.7 g, 34 mmol) and potassium carbonate (7.1 g, 52 mmol) in DMF (10 ml) was stirred at room temperature overnight. Water (30 ml) was added to the reaction mixture, and the reaction was refrigerated overnight. The resultant yellow precipitate was filtered, washed with water, and dried under reduced pressure to provide 6.5 g (71%) of a 1:1 mixture of 5-benzyloxy-1,3-difluoro-2-nitrobenzene and 1-benzyloxy-3,5-difluoro-2-nitrobenzene. The mixture was used directly for the next step without further purification. $^1$H-NMR (CD$_2$Cl$_2$) δ 7.46 to 7.36 (m, 5H), 6.75 to 6.60 (m, 2H), 5.19 (s, 1H), 5.11 (s, 1H); TLC (10% EtOAc/Hex), R$_f$=0.48.

Step 2: Preparation of the title compound
4-Amino-3,5-difluorophenol

A solution of 1:1 mixture of 5-benzyloxy-1,3-difluoro-2-nitrobenzene and 1-benzyloxy-3,5-difluoro-2-nitrobenzene (6.4 g, 24 mmol) from step 1 in methanol (250 ml) was added to a flask containing palladium on carbon (10 wt. %, 720 mg) under nitrogen atmosphere. The mixture was stirred at room temperature under a hydrogen atmosphere overnight. The reaction mixture was filtered through a pad of celite, and the filtrate was concentrated under reduced pressure to provide 3.4 g (97%) of an 1:1 mixture of 4-amino3,5-difluorophenol and 2-amino-3,5-difluorophenol. The mixture was used directly for the next step without further purification. $^1$H-NMR (DMSO-$d_6$) δ 9.50 (br s, 1H), 6.54 to 6.22 (m, 2H), 4.36 (s, 2H); MS GC-MS (M$^+$=146.1), RT=0.87 min.

Method B-4b

Preparation of 4-Amino-2,5-difluorophenol

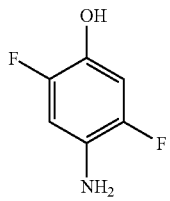

This compound was prepared from 1,2,4-trifluoro-5-nitrobenzene (5.0 g, 28 mmol) in the manner described for 4-amino-3,5-difluorophenol, affording 3.0 g (72.3%) of 4-amino-2,5-difluorophenol. $^1$H-NMR (DMSO-$d_6$) δ 9.04 (s, 1H), 6.67 to 6.46 (m, 2H), 4.64 (s, 2H); MS GC-MS M$^+$=146.1, RT=1.04 min.

Method B-4c

Preparation of 4-Amino-2,3-difluorophenol

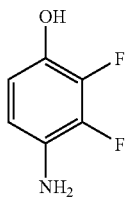

This compound was prepared from 1,2,3-trifluoro-4-nitrobenzene (5.0 g, 28 mmol) in the manner described for 4-amino-3,5-difluorophenol, affording 0.60 g (84%) of 4-amino-2,3-difluorophenol. $^1$H-NMR (DMSO-$d_6$) δ 9.19 (s, 1H), 6.59 to 6.53 (m, 1H), 6.48 to 6.41 (m, 1H), 4.85 (s, 2H); TLC (12% DCM/Hex), $R_f$=0.08.

Method B-5

Preparation of 2-Amino-5-hydroxybenzamide

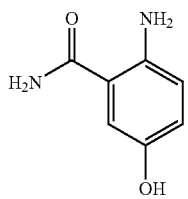

Step 1: Preparation of 5-Benzyloxy-2-nitrobenzonitrile

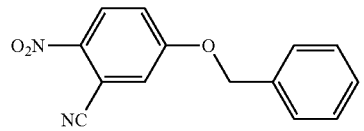

A mixture of 5-fluoro-2-nitrobenzonitrile (15 g, 90 mmol), benzyl alcohol (10.8 g, 100 mmol) and potassium carbonate (18.7 g, 135 mmol) in DMF (20 ml) was stirred at room temperature for 60 h. Water (60 ml) was added to the reaction, and the resultant yellow precipitate out filtered, washed with water, and dried under reduced pressure to provide 17.3 g (75.4%) of 5-benzyloxy-2-nitrobenzonitrile. The compound was used directly for the next step without further purification. MS GC-MS M$^+$=211, RT=6.15 min.

Step 2: Preparation of 5-Benzyloxy-2-nitrobenzamide

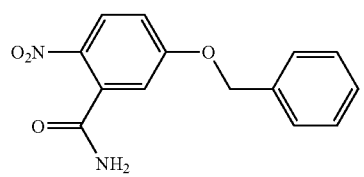

A solution of 5-benzyloxy-2-nitrobenxonitrile (4.5 g, 18 mmol) in acetone (180 ml) and water (90 ml) was treated with sodium percarbonate (contains 25% H2O2, 28 g, 180 mmol), and the mixture was stirred at room temperature for 48 h. The reaction mixture was poured into ethyl acetate (200 ml) and water (100 ml). The biphasic layers were separated, and the organic layer was washed with water (50 ml) and brine (50 ml), dried over Na$_2$SO$_4$, filtered, and concentrated under reduced pressure. The residue was crystallized from ethyl acetate providing 2.7 g (56%) of 5-benzyloxy-2-nitrobenzamide as a white solid. MS GC-MS M$^+$=211, RT=6.15 min.

Step 3: Preparation of the Title Compound 2-Amino-5-hydroxybenzamide

This compound was prepared from 5-benzyloxy-2-nitrobenzamide (2.7 g, 56 mmol) in the manner described for 4-amino-3-fluorophenol, affording 1.5 g (99%) of 2-amino-5-hydroxybenzamide. $^1$H-NMR (CDCl$_3$) δ 7.41 (d, J=8.1 Hz, 1H), 7.16 (dd, J=8.1, 1.6 Hz, 1H), 7.13 (d, J=1, 6 Hz, 1H), 3.93 (s, 3H); MS GC-MS (M$^+$=211, RT=6.15 min).

Method B-6

Preparation of 5-Amino-2,4-dichlorophenol

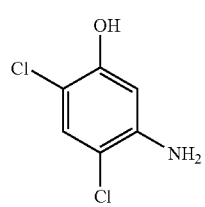

Iron powder (4.03 g, 72.1 mmol) was added slowly to the solution of 2,4-dichloro-5-nitrophenol (3.00 g, 14.4 mmol) in acetic acid (100 ml). After stirring at room temperature overnight, the reaction mixture became milky with formation of a white precipitate. The precipitate was filtered off and the filtrate was concentrated to ca. 20 mL. The residue was diluted with water (100 mL) and neutralized by slow addition of sodium bicarbonate. The mixture was then extracted with methylene chloride (3×150 mL). The organic layer were combined, dried over sodium sulfate, filtered and concentrated to dryness to afford 5-amino-2,4-dichlorophenol (2.20 g, 86%) as a brown solid. $^1$H-NMR (DMSO-$d_6$) δ9.91 (s, 1H), 7.10 (s, 1H), 6.42 (s, 1H), 5.34 (s, 2H); MS LC-MS (M+H)$^+$=178.2, RT=2.10 min.

Method B-7

Preparation of 4-Amino-3-(methylsulfanyl)phenol

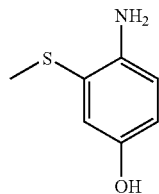

Step 1: Preparation of
3-(Methylsulfanyl)-4-nitrophenol

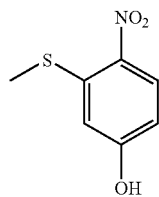

To a solution of 3-fluoro-4-nitrophenol (3.0 g, 19.1 mmol) in anhydrous DMF (100 mL) was added dropwise sodium thiomethoxide (2.57 mL, 38.2 mmol, 2.0 eq) followed by potassium carbonate (7.92 g, 57.3 mmol, 3.0 eq), and the reaction mixture was stirred at RT for 18 h. Water was then added to quench the solution, and the reaction mixture was extracted with EtOAc (3×250 mL). The combined organic layers were washed with water and brine, dried over sodium sulfate, and evaporated under reduced pressure. Purification of the crude using MPLC (biotage) eluted with 20% EtOAc—hexanes afforded 3.25 g (91.9%) of 3-(methylsulfanyl)$_4$-nitrophenol as a yellow solid.

$^1$H-NMR (DMSO-$d_6$) δ11.13 (s, 1H), 8.18 (d, J=9.0 Hz, 1H), 6.79 (d, J=2.7 Hz, 1H), 6.71 (dd, J=9.0, 2.4 Hz, 1H), 2.43 (s, 3H).

Step 2: Preparation of the Title Compound
4-Amino-3-(methylsulfanyl)phenol

This compound was prepared from 3-(Methylsulfanyl)$_4$-nitrophenol (3.2 g, 17.3 mmol) in the manner described for 4-amino-3-fluorophenol, affording 2.18 g (81.3%) of the title compound. $^1$H-NMR (DMSO-$d_6$) δ 8.56 (s, 1H), 6.60 (d, J=2.7 Hz, 1H), 6.53 (d, J=8.7 Hz, 1H), 6.43 (dd, J=8.7, 2.4 Hz, 1H), 2.28 (s, 3H).

General Methods C and D: Preparations of Arylamines of Formula (II)

Compounds of Formula (II) may be prepared as described in one or more of the Examples below:

Method C-1a

Preparation of
4-(4-Aminophenoxy)pyridine-2-carboxylic acid
methylamide

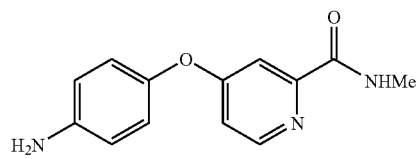

Step 1: Preparation of 4-Chloropyridine-2-carbonyl
chloride hydrochloride

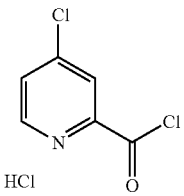

Anhydrous DMF (6.0 mL) was slowly added to SOCl$_2$ (180 mL) between 40° C. and 50° C. The solution was stirred in that temperature range for 10 min., then picolinic acid (60.0 g, 487 mmol) was added in portions over 30 min. The resulting solution was heated at 72° C. for 16 h to generate a yellow solid precipitate. The resulting mixture was cooled to RT, diluted with toluene (500 mL) and concentrated to half its volume. The resulting residue was filtered and the solids were washed with toluene and dried under high vacuum for 4 h to afford 4-chloropyridine-2-carbonyl chloride HCl salt as a yellow solid (92.0 g, 89%).

Step 2: Preparation of 4-Chloropyridine-2-carboxylic
acid methylamide

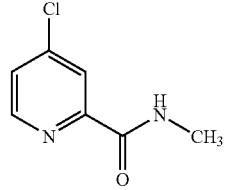

A suspension of methyl 4-chloropyridine-2-carboxylate HCl salt (89.0 g, 428 mmol) in MeOH (75 mL) at 0° C. was treated with a 2.0 M methylamine solution in THF (1 L). The resulting mixture was stored at 3° C. for 5 h, then concentrated under reduced pressure. The resulting solids were suspended in EtOAc (1L) and filtered. The filtrate was washed with a saturated NaCl solution (500 mL), dried over Na$_2$SO$_4$, and concentrated under reduced pressure to afford 4-chloro-N-methyl-2-pyridinecarboxamide as pale-yellow crystals (71.2 g, 97%). $^1$H-NMR (DMSO-d$_6$) δ 2.81 (s, 3H), 7.74 (dd, J=5.1, 2.2 Hz, 1H), 8.00 (d, J=2.2 Hz, 1H), 8.61 (d, J=5.1 Hz, 1H), 8.85 (br d, 1H); CI-MS m/z 171 (MH$^+$); m.p. 41-43° C.

Step 3: Preparation of Title Compound
4-(4-Aminophenoxy)pyridine-2-carboxylic acid methylamide A solution of 4-aminophenol (9.60 g, 88.0 mmol) in anhydrous DMF (150 mL) was treated with potassium tert-butoxide (10.29 g, 91.7 mmol), and the reddish-brown mixture was stirred at RT for 2 h. The contents were treated with 4-chloropyridine-2-carboxylic acid methylamide (15.0 g, 87.9 mmol) and K$_2$CO$_3$ (6.50 g, 47.0 mmol) and then heated at 80° C. for 8 h. The mixture was cooled to RT and partitioned between EtOAc (500 mL) and a saturated NaCl solution (500 mL). The aqueous phase was back-extracted with EtOAc (300 mL). The combined organic layers were washed with brine, dried over Na$_2$SO$_4$, and concentrated under reduced pressure. The resulting solids were dried under reduced pressure at 35° C. for 3 h to afford the title compound (17.9 g, 84%) as a light-brown solid. $^1$H-NMR (DMSO-d$_6$) δ 2.77 (d, J=4.8 Hz, 3H), 5.17 (br s, 2H), 6.64, 6.86 (AA'BB' quartet, J=8.4 Hz, 4H), 7.06 (dd, J=5.5, 2.5 Hz, 1H), 7.33 (d, J=2.5 Hz, 1H), 8.44 (d, J=5.5 Hz, 1H), 8.73 (br d, 1H); HPLC ES-MS m/z 244 (MH$^+$).

Method C-1b

Preparation of
4-(3-Aminophenoxy)pyridine-2-carboxylic acid methylamide

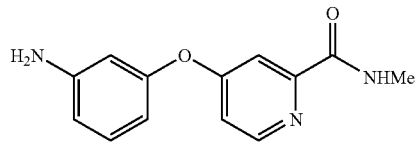

The title compound was prepared in the same manner described for 4-(4-aminophenoxy)pyridine-2-carboxylic acid methylamide, substituting 3-aminophenol for 4-aminophenol. $^1$H-NMR (DMSO-d$_6$) δ 8.75 (br q, J=4.8 Hz, 1H), 8.48 (d, J=6.3 Hz, 1H), 7.39 (d, J=2.1 Hz, 1H), 7.15 to 7.07 (m, 2H), 5.51 to 6.47 (m, 1H), 6.31 to 6.24 (m, 2H), 5.40 (s, 2H), 2.77 (d, J=5.1 Hz, 3H).

Method C-1c

Preparation of
4-(4-Amino-3-fluorophenoxy)pyridine-2-carboxylic acid methylamide

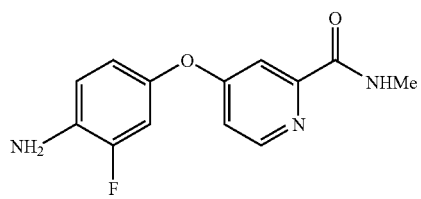

The title compound was prepared in the same manner described for 4-(4-aminophenoxy)pyridine-2-carboxylic acid methylamide, substituting 4-amino-3-fluorophenol for 4-aminophenol. $^1$H-NMR (DMSO-d$_6$) δ 8.74 (br q, J=7.0 Hz, 1H), 8.43 (d, J=4.5 Hz, 1H), 7.32, (d, J=2.1 Hz, 1H), 7.07 (dd, J=4.2, 2.1 Hz, 1H), 6.99 (dd, J=8.7, 1.8 Hz, 1H), 6.82 (t, J=6.6 Hz, 1H), 6.76 (dd, J=6.6, 2.1 Hz, 1H), 5.23 (s, 2H), 2.77 (d, J=3.6 Hz, 3H).

Method C-1d

Preparation of 4-[4-Amino-3-(trifluoromethyl)phenoxy]pyridine-2-carboxylic acid methylamide

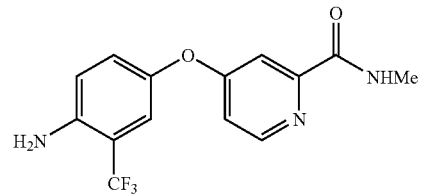

The title compound was prepared in the same manner described for 4-(4-aminophenoxy)pyridine-2-carboxylic acid methylamide, substituting 4-amino-3-trifluoromethylphenol for 4-aminophenol. $^1$H-NMR (DMSO-d$_6$) δ 8.75 (br q, J=6.9 Hz, 1H), 8.44 (d, J=4.2 Hz, 1H), 7.31 (d, J=2.1 Hz, 1H), 7.19 to 7.16 (m, 2H), 7.06 (dd, J=4.2, 1.8 Hz, 1H), 6.92 (d, J=7.2 Hz, 1H), 5.73 (s, 2H), 2.77 (d, J=3.6 Hz, 3H).

Method C-1e

Preparation of
4-(4-Amino-3-methylphenoxy)pyridine-2-carboxylic acid methylamide

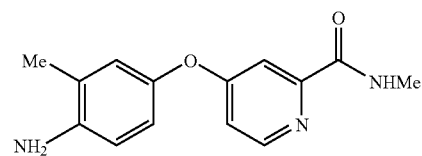

The title compound was prepared in the same manner described for 4-(4-aminophenoxy)pyridine-2-carboxylic acid methylamide, substituting 4-amino-3-methylphenol for 4-aminophenol. $^1$H-NMR (acetone-d$_6$) δ 8.39 (d, J=5.7 Hz, 1H), 8.29 (br s, 1H), 7.51 (dd, J=2.7, 0.6 Hz, 1H), 6.98 (dd, J=5.7, 2.4 Hz, 1H), 6.82 (br s, 1H), 6.77 to 6.76 (m, 2H), 4.56 (br s, 2H), 2.92 (d, J=5.1 Hz, 3H), 2.16 (d, J=1.0 Hz, 3H).

Method C-1f

Preparation of 4-(4-Amino-2-methylphenoxy) Pyridine-2-carboxylic acid methylamide

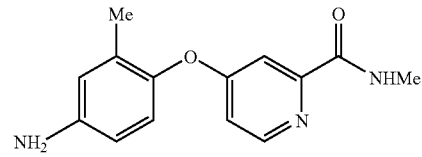

The title compound was prepared in the same manner described for 4-(4-aminophenoxy)pyridine-2-carboxylic acid methylamide, substituting 4-amino-2-methylphenol for 4-aminophenol. ¹H-NMR (DMSO-d₆) δ 8.73 (br q, J=4.8 Hz, 1H), 8.43 (d, J=5.4 Hz, 1H), 7.26 (d, J=2.4 Hz, 1H), 7.02 (dd, J=5.7, 2.7 Hz, 1H), 7.76 (d, J=8.1 Hz, 1H), 6.52 (d, J=3 Hz, 1H), 6.47 (dd, J=8.7, 2.7 Hz, 1H), 5.09 (s, 2H), 2.78 (d, J=3.3 Hz, 3H), 1.91 (s, 3H).

Method C-1g

Preparation of
4-(4-Amino-3-nitrophenoxy)pyridine-2-carboxylic acid methylamide

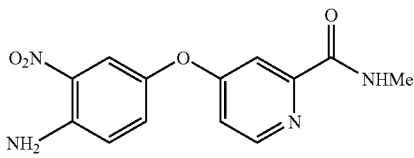

The title compound was prepared in the same manner described for 4-(4-aminophenoxy)pyridine-2-carboxylic acid methylamide, substituting 4-amino-3-nitrophenol for 4-aminophenol. ¹H-NMR (acetone-d₆) δ 8.46 (d, J=5.7 Hz, 1H), 8.31 (br s, 1H), 7.96 (br s, 2H), 7.88 (d, J=2.7 Hz, 1H), 7.56 (dd, J=2.7, 1.0 Hz, 1H), 7.35 (d, J=2.7 Hz, 1H), 717 (br s, 1H), 7.10 (dd, J=5.4, 2.7 Hz, 1H), 2.78 (d, J=3.6 Hz, 3H).

Method C-1h

Preparation of
4-(4-Amino-2-fluorophenoxy)pyridine-2-carboxylic acid methylamide

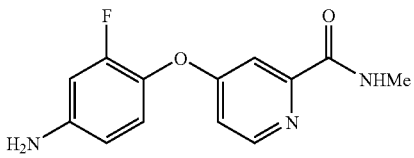

The title compound was prepared in the same manner described for 4-(4-aminophenoxy)pyridine-2-carboxylic acid methylamide, substituting 4-amino-2-fluorophenol for 4-aminophenol. ¹H-NMR (DMSO-d₆) δ 8.75 (br q, J=3.6 Hz, 1H), 8.46 (d, J=4.8 Hz, 1H), 7.31 (d, J=1.8 Hz, 1H), 7.11 (dd, J=4.2, 2.1 Hz, 1H), 6.99 (t, J=6.6 Hz, 1H), 6.50 (dd, J=9.9, 2.1 Hz, 1H), 6.43 to 6.40 (m, 1H), 5.51 (s, 2H), 2.77 (d, J=3.6 Hz, 3H).

Method C-1i

Preparation of
4-(3-Amino-4-chlorophenoxy)pyridine-2-carboxylic acid methylamide

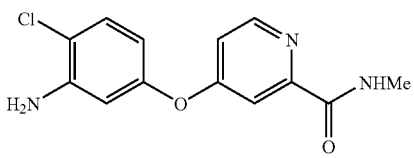

The title compound was prepared in the same manner described for 4-(4-aminophenoxy)pyridine-2-carboxylic acid methylamide, substituting 3-amino-4-chlorophenol for 4-aminophenol. ¹H-NMR (DMSO-d₆): δ 8.76 (m, 1H), 8.47 (d, 1H), 7.39 (s, 1H), 7.24 (d, 1H), 7.15 (dd, 1H), 6.67 (s, 1H), 6.35 (dd, 1H), 5.65 (s, 2H), 2.78 (d, 3H); LC MS m/z 278.1 (MH)⁺, RT=2.36 min.

Method C-1j

Preparation of
4-(3-Amino-2-fluorophenoxy)pyridine-2-carboxylic acid methylamide

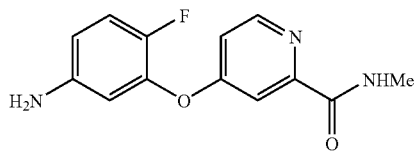

The title compound was prepared in the same manner described for 4-(4-aminophenoxy)pyridine-2-carboxylic acid methylamide, substituting 5-amino-2-fluorophenol for 4-aminophenol. ¹H-NMR (DMSO-d₆): δ 8.77 (br d, J=3.3 Hz, 1H), 8.49 (d, J=4.5 Hz, 1H), 7.35 (d, J=1.8 Hz, 1H), 7.17 (dd, J=4.2, 1.8 Hz, 1H), 7.08 (dd, J=8.1, 6.6 Hz, 1H), 6.49 to 6.42 (m, 2H), 5.27 (s, 2H), 2.77 (d, J=3.0 Hz, 3H).

Method C-1k

Preparation of
4-(3-Amino-4-fluorophenoxy)pyridine-2-carboxylic acid methylamide

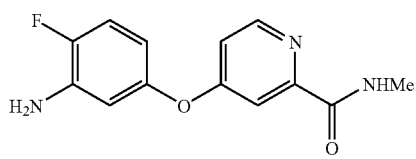

The title compound was prepared in the same manner described for 4-(4-aminophenoxy)pyridine-2-carboxylic acid methylamide, substituting 3-amino-4-fluorophenol for 4-aminophenol. ¹H-NMR (DMSO-d₆) δ 8.75 (br d, J=3.9 Hz, 1H), 8.46 (d, J=4.5 Hz, 1H), 7.35 (d, J=1.8 Hz, 1H), 7.11 (dd, J=4.2, 2.1 Hz, 1H), 7.06 (dd, J=8.4, 6.3 Hz, 1H), 6.50 (dd, J=5.7, 2.4 Hz, 1H), 6.30 to 6.26 (m, 1H), 5.46 (s, 2H), 2.77 (d, J=3.6 Hz, 3H).

Method C-1l

Preparation of 4-(4-Amino-2,5-difluorophenoxy) pyridine-2-carboxylic acid methylamide

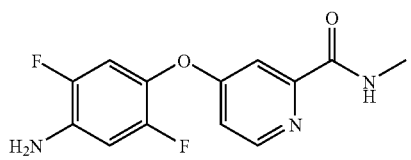

The title compound was prepared in the same manner described for 4-(4-aminophenoxy)pyridine-2-carboxylic acid methylamide, substituting 4-amino-2,5-difluorophenol for 4-aminophenol. $^1$H-NMR (CDCl$_3$) δ 8.34 (d, J=5.7 Hz, 1H), 8.0 (s, 1H), 7.61 (d, J=2.6 Hz, 1H), 6.93 (dd, J=5.3, 2.5 Hz, 1H), 6.82 (dd, J=10.3, 7.0 Hz, 1H), 6.60 (dd, J=11.2, 8.4 Hz, 1H), 3.95 (s, 2H), 2.96 (d, J=5.1 Hz, 3H); MS GC-MS (M$^+$=280.1, RT=2.32 min).

Method C-1m

Preparation of 4-(4-Amino-3,5-difluorophenoxy)pyridine-2-carboxylic acid methylamide

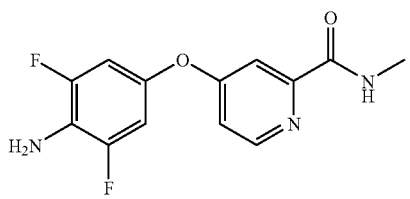

The title compound was prepared in the same manner described for 4-(4-aminophenoxy)pyridine-2-carboxylic acid methylamide, substituting 4-amino-3,5-difluorophenol for 4-aminophenol. $^1$H-NMR (DMSO-d$_6$) δ 8.35 (d, J=5.7 Hz, 1H), 8.0 (s, 1H), 7.63 (d, J=2.1 Hz, 1H), 6.92 (dd, J=5.7, 2.7 Hz, 1H), 7.30 (dd, J=7.3, 1.7 Hz, 2H), 3.75 (s, 2H), 2.97 (d, J=5.3 Hz, 3H); MS GC-MS (M$^+$=280.1, RT=2.27 min).

Method C-1n

Preparation of 4-(4-Amino-2,3-difluorophenoxy)pyridine-2-carboxylic acid methylamide

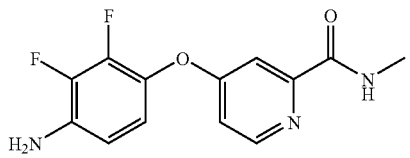

The title compound was prepared in the same manner described for 4-(4-aminophenoxy)pyridine-2-carboxylic acid methylamide, substituting 4-amino-2,3-difluorophenol for 4-aminophenol. $^1$H-NMR (DMSO-d$_6$) δ 8.81-8.75 (m, 1H), 8.50 (d, J=6.0 Hz, 1H), 7.37 (d, J=3.0 Hz, 1H), 7.17 (dd, J=3.0, 6.0 Hz, 1H), 6.94 (ddd, J=2.0, 6.0, 9.0 Hz, 1H), 6.64 (ddd, J=2.0, 6.0, 9.0 Hz, 1H), 5.62 (s, 2H), 2.77 (d, J=5 Hz, 3H); TLC (35% EtOAc/Hex), R$_f$=0.36.

Method C-1o

Preparation of 4-(5-Aminoquinolin-8-yloxy)pyridine-2-carboxylic acid methylamide

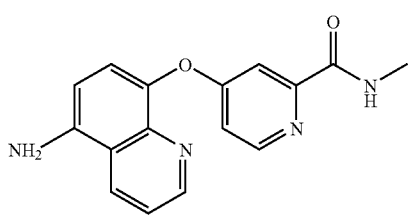

The title compound was prepared in the same manner described for 4-(4-aminophenoxy)pyridine-2-carboxylic acid methylamide, substituting 5-amino-8-hydroxyquinoline for 4-aminophenol. $^1$H-NMR (DMSO-d$_6$) δ 8.72 to 8.66 (m, 2H), 8.60 (dd, J=8.7, 1.8 Hz, 1H), 8.40 (d, J=5.7 Hz, 1H), 7.42 (dd, J=8.7, 4.2 Hz, 1H), 7.37 (d, J=8.4 Hz, 1H), 7.15 (d, J=2.7 Hz, 1H), 7.04 (dd, J=5.4, 2.7 Hz, 1H), 6.73 (d, J=8.1 Hz, 1H), 6.13 (s, 2H), 2.73 (d, J=5.1 Hz, 3H); MS LC-MS (M+H)$^+$=295.2; TLC (5% MeOH/DCM), R$_f$=0.31.

Method C-1p

Preparation of 4-(4-Amino-2-methoxyphenoxy)pyridine-2-carbonitrile

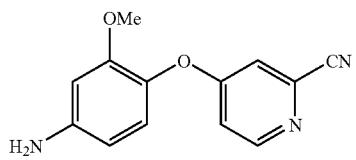

The title compound was prepared in the same manner described for 4-(4-aminophenoxy)pyridine-2-carboxylic acid methylamide, substituting 4-amino-2-methoxyphenol for 4-aminophenol, and 4-chloro-2-cyanopyridine for 4-chloropyridine-2-carboxylic acid methylamide. $^1$H-NMR (DMSO-d$_6$) δ 8.50 (d, J=6.0 Hz, 1H), 7.49 (d, J=2.7 Hz, 1H), 7.00 (dd, J=5.7, 2.4 Hz, 1H), 6.82 (d, J=8.4 Hz, 1H), 6.37 (d, J=2.4 Hz, 1H), 6.16 (dd, J=8.7, 2.7 Hz, 1H), 5.25 (s, 2H), 3.62 (s, 3H); MS LC-MS (M+H)$^+$=242.1.

Method C-1q

Preparation of 4-(4-Amino-3,5-difluoro-phenoxy)pyridine-2-carbonitrile

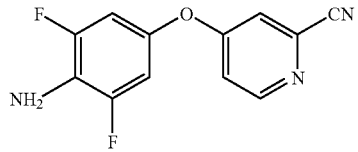

The title compound was prepared in the same manner described for 4-(4-amino-2-methoxyphenoxy)pyridine-2-carbonitrile, substituting 4-amino-3,5-difluorophenol for 4-aminophenol. $^1$H-NMR (DMSO) δ 8.51 (d, J=5.7 Hz, 1H), 7.19 (d, J=2.5 Hz, 1H), 7.00 (dd, J=5.7, J=2.4 Hz, 1H), 6.64 (dd, J=6.7 Hz, J=1.2 Hz, 2H), 3.57 (s, 2H); MS GC-MS (M$^+$=248.6, RT=2.51 min).

Method C-1r

Preparation of 4-(4-Amino-2,5-difluoro-phenoxy)-pyridine-2-carbonitrile

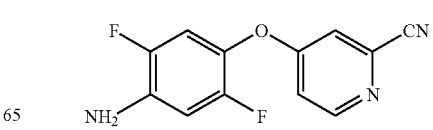

The title compound was prepared in the same manner described for 4-(4-amino-2-methoxyphenoxy)pyridine-2-carbonitrile, substituting 4-amino-2,5-difluorophenol for 4-amino-3,5-difluorophenol. $^1$H-NMR (DMSO-$d_6$) δ 8.56 (d, J=5.9 Hz, 1H), 7.72 (d, J=2.6 Hz, 1H), 7.26-7.17 (m, 2H), 6.72 (dd, J=8.4 Hz, J=12.5 Hz, 1H), 5.56 (s, 2H); MS GC-MS (M$^+$=248.2, RT=2.98 min).

Method C-1s

Preparation of 2-Amino-5-(2-cyanopyridin-4-yloxy)benzamide

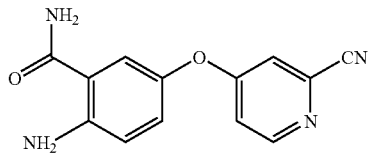

The title compound was prepared in the same manner described for 4-(4-amino-2-methoxyphenoxy)pyridine-2-carbonitrile, substituting 2-amino-5-hydroxy-benzamide for 4-amino-3,5-difluorophenol. $^1$H-NMR (CDCl$_3$) δ 7.41 (d, J=8.1 Hz, 1H), 7.16 (dd, J=8.1, 1.6 Hz, 1H), 7.13 (d, J=1, 6 Hz, 1H), 3.93 (s, 3H); MS GC-MS (M$^+$=211, RT=6.15 min).

Method C-1t

Preparation of 4-(4-Amino-3-chloro-phenoxy)pyridine-2-carboxamide

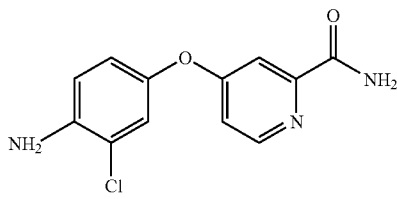

The title compound was prepared in the same manner described for 4-(4-aminophenoxy)pyridine-2-carboxylic acid methylamide, substituting 4-amino-3-chlorophenol for 4-aminophenol, and substituting 4-chloro-2-pyridinecarboxamide for 4-chloropyridine-2-carboxylic acid methylamide. $^1$H-NMR (DMSO-$d_6$) δ 8.45 (d, J=5.4 Hz, 1H), 8.08 (s, 1H), 7.67 (s, 1H), 7.32 (d, J=2.7 Hz, 1H), 7.15 (d, J=2.7 Hz, 1H), 7.09 (dd, J=2.7, 5.4 Hz, 1H), 6.93 to 6.84 (m, 2H), 5.44 (s, 2H); MS LC-MS (M+H)$^+$=264.1, RT=2.40 min.

Method C-1u

Preparation of 4-(4-Amino-3-flurorphenoxy)pyridine-2-carboxamide

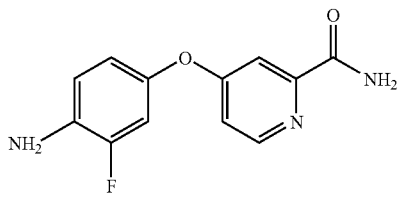

The title compound was prepared in the same manner described for 4-(4-amino-3-chlorophenoxy)pyridine-2-carboxamide, substituting 4-amino-3-fluorophenol for 4-amino-3-chlorophenol. $^1$H-NMR (DMSO-$d_6$) 88.44 (d, J=5.4 Hz, 1H), 8.09 (s, 1H), 7.68 (s, 1H), 7.34 (d, J=2.4 Hz, 1H), 7.10 (dd, J=2.7, 5.7 Hz, 1H), 7.01 (dd, J=2.4, 11.7 Hz, 1H), 6.86 to 6.77 (m, 2H), 5.21 (s, 2H).

Method C-1v

Preparation of 4-(4-Amino-2-chlorophenoxy)pyridine-2-carboxamide

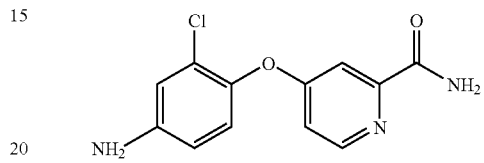

The title compound was prepared in the same manner described for 4-(4-amino-3-chlorophenoxy)pyridine-2-carboxamide, substituting 4-amino-2-chlorophenol for 4-amino-3-chlorophenol. $^1$H-NMR (DMSO-$d_6$) 88.46 (d, J=5.7 Hz, 1H), 8.08 (s, 1H), 7.69 (s, 1H), 7.25 (d, J=2.7 Hz, 1H), 7.08 (dd, J=2.7, 5.7 Hz, 1H), 7.02 (d, J=8.4 Hz, 1H), 6.74 (d, J=2.7 Hz, 1H), 6.59 (dd, J=2.7, 8.7 Hz, 1H), 5.50 (s, 2H); MS LC-MS (MH)$^+$=264.1, RT=1.76 min.

Method C-1w

Preparation of 4-(4-Amino-2-chlorophenoxy)pyridine-2-carboxamide

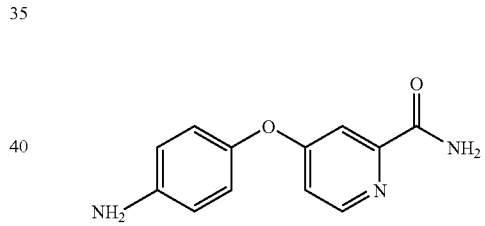

The title compound was prepared in the same manner described for 4-(4-amino-3-chloro-phenoxy)pyridine-2-carboxamide, substituting 4-aminophenol for 4-amino-3-chlorophenol. $^1$H-NMR (DMSO-$d_6$) δ 8.43 (d, J=5.7 Hz, 1H), 8.07 (broad s, 1H), 7.66 (broad s, 1H), 7.31 (d, J=2.7 Hz, 1H), 7.07 (dd, J=5.7 Hz, 2.7 Hz, 1H), 6.85 (d, J=9.0 Hz, 2H), 6.62 (d, J=8.7 Hz, 2H), 5.17 (broad s, 2H).

Method C-2a

Preparation of 4-(4-Amino-2-chlorophenoxy)pyridine-2-carboxylic acid methylamide

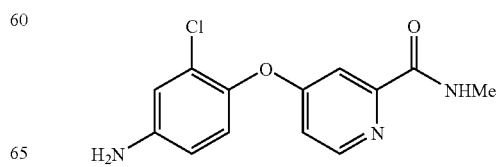

To a stirring N,N'-dimethylamide solution (6 mL) of 2-chloro-4-aminophenol (0.5 g, 3.48 mmol) was slowly added potassium tert-butoxide (0.39 g, 3.48 mmol). After stirring for ca. 25 min., an N,N-dimethylamide solution (4 mL) of 4-chloropiccolinomethylamide (0.46 g, 2.67 mmol) was added, and the contents stirred with heating to 100 C for 16 h. The contents were allowed to cool to room temperature with stirring, and quenched with H$_2$O (5 mL). The contents were extracted with EtOAc, combined organic layers dried over MgSO$_4$, filtered, and concentrated in vacuo. The crude residue was chromatographed (60%→40% EtOAc/Hex gradient) to afford the final product as a dark yellow oil (0.25 g, 34%). $^1$H-NMR (MeOH-d$_4$): δ 8.82 (d, 1H), 7.85 (s, 1H), 7.34 (d, 1H), 7.32(s, 1H), 7.20 (s, 1H), 7.05 (dd, 1H), 3.43 (s, 3H); MS LC-MS [M+H]$^+$=278.2, RT=1.93 min.

Method C-2b

Preparation of 4-(3-Amino-2,4-difluorophenoxy)pyridine-2-carboxylic acid methylamide

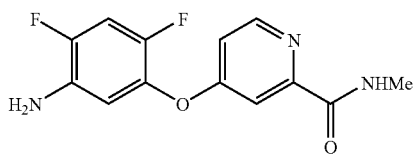

The title compound was prepared in the same manner described for 4-(4-amino-2-chlorophenoxy)pyridine-2-carboxylic acid methylamide, substituting 5-amino-2,4-difluorophenol for 4-amino-2-chlorophenol. $^1$H-NMR (DMSO-d$_6$) δ 8.82 to 8.83 (m, 1H), 8.49 (d, J=5.3 Hz, 1H), 7.29 to 7.39 (m, 2H), 7.14 to 7.19 (m, 1H), 6.68 (t, J=8.5 Hz, 1H), 5.32 (s, 2H), 2.78 (d, J=4.7 Hz, 3H).

Method C-2c

Preparation of 4-(3-Amino-2,4-dichlorophenoxy)pyridine-2-carboxylic acid methylamide

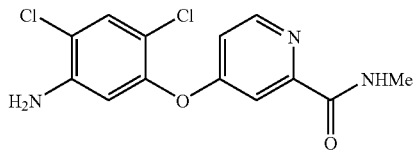

The title compound was prepared in the same manner described for 4-(4-amino-2-chlorophenoxy)pyridine-2-carboxylic acid methylamide, substituting 3-amino-2,4-dichlorophenol for 4-amino-2-chlorophenol. $^1$H-NMR (DMSO-d$_6$) δ 8.80 (q, J=4.8 Hz, 1H), 8.53 (d, J=5.6 Hz, 1H), 7.55 (s, 1H), 7.34 (d, J=2.4 Hz, 1H), 7.17 (m, 1H), 6.71 (s, 1H), 5.83 (s, 2H), 2.79 (d, J=5.0, 3H). MS LC-MS [M+H]$^+$=312.0, RT=3.17 min.

Method C-2d

Preparation of 4-(4-Amino-3-chlorophenoxy)pyridine-2-carboxylic acid methylamide

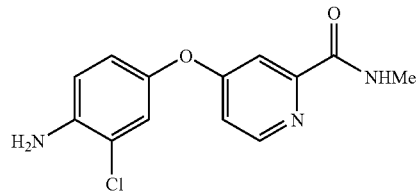

The title compound was prepared in the same manner described for 4-(4-amino-2-chlorophenoxy)pyridine-2-carboxylic acid methylamide, substituting 4-amino-3-chlorophenol for 4-amino-2-chlorophenol. $^1$H-NMR (DMSO-d$_6$) δ 8.76 (m, 1H), 8.47 (d, 1H), 7.35 (s, 1H), 7.15 (s, 1H), 7.06 (dd, 1H), 6.85 to 6.95 (m, 2H), 5.43 (s, 2H), 2.78 (d, 3H); MS LC-MS [M+H]$^+$=278.1 [M+H]$^+$, RT=2.19 min.

Method C-2e

Preparation of 4-[4-Amino-3-(methylsulfanyl)phenoxy]pyridine-2-carboxylic acid methylamide

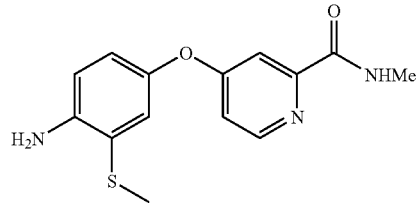

The title compound was prepared in the same manner described for 4-(4-amino-2-chlorophenoxy)pyridine-2-carboxylic acid methylamide, substituting 4-amino-3-methylsulfanylphenol for 4-amino-2-chlorophenol. $^1$H-NMR (DMSO-d$_6$) δ 8.75 (broad q, J=4.8 Hz, 1H), 8.45 (d, J=5.7 Hz, 1H), 7.34 (d, J=2.4 Hz, 1H), 7.07 (dd, J=5.7, 2.7 Hz, 1H), 6.99 (d, J=2.7 Hz, 1H), 6.84 to 6.75 (m, 2H), 5.43 (s, 2H), 2.76 (d, J=4.8 Hz, 3H), 2.35 (s, 3H).

Method C-3a

Preparation of 4-(4-Amino-phenoxy)pyridine-2-carboxylic acid methyl ester

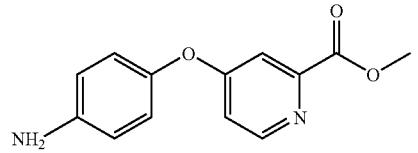

A mixture of 4-(4-Aminophenoxy)pyridine-2-carboxylic acid methylamide (15.0 g, 61.7 mmol) and potassium hydroxide (34.6 g, 617 mmol) in ethanol (400 mL) and water (40 mL) was stirred at 90° C. for 48 h. After cooling to RT, 2.0 N hydrochloric acid was slowly added to the reaction mixture until pH=5. The solvent was removed completely and the residue redissolved in MeOH (400 mL). After slow addition of trimethylsilylchloride (178 mL, 140 mmol, 2.27 eq) at 0° C., the reaction mixture was stirred at reflux for 24 h and cooled to RT. The mixture was filtered, and the filtrate concentrated under reduced pressure and then partitioned between DCM and water. The organic layer was then washed with 1M aqueous sodium bicarbonate solution, dried over $Na_2SO_4$, filtered, and evaporated under reduced pressure. The resulting residue was washed further with $H_2O$ and reextracted with EtOAc/Hex (1:2 v/v) to afford the desired ester (6.27 g, 42%) as a light brown solid. $^1$H-NMR (DMSO-$d_6$) δ 8.51 (d, J=5.7 Hz, 1H), 7.35 (d, J=2.4 Hz, 1H), 7.10 (dd, J=5.7, 2.7 Hz, 1H), 6.86 (dt, J=9.0, 2.4 Hz, 2H), 6.63 (dt, J=8.7, 2.4 Hz, 2H), 5.18 (br s, 2H), 3.86 (s, 3H); MS LC-MS [M+H]$^+$=245, RT=1.04 min; TLC (75% EtOAc/hex), $R_f$=0.20.

Method C-3b

Preparation of
4-(3-Aminophenoxy)pyridine-2-carboxylic acid
methyl ester

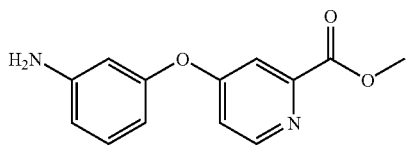

The title compound was prepared in the same manner described for 4-(3-aminophenoxy)pyridine-2-carboxylic acid methyl ester, substituting 4-(3-aminophenoxy)pyridine-2-carboxylic acid methylamide for 4-(4-aminophenoxy)pyridine-2-carboxylic acid methylamide. $^1$H-NMR (CD$_3$OD) δ 8.49 (d, 1H), 7.20 (d, 1H), 7.14 (dd, 1H), 6.64 (dd, 1H), 6.45 (t, 1H), 6.40 (dd, 1H), 3.92 (s, 3H); MS LC-MS [M+H]$^+$=245.1 (MH$^+$), RT=0.52 min.

Method C-4

Preparation of
1-[4-(4-aminophenoxy)pyridin-2-yl]ethanone

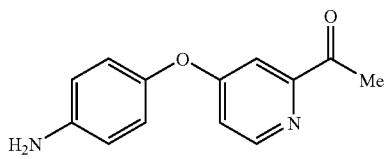

Step 1: Preparation of
4-Chloro-N-methoxy-N-methylpyridine-2-carboxamide

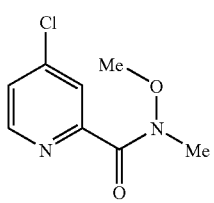

To a mixture of dimethylhydroxylamine HCl (510 mg, 5.18 mmol) and triethylamine (2.16 mL, 15.5 mmol) in anhydrous THF (9.41 mL) and acetonitrile (2.35 mL) was added 4-chloropyridine-2-carbonyl chloride hydrochloride (1.00 g, 4.71 mmol) at 0° C. The reaction mixture was stirred at 0° C. for 2 h then at RT for 16 h. The solvent was removed under reduced pressure and partitioned between EtOAc and water. The organic layer was washed with $H_2O$ and brine, dried over $Na_2SO_4$, and concentrated under reduced pressure. The crude product was purified by MPLC (biotage) eluted with 30% EtOAc/Hex to afford 925 mg (98%) of 4-chloro-N-methoxy-N-methylpyridine-2-carboxamide as an orange oil: TLC (50% EtOAc/Hex), $R_f$=0.31.

Step 2: Preparation of
1-(4-chloropyridin-2-yl)ethanone

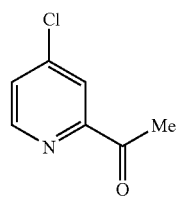

To a 0° C. solution of 1.4 M methyl magnesium bromide in toluene/THF (6.89 mL, 9.65 mmol) in anhydrous THF (8.77 mL) was added a solution of 4-chloro-N-methoxy-N-methylpyridine-2-carboxamide (1.06 g, 5.26 mmol) in anhydrous THF (8.77 mL). The reaction mixture was stirred at RT under $N_2$ for 17 h. The volatile solvent was removed under reduced pressure, and partitioned between EtOAc and water. The organic layer was washed with $H_2O$, brine, dried over $Na_2SO_4$, and concentrated under reduced pressure. The crude product was purified by MPLC (biotage) eluted with 10% EtOAc/Hex to afford 652 mg of 1-(4-chloropyridin-2-yl) ethanone (95.5%) as a white crystalline solid. $^1$H-NMR (Acetone-$d_6$) δ 8.69 (d, J=5.4 Hz, 1H), 7.95 (dd, J=2.1, 1.0 Hz, 1H), 7.71 (dd, J=5.4, 2.1 Hz, 1H), 2.65 (s, 3H); TLC (10% EtOAc/Hex), $R_f$=0.26.

Step 3: Preparation of
1-[4-(4-aminophenoxy)pyridin-2-yl]ethanone

The title compound was prepared in the same manner described for 4-(4-aminophenoxy)pyridine-2-carboxylic acid methylamide, substituting 1-(4-chloropyridin-2-yl)ethanone for 4-chloropyridine-2-carboxylic acid methylamide. $^1$H-NMR (Acetone-$d_6$) δ 8.53 (d, J=5.4 Hz, 1H), 7.36 (d, J=2.7 Hz, 1H), 7.08 (dd, J=5.4, 2.4 Hz, 1H), 6.88 (d, J=9.0 Hz, 2H), 6.77 (d, J=9.0 Hz, 2H), 4.77 (br s, 2H), 2.59 (s, 3H); LC MS m/z 229 (M+H)$^+$, RT=1.11 min; TLC (50% EtOAc/Hex), $R_f$=0.30.

Method C-5a

Preparation of
4-(4-Aminophenoxy)pyridine-2-carboxylic acid
methylcarbamoylmethylamide

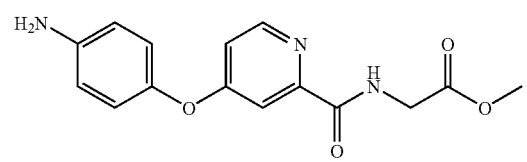

Step 1: Preparation of 4-Chloropyridine-2-carboxylic acid methylcarbamoylmethylamide

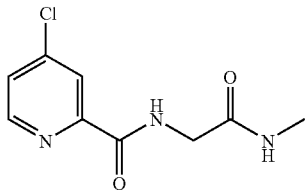

To a solution of 4-chloropyridine-2-carbonyl choride HCl (2.00 g, 9.41 mmol) in THF (16.4 mL) and acetonitrile (9.4 mL) was added 2-amino-N-methylacetamide hydrochloride (1.29 g, 10.35 mmol, 1.1 eq) and triethylamine (5.25 mL, 37.6 mmol, 4.0 eq) at 0° C. The resulting dark brown reaction mixture was stirred at RT for 2 h. The volatile solvent was removed under reduced pressure, and the residue was partitioned between EtOAc and water. The organic layer was washed with water and brine, dried over Na$_2$SO$_4$, filtered, and concentrated under reduced pressure. The crude product was purified on MPLC (biotage) eluted with 100% EtOAc to give 1.4 g (65.3%) of 4-chloropyridine-2-carboxylic acid methylcarbamoyl-N-methylamide as a tan solid: TLC (75% EtOAc/hex), R$_f$=0.14; MS LC-MS [M+H]$^+$=228.

Step 2: Preparation of the title compound 4-(4-Aminophenoxy)pyridine-2-carboxylic acid methylcarbamoylmethylamide The title compound was prepared in the same manner described for 4-(4-aminophenoxy)-pyridine-2-carboxamide, substituting of 4-chloropyridine-2-carboxylic acid N-methylcarbamoylmethylamide for 4-chloro-N-methyl-pyridine-2-carboxamide.
$^1$H-NMR (DMSO-d$_6$) δ 8.86 (t, J=5.7 Hz, 1H), 8.48 (d, J=5.4 Hz, 1H), 7.83 (br d, 1H), 7.32 (d, J=2.7 Hz, 1H), 7.10 (q, J=5.7 Hz, 1H), 6.85 (d, J=8.7 Hz, 2H), 6.63 (d, J=8.7 Hz, 2H), 5.18 (s, 2H), 3.83 (d, J=5.7 Hz, 2H), 2.57 (d, J=4.5 Hz, 3H); MS LC-MS [M+H]$^+$=301; TLC (100% EtOAc), R$_f$=0.10.

Method C-5b

Preparation of 4-(4-Aminophenoxy)pyridine-2-carboxylic acid dimethylcarbamoylmethylamide

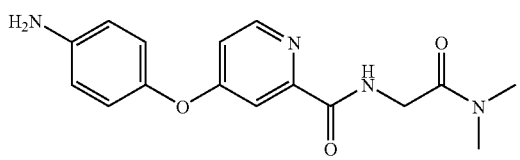

The title compound was prepared in the same manner described for 4-(4-aminophenoxy)pyridine-2-carboxylic acid methylcarbamoylmethylamide, substituting 2-amino-N,N'-dimethylacetamide hydrochloride for 2-amino-N-methylacetamide hydrochloride. $^1$H-NMR (DMSO-d$_6$) δ 8.75 (t, J=4.8 Hz, 1H), 8.49 (d, J=5.4 Hz, 1H), 7.33 (d, J=2.7 Hz, 1H), 7.32 (d, J=2.7 Hz, 1H), 6.86 (d, J=8.7 Hz, 2H), 6.63 (d, J=9.0 Hz, 2H), 5.18 (s, 2H), 4.11 (d, J=5.4 Hz, 2H), 2.96 (s, 3H), 2.85 (s, 3H); MS LC-MS [M+H]$^+$=315.

Method C-5c

Preparation of 4-(4-Amino-3-flurorophenoxy)pyridine-2-carboxylic acid (2-methoxyethyl)amide

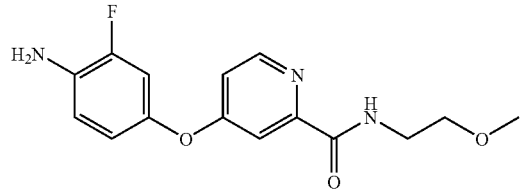

The title compound was prepared in the same manner described for 4-(4-aminophenoxy)pyridine-2-carboxylic acid methylcarbamoylmethylamide, substituting 2-methoxyethylamine for 2-amino-N-methylacetamide hydrochloride. $^1$H-NMR (DMSO-d$_6$) δ 8.66 (br s, 1H), 8.45 (d, J=4.2 Hz, 1H), 7.32 (d, J=1.8 Hz, 1H), 7.09 (dd, J=4.2, 1.8 Hz, 1H), 6.99 (dd, J=9.0, 2.1 Hz, 1H), 6.83 (t, J=6.6 Hz, 1H), 676 (dd, J=6.6, 1.8 Hz, 1H), 5.22 (s, 2H), 3.41 to 3.41 (m, 4H), 3.23 (s, 3H); MS LC-MS [M+H]$^+$=306.

Method D-1a

Preparation of 5-(4-Amino-3-fluorophenoxy)-N-methylnicotinamide

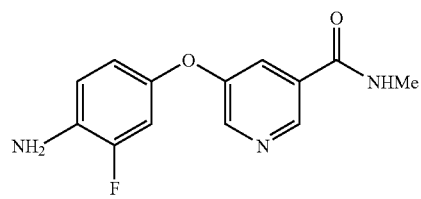

Step 1: Preparation of 5-(4-Nitro-3-fluorophenoxy)nicotinic acid methyl ester

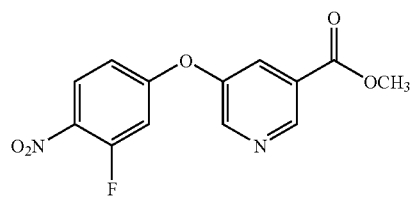

To an ice bath cooled solution of 5-hydroxynicotinic acid methyl ester (5.00 g, 32.65 mmol) in DMF (20 mL) was added sodium hydride (0.78 g, 32.65 mmol). The reaction mixture was stirred at room temperature for 2 hours, and 2,3-difluoro-4-nitrobenzene (5.12 g, 29.68 mmol) was added, and the reaction mixture was stirred at room temperature. After 3 hours the solvent was removed under reduced pressure, and the residue was partitioned between EtOAC (300 mL) and H$_2$O (150 mL). The aqueous layer was extracted with EtOAc (100 mL), and the combined organic layers were dried over Na$_2$SO$_4$, filtered, and the filtrate removed under reduced pressure. The crude product was purified by column chromatography eluted with 50 to 75% EtOAc/Hex to give 2.4 g (28%) of 5-(4-nitro-3-fluorophenoxy)nicotinic acid methyl ester. $^1$H-NMR (CD$_3$OD) δ 9.05 (d, J=1.8 Hz, 1H), 8.70 (d, J=2.7 Hz, 1H), 8.31 (dd, J=2.4, 10.5 Hz, 1H), 8.15-8.14 (m, 1H), 9.06 (dd, J=1.5, 2.1 Hz, 1H), 7.40 (dd, J=8.1, 9.0 Hz, 1H), 3.97 (s, 3H); MS LC-MS [M+H]$^+$=293.1; RT=3.15 min.

Step 2: Preparation of 5-(4-Amino-3-fluorophenoxy)nicotinic acid methyl ester

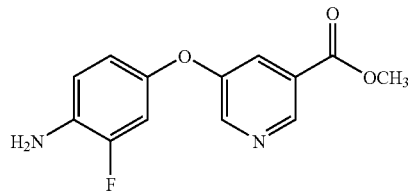

This compound was prepared in the same manner described for 4-amino-3-fluorophenol, substituting 5-(4-nitro-3-fluorophenoxy)nicotinic acid methyl ester for 4-nitro-3-fluorophenol. $^1$H-NMR (CD$_3$OD) δ 8.97 (d, J=1.5 Hz, 1H), 8.71 (d, J=3.0 Hz, 1H), 7.85 to 7.83 (m, 1H), 7.15 to 7.07 (m, 2H), 6.98 to 6.97 (m, 1H), 4.06 (s, 3H); MS LC-MS (MH)+=263.2, RT=2.50 min.

Step 3: Preparation of title compound 5-(4-Amino-3-fluorophenoxy)-N-methylnicotinamide

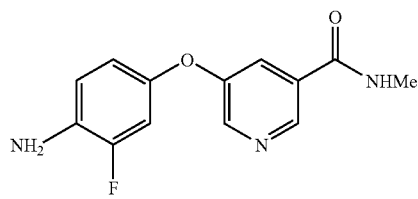

To a solution of 5-(4-amino-3-fluorophenoxy)nicotinic acid methyl ester (0.50 g, 1.91 mmol) in MeOH (2 mL) was added methylamine (0.63 g, 19.1 mmol, 2.0 M in MeOH). The reaction flask was sealed and heated at 40° C. for 4 h. Solvent was removed under reduced pressure, and the crude product was purified by column chromatography eluted with 5% MeOH/CH$_2$Cl$_2$ to give the 0.4 g (80%) of the title compound. $^1$H-NMR (DMSO-d$_6$) δ 8.65 (d, J=1.8 Hz, 1H), 8.62 to 8.60 (m, 1H), 7.54 to 7.52 (m, 1H), 6.94 (dd, J=2.7, 12.0 Hz, 1H), 6.81 to 6.67 (m, 3H), 5.10 (s, 2H), 2.72 (d, J=2.4 Hz, 3H); MS LC-MS [M+H]$^+$=262.2, RT=0.27 min.

Method D-1b

Preparation of 5-(4-Aminophenoxy)-N-methylnicotinamide

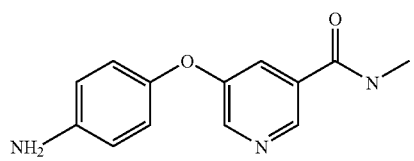

Step 1: Preparation of 5-(4-Aminophenoxy)nicotinic acid methyl ester

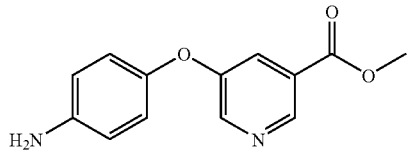

The title compound was prepared in the same manner described 5-(4-Amino-3-fluorophenoxy)nicotinic acid methyl ester, substituting 4-aminophenol for 4-amino-3-fluorophenol. $^1$H NMR (DMSO-d$_6$) δ 8.71 (s, 1H), 8.54 (d, J=2.9 Hz, 1H), 7.47 (t, J=1.9 Hz, 1H), 6.85 (d, J=8.7 Hz, 2H), 6.61 (d, J=8.7 Hz, 2H), 5.12 (br, 2H), 3.81 (s, 3H); MS LC-MS [M+H]$^+$=245.2, RT=1.08 min.

Preparation of the title compound 5-(4-Aminophenoxy)-N-methylnicotinamide

The title compound was prepared in the same manner described for 5-(4-amino-3-fluorophenoxy)-N-methylnicotinamide, substituting 5-(4-aminophenoxy)nicotinic acid methyl ester for 5-(4-amino-3-fluorophenoxy)nicotinic acid methyl ester. $^1$H NMR (DMSO-d$_6$) δ 8.65 (m, 2H), 8.40 (d, J=2.7 Hz, 1H), 7.52 (t, J=2.2 Hz, 1H), 6.84 (d, J=8.7 Hz, 2H), 6.62 (d, J=8.7 Hz, 2H), 5.01 (s, 2H), 2.75 (d, J=4.4 Hz, 3H); MS LC-MS [M+H]$^+$=244.2, RT=0.29 min.

Method D-1c

Preparation of 5-(4-Amino-2-fluorophenoxy)-N-methylnicotinamide

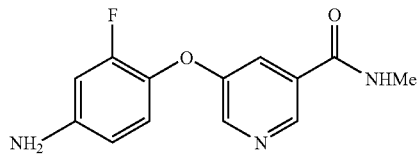

Step 1: Preparation of 5-(4-Amino2-fluorophenoxy)nicotinic acid methyl ester

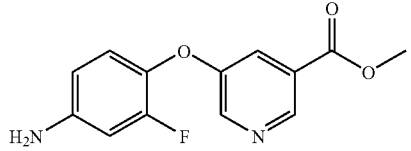

The title compound was prepared in the same manner described 5-(4-Amino-3-fluorophenoxy)nicotinic acid methyl ester, substituting 4-amino-2-fluorophenol for 4-amino-3-fluorophenol. $^1$H NMR (DMSO-d$_6$) δ 7.96 (d, J=1.5 hz, 1H), 7.64 (d, J=3.0 Hz, 1H), 6.88 to 6.87 (m, 1H), 6.16 (t, J=8.7 Hz, 1H), 5.79 to 5.69 (m, 2H), 4.07 (s, 2H), 3.09 (s, 3H); TLC (50% EtOAc/Hex), R$_f$=0.31.

Step 2: Preparation of title compound 5-(4-Amino-2-fluorophenoxy)-N-methylnicotinamide The title compound was prepared in the same manner described for 5-(4-amino-3-fluorophenoxy)-N-methylnicotinamide, substituting 5-(4-amino-2-fluorophenoxy)-nicotinic acid methyl ester for 5-(4-amino-3-fluorophenoxy)nicotinic acid methyl ester. $^1$H NMR (DMSO-$d_6$) δ7.80 (d, J=1.8 Hz, 1H), 7.53 (d, J=2.7 Hz, 1H), 6.83 to 6.81 (m, 1H), 6.15 (t, J=8.7 Hz, 1H), 5.78 to 5.67 (m, 2H), 4.07 (s, 3H), 2.07 (s, 3H).

Method D-2a

Preparation of 4-(4-Aminophenoxymethyl)pyridine-2-carboxylic acid methylamide

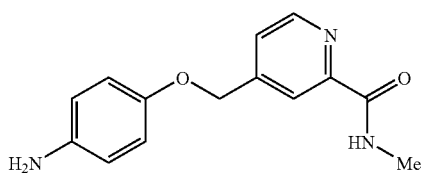

Step 1: Preparation of 2-Methylcarbamoyl-isonicotinic acid ethyl ester

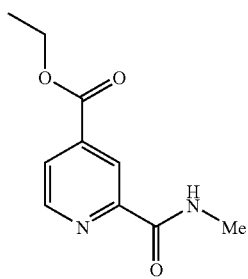

To a 3-necked flask charged with isonicotinic acid ethyl ester (10 mL, 65.4 mmol) in anhydrous N-methylformamide (80.0 mL) at 2.5° C. was added concentrated sulfuric acid (3.67 mL, 65.4 mmol, 1.0 eq) and iron (II) sulfate heptahydrate (4.6 g, 16.4 mmol, 0.25 eq). Hydrogen peroxide (11.1 mL, 98.1 mmol; 30 wt. % solution in water, 1.5 eq) was added dropwise to keep the internal temperature below 25° C. The reaction mixture was stirred at 2.5° C. for 10 min and at RT for 30 min. The reaction mixture was poured into 1M aqueous sodium citrate solution (130 mL), and the resulting orange-yellow suspension was quenched with 5% aqueous sodium bicarbonate solution (150 mL), adjusting the pH to 7. Dichloromethane (100 mL) Was then added, and the organic phase was extracted, washed with water (2×100 mL) and brine (1×100 mL), dried over $Na_2SO_4$, filtered, and evaporated under reduced pressure. The solid was stirred in ice-water and filtered to afford 11.2 g (88.2%) of a yellow solid: TLC (50% EtOAc/Hex), $R_f$=0.25.

Step 2: 4-(hydroxymethyl)-N-methylpyridine-2-carboxamide

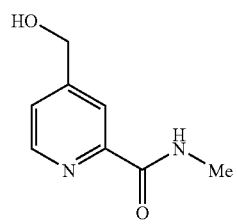

To a solution of 2-methylcarbamoyl-isonicotinic acid ethyl ester (7.77 g, 37.3 mmol) in absolute ethanol (125 mL) was added sodium borohydride (2.82 g, 74.6 mmol, 2.0 eq), and the reaction mixture was stirred at RT under argon for 18 h. The solvent was evaporated under reduced pressure, and the residue was partitioned between EtOAc and water. The aqueous layer was extracted with EtOAc (2×100 mL), and the combined organic layers were dried over $Na_2SO_4$, filtered, and concentrated at reduced pressure to give 5.36 g (86.5%) of 4-(hydroxymethyl)-N-methylpyridine-2-carboxamide as a colorless solid: MS LC-MS [M+H]$^+$=153.

Step 3: Preparation of 4-(4-Nitrophenoxymethyl)pyridine-2-carboxamide

A solution of 4-(hydroxymethyl)-N-methylpyridine-2-carboxamide (117 mg, 0.70 mmol) in DCM (10 mL) was treated with triethylamine (0.11 mL, 0.77 mmol) and methanesulphonylchloride (0.74 mL, 0.70 mmol). The reaction was stirred at 25° C. for 3 h and then quenched with $H_2O$ (10 mL). The layers were separated, and the organic layer was concentrated under reduced pressure to afford the crude benzyl chloride. To a solution of the crude benzyl chloride in anhydrous DMF (10 mL) was added $Cs_2CO_3$ (688 mg, 2.11 mmol) and 4-nitrophenol (0.979 mg, 0.70 mmol). The reaction mixture was heated to 60° C. for 18 h and then partitioned between EtOAc (15 mL) and water (10 mL). The organic layer was extracted with $H_2O$ (4×150 mL), dried ($Na_2SO_4$) and evaporated under reduced pressure to afford 150 mg (74%) of 4-(4-nitrophenoxymethyl)pyridine-2-carboxamide as a light yellow oil. $^1$H-NMR (DMSO-$d_6$): δ 8.78 (br d, J=3.6 Hz, 1H), 6.62 (d, J=3.9 Hz, 1H), 8.21 (d, J=7.2 Hz, 2H), 8.06 (s, 1H), 7.61 (dd, J=3.9, 1.2 Hz, 1H), 7.23 (d, J=6.9 Hz, 2H), 5.45 (s, 2H), 2.81 (d, J=3.6 Hz, 3H); mp 172-174° C.

Step 4: Preparation of title compound 4-(4-Aminophenoxymethyl)pyridine-2-carboxylic acid methylamide The title compound was prepared in the same manner described for 4-amino-3-fluorophenol, substituting 4-(4-nitrophenoxymethyl)pyridine-2-carboxamide for 3-fluoro-4-nitrophenol: MS LC-MS [M+H]$^+$=258.

Method D-2b

Preparation of
4-(3-Aminophenoxymethyl)pyridine-2-carboxylic
acid methylamide

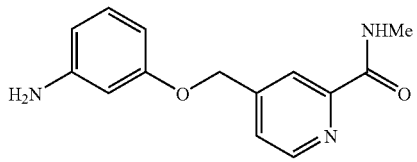

The title compound was prepared in the same manner described for 4-(4-aminophenoxymethyl)pyridine-2-carboxylic acid methylamide, substituting 3-nitrophenol for 4-nitrophenol. $^1$H-NMR (CD$_3$OD) δ 8.40 (d, J=4.5 Hz, 1H), 7.54 (d, J=2.1 Hz, 1H), 7.13 (t, J=6.3 Hz, 1H), 7.00 (dd, J=4.2, 1.8 Hz, 1H), 6.62 to 6.59 (m, 1H), 6.43 (t, J=1.8 Hz, 1H), 6.37 to 6.34 (m, 1H), 4.89 (s, 2H), 2.93 (s, 3H).

Method D-2c

Preparation of 4-(4-Amino-3-fluorophenoxymethyl)pyridine-2-carboxamide

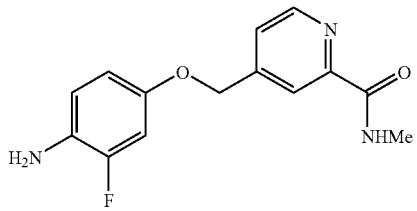

The title compound was prepared in the same manner described for 4-(4-aminophenoxymethyl)pyridine-2-carboxylic acid methylamide, substituting 3-fluoro-4-nitrophenol for 4-nitrophenol. $^1$H-NMR (DMSO-d$_6$) δ 8.77 (br q, J=6.6 Hz, 1H), 8.59 (d, J=3.6 Hz, 1H), 8.02 (s, 1H), 7.56 (dd, J=4.5, 1.5 Hz, 1H), 6.78 (dd, J=9.6, 2.1 Hz, 1H), 6.68 (t, J=7.2 Hz, 1H), 6.60 (dd, J=6.6, 2.4 Hz, 1H), 5.15 (s, 2H), 4.68 (br s, 2H), 2.81 (d, J=3.6 Hz, 3H).

Preparation of Ureas of Formula (I)
General Method E: Substituted Ureas via CDI-Induced Aniline Coupling

EXAMPLE 1

Method E-1a

Preparation of 4-[3-fluoro-4-({[(1-methyl-1H-indazol-5-yl)amino]carbonyl}amino)phenoxy]-N-methylpyridine-2-carboxamide

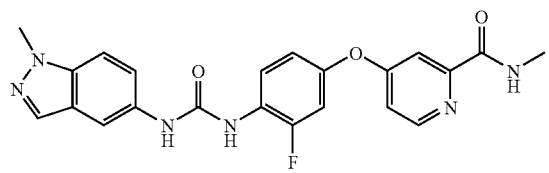

To a solution of 1,1'-carbonyldiimidazole (62 mg, 0.38 mmol) in benzene (2 mL) and CH$_2$Cl$_2$ (1 mL) was added 4-(4-amino-3-fluorophenoxy)-N-methylpyridine-2-carboxamide (100 mg, 0.38 mmol). The resulting solution was stirred at room temperature for 16 h, then was treated with 1-methyl-5-aminoindazole (56 mg, 0.38 mmol). The reaction continued to stir at room temperature for 18 h. The mixture was concentrated under reduced pressure and the residue was triturated with Et$_2$O. The solid was collected by filtration, and then purified by preparative HPLC to afford 44 mg (27%) of the title product. $^1$H-NMR (DMSO-d$_6$) δ 2.78 (d, J=4.8, 3H), 4.01 (s, 3H), 7.02-7.07 (m, 1H), 7.14-7.18 (m, 1H), 7.28-7.36 (m, 2H), 7.39 (d, J=2.9, 1H), 7.52-7.59 (m, 1H), 7.89-7.96 (m, 2H), 8.23 (t, J=9.0, 1H), 8.49 (d, J=4.9, 1H), 8.57-8.63 (m, 1H), 8.71-8.81 (m, 1H), 9.06 (s, 1H); MS LC-MS [M+H]$^+$=435.1; mp 231-234° C.

EXAMPLE 2

Method E-1b

Preparation of Methyl 4-[3-({[(1-methyl-1H-indazol-5-yl)amino]carbonyl}amino)phenoxy]-pyridine-2-carboxylate

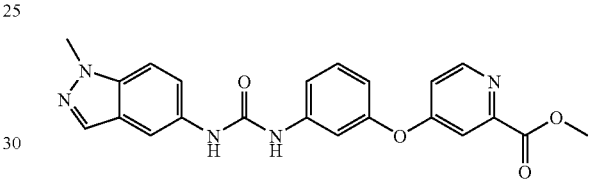

To a solution of 4-(3-amino-phenoxy)-pyridine-2-carboxylic acid methyl ester (0.79 g, 5.35 mmol) in CH$_2$Cl$_2$ (3 mL) was added 1,1'-carbonyldiimidazole (0.87 g, 5.35 mmol), and the reaction mixture was stirred at room temperature for 12 h. A solution of 1-methyl-5-aminoindazol (1.02 g, 6.96 mmol) in CH$_2$Cl$_2$ (4 mL) was added, and the mixture stirred at room temperature an additional 8 h. The mixture was concentrated in vacuo. Purification of the crude product by column chromatography eluted with CH$_2$Cl$_2$/MeOH (95:5) gave 850 mg (38%) of the title compound. $^1$H-NMR (CD$_3$OD) δ 8.57 (dd, 1H), 7.95 (d, 1H), 7.87 (d, 1H), 7.54 (d, 1H), 7.53-7.51 (m, 2H), 7.47-7.32 (m, 2H), 7.32 (d, 1H), 7.21 (dd, 1H), 6.86 (dd, 1H). 4.07 (s, 3H), 3.96 (s, 3H); MS LC-MS [M+H]$^+$=418.2, RT=2.91 min.

EXAMPLE 3

Method E-2

Preparation of N-{4-[(2-acetylpyridin-4-yl)oxy]phenyl}-N'-(1-methyl-1H-indazol-5-yl)urea

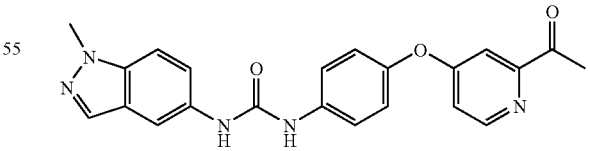

To a solution of 1-methyl-5-aminoindazole (48.4 mg, 0.33 mmol) in anhydrous DCE (1.1 mL) and anhydrous THF (1.1 mL) was added 1,1'-carbonyldiimidazole (65.1 mg, 0.39, 1.2 eq), and the reaction mixture was stirred at 65° C. under argon. After 16 h a solution of 1-[4-(4-aminophenoxy)pyridin-2-yl]ethanone (75 mg, 0.33 mmol, 1.0 eq) in anhydrous DCE (3.3 mL) was added at ambient temperature, and the reaction mixture was stirred at 65° C. under argon for 20 h.

The reaction mixture was partitioned between EtOAc and water, and the organic layer was washed with water and brine, dried over Na$_2$SO$_4$, filtered, and concentrated under reduced pressure. Purification on MPLC (biotage) eluted with 60 to 80% EtOAc/Hex and crystallization from ethyl acetate—hexane afforded 98.2 mg (74.4%) of the title compound as a white solid. $^1$H-NMR (DMSO-d$_6$) δ 8.79 (s, 1H), 8.68 (s, 1H), 8.58 (d, J=5.7 Hz, 1H), 7.93 (d, J=1.0 Hz, 1H), 7.89 (d, J=1.2 Hz, 1H), 7.58 to 7.53 (m, 3H), 7.35 (dd, J=9.0, 2.1 Hz, 1H), 7.26 (d, J=2.7 Hz, 1H), 7.21 (dd, J=5.4, 2.4 Hz, 1H), 7.13 (d, J=8.7 Hz, 2H), 3.99 (s, 3H), 2.59 (s, 3H); MS LC-MS [M+H]$^+$=4.02, RT=2.41 min; TLC (75% EtOAc/Hex), R$_f$=0.11.

EXAMPLE 4

Method E-3a

Preparation of 4-(4-{[(1,3-benzothiazol-6-ylamino)carbonyl]amino}phenoxy)-N-methyl-pyridine-2-carboxamide

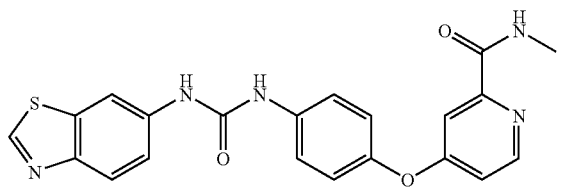

Step 1: Preparation of N-(1-imidazole)-N'-(4-(2-(N-methylcarbamoyl)-4-Pyridyloxy)phenyl)-urea

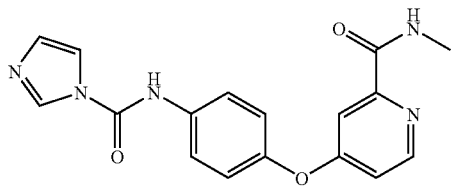

To a slurry of 1,1'-carbonyldiimidazole (6.66 g, 41.1 mmol) and imidazole (2.80 g, 41.1 mmol) in CH$_2$Cl$_2$ (40 mL), was added a solution of 4-(2-(N-methylcarbamoyl)-4-pyridyloxy)aniline (1.0 g, 4.11 mmol) in CH$_2$Cl$_2$ (8 mL) at 0° C. The reaction mixture was stirred at room temperature for 2 h, and then quickly washed with cold water (40 mL). The organic layer was dried with Na$_2$SO$_4$, filtered and concentrated to ca. 16 ml. The crude product in CH$_2$Cl$_2$ was used in the subsequent reaction without further purification.

Step 2: Preparation of title compound 4-(4-{[(1,3-benzothiazol-6-5 ylamino)carbonyl]amino}-phenoxy)-N-methylpyridine-2-carboxamide To a solution of crude N-(1-imidazole)-N'-(4-(2-(N-methylcarbamoyl)-4-pyridyloxy)-phenyl)urea in CH$_2$Cl$_2$ (4 mL) was slowly added a solution of 6-aminobenzothiazole (135 mg, 0.90 mmol) in CH$_2$Cl$_2$ (3 mL) at room temperature. The reaction mixture was heated at 40° C. for 2 d. The resulting precipitate was filtered and washed with CH$_2$Cl$_2$ to afford 256 mg (60%) of the title compound as a white solid. $^1$H-NMR (DMSO-d$_6$) δ 9.22 (s, 1H), 9.02 (s, 1H), 8.93 (s, 1H), 8.78 (q, J=5.1 Hz, 1H), 8.50 (d, J=5.7 Hz, 1H), 8.38 (d, J=1.8 Hz, 1H), 8.00 (d, J=9.0 Hz, 1H), 7.61 (d, J=9.3 Hz, 2H), 7.51 (dd, J=9.3, 2.4 Hz, 1H), 7.39 (d, J=3.0 Hz, 1H), 7.19 to 7.13 (m, 3H), 2.78 (d, J=5.4 Hz, 3H); MS LC-MS [M+H]$^+$=420.2, RT=2.51 min.

EXAMPLE 5

Method E-3b

Preparation of 4-(4-{[(1,3-benzothiazol-6-ylamino)carbonyl]amino}-phenoxy)-N-methylpyridine-2-carboxamide

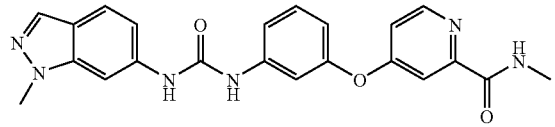

The title compound was prepared in the same manner described for 4-(4{[(1,3-benzothiozol-6-ylamino)carbonyl]amino}phenoxy)-N-methylpyridine-2-carboxyamide, substituting 1-N-methyl-6-aminoindazole for 6-aminobenzothiazole, and substituting 3-(2-(N-methylcarbamoyl)-4-pyridyloxy)aniline for 4-(2-(N-methylcarbamoyl)-4-pyridyloxy)aniline. $^1$H-NMR (CD$_3$OD) δ 8.58 (d, 1H), 7.94 to 7.92 (m, 2H), 7.71 (d, 1H), 7.66 (d, 1H), 7.59 (t, 1H), 7.49 (dd, 1H), 7.33 (dd, 1H), 7.24 (dd, 1H), 7.00 (dd, 1H), 6.97 (dd, 1H), 4.02 (s, 3H), 2.96 (s, 3H); MS LC-MS [M+H]$^+$=417.2, RT=2.46 min.

Additional compounds illustrated in Table 1 were prepared as described above by choosing the appropriate starting materials that are readily available and/or the synthesis of which is taught herein, and using the processes of Method E described above or other standard chemical processes known in the art.

TABLE 1

Examples Synthesized using Method E

| Example | Structure | R$_f$ (TLC solvent) Or RT (min)* | LC/MS ([M + H]+) | Synthesis of (III) or (V)** | Synthesis of (II) | Synthesis of (I) |
|---|---|---|---|---|---|---|
| 6 | 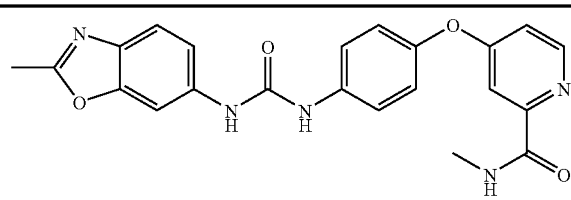 | R$_f$= 0.27 (5% MeOH/ DCM) | 418 | A-2 | C-1 | E-1 |

TABLE 1-continued

Examples Synthesized using Method E

| Example | Structure | R*f* (TLC solvent) Or RT (min)* | LC/MS ([M + H]+) | Synthesis of (III) or (V)** | Synthesis of (II) | Synthesis of (I) |
|---|---|---|---|---|---|---|
| 7 | 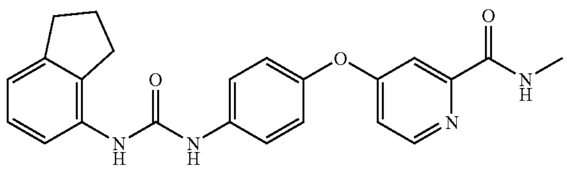 | RT = 2.97 | 403 | comm | C-1 | E-1 |
| 8 | 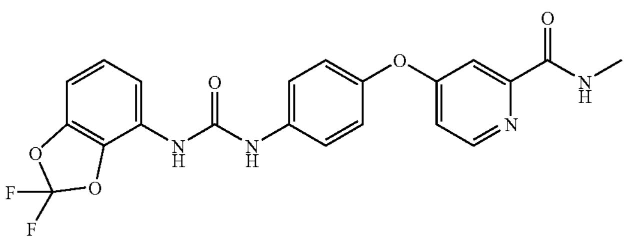 | RT = 3.00 | 443 | comm | C-1 | E-1 |
| 9 | 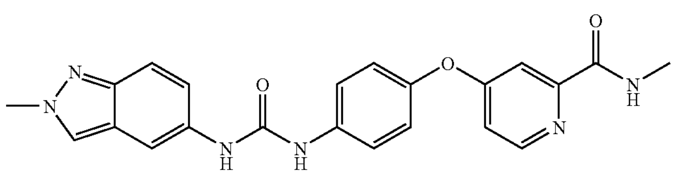 | RT = 2.79 | 417 | comm | C-1 | E-1 |
| 10 | 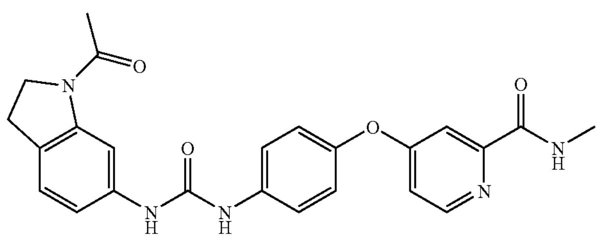 | RT = 2.98 | 446 | comm | C-1 | E-1 |
| 11 | 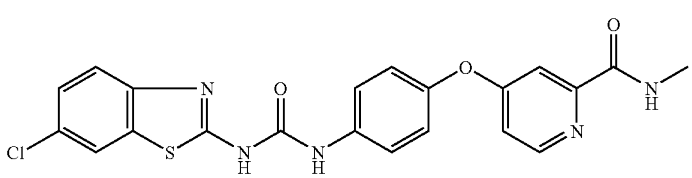 | RT = 3.15 | 454 | comm | C-1 | E-1 |
| 12 | 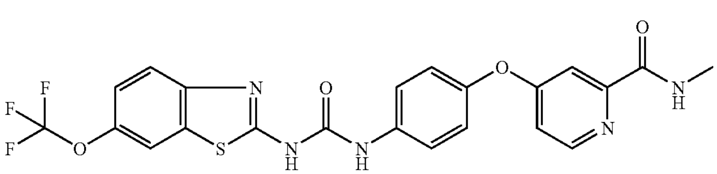 | RT = 3.41 | 504 | comm | C-1 | E-1 |
| 13 | 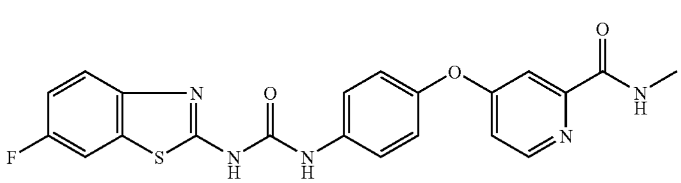 | RT = 2.95 | 438 | comm | C-1 | E-1 |

TABLE 1-continued

Examples Synthesized using Method E

| Example | Structure | R_f (TLC solvent) Or RT (min)* | LC/MS ([M+H]+) | Synthesis of (III) or (V)** | Synthesis of (II) | Synthesis of (I) |
|---|---|---|---|---|---|---|
| 14 | 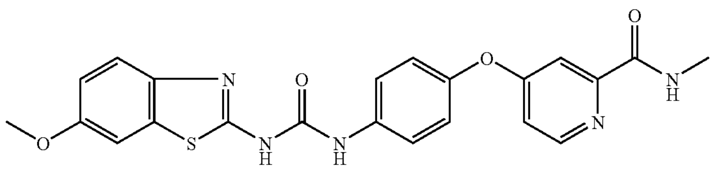 | RT = 2.98 | 450 | comm | C-1 | E-1 |
| 15 | 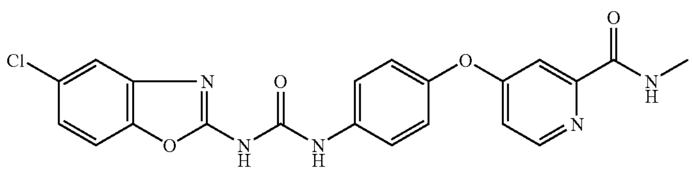 | RT = 3.19 | 438 | comm | C-1 | E-1 |
| 16 | 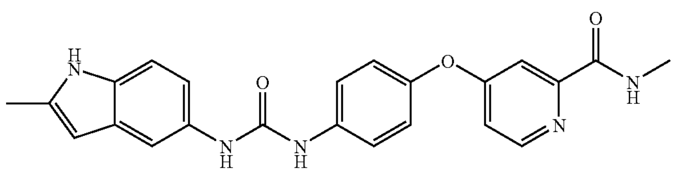 | R_f = 0.43 (100% EtOAc) | 416 | comm | C-1 | E-3 |
| 17 | 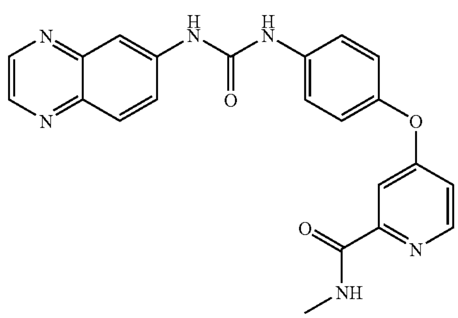 | R_f = 0.16 (100% EtOAc) | 415 | comm | C-1 | E-1 |
| 18 | 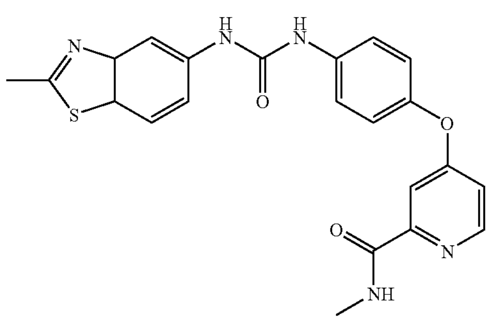 | R_f = 0.30 (100% EtOAc) | 434 | comm | C-1 | E-1 |
| 19 | 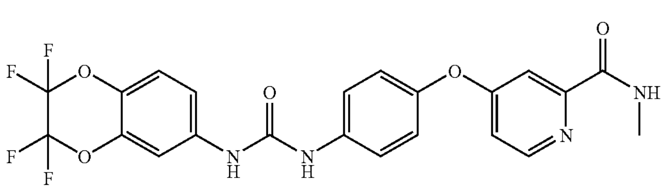 | R_f = 0.27 (5% MeOH/DCM) | 493 | comm | C-1 | E-1 |

TABLE 1-continued

Examples Synthesized using Method E

| Example | Structure | R_f (TLC solvent) Or RT (min)* | LC/MS ([M + H]+) | Synthesis of (III) or (V)** | Synthesis of (II) | Synthesis of (I) |
|---|---|---|---|---|---|---|
| 20 | (2,2-difluoro-benzo[1,3]dioxol-5-yl urea, phenoxy, pyridine-2-carboxamide N-methyl) | R_f = 0.50 (5% MeOH/DCM) | 443 | comm | C-1 | E-1 |
| 21 | (2,3-dihydro-1H-inden-5-yl urea, phenoxy, pyridine-2-carboxamide N-methyl) | RT = 3.49 | 403 | comm | C-1 | E-1 |
| 22 | (1-oxo-2,3-dihydro-1H-inden-5-yl urea, phenoxy, pyridine-2-carboxamide N-methyl) | RT = 2.49 | 417 | comm | C-1 | E-1 |
| 23 | (1-methyl-1H-indazol-5-yl urea, phenoxy, pyridine-2-carboxamide N-methyl) | R_f = 0.48 (7% MeOH/DCM) | 417 | comm | C-1 | E-3 |
| 24 | (1-methyl-1H-indazol-6-yl urea, phenoxy, pyridine-2-carboxamide N-methyl) | R_f = 0.33 (5% MeOH/DCM) | 417 | comm | C-1 | E-3 |
| 25 | (2,3-dihydrobenzofuran-5-yl urea, phenoxy, pyridine-2-carboxamide N-methyl) | R_f = 0.48 (7% MeOH/DCM) | 405 | comm | C-1 | E-3 |
| 26 | (1H-benzotriazol-5-yl urea, phenoxy, pyridine-2-carboxamide N-methyl) | R_f = 0.29 (7% MeOH/DCM) | 404 | comm | C-1 | E-3 |
| 27 | (1H-indazol-6-yl urea, phenoxy, pyridine-2-carboxamide N-methyl) | R_f = 0.38 (7% MeOH/DCM) | 403 | comm | C-1 | E-3 |

TABLE 1-continued

Examples Synthesized using Method E

| Example | Structure | $R_f$ (TLC solvent) Or RT (min)* | LC/MS ([M + H]+) | Synthesis of (III) or (V)** | Synthesis of (II) | Synthesis of (I) |
|---|---|---|---|---|---|---|
| 28 | 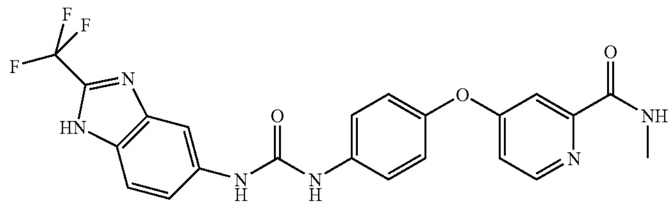 | $R_f$ = 0.44 (7% MeOH/DCM) | 471 | comm | C-1 | E-3 |
| 29 | 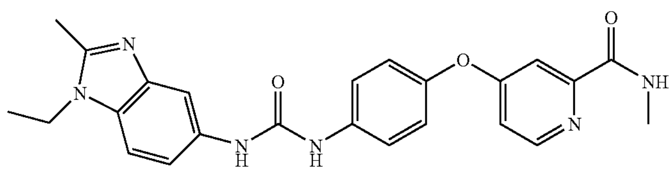 | $R_f$ = 0.58 (7% MeOH/DCM) | 445 | comm | C-1 | E-3 |
| 30 | 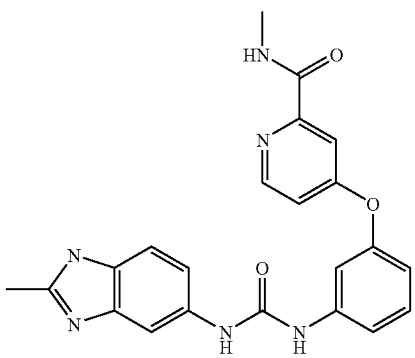 | $R_f$ = 0.27 (5% MeOH/DCM) | 418 | A-2 | C-1 | E-1 |
| 31 | 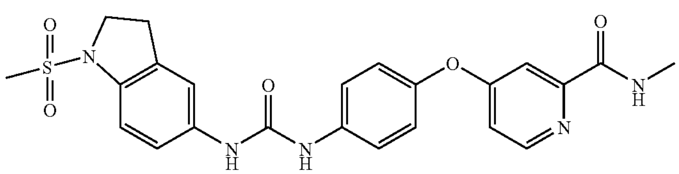 | RT = 3.11 | 482 | comm | C-1 | E-1 |
| 32 | 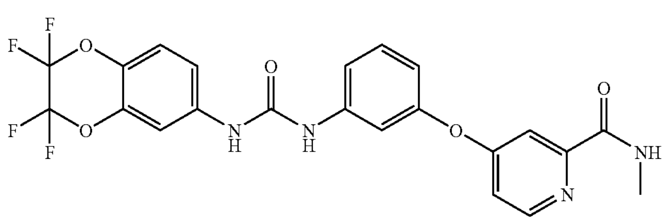 | $R_f$ = 0.40 (5% MeOH/DCM) | 493 | comm | C-1 | E-1 |
| 33 | 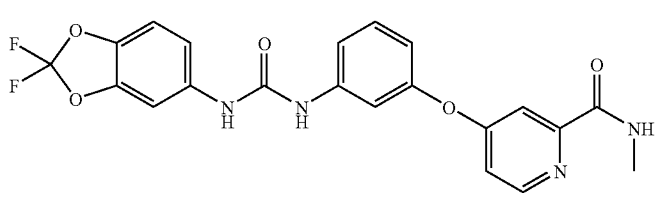 | RT = 3.22 | 443 | comm | C-1 | E-1 |

TABLE 1-continued

Examples Synthesized using Method E

| Example | Structure | R_f (TLC solvent) Or RT (min)* | LC/MS ([M+H]+) | Synthesis of (III) or (V)** | Synthesis of (II) | Synthesis of (I) |
|---|---|---|---|---|---|---|
| 34 | 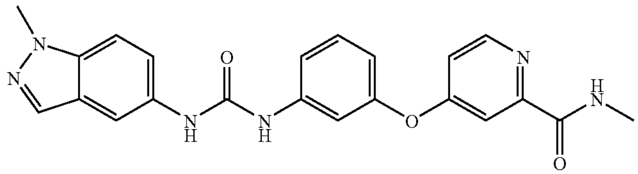 | RT = 2.37 | 417 | comm | C-1 | E-3 |
| 35 | 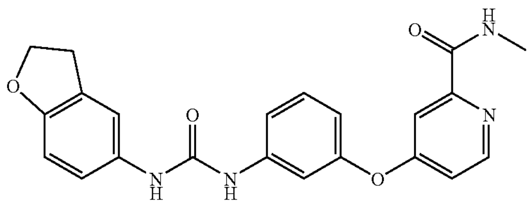 | RT = 2.37 | 405 | comm | C-1 | E-3 |
| 36 | 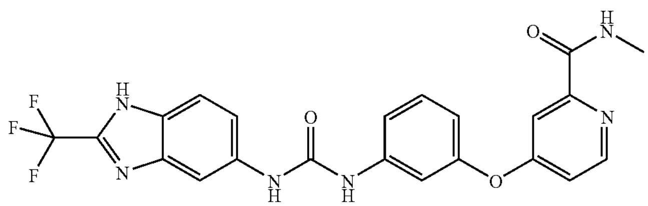 | RT = 2.48 | 471 | comm | C-1 | E-3 |
| 37 | 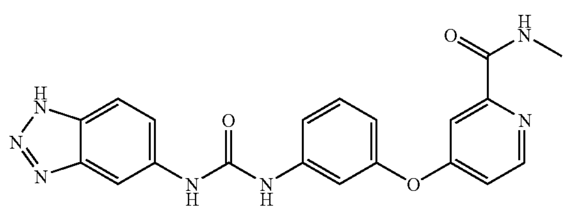 | RT = 2.20 | 404 | comm | C-1 | E-3 |
| 38 | 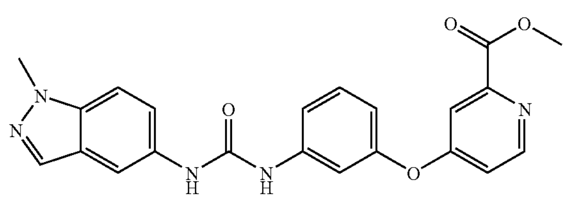 | RT = 2.91 | 418 | comm | C-1 | E-3 |
| 39 | 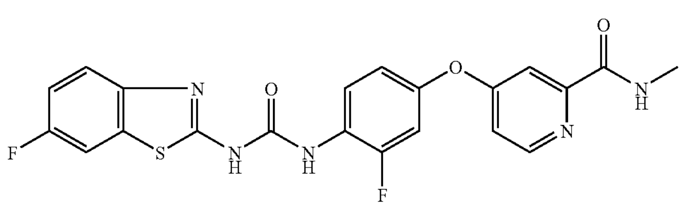 | RT = 3.12 | 456 | B-1 | C-1 | E-1 |
| 40 | 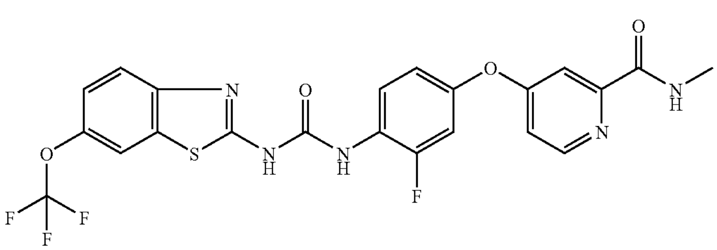 | RT = 3.44 | 522 | B-1 | C-1 | E-1 |

TABLE 1-continued

Examples Synthesized using Method E

| Example | Structure | R$_f$(TLC solvent) Or RT (min)* | LC/MS ([M + H]+) | Synthesis of (III) or (V)** | Synthesis of (II) | Synthesis of (I) |
|---|---|---|---|---|---|---|
| 41 | 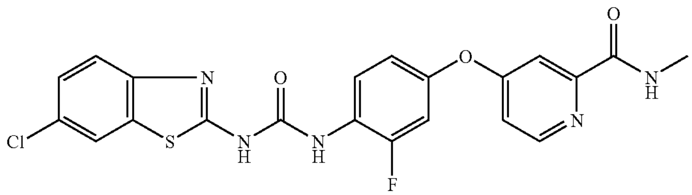 | RT = 2.62 | 472 | B-1 | C-1 | E-1 |
| 42 | 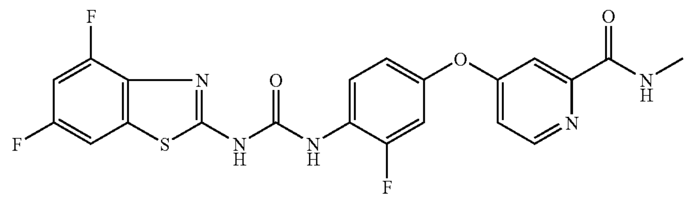 | RT = 3.14 | 474 | B-1 | C-1 | E-1 |
| 43 | 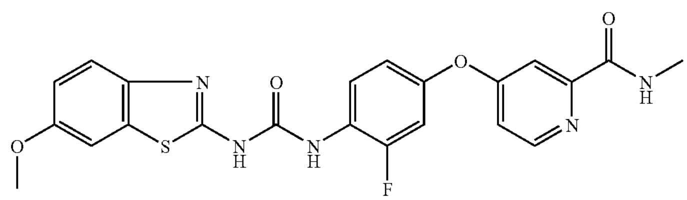 | RT = 2.98 | 468 | B-1 | C-1 | E-1 |
| 44 | 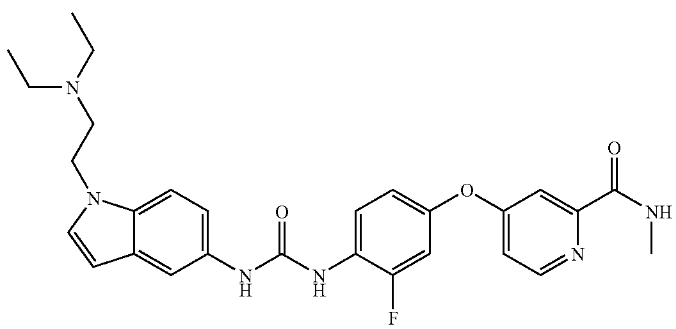 | RT = 2.56 | 519 | A-3 B-1 | C-1 | E-1 |
| 45 | 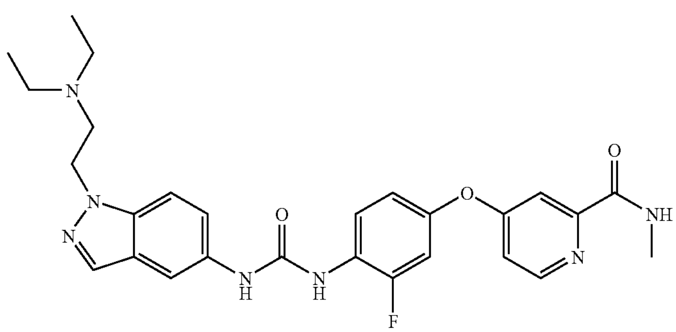 | RT = 2.63 | 520 | A-3 B-1 | C-1 | E-1 |
| 46 | 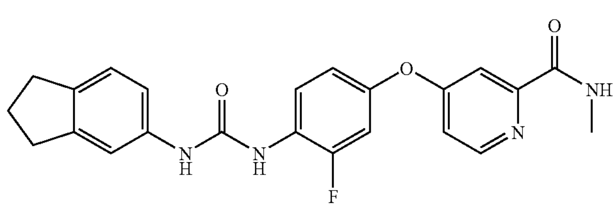 | RT = 3.11 | 421 | B-1 | C-1 | E-1 |

TABLE 1-continued

Examples Synthesized using Method E

| Example | Structure | $R_f$(TLC solvent) Or RT (min)* | LC/MS ([M + H]+) | Synthesis of (III) or (V)** | Synthesis of (II) | Synthesis of (I) |
|---|---|---|---|---|---|---|
| 47 | 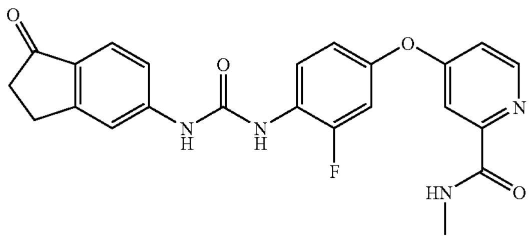 | RT = 2.49 | 435 | B-1 | C-1 | E-1 |
| 48 | 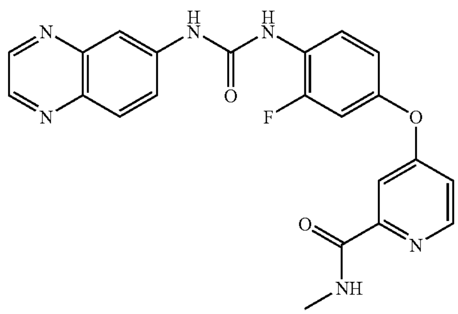 | $R_f$ = 0.38 (100% EtOAc) | 433 | B-1 | C-1 | E-2 |
| 49 | 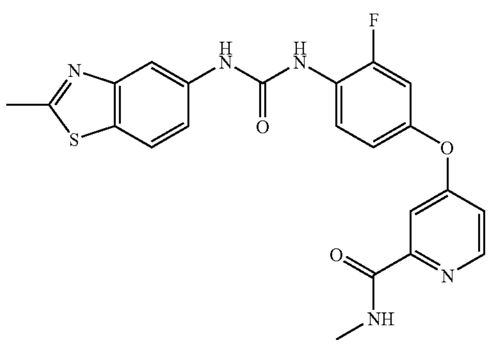 | $R_f$ = 0.56 (100% EtOAc) | 452 | B-1 | C-1 | E-2 |
| 50 | 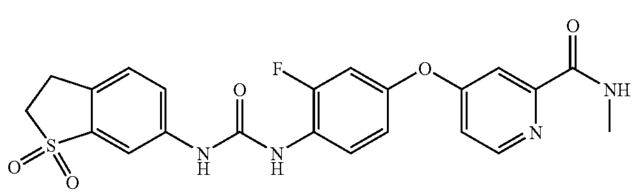 | RT = 2.46 | 471 | A-2 B-1 | C-1 | E-1 |
| 51 | 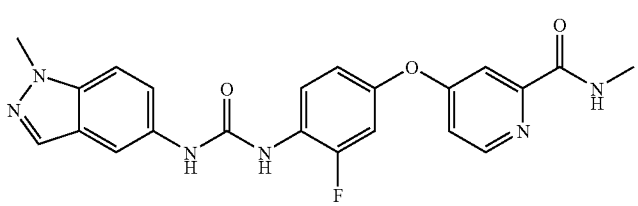 | RT = 1.94 | 432 | B-1 | C-1 | E-1 |
| 52 | 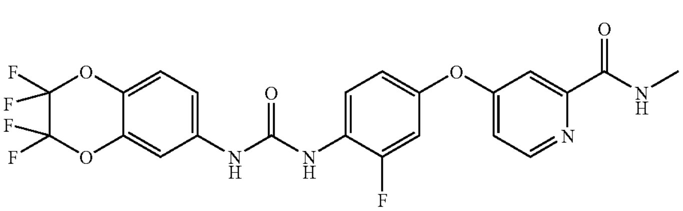 | RT = 3.01 | 511 | B-1 | C-1 | E-1 |

TABLE 1-continued

Examples Synthesized using Method E

| Example | Structure | R$_f$(TLC solvent) Or RT (min)* | LC/MS ([M + H]+) | Synthesis of (III) or (V)** | Synthesis of (II) | Synthesis of (I) |
|---|---|---|---|---|---|---|
| 53 | 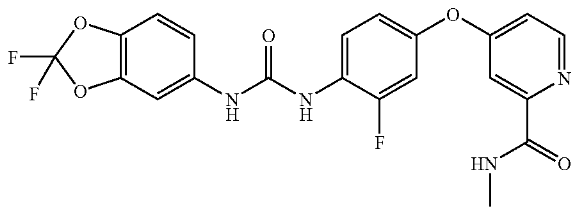 | RT = 2.66 | 461 | B-1 | C-1 | E-1 |
| 54 | 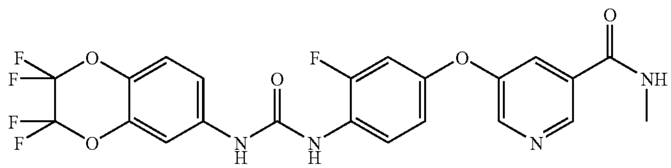 | RT = 3.17 | 511 | B-1 | D-1 | E-1 |
| 55 | 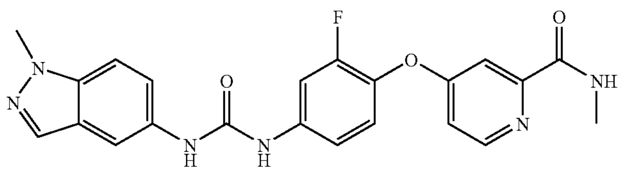 | RT = 2.02 | 435 | B-1 | C-1 | E-1 |
| 56 | 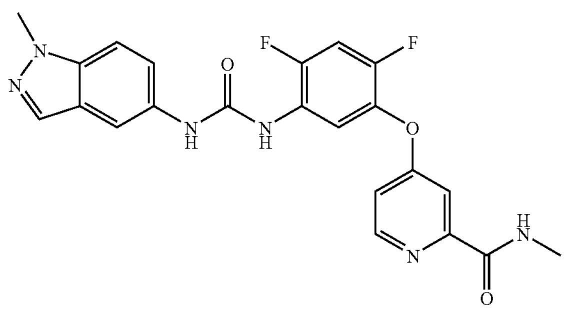 | RT = 2.10 | 453 | B-2 | C-2 | E-1 |
| 57 | 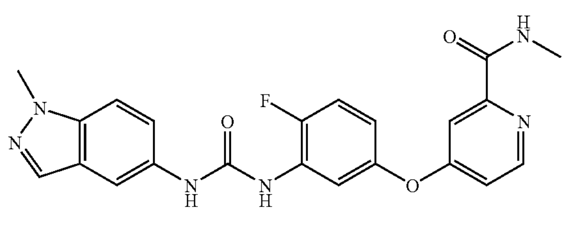 | RT = 1.95 | 435 | B-2 | C-1 | E-1 |
| 58 | 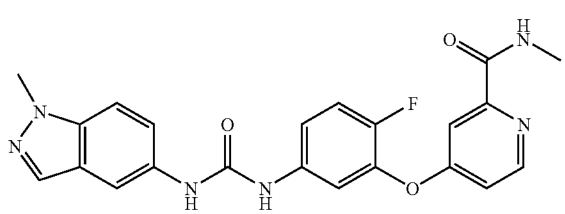 | RT = 2.02 | 435 | B-2 | C-1 | E-1 |

TABLE 1-continued

Examples Synthesized using Method E

| Example | Structure | R_f (TLC solvent) Or RT (min)* | LC/MS ([M+H]+) | Synthesis of (III) or (V)** | Synthesis of (II) | Synthesis of (I) |
|---|---|---|---|---|---|---|
| 59 | 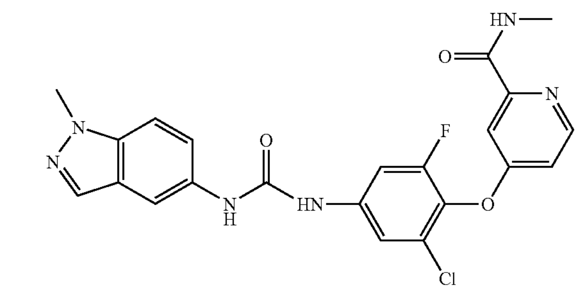 | RT = 2.34 | 469 | B-3 | C-1 | E-1 |
| 60 | 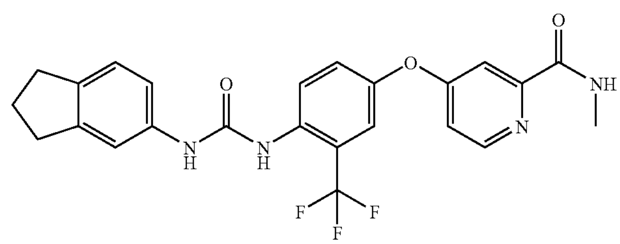 | RT = 2.84 | 471 | B-1 | C-1 | E-1 |
| 61 | 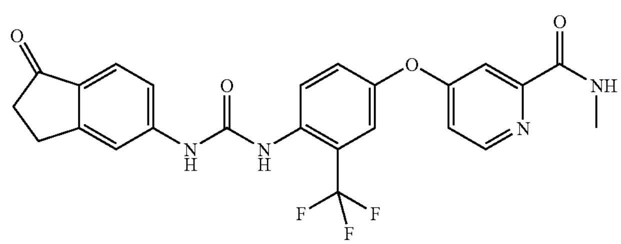 | RT = 2.71 | 485 | B-1 | C-1 | E-1 |
| 62 | 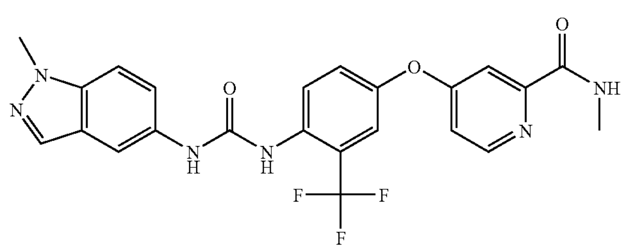 | RT = 2.13 | 485 | B-1 | C-1 | E-1 |
| 63 | 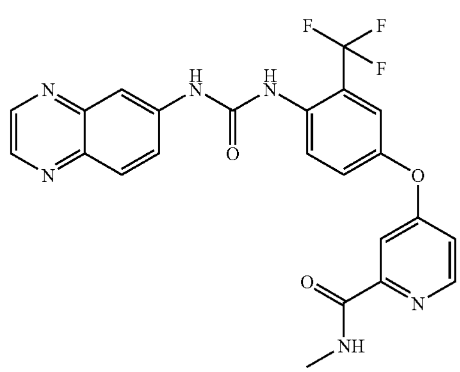 | R_f = 0.42 (100% EtOAc) | 483 | B-1 | C-1 | E-2 |

TABLE 1-continued

Examples Synthesized using Method E

| Example | Structure | R_f (TLC solvent) Or RT (min)* | LC/MS ([M+H]+) | Synthesis of (III) or (V)** | Synthesis of (II) | Synthesis of (I) |
|---|---|---|---|---|---|---|
| 64 | 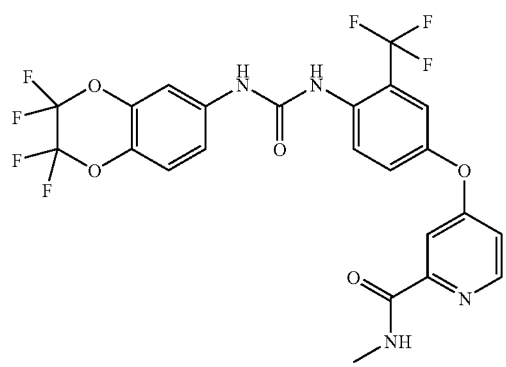 | R_f = 0.35 (50% EtOAc/Hex) | 561 | B-1 | C-1 | E-2 |
| 65 | 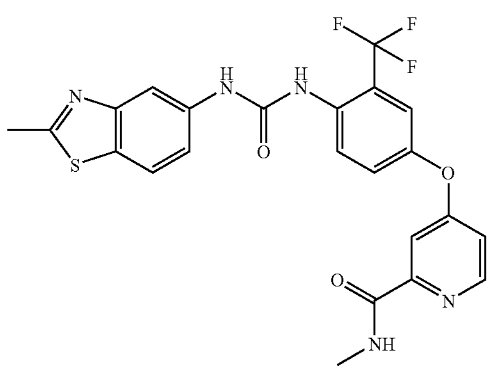 | R_f = 0.63 (100% EtOAc) | 502 | B-1 | C-1 | E-2 |
| 66 | 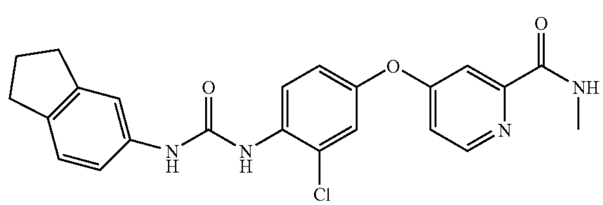 | RT = 2.70 | 451 | comm | C-2 | E-1 |
| 67 | 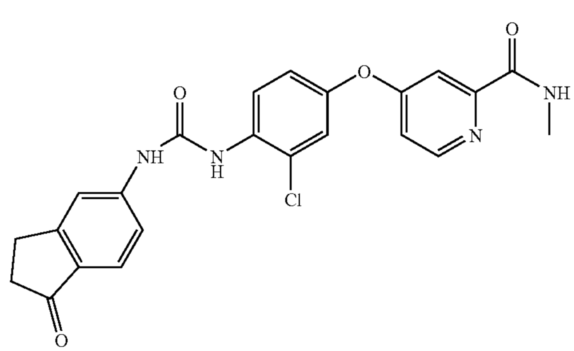 | RT = 3.25 | 437 | comm | C-2 | E-1 |

TABLE 1-continued

Examples Synthesized using Method E

| Example | Structure | R_f (TLC solvent) Or RT (min)* | LC/MS ([M + H]+) | Synthesis of (III) or (V)** | Synthesis of (II) | Synthesis of (I) |
|---|---|---|---|---|---|---|
| 68 | 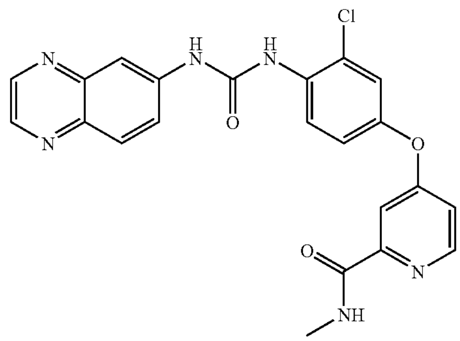 | R_f = 0.41 (100% EtOAc) | 449 | comm | C-2 | E-2 |
| 69 | 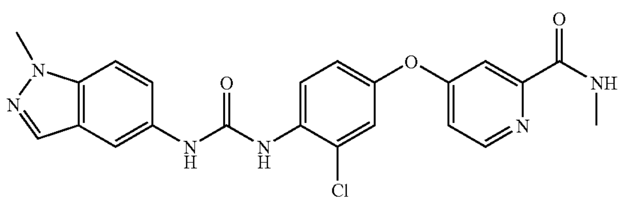 | R_f = 0.52 (5% MeOH/DCM) | 451 | comm | C-2 | E-1 |
| 70 | 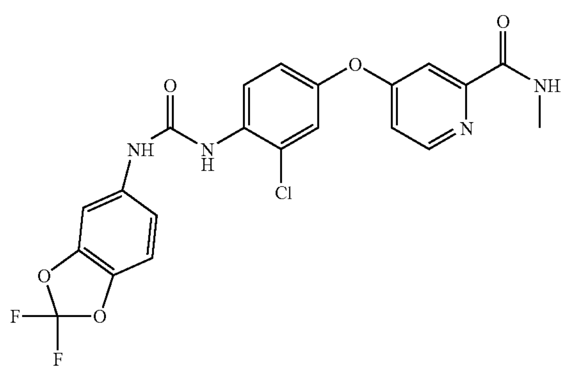 | R_f = 0.37 (50% EtOAc/Hex) | 477 | comm | C-2 | E-1 |
| 71 | 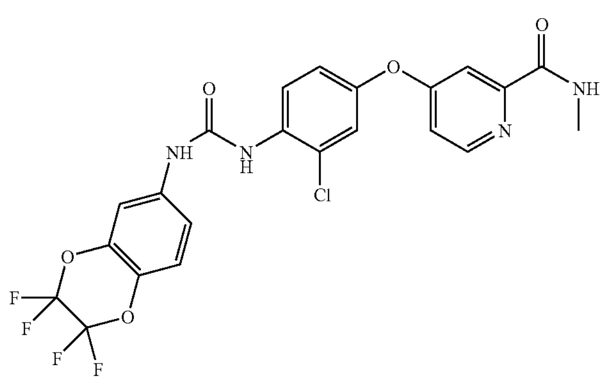 | R_f = 0.26 (50% EtOAc/Hex) | 527 | comm | C-2 | E-1 |

//

TABLE 1-continued

Examples Synthesized using Method E

| Example | Structure | R_f (TLC solvent) Or RT (min)* | LC/MS ([M+H]+) | Synthesis of (III) or (V)** | Synthesis of (II) | Synthesis of (I) |
|---|---|---|---|---|---|---|
| 72 | 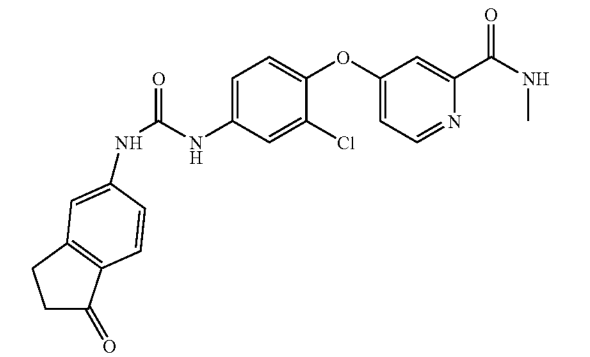 | R_f = 0.46 (50% EtOAc/Hex) | 451 | comm | C-2 | E-1 |
| 73 | 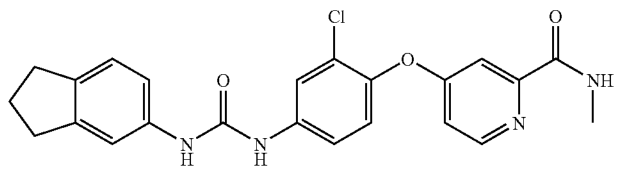 | R_f = 0.56 (5% MeOH/ DCM) | 437 | comm | C-2 | E-1 |
| 74 | 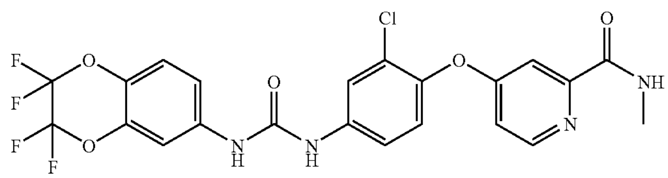 | R_f = 0.57 (5% MeOH/ DCM) | 527 | comm | C-2 | E-1 |
| 75 | 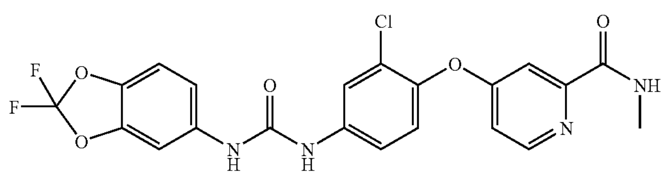 | R_f = 0.57 (5% MeOH/ DCM) | 477 | comm | C-2 | E-1 |
| 76 | 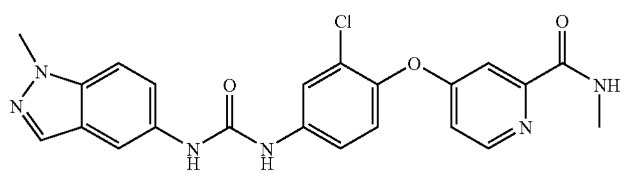 | R_f = 0.23 (5% MeOH/ DCM) | 451 | comm | C-2 | E-1 |
| 77 | 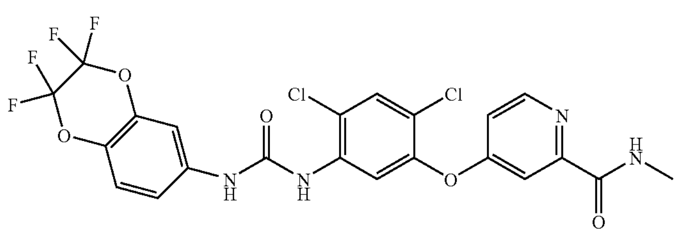 | R_f = 0.47 (5% MeOH/ DCM) | 561 | B-6 | C-2 | E-1 |
| 78 | 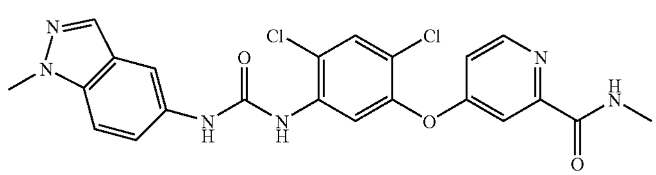 | R_f = 0.38 (5% MeOH/ DCM) | 485 | B-6 | C-2 | E-1 |

TABLE 1-continued

Examples Synthesized using Method E

| Example | Structure | R_f (TLC solvent) Or RT (min)* | LC/MS ([M + H]+) | Synthesis of (III) or (V)** | Synthesis of (II) | Synthesis of (I) |
|---|---|---|---|---|---|---|
| 79 | 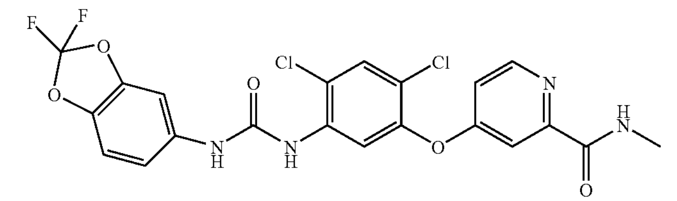 | R_f = 0.47 (5% MeOH/DCM) | 511 | B-6 | C-2 | E-1 |
| 80 | 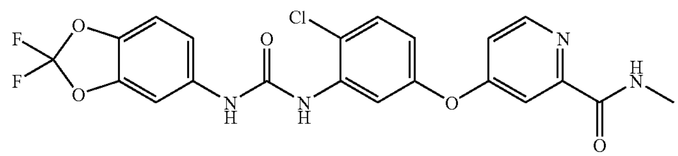 | RT = 3.79 | 477 | comm | C-1 | E-1 |
| 81 | 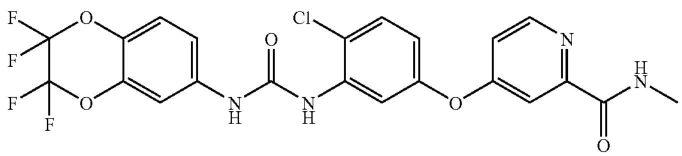 | RT = 3.19 | 527 | comm | C-1 | E-1 |
| 82 | 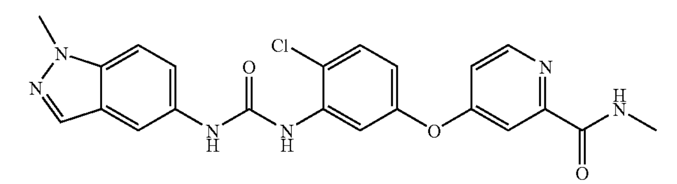 | RT = 3.19 | 451 | comm | C-1 | E-1 |
| 83 | 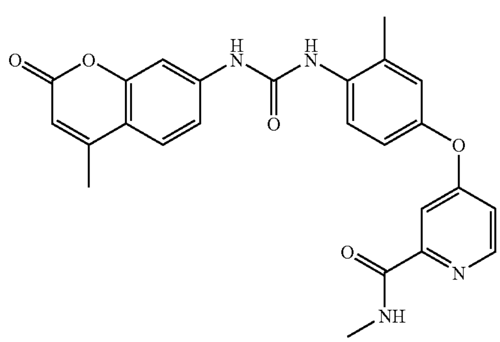 | R_f = 0.64 (100% EtOAc) | 459 | comm | C-1 | E-2 |
| 84 | 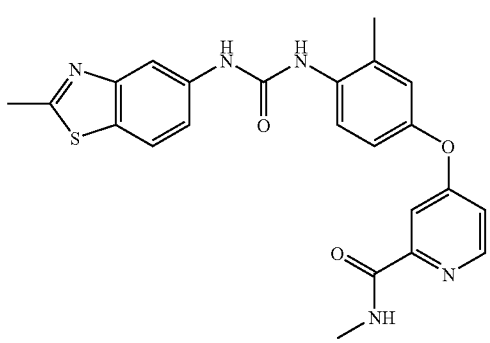 | R_f = 0.35 (100% EtOAc) | 448 | comm | C-1 | E-2 |

TABLE 1-continued

Examples Synthesized using Method E

| Example | Structure | $R_f$(TLC solvent) Or RT (min)* | LC/MS ([M + H]+) | Synthesis of (III) or (V)** | Synthesis of (II) | Synthesis of (I) |
|---|---|---|---|---|---|---|
| 85 | 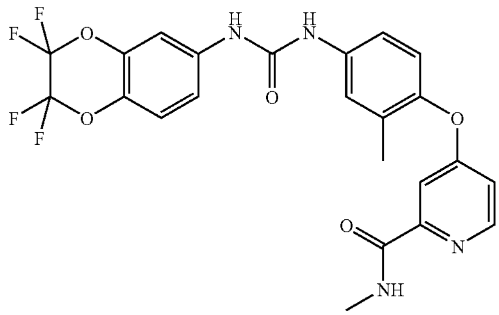 | $R_f$ = 0.16 (50% EtOAc) | 507 | comm | C-1 | E-2 |
| 86 | 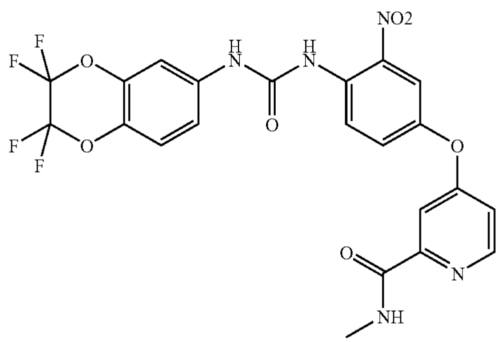 | $R_f$ = 0.41 (50% EtOAc) | 538 | comm | C-1 | E-2 |
| 87 | 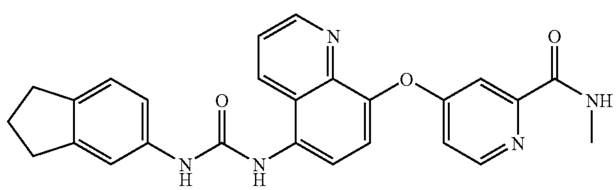 | $R_f$ = 0.45 (15% MeOH/ DCM) | 512 | B-1 | C-1 | E-1 |
| 88 | 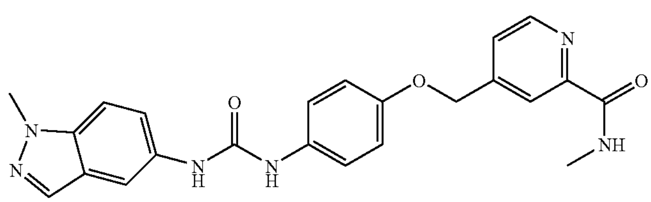 | RT = 1.96 | 431 | comm | D-2 | E-1 |
| 89 | 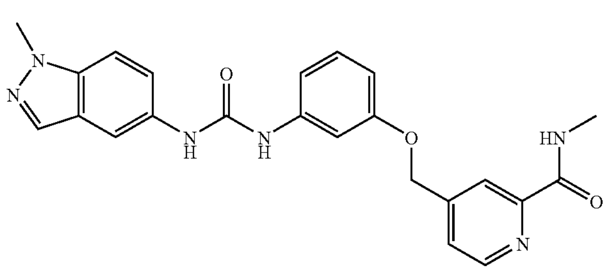 | RT = 2.03 | 431 | comm | D-2 | E-1 |

TABLE 1-continued

Examples Synthesized using Method E

| Example | Structure | R$_f$ (TLC solvent) Or RT (min)* | LC/MS ([M + H]+) | Synthesis of (III) or (V)** | Synthesis of (II) | Synthesis of (I) |
|---|---|---|---|---|---|---|
| 90 | 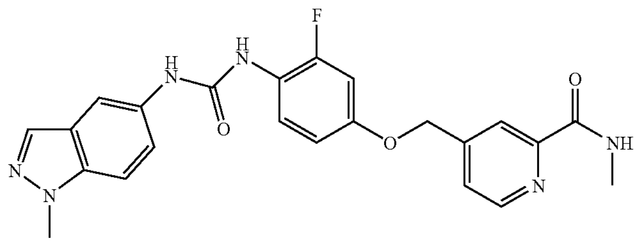 | RT = 2.04 | 448 | comm | D-2 | E-1 |
| 91 | 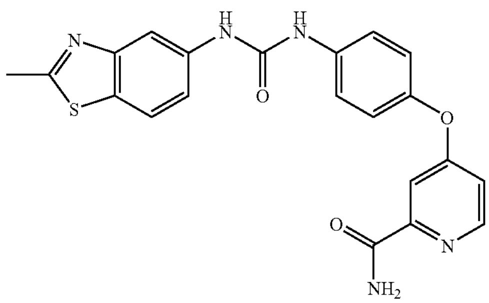 | R$_f$ = 0.19 (100% EtOAc) | 420 | comm | C-1 | E-2 |
| 92 | 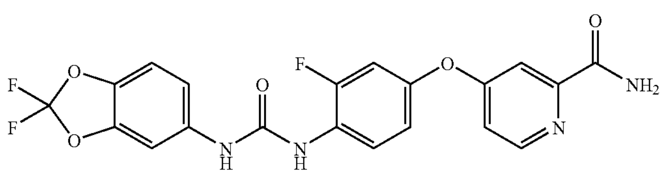 | RT = 3.55 | 447 | B-1 | C-1 | E-1 |
| 93 | 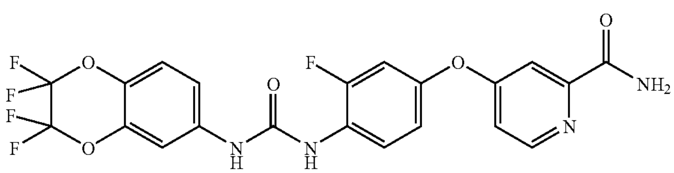 | RT = 3.80 | 497 | B-1 | C-1 | E-1 |
| 94 | 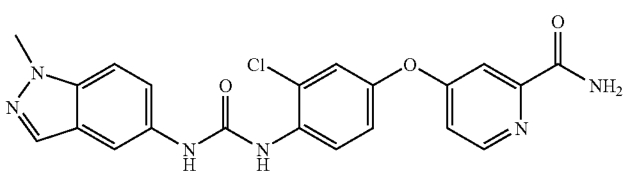 | RT = 3.03 | 437 | comm | C-1 | E-1 |
| 95 | 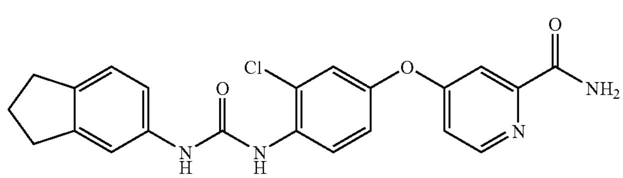 | RT = 3.12 | 423 | comm | C-1 | E-1 |
| 96 | 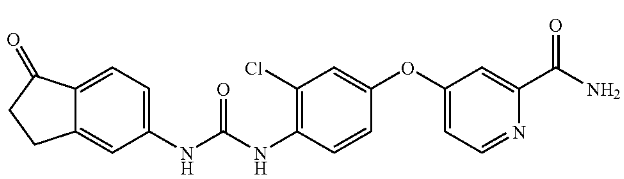 | RT = 2.57 | 437 | comm | C-1 | E-1 |

TABLE 1-continued
Examples Synthesized using Method E
| Example | Structure | R_f (TLC solvent) Or RT (min)* | LC/MS ([M + H]+) | Synthesis of (III) or (V)** | Synthesis of (II) | Synthesis of (I) |
|---|---|---|---|---|---|---|
| 97 | 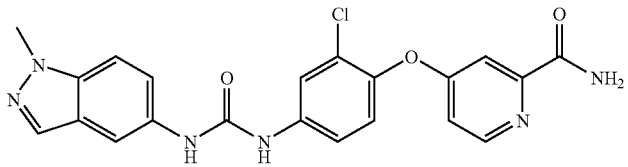 | RT = 2.48 | 437 | comm | C-1 | E-1 |
| 98 | 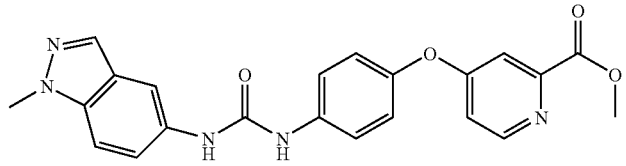 | RT = 2.88 | 418 | comm | C-3 | E-1 |
| 99 | 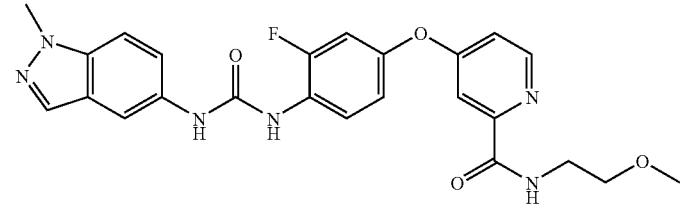 | RT = 2.08 | 479 | B-1 | C-5 | E-1 |
| 100 | 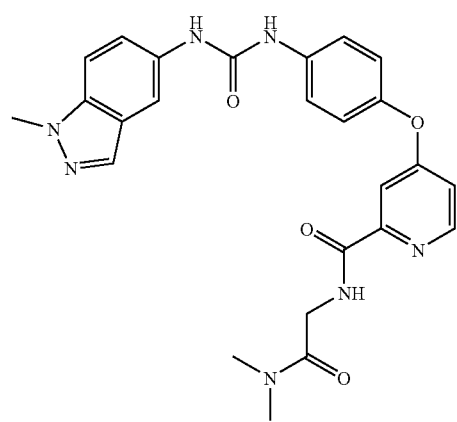 | R_f = 0.58 (10% MeOH/DCM) | 488 | comm | C-5 | E-2 |
| 101 | 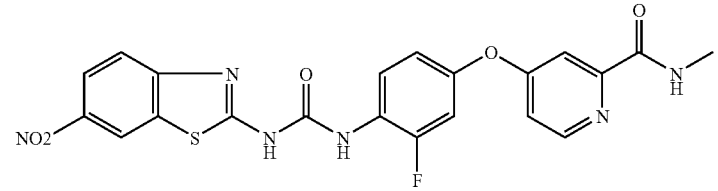 | RT = 3.04 | 483 | B-1 | C-1 | E-1 |
| 102 | 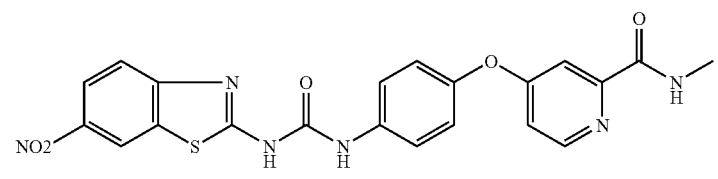 | RT = 3.12 | 465 | comm | C-1 | E-1 |

TABLE 1-continued

Examples Synthesized using Method E

| Example | Structure | R$_f$ (TLC solvent) Or RT (min)* | LC/MS ([M + H]+) | Synthesis of (III) or (V)** | Synthesis of (II) | Synthesis of (I) |
|---|---|---|---|---|---|---|
| 103 | 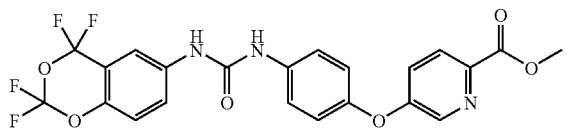 | RT = 3.20 | 456 | comm | C-1 | E-1 |

*The following are the LCMS conditions: HPLC - electrospray mass spectra (HPLC ES-MS) were obtained using a Gilson HPLC system equipped with two Gilson 306 pumps, a Gilson 215 Autosampler, a Gilson diode array detector, a YMC Pro C-18 column (2 × 23 mm, 120 A), and a Micromass LCZ single quadrupole mass spectrometer with z-spray electrospray ionization. Spectra were scanned from 120-1000 amu over 2 seconds. ELSD (Evaporative Light Scattering Detector) data was also acquired as an analog channel. Gradient elution was used with Buffer A as 2% acetonitrile in water with 0.02% TFA and Buffer B as 2% water in Acetonitrile with 0.02% TFA at 1.5 mL/min. Samples were eluted as follows: 90% A for 0.5 min ramped to 95% B over 3.5 min and held at 95% B for 0.5 min and then the column is brought back to initial conditions over 0.1 min. Total run time is 4.8 min.
**comm means commercially available.

Other compounds of Formula I may be prepared using the methods described herein or other methods known in the art, and using the appropriate starting materials and/or intermediates that would be readily recognized by those skilled in the art.

General Method F: Substituted Ureas Via Aniline Addition into Aryl Isocyanates

EXAMPLE 104

Method F-1a

Preparation of N-methyl-4-[4-({[(2,2,4,4-tetrafluoro-4H-1,3-benzodioxin-6-yl)amino]carbonyl}-amino)phenoxy]pyridine-2-carboxamide

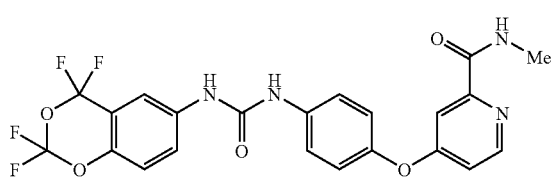

To a slurry of 4-(2-(N-methylcarbamoyl)-4-pyridyloxy) aniline (143 mg, 0.59 mmol) in DCM (1 mL) at 0° C. was added dropwise a solution of 2,2,4,4-tetrafluoro-6-isocyanato-1,3-benzodioxene (150 mg, 0.60 mmol) in DCM (1 mL). The reaction mixture was stirred at room temperature for 12 h. The resulting precipitate was filtered and washed with DCM to afford the desired product (125 mg, 41%) as a white solid.

$^1$H-NMR (DMSO-d$_6$) δ 9.14 (s, 1H), 9.00 (s, 1H), 8.76 (q, J=4.5 Hz, 1H), 8.48 (d, J=5.4 Hz, 1H), 8.10 (d, J=2.7 Hz, 1H), 7.68 (dd, J=9.0, 2.7 Hz, 1H), 7.60 to 7.55 (m, 2H), 7.43 (d, J=9.0 Hz, 1H), 7.36 (d, J=2.4 Hz, 1H), 7.20 to 7.11 (m, 3H), 2.76 (d, J=4.5 Hz, 3H); MS LC-MS [M+H]$^+$=493.1, RT=3.27 min.

EXAMPLE 105

Method F-1b

Preparation of Methyl 4-[3-({[(2,2,4,4-tetrafluoro-4H-1,3-benzodioxin-6-yl)amino]-carbonyl}amino)phenoxy]pyridine-2-carboxylate To a stirring solution of 2,2,4,4-tetrafluoro-6-isocyanato-1,3-benzodioxene (0.816 g, 3.28 mmol) was added 4-(3-aminophenoxy)pyridine-2-carboxylic acid methyl ester (0.800 g, 3.28 mmol) in DCM (13 mL) in portions. The homogenous contents turned white and opaque within 1 min. of addition, and were allowed to stir at room temperature for 12 h. The heterogenous mixture was filtered, and solid product repeatedly washed with DCM to remove residual starting material. The desired product was collected as a white powder, 1.36 g (83%). $^1$H-NMR (DMSO-d$_6$) δ 9.08 (d, 2H), 8.59 (s, 1H), 8.07 (s, 1H), 7.60 (dd, 1H), 7.37 (m, 4H), 7.25 (d, 1H), 7.20 (dd, 1H), 6.80 (d, 1H), 3.82 (s, 3H); MS LC MS [M+H]$^+$=494.1, RT=3.23 min.

EXAMPLE 107

Method F-2

Preparation of 4-(3-fluoro-4-{[(quinoxalin-2-ylamino)carbonyl]amino}phenoxy)-N-methyl-pyridine-2-carboxamide

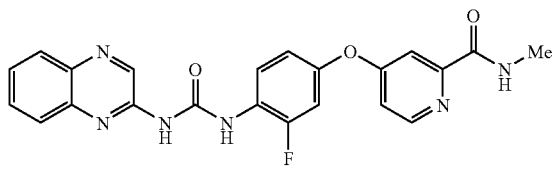

To a solution of 4-[4-amino-3-(fluoro)phenoxy]-N-methylpyridine-2-carboxamide (150.0 mg, 0.57 mmol) in anhydrous THF (5.7 mL) was added triphosgene (63 mg, 0.21 mmol, 0.37 eq) and diisopropylethyl amine (0.12 mL, 0.69 mmol, 1.2 eq), and the reaction mixture was stirred at 75° C. After 3 h a solution of 2-aminoquinoxaline (83.3 mg, 0.57 mmol, 1.0 eq) in anhydrous DMF (2.8 mL) was added, and the reaction mixture was stirred at 75° C. for 17 h. The reaction mixture was partitioned between EtOAc and water, and the organic layer was washed with water and brine, dried over MgSO$_4$, filtered, and evaporated under reduced pressure. The crude was absorbed onto silica and purified by MPLC (biotage) eluted with 10% MeOH/EtOAc. Trituration from DCM/MeOH afforded 25.0 mg (10.1%) of the title product as a yellow solid. $^1$H-NMR (DMSO-d$_6$) δ 11.75 (s, 1H), 10.75 (s, 1H), 8.89 (s, 1H), 8.79 (br q, J=5.1 Hz, 1H), 8.53 (d, J=6.0 Hz, 1H), 8.38 (t, J=9.0 Hz, 1H), 8.01 (d, J=8.1 Hz, 1H), 7.82 (d, J=3.9 Hz, 2H), 7.70 to 7.64 (m, 1H), 7.47 to 7.42 (m, 2H), 7.20 (dd, J=5.4, 2.4 Hz, 1H), 7.14 (d, J=8.7 Hz, 1H) 2.78 (d, J=4.8 Hz, 3H); TLC (100% EA), R$_f$=0.20; MS LC-MS [M+H]$^+$=433), RT=2.86 min.

EXAMPLE 108

Method F-3

Preparation of 4-(3-{[(1H-indazol-5-ylamino)carbonyl]amino}phenoxy)-N-methylpyridine-2-carboxamide dihydrochloride

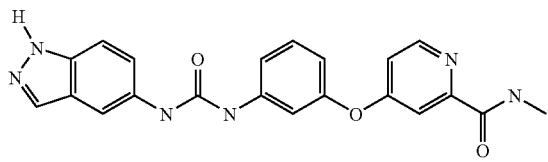

Step 1: Preparation of 5-Isocyanato-indazole-1-carboxylic acid tert-butyl ester

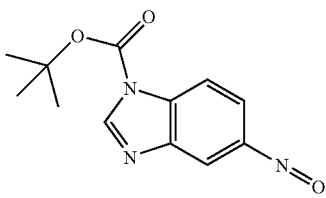

A 0° C. mixture of 1.93M solution of phosgene in toluene (8.9 mL, 17 mmol) and CH$_2$Cl$_2$ (80 mL) was added dropwise a solution of 5-amino-indazole-1-carboxylic acid tert-butyl ester (2 g, 8.5 mmol) and pyridine (3.5 mL, 43 mmol) in CH$_2$Cl$_2$ (20 mL). The reaction mixture was stirred for 1.5 h, then concentrated under reduced pressure. The residue was dissolved in CH$_2$Cl$_2$ (100 mL) and was used without further purification.

Step 2: Preparation of N-(1-tert-Butylcarboxyl-indazo-5-yl)-N'-[(3-(2-(N-methylcarboxyl)-4-Pyridyloxy)phenyl]urea

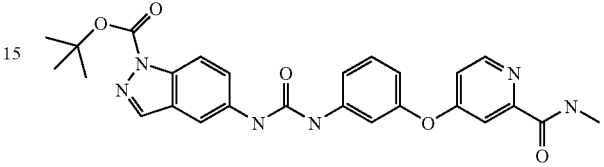

To a solution of 4-(3-Aminophenoxy)pyridine-2-carboxamide (108 mg, 0.39 mmol) in CH$_2$Cl$_2$ (5 mL) was added the solution of crude 5-isocyanato-indazole-1-carboxylic acid tert-butyl ester (0.39 mmol) in CH$_2$Cl$_2$ (5 mL). The reaction mixture was is stirred at room temperature for 12 days. The resulting slurry was diluted with about 1 mL MeOH. The resulting clear solution was purified by MPLC (Biotage) eluted with 70% EtOAc/hex followed by 100% EtOAc to get N-(1-tert-Butylcarboxyl-indazo-5-yl)-N'-[(3-(2-(N-methylcarboxyl)-4-pyridyloxy)phenyl]urea (63 mg, 32%) as a white solid: TLC (80% EtOAc/hex) R$_f$=0.36; ES-LCMS (rel abundance) m/z 503 (MH$^+$, 100%); HRMS calc 503.203744, found 503.20344.

Step 3: Preparation of the title compound 4-(3-{[(1H-indazol-5-ylamino)carbonyl]amino}-phenoxy)-N-methylpyridine-2-carboxamide dihydrochloride N-(1-tert-Butylcarboxyl-indazo-5-yl)-N'-[(3-(2-(N-methylcarboxyl)-4-pyridyloxy)-phenyl]urea (29 mg, 0.06 mmol) was taken up into a 2M HCl solution in ether (5 mL, 10 mmol). The reaction mixture was stirred overnight. The resulting mixture was concentrated under reduced pressure to get the title compound (28 mg, 100%) as a yellow solid: free base TLC (EtOAc) R$_f$ 0.27; ES-LCMS (rel abundance) m/z 403 (MH$^+$, 100%); HRMS calc 403.15132, found 403.15112. Additional compounds illustrated in Table 2 were prepared as described above by choosing the appropriate starting materials that are readily available and/or the synthesis of which is taught herein, and using the processes of Method F described above or other standard chemical processes known in the art.

TABLE 2

Examples Synthesized using Method F

| Example | Structure | R$_f$(TLC solvent) Or RT (min)* | LC/MS ([M + H]+) | Synthesis of (V)** | Synthesis of (II) | Synthesis of (I) |
|---|---|---|---|---|---|---|
| 109 | 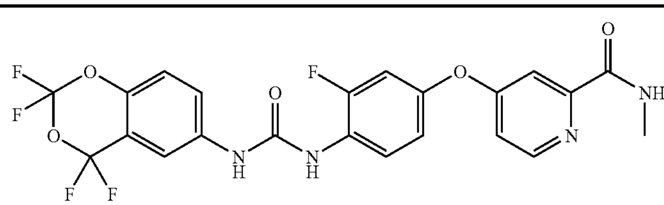 | R$_f$= 0.52 (5% MeOH/ DCM) | 511 | B-1 | C-1 | F-1 |

TABLE 2-continued

Examples Synthesized using Method F

| Example | Structure | R$_f$(TLC solvent) Or RT (min)* | LC/MS ([M + H]+) | Synthesis of (V)** | Synthesis of (II) | Synthesis of (I) |
|---|---|---|---|---|---|---|
| 110 | 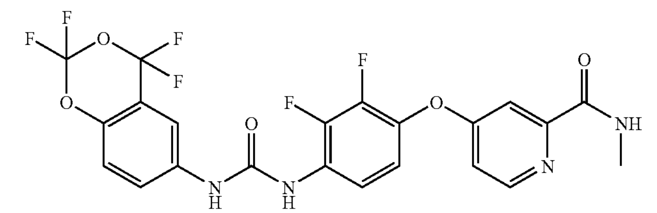 | R$_f$ = 0.22 (35% EtOAc/Hex) | 529 | B-4 | C-1 | F-1 |
| 111 | 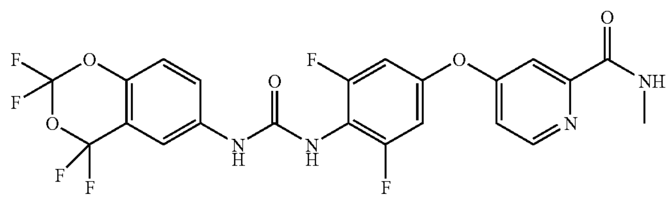 | R$_f$ = 0.07 (50% EtOAc/Hex) | 529 | B-4 | C-1 | F-1 |
| 112 | 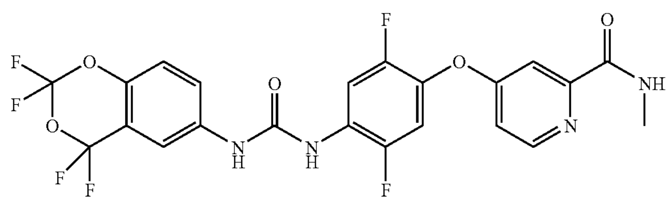 | R$_f$ = 0.11 (50% EtOAc/Hex) | 529 | B-4 | C-1 | F-1 |
| 113 | 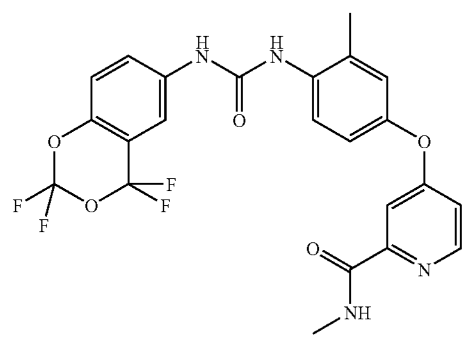 | R$_f$ = 0.18 (50% EtOAc/Hex) | 507 | comm | C-1 | F-1 |
| 114 | 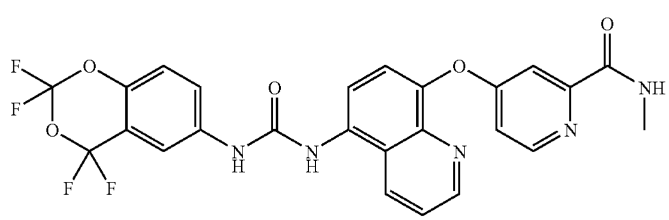 | R$_f$ = 0.25 (15% MeOH/DCM) | 544 | B-1 | C-1 | F-1 |
| 115 | 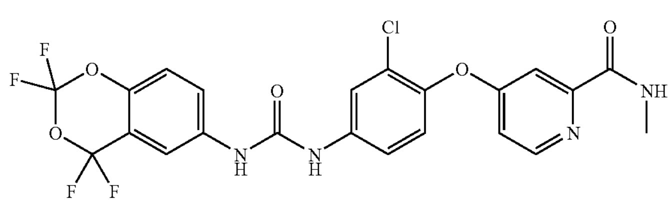 | R$_f$ = 0.13 (50% EtOAc/Hex) | 527 | comm | C-2 | F-1 |

TABLE 2-continued

Examples Synthesized using Method F

| Example | Structure | $R_f$(TLC solvent) Or RT (min)* | LC/MS ([M + H]+) | Synthesis of (V)** | Synthesis of (II) | Synthesis of (I) |
|---|---|---|---|---|---|---|
| 116 | 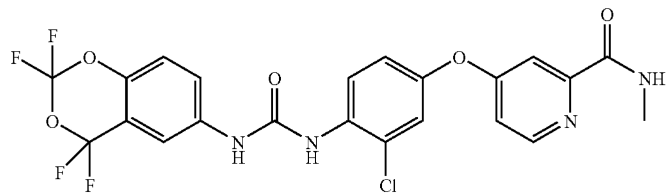 | $R_f$ = 0.20 (50% EtOAc/Hex) | 527 | comm | C-2 | F-1 |
| 117 | 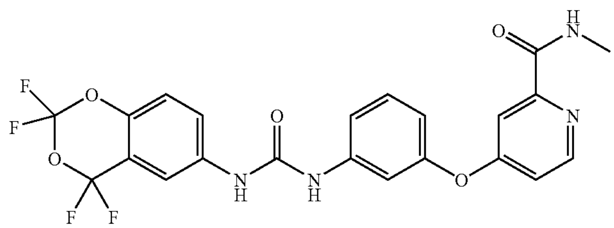 | RT = 3.31 | 493 | comm | C-1 | F-1 |
| 118 | 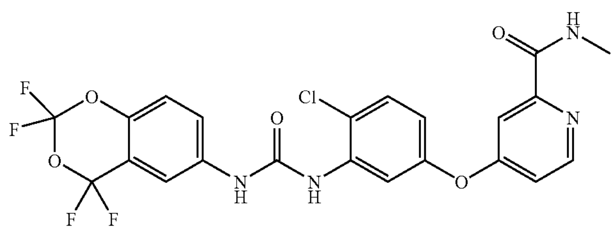 | RT = 3.97 | 527 | comm | C-1 | F-1 |
| 119 | 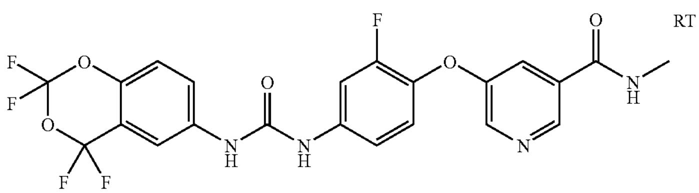 | RT = 3.64 | 511 | comm | D-1 | F-1 |
| 120 | 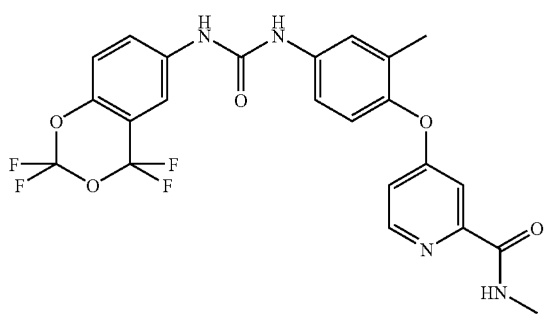 | $R_f$ = 0.20 (50% EtOAc/Hex) | 507 | comm | C-1 | F-1 |
| 121 | 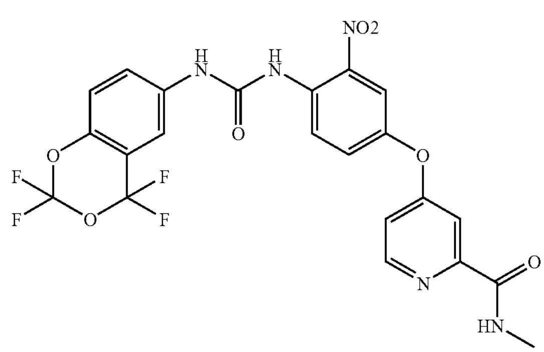 | $R_f$ = 0.35 (50% EtOAc/Hex) | 538 | comm | C-1 | F-1 |

TABLE 2-continued

Examples Synthesized using Method F

| Example | Structure | $R_f$(TLC solvent) Or RT (min)* | LC/MS ([M + H]+) | Synthesis of (V)** | Synthesis of (II) | Synthesis of (I) |
|---|---|---|---|---|---|---|
| 122 | 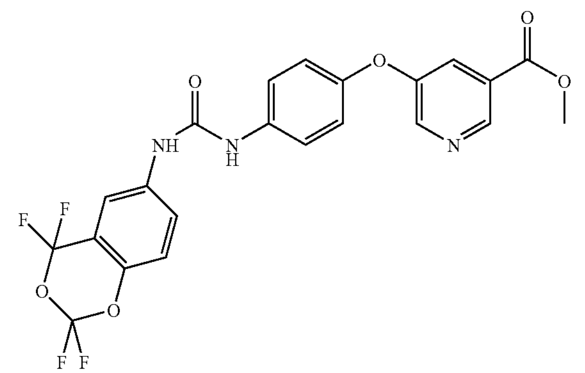 | $R_f$ = 0.59 (75% EtOAc/Hex) | 494 | comm | D-1 | F-1 |
| 123 | 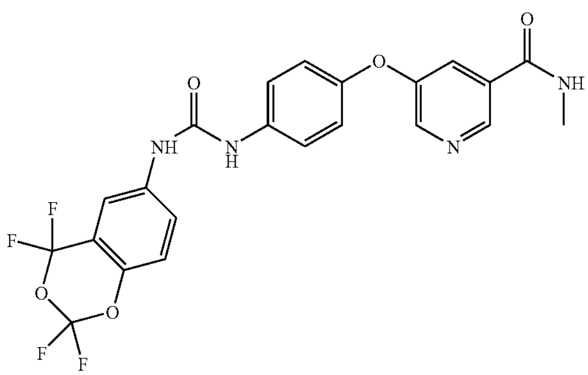 | $R_f$ = 0.45 (10% MeOH/ DCM) | 493 | comm | D-1 | F-1 |
| 124 | 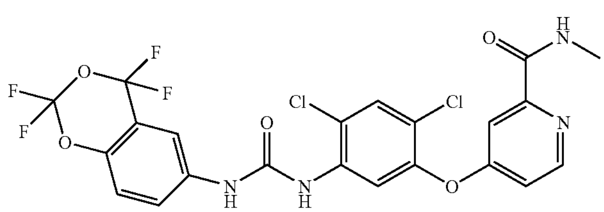 | $R_f$ = 0.76 (75% EtOAc/Hex) | 561 | B-6 | C-2 | F-1 |
| 125 | 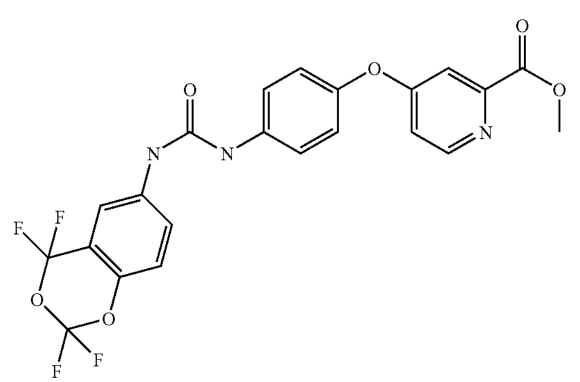 | RT = 3.23 | 493 | comm | C-3 | F-1 |

TABLE 2-continued

Examples Synthesized using Method F

| Example | Structure | $R_f$(TLC solvent) Or RT (min)* | LC/MS ([M + H]+) | Synthesis of (V)** | Synthesis of (II) | Synthesis of (I) |
|---|---|---|---|---|---|---|
| 126 | 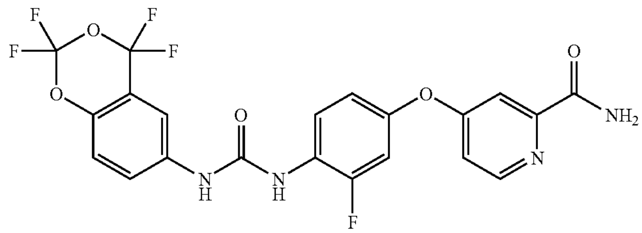 | $R_f$ = 0.35 (60% EtOAc/Hex) | 497 | B-1 | C-1 | F-1 |
| 127 | 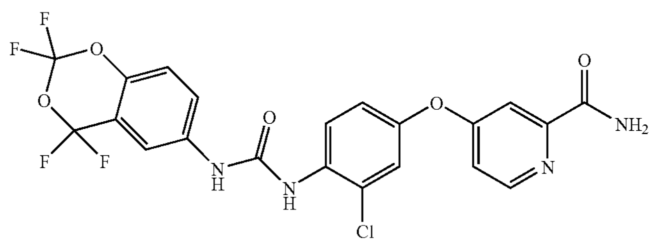 | RT = 3.37 | 513 | comm | C-1 | F-1 |
| 128 | 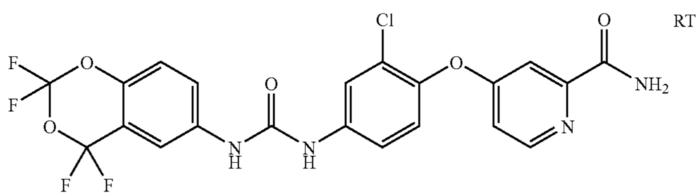 | RT = 3.85 | 513 | comm | C-1 | F-1 |
| 129 | 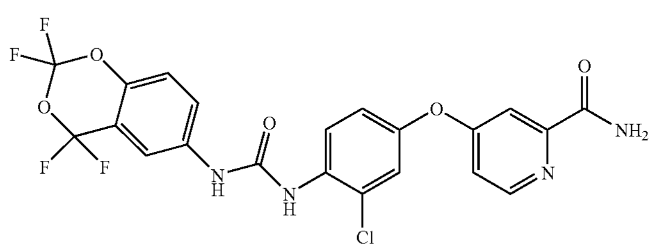 | RT = 3.37 | 513 | comm | C-1 | F-1 |
| 130 | 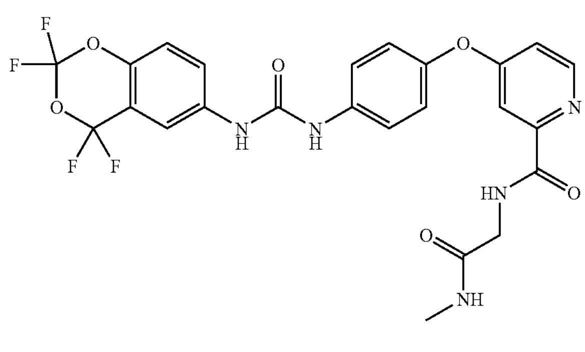 | $R_f$ = 0.16 (5% MeOH/ EtOAc) | 550 | comm | C-5 | F-1 |

TABLE 2-continued

Examples Synthesized using Method F

| Example | Structure | R$_f$(TLC solvent) Or RT (min)* | LC/MS ([M + H]+) | Synthesis of (V)** | Synthesis of (II) | Synthesis of (I) |
|---|---|---|---|---|---|---|
| 131 | 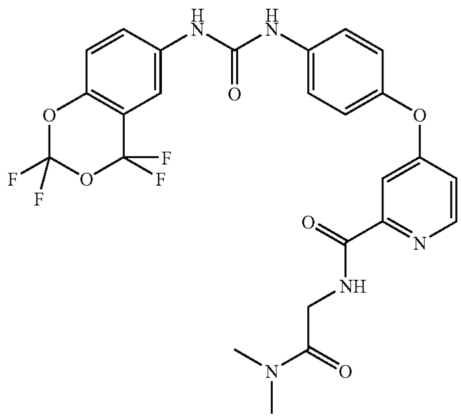 | R$_f$ = 0.55 (10% MeOH/ DCM) | 564 | comm | C-5 | F-1 |
| 132 | 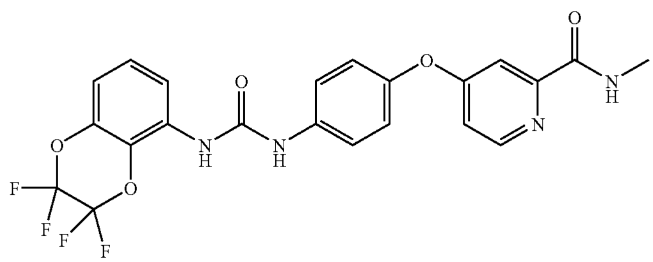 | RT = 3.33 | 493 | comm | C-1 | F-1 |
| 133 | 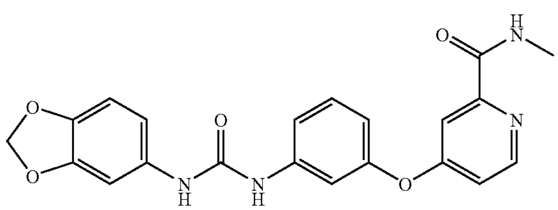 | RT = 2.64 | 407 | comm | C-1 | F-1 |
| 134 | 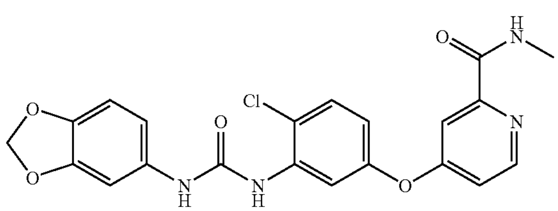 | RT = 3.41 | 441 | comm | C-1 | F-1 |
| 135 | 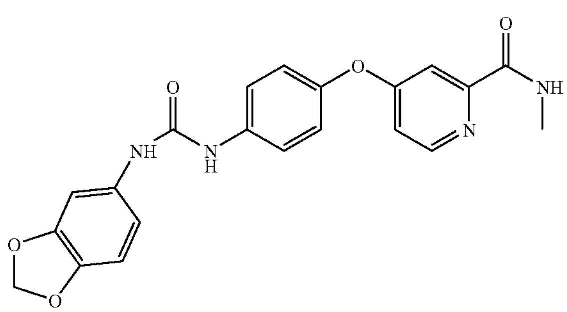 | R$_f$ = 0.50 (5% MeOH/ DCM) | 407 | comm | C-1 | F-1 |

TABLE 2-continued

Examples Synthesized using Method F

| Example | Structure | R*f*(TLC solvent) Or RT (min)* | LC/MS ([M + H]+) | Synthesis of (V)** | Synthesis of (II) | Synthesis of (I) |
| --- | --- | --- | --- | --- | --- | --- |
| 136 | 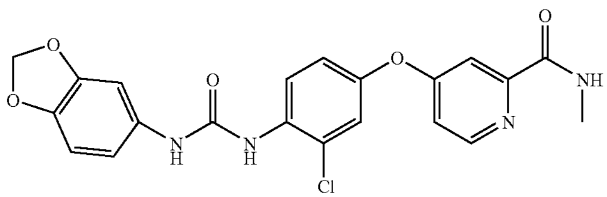 | R*f* = 0.36 (50% EtOAc/Hex) | 441 | comm | C-2 | F-1 |
| 137 | 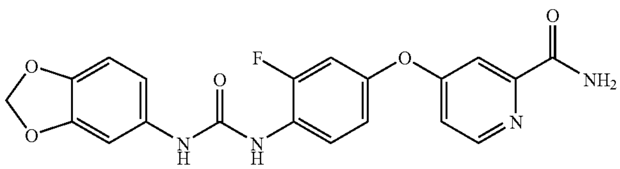 | RT = 2.58 | 411 | A-1 | C-1 | F-1 |
| 138 | 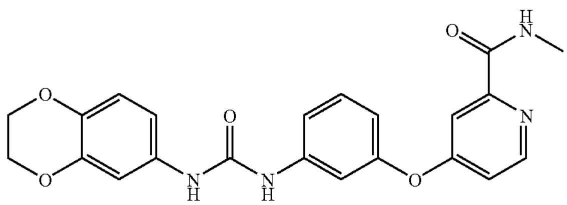 | RT = 2.62 | 421 | comm | C-1 | F-1 |
| 139 | 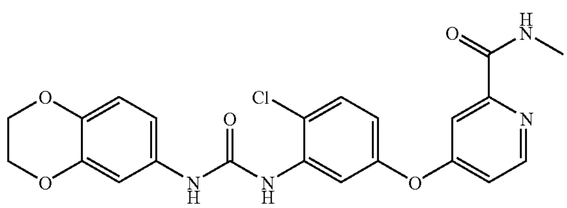 | RT = 3.28 | 455 | comm | C-1 | F-1 |
| 140 | 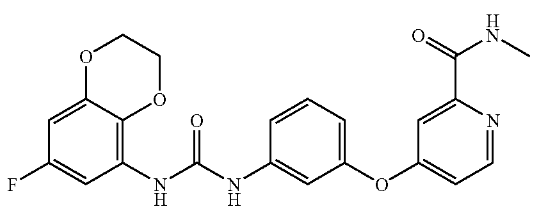 | RT = 3.36 | 461 (Na+) | comm | C-1 | F-1 |
| 141 | 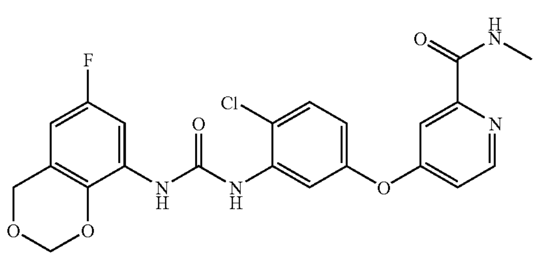 | RT = 3.58 | 495 (Na+) | comm | C-1 | F-1 |

TABLE 2-continued

Examples Synthesized using Method F

| Example | Structure | $R_f$(TLC solvent) Or RT (min)* | LC/MS ([M + H]+) | Synthesis of (V)** | Synthesis of (II) | Synthesis of (I) |
|---|---|---|---|---|---|---|
| 142 | 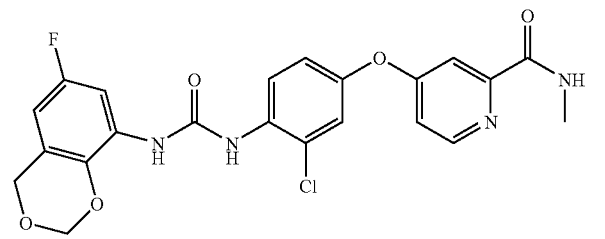 | $R_f$ = 0.40 (50% EtOAc/Hex) | 473 | comm | C-1 | F-1 |
| 143 | 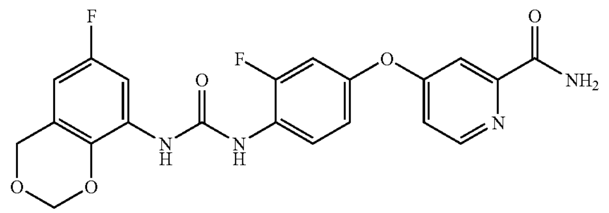 | RT = 2.84 | 443 | B-1 | C-1 | F-1 |
| 144 | 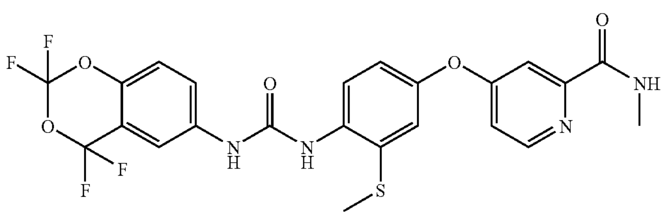 | RT = 3.55 | 539 | B-7 | C-2 | F-1 |

*The following are the LCMS conditions: HPLC - electrospray mass spectra (HPLC ES-MS) were obtained using a Gilson HPLC system equipped with two Gilson 306 pumps, a Gilson 215 Autosampler, a Gilson diode array detector, a YMC Pro C-18 column (2 × 23 mm, 120 A), and a Micromass LCZ single quadrupole mass spectrometer with z-spray electrospray ionization. Spectra were scanned from 120-1000 amu over 2 seconds. ELSD (Evaporative Light Scattering Detector) data was also acquired as an analog channel. Gradient elution was used with Buffer A as 2% acetonitrile in water with 0.02% TFA and Buffer B as 2% water in Acetonitrile with 0.02% TFA at 1.5 mL/min. Samples were eluted as follows: 90% A for 0.5 min ramped to 95% B over 3.5 min and held at 95% B for 0.5 min and then the column is brought back to initial conditions over 0.1 min. Total run time is 4.8 min.
**comm means commercially available.

Other compounds of Formula I may be prepared using the methods described herein or other methods known in the art, and using the appropriate starting materials and/or intermediates that would be readily recognized by those skilled in the art.

General Methods G and H: Preparations of Extended Amides via Ester Displacement by Nucleophilic Alkyl Amines

EXAMPLE 145

Method G-1a

Preparation of N-[3-(1H-imidazol-1-yl)propyl]-4-[4-({[(2,2,4,4-tetrafluoro-4H-1,3-benzodioxin-6-yl)amino]carbonyl}amino)phenoxy]pyridine-2-carboxamide To a mixture of methyl 4-[4-({[(2,2,4,4-tetrafluoro-4H-1,3-benzodioxin-6-yl)amino]-carbonyl}amino)phenoxy]pyridine-2-carboxylate (80 mg, 0.16 mmol) and magnesium chloride (16 mg, 0.16 mmol) in THF (2 ml) was added 1-(3-aminopropyl)imidazole (0.04 mL, 0.32 mmol) at room temperature. The reaction mixture was stirred at room temperature for 3 d. The solid was filtered and washed with 10% MeOH in CH$_2$Cl$_2$. The combined filtrate was concentrated to dryness and the residue was purified by column chromatography, eluting with 2 to 5% MeOH/CH$_2$Cl$_2$ to afford 44 mg (45%) of the title compound as a white solid. $^1$H-NMR (DMSO-d$_6$) δ 9.19 (s, 1H), 9.05 (s, 1H), 8.97 (t, 1H), 8.54 (d, 1H), 8.13 (d, 1H), 7.70-7.58 (m, 4H), 7.42 (d, 1H), 7.38 (d, 1H), 7.19-7.16 (m, 4H), 6.87 (s, 1H), 3.97 (t, 2H), 3.24 (q, 2H), 1.95 (quin, 2H); MS LC-MS(MH)$^+$=587.1, RT=3.14 min.

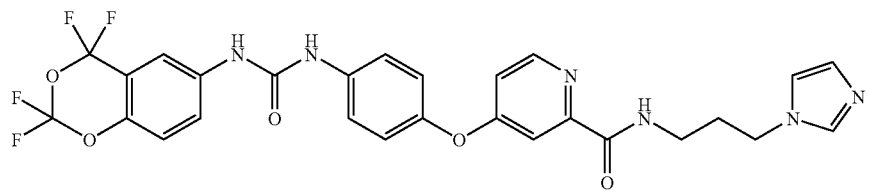

EXAMPLE 146

Method G-1b

Preparation of N-(2-pyrrolidin-1-ylethyl)₄-[4-({[(2,2,4,4-tetrafluoro-4H-1,3-benzodioxin-6-yl)-amino]carbonyl}amino)phenoxy]pyridine-2-carboxamide

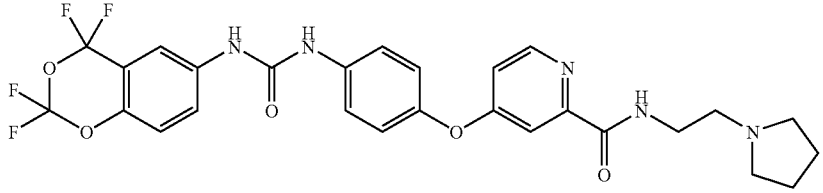

The title compound was prepared in the same manner described for N-[3-(1H-imidazol-1-yl)propyl]-4-[4-({[(2,2,4,4-tetrafluoro-4H-1,3-benzodioxin-6-yl)amino]carbonyl}-amino)phenoxy]pyridine-2-carboxamide, substituting 1-(2-aminoethyl)pyrrolidone for 1-(3-aminopropyl)imidazole. ¹H-NMR (MeOH-d₄) δ 8.45 (d, 1H), 8.00 (d, 1H), 7.65 (dd, 1H), 7.56 (m, 3H), 7.22 (d, 1H), 7.10 (m, 2H), 7.04 (dd, 1H), 3.57 (t, 2H), 2.77 (t, 2H), 2.67 (m, 4H), 1.83 (m, 4H); MS LC-MS [M+H]⁺=576.2, RT=3.16 min.

EXAMPLE 147

Method G-1c

Preparation of N-cyclopropyl-4-[4-({[(1-methyl-1H-indazol-5-yl)amino]-carbonyl}amino)phenoxy]pyridine-2-carboxamide

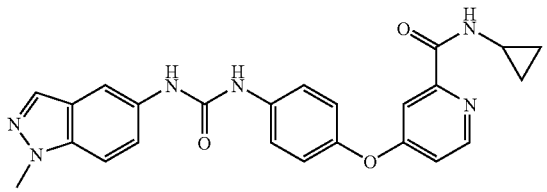

The title compound was prepared in the same manner described for N-[3-(1H-imidazol-1-yl)propyl]-4-[4-({[(2,2,4,4-tetrafluoro-4H-1,3-benzodioxin-6-yl)amino]carbonyl}-amino)phenoxy]pyridine-2-carboxamide, substituting cyclopropylamine for 1-(3-aminopropyl)imidazole and 4-[4-({[(1-methyl-1H-indazol-5-yl)amino]-carbonyl}amino)-phenoxy]pyridine-2-carboxamide for methyl 4-[4-({[(2,2,4,4-tetrafluoro-4H-1,3-benzodioxin-6-yl)amino]carbonyl}amino)phenoxy]pyridine-2-carboxylate. ¹H-NMR (MeOH-d₄/CD₂Cl₂) δ 8.42 (d, J=5.5 Hz, 1H), 7.92 (s, 1H), 7.88 (d, J=2.0 Hz, 1H), 7.45-7.57 (m, 5H), 7.08 (m, 2H), 7.02 (dd, J=5.5, 2.6 Hz, 1H), 4.04 (s, 3H), 2.84 (m, 1H), 0.81 (m, 2H), 0.65 (m, 2H); MS LC-MS [M+H]⁺=443.2, RT=2.51 min.

EXAMPLE 148

Method H-1a

Preparation of 4-[3-({[(1-methyl-1H-indazol-5-yl)amino]carbonyl}amino)phenoxy]-N-(2-piperidin-1-ylethyl)pyridine-2-carboxamide

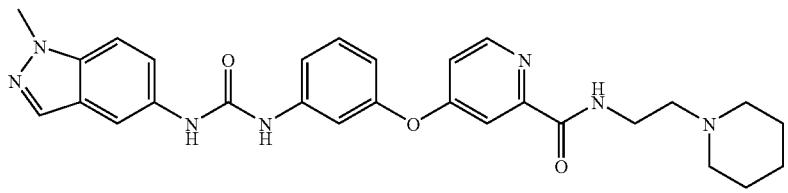

Step 1: Preparation of 4-[3-({[(1-methyl-1H-indazol-5-yl)amino]carbonyl}amino)phenoxy]-pyridine-2-carboxylic acid

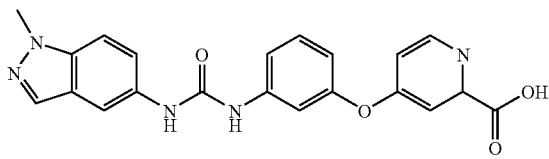

A mixture of N-methyl-4-[3-({[(1-methyl-1H-indazol-5-yl)amino]carbonyl}amino)-phenoxy]pyridine-2-carboxamide (80 mg, 0.19 mmol) and powdered potassium hydroxide (0.03 g, 0.56 mmol) was dissolved in MeOH/H₂O (4 mL, 3:1), and the reaction mixture was heated at 40° C. for 3 h. The solvent was removed in vacuo, the crude residue dissolved in H₂O (5 mL), and precipitated on being neutralized with aq. 1N HCl. The precipitated solid was washed with water and then CH₂Cl₂ to give 0.55 g (70%) of the carboxylic acid. ¹H-NMR (DMSO-d₆) δ 9.97 (s, 1H), 9.77 (s, 1H), 8.46 (d, 1H), 7.93 (s, 1H), 7.90 (s, 1H), 7.51 (d, 1H), 7.43-7.34 (m, 5H), 7.07 (dd, 1H), 6.73 (dd, 1H), 3.97 (s, 3H); MS LC-MS (M+H)⁺=404.1, RT=2.45 min.

Step 2: Preparation of the title compound 4-[3-({[(1-methyl-1H-indazol-5-yl)amino]carbonyl}-amino)phenoxy]-N-(2-piperidin-1-ylethyl)pyridine-2-carboxamide 4-[3-({[(1-methyl-1H-indazol-5-yl)amino]carbonyl}amino)phenoxy]-pyridine-2-carboxylic acid (0.07 g, 0.17 mmol) was dissolved in DMF (2.5 mL), followed by sequential addition of 1-(2-aminoethyl)piperidine (0.02 g, 0.17 mmol), 1-hydroxybenzotriazole (0.05 g, 0.38 mmol), 1-[3-(dimethylamino) propyl]-3-ethylcarbodiimide hydrochloride (0.05 g, 0.26 mmol), and N-methylmorpholine (0.04 g, 0.38 mmol). The mixture was stirred at room temperature for 12 h, and the solvent was removed in vacuo. The crude residue was dissolved in CH₂Cl₂ (10 mL), and washed with H₂O (3 mL). The solvent was removed in vacuo, and the crude product was purified by preparative HPLC. The isolated product was washed with aq. Na$_2$CO$_3$ to give 0.07 g (78%) of the title compound. $^1$H-NMR (CD$_3$OD) δ 8.51 (d, 1H), 7.91 (s, 1H), 7.84 (d, 1H), 7.59 (d, 1H), 7.50-7.46 (m, 2H), 7.41-7.36 (m, 2H), 7.26 (dd, 1H), 7.10 (dd, 1H), 6.81-6.77 (dd, 1H), 4.03 (s, 3H), 3.60 (t, 2H), 2.78-2.71 (m, 6H), 1.69-1.51 (m, 6H); MS LC-MS (M+H)$^+$=514.3, RT=2.62 min.

EXAMPLE 149

Method H-1b

Preparation of 4-[3-({[(1-methyl-1H-indazol-5-yl)amino]carbonyl}amino)phenoxy]-N-Pyridin-3-ylpyridine-2-carboxamide

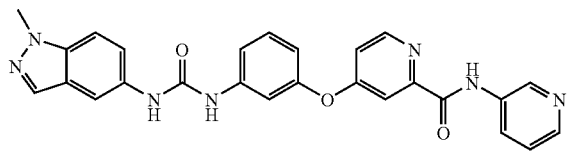

The title compound was prepared in the same manner described for 4-[3-({[(1-methyl-1H-indazol-5-yl)amino]carbonyl}-amino)phenoxy]-N-(2-piperidin-1-ylethyl)pyridine-2-carbox-amide, substituting 3-aminopyridine for 1-(2-aminoethyl)piperidine. $^1$H-NMR (DMSO-d$_6$) δ 10.39 (s, 1H), 8.93 (s, 1H), 8.72 (s, 1H), 8.63 (d, J=5.4 Hz, 1H), 8.38 to 8.36 (m, 1H), 8.19 (d, J=8.4 Hz, 1H), 7.91 to 7.86 (m, 3H), 7.85 to 7.51 (m, 3H), 7.42 (t, J=2.1 Hz, 1H), 7.52 to 7.17 (m, 4H), 6.85 (dd, J=2.4, 1.5 Hz, 1H), 3.98 (s, 3H); MS LC-MS (M+H)$^+$=480.1, RT=2.81 min.

Method I: General Method for the Synthesis of Carboxamide Through Hydrolysis of Nitrile

EXAMPLE 150

Method I

Preparation of 4-[3,5-difluoro-4-({[(2,2,4,4-tetrafluoro-4H-1,3-benzodioxin-6-yl)amino]-carbonyl}amino)phenoxy]pyridine-2-carboxamide

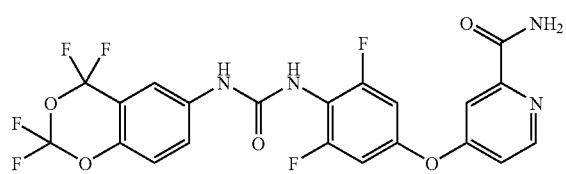

A solution of N-{4-[(2-cyanopyridin-4-yl)oxy]-2,6-difluorophenyl}-N'-(2,2,4,4-tetra-fluoro-4H-1,3-benzodioxin-6-yl)urea (100 mg, 0.20 mmol) in acetone (2 ml) and water (1 ml) was treated with sodium percarbonate (contain 25% H$_2$O$_2$, 320 mg, 2.0 mmol), and the mixture was stirred at room temperature overnight. The reaction mixture was partitioned between ethyl acetate (20 ml) and water (10 ml). The organic layer was washed with water (10 ml) and brine (5 ml), dried over Na$_2$SO$_4$, filtered, and concentrated under reduced pressure. The residue was crystallized from methanol providing 42 mg (41%) of title compound as a white solid. $^1$H-NMR (DMSO-d$_6$) δ 9.48 (s, 1H), 8.56 (d, J=6.0 Hz, 1H), 8.31 (s, 1H), 8.15 (s, 1H), 8.07 (d, J=2.2 Hz, 1H), 7.74 (s, 1H), 7.68 (dd, J=9.2, 2.7 Hz, 1H), 7.46 (d, J=2.3 Hz, 1H), 7.41 (d, J=9.3 Hz, 1H), 7.25 (m, 2H); MS GC-MS M$^+$=515.0, RT=3.63 min.

General Method J: Oxidations

EXAMPLE 151

Method J-1

Preparation of N-methyl-4-[3-({[(2,2,4,4-tetrafluoro-4H-1,3-benzodioxin-6-yl)amino]carbonyl}amino)phenoxy]pyridine-1-oxo-2-carboxamide

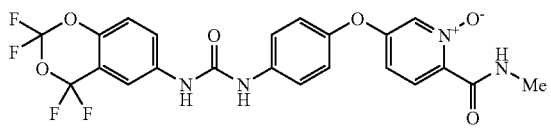

To a solution of N-methyl-4-[3-({[(2,2,4,4-tetrafluoro-4H-1,3-benzodioxin-6-yl)amino]carbonyl}amino)phenoxy]pyridine-2-carboxamide (100 mg, 0.20 mmol) in DCM (3 mL) and THF (3 mL) was added mCPBA (140 mg, 0.81 mmol). This was stirred for 48 h and the precipitate that formed was collected, and washed with DCM and MeOH to afford 53 mg (48%) of the title compound as a white solid. $^1$H-NMR (DMSO-d$_6$) δ11.37 (br q, J=4.8 Hz, 1H), 9.14 (d, J=15.6 Hz, 2H), 8.40 (d, J=7.2 Hz, 1H), 8.08 (d, J=2.7 Hz, 1H), 7.63 (dd, J=9.3, 2.4 Hz, 1H), 7.59 (d, J=3.6 Hz, 1H), 7.49 (t, J=1.8 Hz, 1H), 7.44 to 7.38 (m, 2H), 7.33 to 7.26 (m, 2H), 6.87 to 6.83 (m, 1H), 2.85 (d, J=5.1 Hz, 3H); MS LC-MS (M+H)$^+$=509.2, RT=3.54 min.

EXAMPLE 152

Method J-2

N-Methyl-4-[3-(methylsulfonyl)-4-({[(2.2,4,4-tetrafluoro-4H-1,3-benzodioxin-6-yl)amino]-carbonyl}amino)phenoxy]pyridine-2-carboxamide

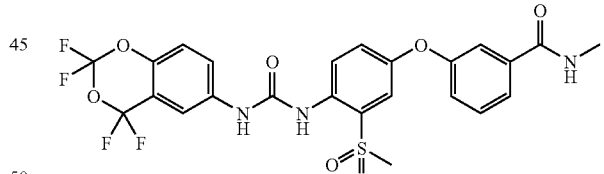

To N-methyl-4-[3-(methylthio)-4-({[(2,2,4,4-tetrafluoro-4H-1,3-benzodioxin-6-yl)-amino]carbonyl}amino)phenoxy]pyridine-2-carboxamide (150 mg, 0.28 mmol) in anhydrous 1:1 v/v DCM/THF (3.0 mL) at 0° C. was added mCPBA (162.7 mg, 0.61 mmol, 2.2 eq, and the reaction mixture was stirred at RT for 17 h. The reaction mixture was poured into aqueous saturated sodium thiosulfate solution and extracted with EtOAc (3×100 mL). The combined organic layers were washed with brine, dried over sodium sulfate, filtered, and evaporated under reduced pressure to give 73.3 mg (46.1%) of the title compound as a white solid. $^1$H-NMR (DMSO-d$_6$) δ 10.31 (s, 1H), 8.81 (q, J=5.4 Hz, 1H), 8.71 (s, 1H), 8.55 (d, J=5.7 Hz, 1H), 8.23 (d, J=9.0 Hz, 1H), 8.15 (d, J=2.4 Hz, 1H), 7.70 to 7.59 (m, 3H), 7.47 (s, 1H), 7.45 (d, J=6.9 Hz, 1H), 7.21 (dd, J=5.4, 2.4 Hz, 1H), 3.37 (s, 3H), 2.79 (d, J=5.1 Hz, 3H); MS LC-MS (M+H)$^+$=571.1, RT=3.81 min; m.p. 222-223.5° C.

Additional compounds illustrated in Table 3 were prepared as described above by choosing the appropriate starting materials that are readily available and/or the synthesis of which is taught herein, and using the processes of Methods G, H, and/or I described above or other standard chemical processes known in the art.

TABLE 3

Examples Synthesized using Methods G, H or I

| Example | Structure | R_f (TLC solvent) Or RT (min)* | LC/MS ([M + H]+) | Synthesis of (III) and/or (V)** | Synthesis of Ureas (VI) or (VIII) | Synthesis of (I)* |
|---|---|---|---|---|---|---|
| 153 | 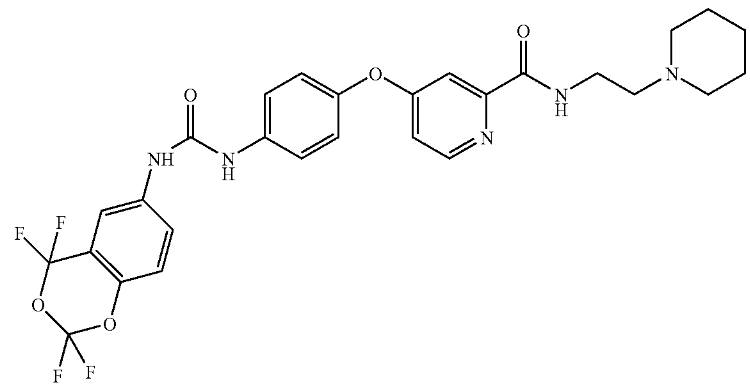 | R_f = 0.46 (10% MeOH/DCM) | 590 | C-3 | F-1 | G |
| 154 | 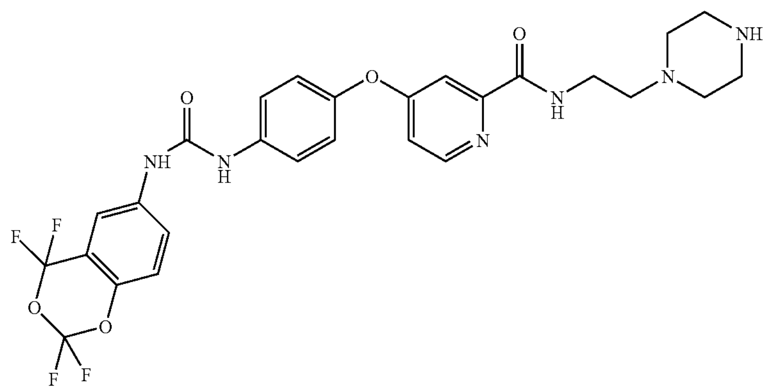 | RT = 2.92 | 591 | C-3 | F-1 | G |
| 155 | 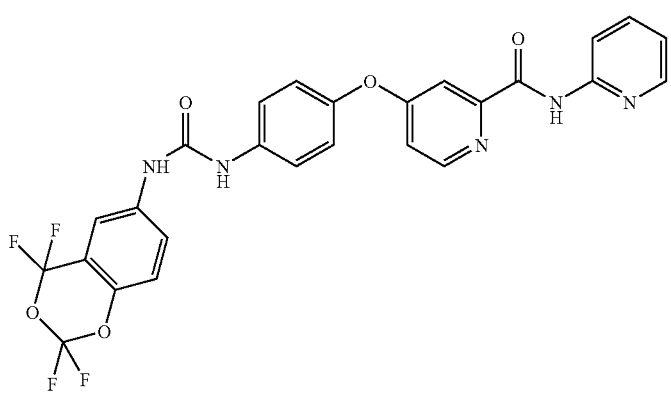 | R_f = 0.38 (67% EtOAc/Hex) | 556 | C-3 | F-1 | G |
| 156 | 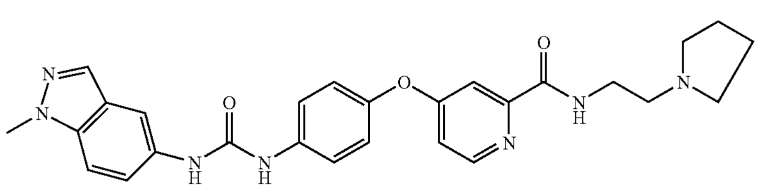 | RT = 2.52 | 500 | C-3 | E-1 | G |

TABLE 3-continued

Examples Synthesized using Methods G, H or I

| Example | Structure | R$_f$ (TLC solvent) Or RT (min)* | LC/ MS ([M + H]+) | Synthesis of (III) and/or (V)** | Synthesis of Ureas (VI) or (VIII) | Synthesis of (I)* |
|---|---|---|---|---|---|---|
| 157 | 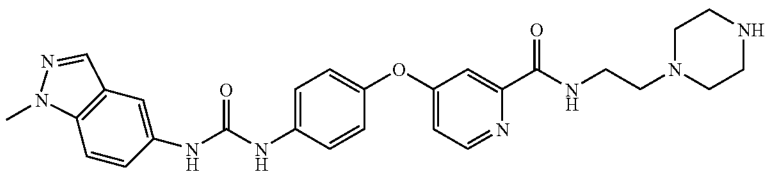 | R$_f$ = 0.29 (25% MeOH/ DCM) | 515 | C-3 | E-1 | G |
| 158 | 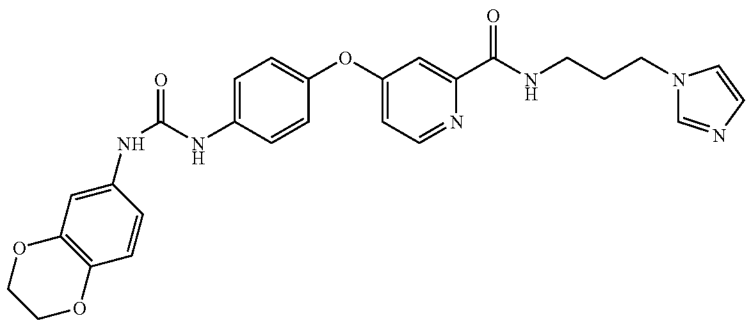 | R$_f$ = 0.44 (7% MeOH/ DCM) | 515 | C-3 | F-1 | G |
| 159 | 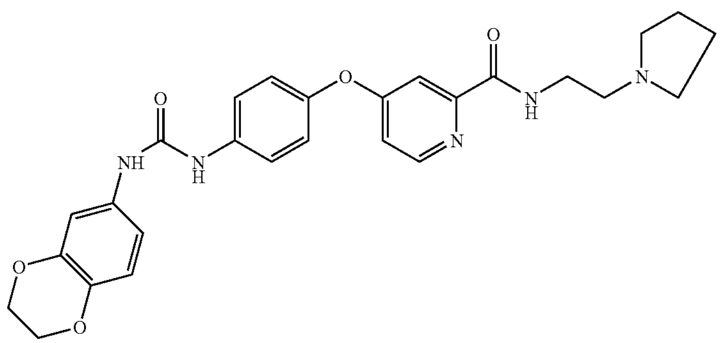 | R$_f$ = 0.46 (15% MeOH/ DCM) | 504 | C-3 | F-1 | G |
| 160 | 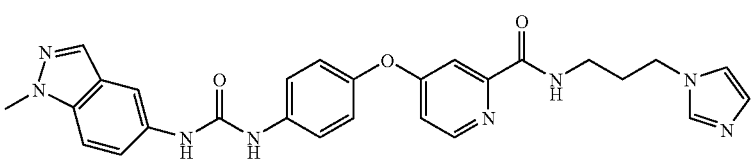 | R$_f$ = 0.23 (15% MeOH/ DCM) | 511 | C-3 | E-1 | G |
| 161 | 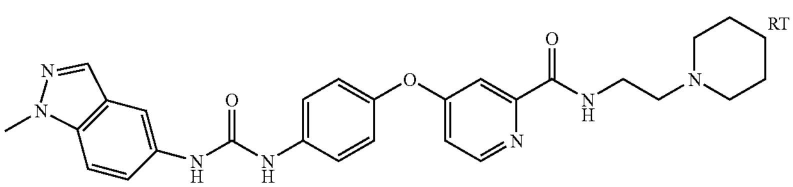 | RT = 2.56 | 514 | C-3 | E-1 | G |
| 162 | 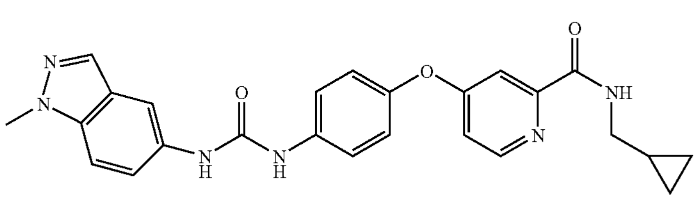 | R$_f$ = 0.40 (75% EtOAc/ Hex) | 457 | C-3 | E-1 | G |

TABLE 3-continued

Examples Synthesized using Methods G, H or I

| Example | Structure | R_f (TLC solvent) Or RT (min)* | LC/MS ([M + H]+) | Synthesis of (III) and/or (V)** | Synthesis of Ureas (VI) or (VIII) | Synthesis of (I)* |
|---|---|---|---|---|---|---|
| 163 | 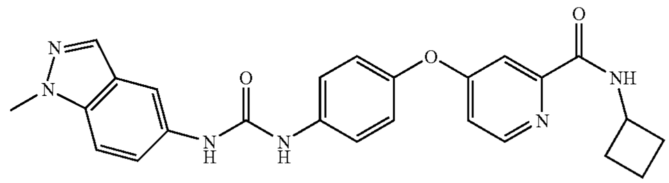 | R_f = 0.42 (75% EtOAc/Hex) | 457 | C-3 | E-1 | G |
| 164 | 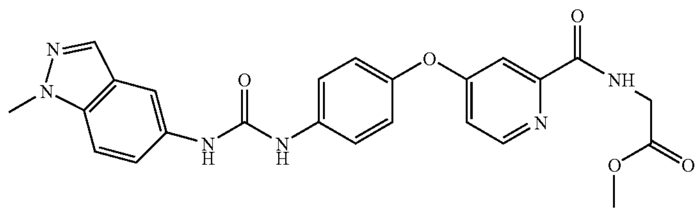 | RT = 2.51 | 475 | C-3 | E-1 | G |
| 165 | 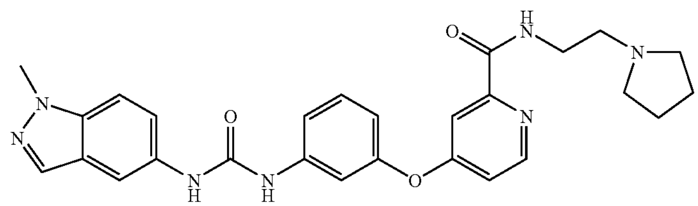 | Rt = 2.58 | 500 | C-1 | E-1 | H |
| 166 | 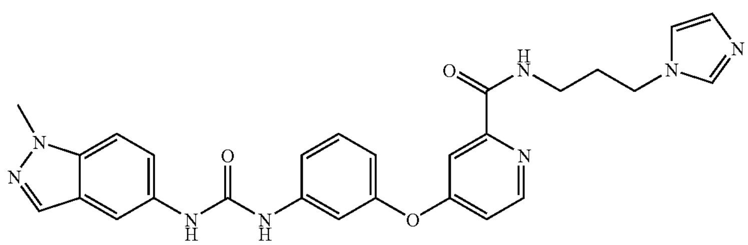 | RT = 2.57 | 511 | C-1 | E-1 | H |
| 167 | 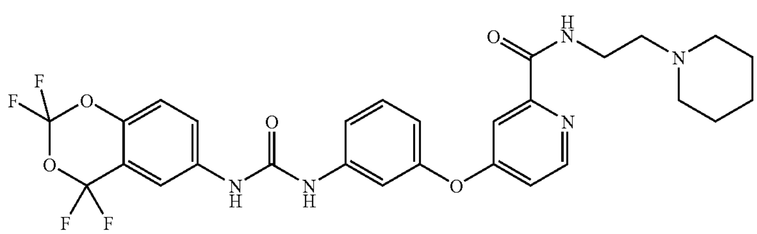 | RT = 3.18 | 590 | C-1 | F-1 | H |
| 168 | 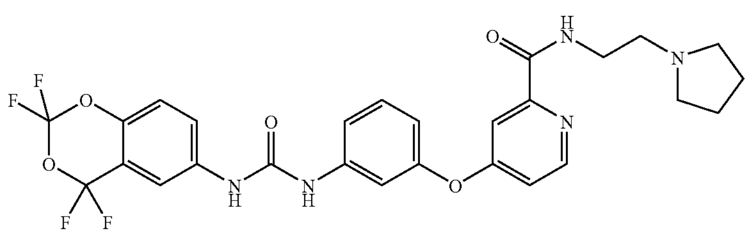 | RT = 3.13 | 576 | C-1 | F-1 | H |

TABLE 3-continued

Examples Synthesized using Methods G, H or I

| Example | Structure | $R_f$ (TLC solvent) Or RT (min)* | LC/ MS ([M + H]+) | Synthesis of (III) and/or (V)** | Synthesis of Ureas (VI) or (VIII) | Synthesis of (I)* |
|---|---|---|---|---|---|---|
| 169 | 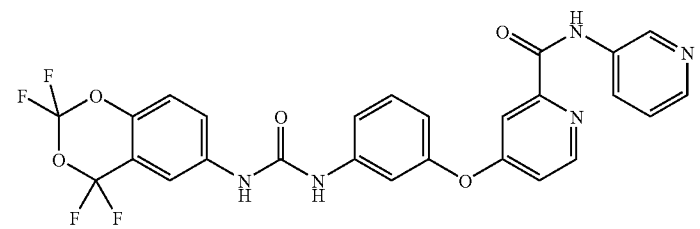 | RT = 3.69 | 556 | C-1 | F-1 | H |
| 170 | 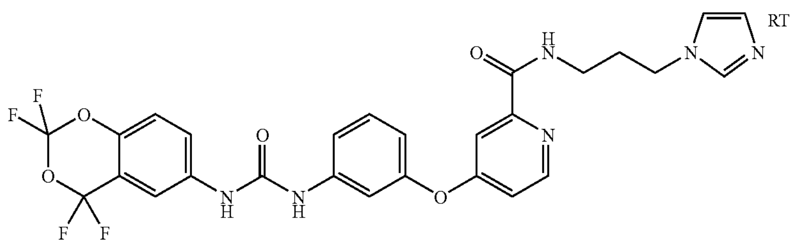 | RT = 2.74 | 587 | C-1 | F-1 | H |
| 171 | 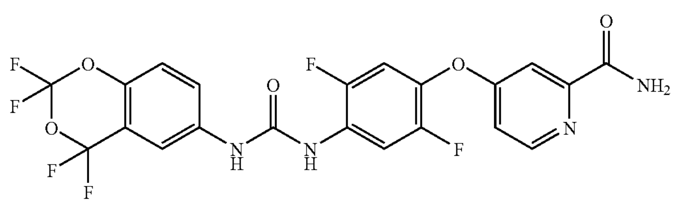 | $R_f$ = 0.33 (50% EtOAc/ Hex) | 515 | B-4 C-1 | F-1 | I |
| 172 | 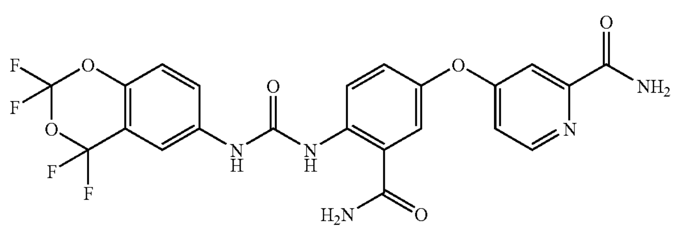 | RT = 3.61 | 522 | B-5 C-1 | F-1 | I |
| 173 | 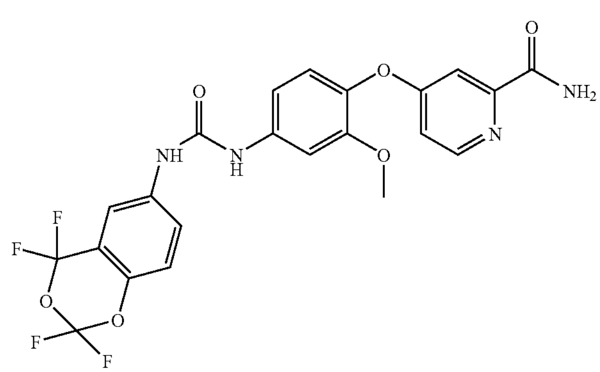 | RT = 3.31 | 509 | B-1 C-1 | F-1 | I |

TABLE 3-continued

Examples Synthesized using Methods G, H or I

| Example | Structure | R_f (TLC solvent) Or RT (min)* | LC/ MS ([M + H]+) | Synthesis of (III) and/or (V)** | Synthesis of Ureas (VI) or (VIII) | Synthesis of (I)* |
|---|---|---|---|---|---|---|
| 174 | 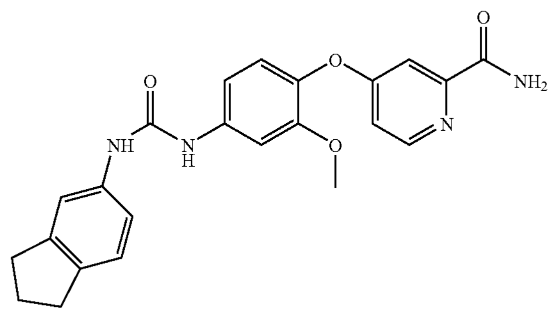 | RT = 3.39 | 419 | B-1 C-1 | E-1 | I |

*The following are the LCMS conditions: HPLC - electrospray mass spectra (HPLC ES-MS) were obtained using a Gilson HPLC system equipped with two Gilson 306 pumps, a Gilson 215 Autosampler, a Gilson diode array detector, a YMC Pro C-18 column (2 × 23 mm, 120 Å), and a Micromass LCZ single quadrupole mass spectrometer with z-spray electrospray ionization. Spectra were scanned from 120-1000 amu over 2 seconds. ELSD (Evaporative Light Scattering Detector) data was also acquired as an analog channel. Gradient elution was used with Buffer A as 2% acetonitrile in water with 0.02% TFA and Buffer B as 2% water in Acetonitrile with 0.02% TFA at 1.5 mL/min. Samples were eluted as follows: 90% A for 0.5 min ramped to 95% B over 3.5 min and held at 95% B for 0.5 min and then the column is brought back to initial conditions over 0.1 min. Total run time is 4.8 min.
**comm means commercially available.

Biological Tests
c-Raf (Raf-1) Biochemical Assay
Purification of Proteins Used in the Assay The c-Raf biochemical assay was performed with a c-Raf enzyme that was activated (phosphorylated) by Lck kinase. Lck-activated c-Raf (Lck/c-Raf) was produced in Sf9 insect cells by co-infecting cells with baculoviruses expressing, under the control of the polyhedrin promoter, GST-c-Raf (from amino acid 302 to amino acid 648) and Lck (full-length). Both baculoviruses were used at the multiplicity of infection of 2.5 and the cells were harvested 48 hours post infection.

MEK-1 protein was produced in Sf9 insect cells by infecting cells with the baculovirus expressing GST-MEK-1 (full-length) fusion protein at the multiplicity of infection of 5 and harvesting the cells 48 hours post infection. Similar purification procedure was used for GST-c-Raf 302-648 and GST-MEK-1.

Transfected cells were suspended at 100 mg of wet cell biomass per mL in a buffer containing 10 mM sodium phosphate, 140 mM sodium chloride pH 7.3, 0.5% Triton X-100 and the protease inhibitor cocktail. The cells were disrupted with Polytron homogenizer and centrifuged 30,000 g for 30 minutes. The 30,000 g supernatant was applied onto GSH-Sepharose. The resin was washed with a buffer containing 50 mM Tris, pH 8.0, 150 mM NaCl and 0.01% Triton X-100. The GST-tagged proteins were eluted with a solution containing 100 mM Glutathione, 50 mM Tris, pH 8.0, 150 mM NaCl and 0.01% Triton X-100. The purified proteins were dialyzed into a buffer containing 20 mM Tris, pH 7.5, 150 mM NaCl and 20% Glycerol.

Biochemical Assay Protocol and Results

The compounds were serially diluted in DMSO using three-fold dilutions to stock concentrations ranging typically from 50 μM to 20 nM (final concentrations in the assay range from 1 μM to 0.4 nM). The c-Raf biochemical assay was performed as a radioactive filtermat assay in 96-well Costar polypropylene plates (Costar 3365). The plates were loaded with 75 μL solution containing 50 mM HEPES pH 7.5, 70 mM NaCl, 80 ng of Lck/c-Raf and 1 μg MEK-1. Subsequently, 2 μL of the serially diluted individual compounds were added to the reaction, prior to the addition of ATP. The reaction was initiated with 25 μL ATP solution containing 5 μM ATP and 0.3 μCi [33P]-ATP. The plates were sealed and incubated at 32° C. for 1 hour. The reaction was quenched with the addition of 50 μl of 4% Phosphoric Acid and harvested onto P30 filtermats (PerkinElmer) using a Wallac Tomtec Harvester. Filtermats were washed with 1% Phosphoric Acid first and deionized $H_2O$ second. The filters were dried in a microwave, soaked in scintillation fluid and read in a Wallac 1205 Betaplate Counter (Wallac Inc., Atlanta, Ga., U.S.A.). The results were expressed as percent inhibition.

% Inhibition=$[100-(T_{ib}/T_i)] \times 100$ where $T_{ib}$=(counts per minute with inhibitor)−(background)

$T_i$=(counts per minute without inhibitor)−(background)

Compounds of examples 1-174 show >40% inhibition at 1 micromolar in this assay. Furthermore, compounds of examples 1, 4, 5, 8, 15, 19, 21, 23, 25, 32, 33-36, 39-43, 46-63, 66-86, 92-94, 96, 97, 101, 104, 107, 109-114, 116, 118-121, 123-131, 133, 134, 136-144, 149, 151, 152, 154, 164, 165, 167, and 170-174 show >80% inhibition of c-Raf kinase at 1 micromolar.

It is believed that one skilled in the art, using the preceding information and information available in the art, can utilize the present invention to its fullest extent.

It should be apparent to one of ordinary skill in the art that changes and modifications can be made to this invention without departing from the spirit or scope of the invention as it is set forth herein.

All publications and patents cited above are incorporated herein by reference

What is claimed is:

1. A compound of formula (I):

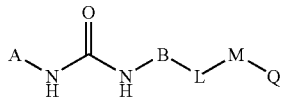

wherein

A is a bicyclic heterocycle which is:
(1) benzimidazolyl
(2) 1,3-benzothiazolyl
(3) 1,2,3-benzotriazolyl
(4) 1,3-benzoxazolyl
(5) 2,3-dihydro-1H-indolyl
(6) 2,3-dihydro-1H-indenyl
(7) 1,1-dioxido-2,3-dihydro-1-benzothienyl
(8) 1H-indazolyl
(9) 2H-indazolyl
(10) 1H-indolyl
(11) 2H-chromenyl
(12) quinoxalinyl or
(13) one of the formulae

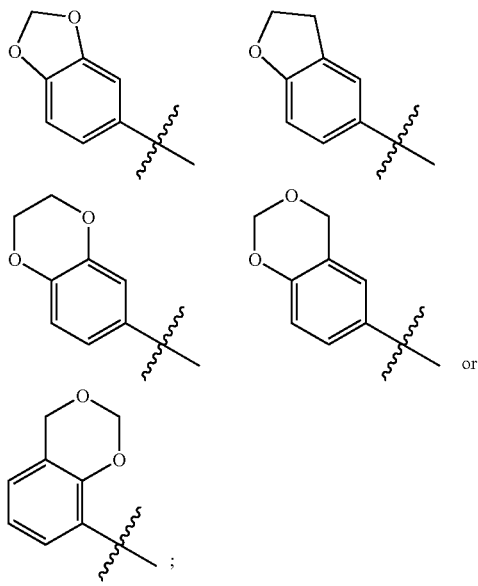

optionally substituted with 1-4 substituents which are independently $R^1$, $OR^1$, $S(O)_pR^1$, $C(O)R^1$, $C(O)OR^1$, $C(O)NR^1R^2$, halogen, oxo, cyano, or nitro;

B is phenyl, naphthyl, or pyridyl, optionally substituted with 1-4 substituents which are independently $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_6$ dialkylamino, carboxyamide, halogen, cyano, nitro or $S(O)_pR^7$;

L is:
(a) —$(CH_2)_m$—O—$(CH_2)_l$—,
(b) —$(CH_2)_m$—$(CH_2)_l$—,
(c) —$(CH_2)_m$—C(O)—$(CH_2)_l$—,
(d) —$(CH_2)_m$—$NR^3$—$(CH_2)_l$—,
(e) —$(CH_2)_m$—$NR^3C(O)$—$(CH_2)_l$—,
(f) —$(CH_2)_m$—S—$(CH_2)_l$—,
(g) —$(CH_2)_m$—$C(O)NR^3$—$(CH_2)_l$—, or
(h) a single bond;

m and l are integers independently selected from 0-4;

M is a pyridine ring, optionally substituted with 1-3 substituents which are independently $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_6$ dialkylamino, halogen, or nitro;

Q is $C(O)R^4$, $C(O)OR^4$ or $C(O)NR^4R^5$;

each of $R^1$, $R^2$, $R^3$, $R^4$ and $R^5$ is independently:
(a) hydrogen,
(b) $C_1$-$C_5$ linear, branched, or cyclic alkyl,
(c) phenyl,
(d) $C_1$-$C_3$ alkyl-phenyl,
(e) up to per-halo substituted $C_1$-$C_5$ linear or branched alkyl,
(f) —$(CH_2)_q$—X, wherein X is a 5 or 6 membered heterocyclic ring, containing at least one atom selected from oxygen, nitrogen and sulfur, which is saturated, partially saturated, or aromatic, or a 8-10 membered bicyclic heteroaryl having 1-4 heteroatoms which are O, N or S, or
(g) —$(CH_2)_q$—Y, where Y is $C(O)R^6$, $C(O)OR^6$ and $C(O)NR^6R^7$;

each of $R^6$-$R^7$ is independently:
(a) hydrogen,
(b) $C_1$-$C_5$ linear, branched, or cyclic alkyl,
(c) phenyl,
(d) $C_1$-$C_3$ alkyl-phenyl, or
(e) up to per-halo substituted $C_1$-$C_5$ linear or branched alkyl;

each of $R^1$, $R^2$, $R^3$, $R^4$, $R^5$, $R^6$ and $R^7$, other than per-halo substituted $C_1$-$C_5$ linear or branched alkyl, is optionally substituted with 1-3 substituents which are independently $C_1$-$C_5$ linear or branched alkyl, up to perhalo substituted $C_1$-$C_5$ linear or branched alkyl, $C_1$-$C_3$ alkoxy, hydroxy, carboxy, amino, $C_1$-$C_3$ alkylamino, $C_1$-$C_6$ dialkylamino, halogen, cyano, or nitro;

p is an integer selected from 0, 1, or 2; and q is an integer selected from 1, 2, 3, or 4, or a pharmaceutically acceptable salt of formula I or an oxidized derivative of formula I wherein one or more urea nitrogens are substituted with a hydroxyl group, or an oxidized derivative of formula I wherein the nitrogen atom of pyridine ring M is in the oxide form, or a methyl, ethyl, propyl, isopropyl, butyl, isobutyl, pentyl ester or phenyl $C_1$-$C_5$ alkyl ester of formula I at a carboxylic acid group or amide group.

2. A compound of claim 1 wherein A and B follow one of the following combinations:

A=1H-benzimidazol-5-yl; and B=phenyl, pyridinyl or naphthyl,

A=1H-benzimidazol-6-yl; and B=phenyl, pyridinyl or naphthyl,

A=1,3-benzodioxin-6-yl; and B=phenyl, pyridinyl or naphthyl,

A=1,3-benzodioxin-7-yl; and B=phenyl, pyridinyl or naphthyl,

A=1,3-benzodioxin-8-yl; and B=phenyl, pyridinyl or naphthyl,

A=1,3-benzodioxol-4-yl; and B=phenyl, pyridinyl or naphthyl,

A=1,3-benzodioxol-5-yl; and B=phenyl, pyridinyl or naphthyl,

A=1,3-benzothiazol-2-yl; and B=phenyl, pyridinyl or naphthyl,

A=1,3-benzothiazol-5-yl; and B=phenyl, pyridinyl or naphthyl,
A=1,3-benzothiazol-6-yl; and B=phenyl, pyridinyl or naphthyl,
A=1,2,3-benzotriazol-5-yl; and B=phenyl, pyridinyl or naphthyl,
A=1,3-benzoxazol-2-yl; and B=phenyl, pyridinyl or naphthyl, or
A=1,3-benzoxazol-6-yl; and B=phenyl, pyridinyl or naphthyl.

3. A compound of claim 1 wherein A and B follow one of the following combinations:
A=1H-benzimidazolyl; and B=phenyl or pyridinyl,
A=1,3-benzodioxinyl; and B=phenyl or pyridinyl,
A=1,3-benzodioxolyl; and B=phenyl or pyridinyl,
A=1,3-benzothiazolyl; and B=phenyl or pyridinyl,
A=1,2,3-benzotriazolyl; and B=phenyl or pyridinyl, or
A=1,3-benzoxazolyl; and B=phenyl or pyridinyl.

4. A compound of claim 1 wherein A and B follow one of the following combinations:
A=1H-benzimidazol-5-yl; and B=phenyl or pyridinyl,
A=1H-benzimidazol-6-yl; and B=phenyl or pyridinyl,
A=1,3-benzodioxin-6-yl; and B=phenyl or pyridinyl,
A=1,3-benzodioxin-7-yl; and B=phenyl or pyridinyl,
A=1,3-benzodioxin-8-yl; and B=phenyl or pyridinyl,
A=1,3-benzodioxol-4-yl; and B=phenyl or pyridinyl,
A=1,3-benzodioxol-5-yl; and B=phenyl or pyridinyl,
A=1,3-benzothiazol-2-yl; and B=phenyl or pyridinyl,
A=1,3-benzothiazol-5-yl; and B=phenyl or pyridinyl,
A=1,3-benzothiazol-6-yl; and B=phenyl or pyridinyl,
A=1,2,3-benzotriazol-5-yl; and B=phenyl or pyridinyl,
A=1,3-benzoxazol-2-yl; and B=phenyl or pyridinyl, or
A=1,3-benzoxazol-6-yl; and B=phenyl or pyridinyl.

5. A compound of claim 1 wherein A and B follow one of the following combinations:
A=2,3-dihydro-1,4-benzodioxin-5-yl; and B=phenyl, pyridinyl or naphthyl,
A=2,3-dihydro-1,4-benzodioxin-6-yl; and B=phenyl, pyridinyl or naphthyl,
A=2,3-dihydro-1-benzofuran-5-yl; and B=phenyl, pyridinyl or naphthyl,
A=2,3-dihydro-1H-indol-5-yl; and B=phenyl, pyridinyl or naphthyl,
A=2,3-dihydro-1H-indol-6-yl; and B=phenyl, pyridinyl or naphthyl,
A=2,3-dihydro-1H-inden-4-yl; and B=phenyl, pyridinyl or naphthyl,
A=2,3-dihydro-1H-inden-5-yl; and B=phenyl, pyridinyl or naphthyl,
A=1,1-dioxido-2,3-dihydro-1-benzothien-6-yl; and B=phenyl, pyridinyl or naphthyl.

6. A compound of claim 1 wherein A and B follow one of the following combinations:
A=2,3-dihydro-1,4-benzodioxin-5-yl; and B=phenyl or pyridinyl,
A=2,3-dihydro-1,4-benzodioxin-6-yl; and B=phenyl or pyridinyl,
A=2,3-dihydro-1-benzofuran-5-yl; and B=phenyl or pyridinyl,
A=2,3-dihydro-1H-indol-5-yl; and B=phenyl or pyridinyl,
A=2,3-dihydro-1H-indol-6-yl; and B=phenyl or pyridinyl,
A=2,3-dihydro-1H-inden-4-yl; and B=phenyl or pyridinyl,
A=2,3-dihydro-1H-inden-5-yl; and B=phenyl or pyridinyl, or
A=1,1-dioxido-2,3-dihydro-1-benzothien-6-yl; and B=phenyl or pyridinyl.

7. A compound of claim 1 wherein A and B follow one of the following combinations:
A=1H-indazol-5-yl; and B=phenyl, pyridinyl or naphthyl,
A=2H-indazol-5-yl; and B=phenyl, pyridinyl or naphthyl,
A=1H-indazol-6-yl; and B=phenyl, pyridinyl or naphthyl,
A=1H-indol-5-yl; and B=phenyl, pyridinyl or naphthyl,
A=2-oxo-2H-chromen-7-yl; and B=phenyl, pyridinyl or naphthyl or
A=1oxo-2,3-dihydro-1H-inden-5-yl; and B=phenyl, pyridinyl or naphthyl.

8. A compound of claim 1 wherein A and B follow one of the following combinations:
A=1H-indazol-5-yl; and B=phenyl or pyridinyl,
A=2H-indazol-5-yl; and B=phenyl or pyridinyl,
A=1H-indazol-6-yl; and B=phenyl or pyridinyl,
A=1H-indol-5-yl; and B=phenyl or pyridinyl,
A=2-oxo-2H-chromen-7-yl; and B=phenyl or pyridinyl, or
A=1-oxo-2,3-dihydro-1H-inden-5-yl; and B=phenyl or pyridinyl.

9. A compound of claim 1 wherein A and B follow one of the following combinations:
A=quinoxalin-2-yl; and B=phenyl, pyridinyl or naphthyl or
A=quinoxalin-6-yl; and B=phenyl, pyridinyl or naphthyl.

10. A compound of claim 1 wherein A and B follow one of the following combinations:
A=quinoxalin-2-yl; and B=phenyl or pyridinyl, or
A=quinoxalin-6-yl; and B=phenyl or pyridinyl.

11. A compound as in claim 1 wherein L is —O— or —S—.

12. A compound which is:
N-methyl-4-[3-({[(2-methyl-1,3-benzoxazol-6-yl)amino]carbonyl}amino)phenoxy]pyridine-2-carboxamide
4-[4-({[(1-acetyl-2,3-dihydro-1H-indol-6-yl)amino]carbonyl}amino)phenoxy]-N-methylpyridine-2-carboxamide
4-[4-({[(6-chloro-1,3-benzothiazol-2-yl)amino]carbonyl}amino)phenoxy]-N-methylpyridine-2-carboxamide
N-methyl-4-{4-[({[6-(trifluoromethoxy)-1,3-benzothiazol-2-yl]amino}carbonyl)amino]phen-oxy}pyridine-2-carboxamide
4-[4-({[(6-fluoro-1,3-benzothiazol-2-yl)amino]carbonyl}amino)phenoxy]-N-methylpyridine-2-carboxamide
4-[3-fluoro-4-({[(6-fluoro-1,3-benzothiazol-2-yl)amino]carbonyl}amino)phenoxy]-N-methylpyridine-2-carboxamide
4-{3-fluoro-4-[({[6-(trifluoromethoxy)-1,3-benzothiazol-2-yl]amino}carbonyl)amino]phen-oxy}-N-methylpyridine-2-carboxamide;
4-[4-({[(6-methoxy-1,3-benzothiazol-2-yl)amino]carbonyl}amino)phenoxy]-N-methylpyridine-2-carboxamide
4-[4-({[(6-methoxy-1,3-benzothiazol-2-yl)amino]carbonyl}amino)phenoxy]-N-methylpyridine-2-carboxamide
4-[4-({[(5-chloro-1,3-benzoxazol-2-yl)amino]carbonyl}amino)phenoxy]-N-methylpyridine-2-carboxamide
4-[4-({[(5-chloro-1,3-benzoxazol-2-yl)amino]carbonyl}amino)phenoxy]-N-methylpyridine-2-carboxamide
4-[4-({[(6-chloro-1,3-benzothiazol-2-yl)amino]carbonyl}amino)-3-fluorophenoxy]-N-methylpyridine-2-carboxamide 4-[4-({[(6-chloro-1,3-benzothiazol-2-yl)amino]carbonyl}amino)-3-fluorophenoxy]-N-methylpyridine-2-carboxamide 4-(2-chloro-4-{[(2,3-dihydro-1H-inden-5-ylamino)carbonyl]amino}phenoxy)-N-methylpyridine-2-carboxamide 4-[(5-{[(2,3-dihydro-1H-inden-5-ylamino)carbonyl]amino}quinolin-8-yl)oxy]-N-methylpyridine-2-carboxamide 4-[4-({[(4,6-difluoro-1,3-benzothiazol-2-yl)amino]carbonyl}amino)-3-fluorophenoxy]-N-methylpyridine-2-carboxamide 4-[3-fluoro-4-({[(6-methoxy-1,3-benzothiazol-2-yl)amino]carbonyl}amino)phenoxy]-N-methylpyridine-2-carboxamide 4-(4-{[({1-[2-(diethylamino)ethyl]-1H-indol-5-yl}amino)carbonyl]amino}-3-fluorophenoxy)-N-methylpyridine-2-carboxamide;

4-(4-{[(2,3-dihydro-1H-inden-5-ylamino)carbonyl]amino}-3-fluorophenoxy)-N-methylpyridine-2-carboxamide 4-[3-fluoro-4-({[(1-oxo-2,3-dihydro-1H-inden-5-yl)amino]carbonyl}amino)phenoxy]-N-methylpyridine-2-carboxamide 4-[4-({[(1,1-dioxido-2,3-dihydro-1-benzothien-6-yl)amino]carbonyl}amino) -3-fluorophenoxy]-N-methylpyridine-2-carboxamide 4-[3-fluoro-4-({[(1methyl-1H-indazol-5-yl)amino]carbonyl}amino)phenoxy]-N-methylpyridine-2-carboxamide 4-[2-fluoro-4-({[(1methyl-1H-indazol-5-yl)amino]carbonyl}amino)phenoxy]-N-methylpyridine-2-carboxamide 4-[2,4-difluoro-5-({[(1methyl-1H-indazol-5-yl)amino]carbonyl}amino)phenoxy]-N-methylpyridine-2-carboxamide N-methyl-4-[4-({[(1methyl-1H-indazol-5-yl)amino]carbonyl}amino)-3-(trifluoromethyl)-phenoxy]pyridine-2-carboxamide 4-[4-fluoro-3-({[(1methyl-1H-indazol-5-yl)amino]carbonyl}amino)phenoxy]-N-methylpyridine-2-carboxamide 4-[2-fluoro-5-({[(1methyl-1H-indazol-5-yl)amino]carbonyl}amino)phenoxy]-N-methylpyridine-2-carboxamide 4-[2-chloro-6-fluoro-4-({[(1methyl-1H-indazol-5-yl)amino]carbonyl}amino)phenoxy]-N-methylpyridine-2-carboxamide 4-[3-fluoro-4-({[(1methyl-1H-indazol-5-yl)amino]carbonyl}amino)phenoxy]-N-(2-methoxyethyl)pyridine-2-carboxamide 4-[3-fluoro-4-({[(2,2,3,3-tetrafluoro-2,3-dihydro-1,4-benzodioxin-6-yl)amino]carbonyl}-amino)phenoxy]-N-methylpyridine-2-carboxamide 4-[4-({[(2,2-difluoro-1,3-benzodioxol-5-yl)amino]carbonyl}amino)-3-fluorophenoxy]-N-methylpyridine-2-carboxamide N-methyl-4-(4-{[(quinoxalin-6-ylamino)carbonyl]amino}phenoxy)pyridine-2carboxamide 4-(3-fluoro-4-{[(quinoxalin-6-ylamino)carbonyl]amino}phenoxy)-N-methylpyridine-2-carboxamide N-methyl-4-[4-{[(quinoxalin-6-ylamino)carbonyl]amino}-3-(trifluoromethyl)phenoxy]-pyridine-2-carboxamide 4-(3-chloro-4-{[(quinoxalin-6-ylamino)carbonyl]amino}phenoxy)-N-methylpyridine-2-carboxamide N-methyl-4-[4-({[(2,2,3,3-tetrafluoro-2,3-dihydro-1,4-benzodioxin-6-yl)amino]carbonyl}-amino)-3-(trifluoromethyl)phenoxy]pyridine-2-carboxamide 4-[4-({[(2-methyl-1,3-benzothiazol-5-yl)amino]carbonyl}amino)phenoxy]pyridine-2-carboxamide N-methyl-4-[4-({[(2-methyl-1,3-benzothiazol-5-yl)amino]carbonyl}amino)-3-(trifluoro-methyl)phenoxy]pyridine-2-carboxamide N-methyl-4-[3-methyl-4-({[(4-methyl-2-oxo-2H-chromen-7-yl)amino]carbonyl}amino)-phenoxy]pyridine-2-carboxamide N-methyl-4-[3-methyl-4-({[(2-methyl-1,3-benzothiazol-5-yl)amino]carbonyl}amino)-phenoxy]pyridine-2-carboxamide 4-[3-fluoro-4-({[(2-methyl-1,3-benzothiazol-5-yl)amino]carbonyl}amino)phenoxy]-N-methylpyridine-2-carboxamide N-methyl-4-{[3-({[(1methyl-1H-indazol-5-yl)amino]carbonyl}amino)phenoxy]methyl}-pyridine-2-carboxamide 4-{[3-fluoro-4-({[(1-methyl-1H-indazol-5-yl)amino]carbonyl}amino)phenoxy]methyl}-N-methylpyridine-2-carboxamide 4-[2-chloro-4-({[(1methyl-1H-indazol-5-yl)amino]carbonyl}amino)phenoxy]N-methylpyridine-2-carboxamide N-methyl-4-[3-({[(2,2,3,3-tetrafluoro-2,3-dihydro-1,4-benzodioxin-6-yl)amino]carbonyl}-amino)phenoxy]pyridine-2-carboxamide N-methyl -4-[4-({[(2,2,3,3-tetrafluoro-2,3-dihydro-1,4-benzodioxin-6-yl)amino]carbonyl}-amino)phenoxy]pyridine-2-carboxamide 4-[3-({[(2,2-difluoro-1,3-benzodioxol-5-yl)amino]carbonyl}amino)phenoxy]-N-methylpyridine-2-carboxamide 4-[4-({[(2,2-difluoro-1,3-benzodioxol-5-yl)amino]carbonyl}amino)phenoxy]-N-methylpyridine-2-carboxamide 4-[2-chloro-4-({[(2,2,3,3-tetrafluoro-2,3-dihydro-1,4-benzodioxin-6-yl)amino]carbonyl}-amino)phenoxy]-N-methylpyridine-2-carboxamide 4-[2-chloro-4-({[(2,2-difluoro-1,3-benzodioxol-5-yl)amino]carbonyl}amino)phenoxy]-N-methylpyridine-2-carboxamide 4-[3-chloro-4-({[(1methyl-1H-indazol-5-yl)amino]carbonyl}amino)phenoxy]-N-methylpyridine-2-carboxamide N-methyl-4-[3-({[(1methyl-1H-indazol-5-yl)amino]carbonyl}amino)phenoxy]pyridine-2-carboxamide N-methyl-4-[3-({[(1methyl-1H-indazol-6-yl)amino]carbonyl}amino)phenoxy]pyridine-2-carboxamide 4-(3-{[(2,3-dihydro-1-benzofuran-5-ylamino)carbonyl]amino}phenoxy)-N-methylpyridine-2-carboxamide N-methyl-4-{3-[({[2-(trifluoromethyl)-1H-benzimidazol-5-yl]amino}carbonyl)amino]-phenoxy}pyridine-2-carboxamide 4-[4-chloro-3-({[(1methyl-1H-indazol-5-yl)amino]carbonyl}amino)phenoxy]-N-methyl-pyridine-2-carboxamide 4-[4-chloro-3-({[(2,2,3,3-tetrafluoro-2,3-dihydro-1,4-benzodioxin-6-yl)amino]-carbonyl}amino)phenoxy]-N-methylpyridine-2-carboxamide 4-[4-chloro-3-({[(2,2-difluoro-1,3-benzodioxol-5-yl)amino]carbonyl}amino)phenoxy]-N-methylpyridine-2-carboxamide 4-[3-chloro-4-({[(1methyl-1H-indazol-5-yl)amino]carbonyl}amino)phenoxy]pyridine-2-carboxamide 4-[2-chloro-4-({[(1methyl-1H-indazol-5-yl)amino]carbonyl}amino)phenoxy]pyridine-2-carboxamide
4-[4-({[(2,2-difluoro-1,3-benzodioxol-5-yl)amino]carbonyl}amino)-3-fluorophenoxy)-pyridine-2-carboxamide
4-[3-fluoro-4-({[(2,2,3,3-tetrafluoro-2,3-dihydro-1,4-benzodioxin-6-yl)amino]carbonyl}-amino)phenoxy]pyridine-2-carboxamide
4-(4-{[(2,3-dihydro-1H-inden-5-ylamino)carbonyl]amino}phenoxy)-N-methylpyridine-2-carboxamide
N-methyl-4-[4-({[(1oxo-2,3-dihydro-1H-inden-5-yl)amino]carbonyl}amino)phenoxy]-pyridine-2-carboxamide
5-[3-fluoro-4-({[(2,2,3,3-tetrafluoro-2,3-dihydro-1,4-benzodioxin-6-yl)amino]carbonyl}-amino)phenoxy]-N-methylnicotinamide
4-[4-{[(2,3-dihydro-1H-inden-5-ylamino)carbonyl]amino}-3-(trifluoromethyl)phenoxy]-N-methylpyridine-2-carboxamide
N-methyl-4-[4-({[(1oxo-2,3-dihydro-1H-inden-5-yl)amino]carbonyl}amino) -3-(trifluoromethyl)phenoxy]pyridine-2-carboxamide
4-(3-chloro-4-{[(2,3-dihydro-1H-inden-5-ylamino)carbonyl]amino}phenoxy)pyridine-2-carboxamide
4-[3-chloro-4-({[(1oxo-2,3-dihydro-1H-inden-5-yl)amino]carbonyl}amino)phenoxy]-pyridine-2-carboxamide
N-methyl-4-[4-{[(1methyl-1H-indazol-6-yl)amino]carbonyl}amino)phenoxy]pyridine-2-carboxamide
4-(4-{[(1,3-benzothiazol-6-ylamino)carbonyl]amino}phenoxy)-N-methylpyridine-2-carboxamide
N-methyl-4-[4-({[(1methyl-1H-indazol-5-yl)amino]carbonyl}amino)phenoxy]pyridine-2-carboxamide
4-(4-{[(2,3-dihydro-1-benzofuran-5-ylamino)carbonyl]amino}phenoxy)-N-methylpyridine-2-carboxamide
4-[2,4-dichloro-5-({[(2,2,3,3-tetrafluoro-2,3-dihydro-1,4-benzodioxin-6-yl)amino]carbonyl}-amino)phenoxy]-N-methylpyridine-2-carboxamide
4-[2,4-dichloro-5-({[(1methyl-1H-indazol-5-yl)amino]carbonyl}amino)phenoxy]-N-methylpyridine-2-carboxamide
4-[3-chloro-4-({[(2,2-difluoro-1,3-benzodioxol-5-yl)amino]carbonyl}amino)phenoxy]-N-methylpyridine-2-carboxamide
4-[3-chloro-4-({[(2,2,3,3-tetrafluoro-2,3-dihydro-1,4-benzodioxin-6-yl)amino]carbonyl}-amino)phenoxy]-N-methylpyridine-2-carboxamide;
4-(3-chloro-4-{[(2,3-dihydro-1H-inden-5-ylamino)carbonyl]amino}phenoxy)-N-methylpyridine-2-carboxamide
4-(3-chloro-4-{[(2,3-dihydro-1H-inden-5-ylamino)carbonyl]amino}phenoxy)-N-methylpyridine-2-carboxamide;
4-[3-chloro-4-({[(1oxo-2,3-dihydro-1H-inden-5-yl)amino]carbonyl}amino)phenoxy]-N-methylpyridine-2-carboxamide;
4-[2-chloro-4-({[(1oxo-2,3-dihydro-1H-inden-5-yl)amino]carbonyl}amino)phenoxy]-N-methylpyridine-2-carboxamide
4-(3-chloro-4-{[(2,3-dihydro-1H-inden-5-ylamino)carbonyl]amino}phenoxy)-N-methylpyridine-2-carboxamide
4-(3-chloro-4-{[(2,3-dihydro-1H-inden-5-ylamino)carbonyl]amino}phenoxy)-N-methylpyridine-2-carboxamide
4-[2,4-dichloro-5-({[(2,2-difluoro-1,3-benzodioxol-5-yl)amino]carbonyl}amino)phenoxy]-N-methylpyridine-2-carboxamide
N-methyl-4-{4-[({[1(methylsulfonyl)-2,3-dihydro-1H-indol-5-yl]amino}carbonyl)amino]-phenoxy}pyridine-2-carboxamide
N-methyl-4-[3-nitro-4-({[(2,2,3,3-tetrafluoro-2,3-dihydro-1,4-benzodioxin-6-yl)amino]-carbonyl}amino)phenoxy]pyridine-2-carboxamide
N-methyl-4-[2-methyl-4-({[(2,2,3,3-tetrafluoro-2,3-dihydro-1,4-benzodioxin -6-yl)amino]-carbonyl}amino)phenoxy]pyridine-2-carboxamide
4-[2,3-difluoro-4-({[(2,2,4,4-tetrafluoro-4H-1,3-benzodioxin-6-yl)amino]carbonyl}amino)-phenoxy]-N-methylpyridine-2-carboxamide
4-[3,5-difluoro-4-({[(2,2,4,4-tetrafluoro-4H-1,3-benzodioxin-6-yl)amino]carbonyl}amino)-phenoxy]-N-methylpyridine-2-carboxamide
4-[2,5-difluoro-4-({[(2,2,4,4-tetrafluoro-4H-1,3-benzodioxin-6-yl)amino]carbonyl}amino)-phenoxy]-N-methylpyridine-2-carboxamide
N-methyl-4-[4({[(2,2,3,3-tetrafluoro-2,3-dihydro-1,4-benzodioxin-5-yl)amino]carbonyl}-amino)phenoxy]pyridine-2-carboxamide trifluoroacetate
4-[3-fluoro-4-({[(2,2,4,4-tetrafluoro-4H-1,3-benzodioxin-6-yl)amino]carbonyl}-amino)phenoxy]-pyridine-2-carboxamide
4-[3-fluoro-4-({[(2,2,4,4-tetrafluoro-4H-1,3-benzodioxin-6-yl)amino]carbonyl}amino)-phenoxy]pyridine-2-carboxamide
N-methyl-4-{[5-({[(2,2,4,4-tetrafluoro-4H-1,3-benzodioxin-6-yl)amino]carbonyl}amino)-quinolin-8-yl]oxy}pyridine-2-carboxamide
4-(3-{[(1H-indazol-5-ylamino)carbonyl]amino}phenoxy)-N-methylpyridine-2-carboxamide dihydrochloride
N-[2-(methylamino)-2-oxoethyl]-4-[4-({[(2,2,4,4-tetrafluoro-4H-1,3-benzodioxin-6-yl)amino]carbonyl}amino)phenoxy]pyridine-2-carboxamide
4-(3-fluoro-4-{[(quinoxalin-2-ylamino)carbonyl]amino}phenoxy)-N-methylpyridine-2-carboxamide
N-[2-(dimethylamino)-2-oxoethyl]-4-[4-({[(2,2,4,4-tetrafluoro-4H-1,3-benzodioxin-6-yl)amino]carbonyl}amino)phenoxy]pyridine-2-carboxamide
N-methyl-4-[3-methyl-4-{[(2,2,4,4-tetrafluoro-4H-1,3-benzodioxin-6-yl)amino]carbonyl}-amino)phenoxy]pyridine-2-carboxamide
Methyl 4-[3-({[(2,2,4,4-tetrafluoro-4H-1,3-benzodioxin-7-yl)amino]carbonyl}-amino)phenoxy]-pyridine-2-carboxylate
4-[3-chloro-4-({[(2,2,4,4-tetrafluoro-4H-1,3-benzodioxin -6yl)amino]carbonyl}amino)-phenoxy]-N-methylpyridine-2-carboxamide
4-[3-chloro-4-({[(2,2,4,4-tetrafluoro-4H-1,3-benzodioxin-6-yl)amino]carbonyl}amino)-phenoxy]pyridine-2-carboxamide
4-(3-{[(1,3-benzodioxol-5-ylamino)carbonyl]amino}phenoxy)-N -methylpyridine-2-carboxamide
N-methyl-4-[3-({[(2,2,4,4-tetrafluoro-4H-1,3-benzodioxin-6-yl)amino]carbonyl}amino)-phenoxy]pyridine-2-carboxamide
4-(3-{[(2,3-dihydro-1,4-benzodioxin-6-ylamino)carbonyl]amino}phenoxy)-N-methylpyridine-2-carboxamide
4-[4-chloro-3-({[(2,2,4,4-tetrafluoro-4H-1,3-benzodioxin-6-yl)amino]carbonyl}amino)-phenoxy]-N-methylpyridine-2-carboxamide 5-[2-fluoro-4-({[(2,2,4,4-tetrafluoro-4H-1,3-benzo-dioxin-6-yl)amino]carbonyl}amino)-phenoxy]-N-methylnicotinamide 4-[2-chloro-4-({[(2,2,4,4-tetrafluoro-4H-1,3-benzo-dioxin-6-yl)amino]carbonyl}amino)-phenoxy]pyridine-2-carboxamide 4-[3-chloro-4-({[(2,2,4,4-tetrafluoro-4H-1,3-benzo-dioxin-6-yl)amino]carbonyl}amino)-phenoxy]pyridine-2-carboxamide 4-[3-fluoro-4-({[(2,2,4,4-tetrafluoro-4H-1,3benzodioxin-6-yl)amino]carbonyl}amino)-phenoxy]pyridine-2-carboxamide 4-[3-fluoro-4-({[(2,2,4,4-tetrafluoro-4H-1,3-benzo-dioxin-6-yl)amino]carbonyl}amino)-phenoxy]pyridine-2-carboxamide 4-(3-{[(1,3-benzodioxol-5-ylamino)carbonyl]amino}-4-chlorophenoxy)-N-methylpyridine-2-carboxamide 4-[4-chloro-3-({[(6-fluoro-4H-1,3-benzodioxin-8-yl)amino]carbonyl}amino)phenoxy]-N-methylpyridine-2-carboxamide 4-(4-{[(1,3-benzodioxol -5-ylamino)carbonyl]amino}-3-fluorophenoxy)pyridine-2-carboxamide 4-[3-fluoro-4-({[(6-fluoro-4H-1,3-benzodioxin-8-yl)amino]carbonyl}amino)phenoxy]-pyridine-2-carboxamide 4-(4-chloro-3-{[(2,3-dihydro-1,4-benzodioxin-6-ylamino)carbonyl]amino}phenoxy)-N-methylpyridine-2-carboxamide 4-[3-({[(7-fluoro-2,3-dihydro-1,4-benzodioxin-5-yl)amino]carbonyl}amino)phenoxy]-N-methylpyridine-2-carboxamide 4-[3-fluoro-4-({[(2,2,4,4-tetrafluoro-4H-1,3-benzo-dioxin-6-yl)amino]carbonyl}amino)-phenoxy]-N-methylpyridine-2-carboxamide 4-(4-{[(1,3-benzodioxol -5-ylamino)carbonyl] amino}phenoxy)-N-methylpyridine-2-carboxamide N-methyl-4-[4-({[(2,2,4,4-tetrafluoro-4H-1,3-benzo-dioxin-6-yl)amino]carbonyl}amino)-phenoxy]pyridine-2-carboxamide Methyl 4-[4-({[(2,2,4,4-tetrafluoro-4H-1,3-benzodioxin-6-yl)amino]carbonyl}-amino)phenoxy]pyridine-2-carboxylate Methyl 5-[4-({[(2,2,4,4-tetrafluoro-4H-1,3-benzodioxin-6-yl)amino]carbonyl}amino)-phenoxy]nicotinate 4-[2,4-dichloro-5-({[(2,2,4,4-tetrafluoro-4H-1,3-benzo-dioxin-6-yl)amino]carbonyl}amino)-phenoxy]-N-methylpyridine-2-carboxamide N-methyl-5-[4-({[(2,2,4,4-tetrafluoro-4H-1,3-benzo-dioxin-6-yl)amino]carbonyl}amino)-phenoxy]nicotinamide 4-(4-{[(1,3-benzodioxol-5-ylamino)carbonyl]amino}-3-chlorophenoxy)-N-methylpyridine-2-carboxamide 4-[3-chloro-4-({[(6-fluoro-4H-1,3-benzodioxin-8-yl)amino]carbonyl}amino)phenoxy]-N-methylpyridine-2-carboxamide N-methyl-4-[2-methyl-4-({[(2,2,4,4-tetrafluoro-4H-1,3-benzodioxin-6-yl)amino]carbonyl}-amino)phenoxy]pyridine-2-carboxamide N-methyl-4-[3-nitro-4-({[(2,2,4,4-tetrafluoro-4H-1,3-benzodioxin-6-yl)amino]carbonyl}-amino)phenoxy]pyridine-2-carboxamide N-methyl-4-[3-({[(2,2,4,4-tetrafluoro-4H-1,3-benzo-dioxin-6-yl)amino]carbonyl}amino)-phenoxy]pyridine-2-carboxamide 1-oxide 4-[3-({[(1-methyl-1H-indazol-5-yl)amino]carbonyl}amino)phenoxy]-N-(2-pipendin-1-ylethyl)pyridine-2-carboxamide 4-[3-({[(1-methyl-1H-indazol-5-yl)amino]carbonyl}amino)phenoxy]-N-(2-pyrrolidin-1-ylethyl)pyridine-2-carboxamide 4-[3-({[(1-methyl-1H-indazol-5-yl)amino]carbonyl}amino)phenoxy]-N-pyridin-3-ylpyridine-2-carboxamide N-[3-(1H-imidazol-1-yl)propyl]-4-[3-({[(1-methyl-1H-indazol-5-yl)amino]carbonyl}amino)-phenoxy]pyridine-2-carboxamide N-(2-pipendin-1-ylethyl)-4-[3-({[(2,2,4,4-tetrafluoro-4H-1,3-benzodioxin-6-yl)amino]-carbonyl}amino)phenoxy]pyridine-2-carboxamide N-(2-pyrrolidin-1-ylethyl)-4-[3-({[(2,2,4,4-tetrafluoro-4H-1,3-benzodioxin-6-yl)amino]-carbonyl}amino)phenoxy]pyridine-2-carboxamide N-pyridin-3-yl-4-[3-({[(2,2,4,4-tetrafluoro-4H-1,3-benzodioxin-6-yl)amino]carbonyl}-amino)phenoxy]pyridine-2-carboxamide N-[3-(1H-imidazol-1yl)propyl]-4-[3-({[(2,2,4,4-tetrafluoro-4H-1,3-benzodioxin-6-yl)amino]-carbonyl}amino)phenoxy]pyridine-2-carboxamide N-[3-(1H-imidazol-1-yl)propyl]-4-[4-({[(2,2,4,4-tetrafluoro-4H-1,3-benzodioxin-6-yl)amino]-carbonyl}amino)phenoxy]pyridine-2-carboxamide N-(2-pyrrolidin-1-ylethyl)-4-[4-({[(2,2,4,4-tetrafluoro-4H-1,3-benzodioxin-6-yl)amino]-carbonyl}amino)phenoxy]pyridine-2-carboxamide N-(2-piperidin-1-ylethyl)-4-[4-({[(2,2,4,4-tetrafluoro-4H-1,3-benzodioxin-6-yl)amino]-carbonyl}amino)phenoxy]pyridine-2-carboxamide N-(2-piperazin-1-ylethyl)-4-[4-({[(2,2,4,4-tetrafluoro-4H-1,3-benzodioxin-6-yl)amino]-carbonyl}amino)phenoxy]pyridine-2-carboxamide N-pyridin-2-yl-4-[4-({[(2,2,4,4-tetrafluoro-4H-1,3-benzodioxin-6-yl)amino]carbonyl}amino)-phenoxy]pyridine-2-carboxamide 4-[4-({[(1methyl-1H-indazol-5-yl)amino]carbonyl}amino)phenoxy]-N-(2-pyrrolidin-1-ylethyl)pyridine-2-carboxamide 4-[4-({[(1methyl-1H-indazol-5-yl)amino]carbonyl}amino)phenoxy]-N-(2-piperazin-1ylethyl)pyridine-2-carboxamide 4-[2-methoxy-4-({[(2,2,4,4-tetrafluoro-4H-1,3-benzo-dioxin-6-yl)amino]carbonyl}amino)-phenoxy]pyridine-2-carboxamide 4-(4-{[(2,3-dihydro-1H-inden-5-ylamino)carbonyl]amino}-2-methoxyphenoxy)pyridine-2-carboxamide 4-[2,5-difluoro-4-({[(2,2,4,4-tetrafluoro-4H-1,3-benzo-dioxin-6-yl)amino]carbonyl}amino)-phenoxy]pyridine-2-carboxamide 4-[3,5-difluoro-4-({[(2,2,4,4-tetrafluoro-4H-1,3-benzo-dioxin-6-yl)amino]carbonyl}amino)-phenoxy]pyridine-2-carboxamide 4-[3-(aminocarbonyl)-4-({[(2,2,4,4-tetrafluoro-4H-1,3-benzodioxin-6-yl)amino]carbonyl}-amino)phenoxy]pyridine-2-carboxamide N-methyl-4-[3-(methylsulfonyl)-4-({[(2,2,4,4-tetrafluoro-4H-1,3-benzodioxin-6-yl)amino]carbonyl}amino)phenoxy]pyridine-2-carboxamide N-methyl-4-[3-(methylthio)-4-({[(2,2,4,4-tetrafluoro-4H-1,3-benzodioxin-6-yl)amino]carbonyl}amino)phenoxy]pyridine-2-carboxamide 4-[3-fluoro-4-({[(6-nitro-1,3-benzothiazol-2-yl)amino]carbonyl}amino)phenoxy]-N-methylpyridine-2-carboxamide N-methyl-4-[4-({[(6-nitro-1,3-benzothiazol-2-yl)amino]carbonyl}amino)phenoxy]pyridine-2-carboxamide 4-[4-({[(4,6-difluoro-1,3-benzothiazol-2-yl)amino]
carbonyl}amino)phenoxy]-N-methylpyridine-2-carboxamide
N-methyl-4-[4-({[(2-methyl-1,3-benzoxazol-6-yl)amino]
carbonyl}amino)phenoxy]pyridine-2-carboxamide
4-(4-{[(2,3-dihydro-1H-inden-4-ylamino)carbonyl]
amino}phenoxy)-N-methylpyridine-2-carboxamide
4-[4-({[(2,2-difluoro-1,3-benzodioxol-4-yl)amino]
carbonyl}amino)phenoxy]-N-methylpyridine-2-carboxamide
N-methyl-4-[4-({[(2-methyl-2H-indazol-5-yl)amino]
carbonyl}amino)phenoxy]pyridine-2-carboxamide
4-(4-{[({1-[2-(diethylamino)ethyl]-1H-indazol-5-yl}amino)carbonyl]amino}-3-fluorophenoxy)-N-methylpyridine-2-carboxamide
N-methyl-4-[4-({[(2-methyl-1H-indol-5-yl)amino]
carbonyl}amino)phenoxy]pyridine-2-carboxamide
N-{4-[(2-acetylpyridin-4-yl)oxy]phenyl}-N'-(1-methyl-1H-indazol-5- yl)urea
N-[2-(dimethylamino)-2-oxoethyl]-4 -[4-({[(1methyl-1H-indazol-5-yl)amino]carbonyl}-aminophenoxy]pyridine-2-carboxamide
N-methyl-4-[4-({[(2-methyl-1,3-benzothiazol-5-yl)
amino]carbonyl}amino)phenoxy]pyridine-2-carboxamide
N-methyl-4-{[4-({[(1methyl-1H-indazol-5-yl)amino]
carbonyl}amino)phenoxy]methyl}-pyridine-2-carboxamide
4-(3-{[(1H-1,2,3-benzotriazol-5-ylamino)carbonyl]
amino}phenoxy)-N-methylpyridine-2-carboxamide
Methyl 4-[3-({[(1methyl-1H-indazol-5-yl)amino]
carbonyl}amino)phenoxy]pyridine-2-carboxylate
4-(4-{[(1H-1,2,3-benzotriazol-5-ylamino)carbonyl]
amino}phenoxy)-N-methylpyridine-2-carboxamide
4-(4-{[(1H-indazol-6-ylamino)carbonyl]
amino}phenoxy)-N-methylpyridine-2-carboxamide
N-methyl-4-{4-[({[2-(trifluoromethyl)-1H-benzimidazol-5-yl]amino}carbonyl)amino]-phenoxy}pyridine-2-carboxamide
4-[4-({[(1-ethyl-2-methyl-1H-benzimidazol-5-yl)amino]
carbonyl}amino)phenoxy]-N-methylpyridine-2-carboxamide
Methyl 4-[4-({[(1methyl-1H-indazol-5-yl)amino]
carbonyl}amino)phenoxy]pyridine-2-carboxylate
4-[2-chloro-4-({[(2,2,4,4-tetrafluoro-4H-1,3-benzodioxin-7-yl)amino]carbonyl}amino)-phenoxy]-N-methylpyridine-2-carboxamide
4-(4-{[(2,3-dihydro-1,4-benzodioxin-6-ylamino)carbonyl]amino}phenoxy)-N-[3-(1H-imidazol-1-yl)propyl]pyridine-2-carboxamide
4-(4-{[(2,3-dihydro-1,4-benzodioxin-6-ylamino)carbonyl]amino}phenoxy)-N-(2-pyrrolidin-1-ylethyl)pyridine-2-carboxamide
N-[3-(1H-imidazol-1yl)propyl]-4-[4-({[(1methyl-1H-indazol-5-yl)amino]carbonyl}amino)-phenoxy]pyridine-2-carboxamide
4-[4-({[(1methyl-1H-indazol-5-yl)amino]
carbonyl}amino)phenoxy]-N-(2-piperidin-1-ylethyl)pyridine-2-carboxamide
N-cyclopropyl-4-[4-({[(1methyl-1H-indazol-5-yl)amino]
carbonyl}amino)phenoxy]pyridine-2-carboxamide
N-(cyclopropylmethyl)-4-[4-({[(1methyl-1H-indazol-5-yl)amino]carbonyl}amino)phenoxy]-pyridine-2-carboxamide
N-cyclobutyl-4-[4-({[(1methyl-1H-indazol-5-yl)amino]
carbonyl}amino)phenoxy]pyridine-2-carboxamide or
Methyl-N-({4-[4-({[(1methyl-1H-indazol-5-yl)amino]
carbonyl}amino)phenoxy]pyridin-2-yl}carbonyl)glycinate.

13. A pharmaceutical composition which comprises an effective amount of at least one compound of claim 1 and a physiologically acceptable carrier.

14. A compound of formula (I):

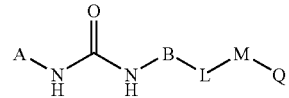

wherein
Q is $C(O)R^4$, $C(O)OR^4$ or $C(O)NR^4R^5$;
wherein A is a bicyclic heterocycle which is:
(1) benzimidazol-5-yl
(2) benzimidazol-6-yl
(3) 1,3-benzothiazol-2-yl
(4) 1,3-benzothiazol-5-yl
(5) 1,3-benzothiazol-6-yl
(6) 1,2,3-benzotriazol-5-yl
(7) 1,3-benzoxazol-2-yl
(8) 1,3-benzoxazol-6-yl
(9) 2,3-dihydro-1H-indol-5-yl
(10) 2,3-dihydro-1H-indol-6-yl
(11) 2,3-dihydro-1H-inden-4-yl
(12) 2,3-dihydro-1H-inden-5-yl
(13) 1,1-dioxido-2,3-dihydro-1-benzothien-6-yl
(14) 1H-indazol-5-yl
(15) 2H-indazol-5-yl
(16) 1H-indazol-6-yl
(17) 1H-indol-5-yl
(18) 2-oxo-2H-chromen-7-yl
(19) 1-oxo-2,3-dihydro-1 H-inden-5-yl
(20) quinoxalin-2-yl
(21) quinoxalin-6-yl, or
(22) one of the formulae

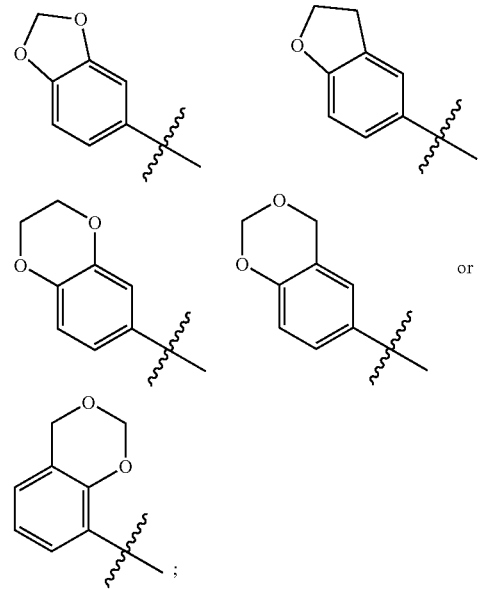

optionally substituted with 1-4 substituents which are independently $R^1$, $OR^1$,
  $S(O)_pR^1$, $C(O)R^1$, $C(O)OR^1$, $C(O)NR^1R^2$, halogen, oxo, cyano, or nitro,
 B is phenyl, optionally substituted with 1-4 substituents which are independently $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_6$ dialkylamino, carboxyamide, halogen, cyano, nitro or $S(O)_pR^7$;
 L is:
  (a) —(CH$_2$)$_m$—O—(CH$_2$)$_l$—,
  (b) —(CH$_2$)$_m$—(CH$_2$)$_l$—,
  (c) —(CH$_2$)$_m$—C(O)—(CH$_2$)$_l$—,
  (d) —(CH$_2$)$_m$—NR$^3$—(CH$_2$)$_l$—,
  (e) —(CH$_2$)$_m$—NR$^3$C(O)—(CH$_2$)$_l$—,
  (f) —(CH$_2$)$_m$—S—(CH$_2$)$_l$—,
  (g) —(CH$_2$)$_m$—C(O)NR$^3$—(CH$_2$)$_l$—, or
  (h) a single bond;
 m and l are integers independently selected from 0-4;
 M is a pyridine ring, optionally substituted with 1-3 substituents which are independently $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_6$ dialkylamino, halogen, or nitro;
 Q is $C(O)R^4$, $C(O)OR^4$ or $C(O)NR^4R^5$;
 each of $R^1$, $R^2$, $R^3$, $R^4$ and $R^5$, is independently:
  (a) hydrogen,
  (b) $C_1$-$C_5$ linear, branched, or cyclic alkyl,
  (c) phenyl,
  (d) $C_1$-$C_3$ alkyl-phenyl,
  (e) up to per-halo substituted $C_1$-$C_5$ linear or branched alkyl,
  (f) —(CH$_2$)$_q$—X, wherein X is a 5 or 6 membered heterocyclic ring, containing at least one atom selected from oxygen, nitrogen and sulfur, which is saturated, partially saturated, or aromatic, or a 8-10 membered bicyclic heteroaryl having 1-4 heteroatoms which are O, N or S, or
  (g) —(CH$_2$)$_q$—Y, where Y is $C(O)R^6$, $C(O)OR^6$ and $C(O)NR^6R^7$;
 each of $R^6$-$R^7$ is independently:
  (a) hydrogen,
  (b) $C_1$-$C_5$ linear, branched, or cyclic alkyl,
  (c) phenyl,
  (d) $C_1$-$C_3$ alkyl-phenyl, or
  (e) up to per-halo substituted $C_1$-$C_5$ linear or branched alkyl;
 each of $R^1$, $R^2$, $R^3$, $R^4$, $R^5$, $R^6$ and $R^7$, other than per-halo substituted $C_1$-$C_5$ linear or branched alkyl, is optionally substituted with 1-3 substituents which are independently $C_1$-$C_5$ linear or branched alkyl, up to perhalo substituted $C_1$-$C_5$ linear or branched alkyl, $C_1$-$C_3$ alkoxy, hydroxy, carboxy, amino, $C_1$-$C_3$ alkylamino, $C_1$-$C_6$ dialkylamino, halogen, cyano, or nitro;
 p is an integer selected from 0, 1, or 2; and
 q is an integer selected from 1, 2, 3, or 4,
 or a pharmaceutically acceptable salt of formula I or an oxidized derivative of formula I wherein one or more urea nitrogens are substituted with a hydroxyl group, or an oxidized derivative of formula I wherein the nitrogen atom of pyridine ring M is in the oxide form, or a methyl, ethyl, propyl, isopropyl, butyl, isobutyl, pentyl ester or phenyl $C_1$-$C_5$ alkyl ester of formula I at a carboxylic acid group or amide group.

15. A compound of claim 14 wherein A is
 (1) benzimidazol-5-yl
 (2) benzimidazol-6-yl
 (8) 1,3-benzoxazol-6-yl
 (9) 2,3-dihydro-1H-indol-5-yl
 (10) 2,3-dihydro-1H-indol-6-yl
 (11) 2,3-dihydro-1H-inden-4-yl
 (12) 2,3-dihydro-1H-inden-5-yl
 (13) 1,1-dioxido-2,3-dihydro-1-benzothien-6-yl
 (14) 1H-indazol-5-yl
 (15) 2H-indazol-5-yl
 (16) 1H-indazol-6-yl
 (17) 1H-indol-5-yl
 (18) quinoxalin-2-yl
 (19) quinoxalin-6-yl, or
 (20) one of the formulae

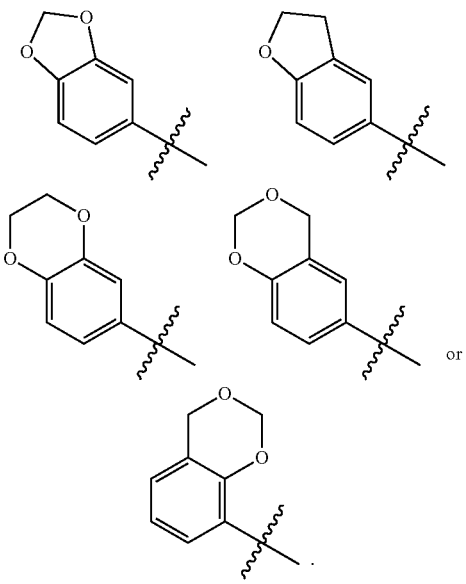

16. A compound of claim 14 wherein the optional substituents on bicyclic heterocycle A are independently $R^1$, $OR^1$, and halogen.

17. A compound as in claim 16 wherein B is phenyl optionally substituted with 1-4 substituents which are halogen.

18. A compound of claim 17 wherein L is —O—.

19. A compound of claim 18 wherein Q is $C(O)NR^4R^5$ and each of $R^4$ and $R^5$ is independently hydrogen or $C_1$-$C_5$ alkyl.

20. A compound of formula (I):

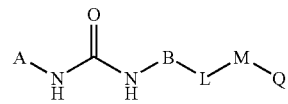

wherein
 A is a bicyclic heterocycle which is:
 (1) benzimidazol-5-yl
 (2) benzimidazol-6-yl
 (8) 1,3-benzoxazol-6-yl
 (9) 2,3-dihydro-1H-indol-5-yl
 (10) 2,3-dihydro-1H-indol-6-yl
 (11) 2,3-dihydro-1H-inden-4-yl
 (12) 2,3-dihydro-1H-inden-5-yl

(13) 1,1-dioxido-2,3-dihydro-1-benzothien-6-yl
(14) 1H-indazol-5-yl
(15) 2H-indazol-5-yl
(16) 1H-indazol-6-yl
(17) 1H-indol-5-yl
(18) quinoxalin-2-yl
(19) quinoxalin-6-yl, or
(20) one of the formulae

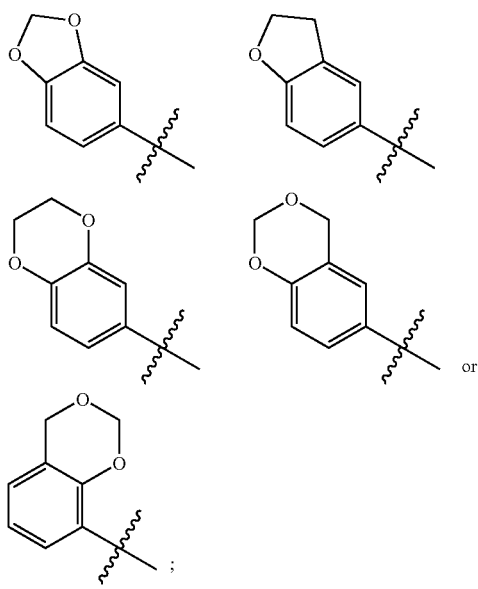

optionally substituted with 1-4 substituents which are independently $R^1$, $OR^1$, $S(O)_pR^1$, $C(O)R^1$, $C(O)OR^1$, $C(O)NR^1R^2$, halogen, oxo, cyano, or nitro,
  B is phenyl, optionally substituted with halogen,
  L is —O—,
  M is a pyridine ring substituted only with Q,
  Q is $C(O)NHR^5$ and $R^5$ is independently hydrogen or $C_1$-$C_5$ alkyl,
  and p is an integer selected from 0, 1, or 2
  or a pharmaceutically acceptable salt of formula I or an oxidized derivative of formula I wherein one or more urea nitrogens are substituted with a hydroxyl group, or an oxidized derivative of formula I wherein the nitrogen atom of pyridine ring M is in the oxide form, or a methyl, ethyl, propyl, isopropyl, butyl, isobutyl, pentyl ester or phenyl $C_1$-$C_5$ alkyl ester of formula I at a carboxylic acid group or amide group.

21. A compound of formula (I):

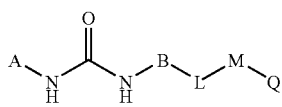

I wherein
A is a bicyclic heterocycle which is:
(1) benzimidazolyl
(2) 1,3-benzothiazolyl
(3) 1,2,3-benzotriazolyl
(4) 1,3-benzoxazolyl
(5) 2,3-dihydro-1H-indolyl
(6) 2,3-dihydro-1H-indenyl
(7) 1,1-dioxido-2,3-dihydro-1-benzothienyl
(8) 1H-indazolyl
(9) 2H-indazolyl
(10) 1H-indolyl
(11) 2H-chromenyl
(12) quinoxalinyl or
(13) one of the formulae

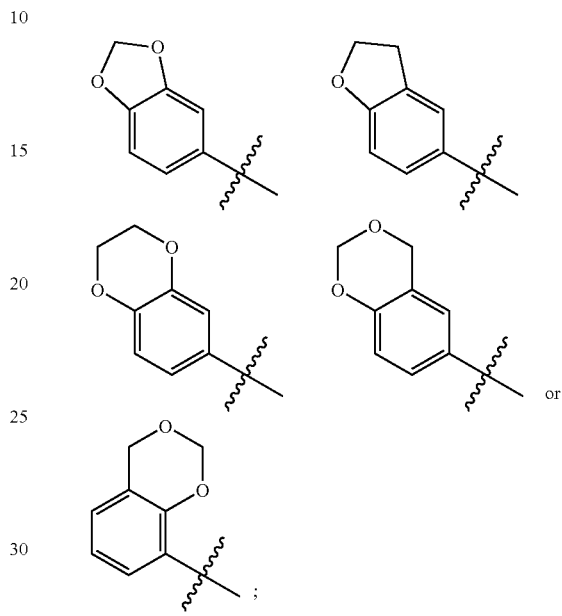

optionally substituted with 1-4 substituents which are independently $R^1$, $OR^1$, $S(O)_pR^1$, $C(O)R^1$, $C(O)OR^1$, $C(O)NR^1R^2$, halogen, oxo, cyano, or nitro;
  B is quinolinyl, optionally substituted with 1-4 substituents which are independently $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_6$ dialkylamino, carboxyamide, halogen, cyano, nitro or $S(O)_pR^7$;
  L is:
  (a) —$(CH_2)_m$—O—$(CH_2)_l$—,
  (b) —$(CH_2)_m$—$(CH_2)_l$—,
  (c) —$(CH_2)_m$—C(O)—$(CH_2)_l$—,
  (d) —$(CH_2)_m$—$NR^3$—$(CH_2)_l$—,
  (e) —$(CH_2)_m$—$NR^3C(O)$—$(CH_2)_l$—,
  (f) —$(CH_2)_m$—S—$(CH_2)_l$—,
  (g) —$(CH_2)_m$—$C(O)NR^3$—$(CH_2)_l$—, or
  (h) a single bond;
  m and l are integers independently selected from 0-4;
  M is a pyridine ring, optionally substituted with 1-3 substituents which are independently $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_6$ dialkylamino, halogen, or nitro;
  Q is $C(O)R^4$, $C(O)OR^4$ or $C(O)NR^4R^5$;
  each of $R^1$, $R^2$, $R^3$, $R^4$ and $R^5$ is independently:
  (a) hydrogen,
  (b) $C_1$-$C_5$ linear, branched, or cyclic alkyl,
  (c) phenyl,
  (d) $C_1$-$C_3$ alkyl-phenyl,
  (e) up to per-halo substituted $C_1$-$C_5$ linear or branched alkyl, (f) —(CH$_2$)$_q$-X, wherein X is a 5 or 6 membered heterocyclic ring, containing at least one atom selected from oxygen, nitrogen and sulfur, which is saturated, partially saturated, or aromatic, or a 8-10 membered bicyclic heteroaryl having 1-4 heteroatoms which are O, N or S, or (g) —(CH$_2$)$_q$-Y, where Y is C(O)R$^6$, C(O)OR$^6$ and C(O)NR$^6$R$^7$;

each of R$^6$-R$^7$ is independently:
(a) hydrogen,
(b) C$_1$-C$_5$ linear, branched, or cyclic alkyl,
(c) phenyl,
(d) C$_1$-C$_3$ alkyl-phenyl, or
(e) up to per-halo substituted C$_1$-C$_5$ linear or branched alkyl;

each of R$^1$, R$^2$, R$^3$, R$^4$, R$^5$, R$^6$ and R$^7$, other than per-halo substituted C$_1$-C$_5$ linear or branched alkyl, is optionally substituted with 1-3 substituents which are independently C$_1$-C$_5$ linear or branched alkyl, up to perhalo substituted C$_1$-C$_5$ linear or branched alkyl, C$_1$-C$_3$ alkoxy, hydroxy, carboxy, amino, C$_1$-C$_3$ alkylamino, C$_1$-C$_6$ dialkylamino, halogen, cyano, or nitro;

p is an integer selected from 0, 1, or 2; and
q is an integer selected from 1, 2, 3, or 4,
or a pharmaceutically acceptable salt of formula I or an oxidized derivative of formula I wherein one or more urea nitrogens are substituted with a hydroxyl group, or an oxidized derivative of formula I wherein the nitrogen atom of pyridine ring M is in the oxide form, or a methyl, ethyl, propyl, isopropyl, butyl, isobutyl, pentyl ester or phenyl C$_1$-C$_5$ alkyl ester of formula I at a carboxylic acid group or amide group.

22. A compound of claim 1 wherein A and B follow one of the following combinations:
A=1H-benzimidazol-5-yl; and B=quinolinyl,
A=1H-benzimidazol-6-yl; and B=quinolinyl,
A=1,3-benzodioxin-6-yl; and B=quinolinyl,
A=1,3-benzodioxin-7-yl; and B=quinolinyl,
A=1,3-benzodioxin-8-yl; and B=quinolinyl,
A=1,3-benzodioxol-4-yl; and B=quinolinyl,
A=1,3-benzodioxol-5-yl; and B=quinolinyl,
A=1,3-benzothiazol-2-yl; and B=quinolinyl,
A=1,3-benzothiazol-5-yl; and B=quinolinyl,
A=1,3-benzothiazol-6-yl; and B=quinolinyl,
A=1,2,3-benzotriazol-5-yl; and B=quinolinyl,
A=1,3-benzoxazol-2-yl; and B=quinolinyl or
A=1,3-benzoxazol-6-yl; and B=quinolinyl.

23. A compound of claim 1 wherein A and B follow one of the following combinations:
A=2,3-dihydro-1,4-benzodioxin-5-yl; and B=quinolinyl,
A=2,3-dihydro-1,4-benzodioxin-6-yl; and B=quinolinyl,
A=2,3-dihydro-1-benzofuran-5-yl; and B=quinolinyl,
A=2,3-dihydro-1H-indol-5-yl; and B=quinolinyl,
A=2,3-dihydro-1H-indol-6-yl; and B=quinolinyl,
A=2,3-dihydro-1H-inden-4-yl; and B=quinolinyl,
A=2,3-dihydro-1H-inden-5-yl; and B=quinolinyl, or
A=1,1-dioxido-2,3-dihydro-1-benzothien-6-yl; and B=quinolinyl.

24. A compound of claim 1 wherein A and B follow one of the following combinations:
A=1H-indazol-5-yl; and B=quinolinyl,
A=2H-indazol-5-yl; and B=quinolinyl,
A=1H-indazol-6-yl; and B=quinolinyl,
A=1H-indol-5-yl; and B=quinolinyl,
A=2-oxo-2H-chromen-7-yl; and B=quinolinyl or
A=1-oxo-2,3-dihydro-1H-inden-5-yl and B=quinolinyl.

25. A compound of claim 1 wherein A and B follow one of the following combinations:
A=quinoxalin-2-yl; and B=quinolinyl or
A=quinoxalin-6-yl; and B=quinolinyl.

26. A compound as in claim 21 wherein L is —O——S—.

27. A pharmaceutical composition which comprises an effective amount of at least one compound of claim 21 and a physiologically acceptable carrier.

28. A compound of formula (I):

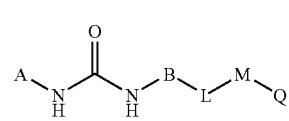

wherein
Q is C(O)R$^4$, C(O)OR$^4$ or C(O)NR$^4$R$^5$;
wherein A is a bicyclic heterocycle which is:
(1) benzimidazol-5-yl
(2) benzimidazol-6-yl
(3) 1,3-benzothiazol-2-yl
(4) 1,3-benzothiazol-5-yl
(5) 1,3-benzothiazol-6-yl
(6) 1,2,3-benzotriazol-5-yl
(7) 1,3-benzoxazol-2-yl
(8) 1,3-benzoxazol-6-yl
(9) 2,3-dihydro-1H-indol-5-yl
(10) 2,3-dihydro-1H-indol-6-yl
(11) 2,3-dihydro-1H-inden-4-yl
(12) 2,3-dihydro-1H-inden-5-yl
(13) 1,1-dioxido-2,3-dihydro-1-benzothien-6-yl
(14) 1H-indazol-5-yl
(15) 2H-indazol-5-yl
(16) 1H-indazol-6-yl
(17) 1H-indol-5-yl
(18) 2-oxo-2H-chromen-7-yl
(19) 1-oxo-2,3-dihydro-1H-inden-5-yl
(20) quinoxalin-2-yl
(21) quinoxalin-6-yl, or
(22) one of the formulae

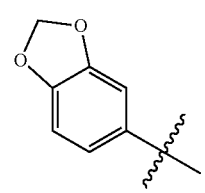 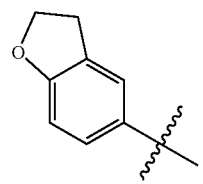

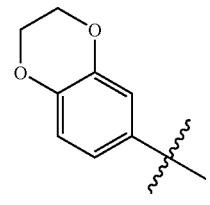 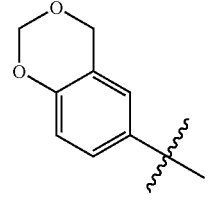 or

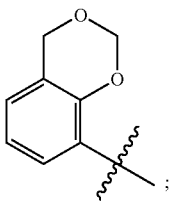

optionally substituted with 1-4 substituents which are independently $R^1$, $OR^1$, $S(O)_p R^1$, $C(O)R^1$, $C(O)OR^1$, $C(O)NR^1R^2$, halogen, oxo, cyano, or nitro B is quinolinyl, optionally substituted with 1-4 substituents which are independently $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_6$ dialkylamino, carboxyamide, halogen, cyano, nitro or $S(O)_p R^7$;

L is:
(a) —$(CH_2)_m$—O—$(CH_2)_l$—,
(b) —$(CH_2)_m$—$(CH_2)_l$—,
(c) —$(CH_2)_m$—C(O)—$(CH_2)_l$—,
(d) —$(CH_2)_m$—$NR^3$—$(CH_2)_l$—,
(e) —$(CH_2)_m$—$NR^3$C(O)—$(CH_2)_l$—,
(f) —$(CH_2)_m$—S—$(CH_2)_l$—,
(g) —$(CH_2)_m$—C(O)$NR^3$—$(CH_2)_l$—, or
(h) a single bond;

m and l are integers independently selected from 0-4;

M is a pyridine ring, optionally substituted with 1-3 substituents which are independently $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_6$ dialkylamino, halogen, or nitro;

each of $R^1$, $R^2$, $R^3$, $R^4$ and $R^5$, is independently:
(a) hydrogen,
(b) $C_1$-$C_5$ linear, branched, or cyclic alkyl,
(c) phenyl,
(d) $C_1$-$C_3$ alkyl-phenyl,
(e) up to per-halo substituted $C_1$-$C_5$ linear or branched alkyl,
(f) —$(CH_2)_q$—X, wherein X is a 5 or 6 membered heterocyclic ring, containing at least one atom selected from oxygen, nitrogen and sulfur, which is saturated, partially saturated, or aromatic, or a 8-10 membered bicyclic heteroaryl having 1-4 heteroatoms which are O, N or S, or
(g) —$(CH_2)_q$—Y, where Y is $C(O)R^6$, $C(O)OR^6$ and $C(O)NR^6R^7$;

each of $R^6$-$R^7$ is independently:
(a) hydrogen,
(b) $C_1$-$C_5$ linear, branched, or cyclic alkyl,
(c) phenyl,
(d) $C_1$-$C_3$ alkyl-phenyl, or
(e) up to per-halo substituted $C_1$-$C_5$ linear or branched alkyl;

each of $R^1$, $R^2$, $R^3$, $R^4$, $R^5$, $R^6$ and $R^7$, other than per-halo substituted $C_1$-$C_5$ linear or branched alkyl, is optionally substituted with 1-3 substituents which are independently $C_1$-$C_5$ linear or branched alkyl, up to perhalo substituted $C_1$-$C_5$ linear or branched alkyl, $C_1$-$C_3$ alkoxy, hydroxy, carboxy, amino, $C_1$-$C_3$ alkylamino, $C_1$-$C_6$ dialkylamino, halogen, cyano, or nitro;

p is an integer selected from 0, 1, or 2; and
q is an integer selected from 1, 2, 3, or 4, or a pharmaceutically acceptable salt of formula I or an oxidized derivative of formula I wherein one or more urea nitrogens are substituted with a hydroxyl group, or an oxidized derivative of formula I wherein the nitrogen atom of pyridine ring M is in the oxide form, or a methyl, ethyl, propyl, isopropyl, butyl, isobutyl, pentyl ester or phenyl $C_1$-$C_5$ alkyl ester of formula I at a carboxylic acid group or amide group.

29. A compound of claim 28 wherein A is
(1) benzimidazol-5-yl
(2) benzimidazol-6-yl
(8) 1,3-benzoxazol-6-yl
(9) 2,3-dihydro-1H-indol-5-yl
(10) 2,3-dihydro-1H-indol-6-yl
(11) 2,3-dihydro-1H-inden-4-yl
(12) 2,3-dihydro-1H-inden-5-yl
(13) 1,1-dioxido-2,3-dihydro-l-benzothien-6-yl
(14) 1H-indazol-5-yl
(15) 2H-indazol-5-yl
(16) 1H-indazol-6-yl
(17) 1H-indol-5-yl
(18) quinoxalin-2-yl
(19) quinoxalin-6-yl, or
(20) one of the formulae

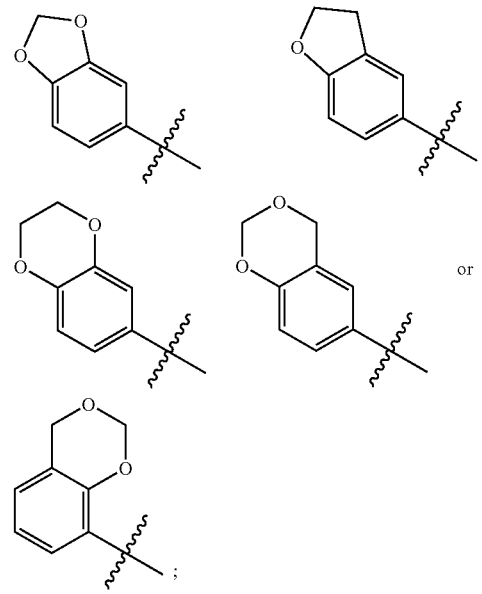

30. A compound of claim 28 wherein the optional substituents on bicyclic heterocycle A are independently $R^1$, $OR^1$, and halogen.
31. A compound of claim 30 wherein L is —O—.
32. A compound of claim 31 wherein Q is $C(O)NR^4R^5$ and each of $R^4$ and $R^5$ is independently hydrogen or $C_1$-$C_5$ alkyl.

* * * * *

UNITED STATES PATENT AND TRADEMARK OFFICE
CERTIFICATE OF CORRECTION

| | |
|---|---|
| PATENT NO. | : 8,076,488 B2 |
| APPLICATION NO. | : 10/788426 |
| DATED | : December 13, 2011 |
| INVENTOR(S) | : Jacques Dumas et al. |

It is certified that error appears in the above-identified patent and that said Letters Patent is hereby corrected as shown below:

Column 132, Line 9 reads: "A=1oxo-2,3-dihydro-1H-inden-5-yl; and B=phenyl," should read
-- A=1-oxo-2,3-dihydro-1H-inden-5-yl; and B=phenyl, --.

Column 133, Line 29 reads: "4-[3-fluoro-4-({[(1methyl-1H-indazol-5-yl)amino]" should read
-- 4-[3-fluoro-4-({[(1-methyl-1H-indazol-5-yl)amino] --.

Column 133, Line 32 reads: "4-[2-fluoro-4-({[(1methyl-1H-indazol-5-yl)amino]" should read
-- 4-[2-fluoro-4-({[(1-methyl-1H-indazol-5-yl)amino] --.

Column 133, Line 35 reads: "4-[2,4-difluoro-5-({[(1methyl-1H-indazol-5-yl)amino]" should read
-- 4-[2,4-difluoro-5-({[(1-methyl-1H-indazol-5-yl)amino] --.

Column 133, Line 38 reads: "N-methyl-4-[4-({[(1methyl-1H-indazol-5-yl)amino]" should read
-- N-methyl-4-[4-({[(1-methyl-1H-indazol-5-yl)amino] --.

Column 133, Line 41 reads: "4-[4-fluoro-3-({[(1methyl-1H-indazol-5-yl)amino]" should read
-- 4-[4-fluoro-3-({[(1-methyl-1H-indazol-5-yl)amino] --.

Column 133, Line 44 reads: "4-[2-fluoro-5-({[(1methyl-1H-indazol-5-yl)amino]" should read
-- 4-[2-fluoro-5-({[(1-methyl-1H-indazol-5-yl)amino] --.

Column 133, Line 47 reads: "4-[2-chloro-6-fluoro-4-({[(1methyl-1H-indazol-5-yl)" should read
-- 4-[2-chloro-6-fluoro-4-({[(1-methyl-1H-indazol-5-yl) --.

Column 133, Line 50 reads: "4-[3-fluoro-4-({[(1methyl-1H-indazol-5-yl)amino]" should read
-- 4-[3-fluoro-4-({[(1-methyl-1H-indazol-5-yl)amino] --.

Column 134, Line 18 reads: ''N-methyl-4-{[3-({[(1methyl-1H-indazol-5-yl)amino]" should read
-- N-methyl-4-{[3-({[(1-methyl-1H-indazol-5-yl)amino] --.

Signed and Sealed this
Thirteenth Day of March, 2012

David J. Kappos
*Director of the United States Patent and Trademark Office*

CERTIFICATE OF CORRECTION (continued)
U.S. Pat. No. 8,076,488 B2

Column 134, Line 24 reads: "4-[2-chloro-4-({[(1methyl-1H-indazol-5-yl)amino]" should read
-- 4-[2-chloro-4-({[(1-methyl-1H-indazol-5-yl)amino] --.

Column 134, Line 45 reads: "4-[3-chloro-4-({[(1methyl-1H-indazol-5-yl)amino]" should read
-- 4-[3-chloro-4-({[(1-methyl-1H-indazol-5-yl)amino] --.

Column 134, Line 48 reads: "N-methyl-4-[3-({[(1methyl-1H-indazol-5-yl)amino]" should read
-- N-methyl-4-[3-({[(1-methyl-1H-indazol-5-yl)amino] --.

Column 134, Line 50 reads: "N-methyl-4-[3-({[(1methyl-1H-indazol-6-yl)amino]" should read
-- N-methyl-4-[3-({[(1-methyl-1H-indazol-6-yl)amino] --.

Column 134, Line 57 reads: "4-[4-chloro-3-({[(1methyl-1H-indazol-5-yl)amino]" should read
-- 4-[4-chloro-3-({[(1-methyl-1H-indazol-5-yl)amino] --.

Column 134, Line 66 reads: "4-[3-chloro-4-({[(1methyl-1H-indazol-5-yl)amino]" should read
-- 4-[3-chloro-4-({[(1-methyl-1H-indazol-5-yl)amino] --.

Column 135, Line 1 reads: "4-[2-chloro-4-({[(1methyl-1H-indazol-5-yl)amino]" should read
-- 4-[2-chloro-4-({[(1-methyl-1H-indazol-5-yl)amino] --.

Column 135, Line 11 reads: "N-methyl-4-[4-({[(1oxo-2,3-dihydro-1H-inden-5-yl)" should read
-- N-methyl-4-[4-({[(1-oxo-2,3-dihydro-1H-inden-5-yl) --.

Column 135, Line 21 reads: "N-methyl-4-[4-({[(1oxo-2,3-dihydro-1H-inden-5-yl)" should read
-- N-methyl-4-[4-({[(1-oxo-2,3-dihydro-1H-inden-5-yl) --.

Column 135, Line 29 reads: "N-methyl-4-[4-({[(1methyl-1H-indazol-6-yl)amino]" should read
-- N-methyl-4-[4-({[(1-methyl-1H-indazol-6-yl)amino] --.

Column 135, Line 33 reads: "N-methyl-4-[4-({[(1methyl-1H-indazol-5-yl)amino]" should read
-- N-methyl-4-[4-({[(1-methyl-1H-indazol-5-yl)amino] --.

Column 135, Line 41 reads: "4-[2,4-dichloro-5-({[(1methyl-1H-indazol-5-yl)amino]" should read
-- 4-[2,4-dichloro-5-({[(1-methyl-1H-indazol-5-yl)amino] --.

Column 135, Line 56 reads: "4-[3-chloro-4-({[(1oxo-2,3-dihydro-1H-inden-5-yl)" should read
-- 4-[3-chloro-4-({[(1-oxo-2,3-dihydro-1H-inden-5-yl) --.

Column 135, Line 59 reads: "4-[2-chloro-4-({[(1oxo-2,3-dihydro-1H-inden-5-yl)" should read
-- 4-[2-chloro-4-({[(1-oxo-2,3-dihydro-1H-inden-5-yl) --.

Column 138, Line 37 reads: "4-[4-({[(1methyl-1H-indazol-5-yl)amino]" should read
-- 4-[4-({[(1-methyl-1H-indazol-5-yl)amino] --.

CERTIFICATE OF CORRECTION (continued)
U.S. Pat. No. 8,076,488 B2

Column 138, Line 40 reads: "4-[4-({[(1methyl-1H-indazol-5-yl)amino]" should read
-- 4-[4-({[(1-methyl-1H-indazol-5-yl)amino] --.

Column 139, Line 21 reads: "N-[2-(dimethylamino)-2-oxoethyl]-4-[4-({[(1methyl-" should read
-- N-[2-(dimethylamino)-2-oxoethyl]-4-[4-({[(1-methyl- --.

Column 139, Line 27 reads: "N-methyl-4-{[4-({[(1methyl-1H-indazol-5-yl)amino]" should read
-- N-methyl-4-{[4-({[(1-methyl-1H-indazol-5-yl)amino] --.

Column 139, Line 32 reads: "Methyl 4-[3-({[(1methyl-1H-indazol-5-yl)amino]" should read
-- Methyl 4-[3-({[(1-methyl-1H-indazol-5-yl)amino] --.

Column 139, Line 44 reads: "Methyl 4-[4-({[(1methyl-1H-indazol-5-yl)amino]" should read
-- Methyl 4-[4-({[(1-methyl-1H-indazol-5-yl)amino] --.

Column 139, Line 55 reads: "N-[3-(1H-imidazol-1-yl)propyl]-4-[4-({[(1methyl-1H-in-" should read
-- N-[3-(1H-imidazol-1-yl)propyl]-4-[4-({[(1-methyl-1H-in- --.

Column 139, Line 58 reads: "4-[4-({[(1methyl-1H-indazol-5-yl)amino]" should read
-- 4-[4-({[(1-methyl-1H-indazol-5-yl)amino] --.

Column 139, Line 61 reads: "N-cyclopropyl-4-[4-({[(1methyl-1H-indazol-5-yl)amino]" should read
-- N-cyclopropyl-4-[4-({[(1-methyl-1H-indazol-5-yl)amino] --.

Column 139, Line 63 reads: "N-(cyclopropylmethyl)-4-[4-({[(1methyl-1H-indazol-5-yl)amino]"
should read -- N-(cyclopropylmethyl)-4-[4-({[(1-methyl-1H-indazol-5-yl)amino] --.

Column 139, Line 66 reads: "N-cyclobutyl-4-[4-({[(1methyl-1H-indazol-5-yl)amino]" should read
-- N-cyclobutyl-4-[4-({[(1-methyl-1H-indazol-5-yl)amino] --.

Column 140, Line 1 reads: "Methyl-N-({4-[4-({[(1methyl-1H-indazol-5-yl)amino]" should read
-- Methyl-N-({4-[4-({[(1-methyl-1H-indazol-5-yl)amino] --.